US010239869B2

(12) United States Patent
Ramdas et al.

(10) Patent No.: US 10,239,869 B2
(45) Date of Patent: Mar. 26, 2019

(54) SULFONAMIDE COMPOUNDS AS VOLTAGE-GATED SODIUM CHANNEL MODULATORS

(71) Applicant: LUPIN LIMITED, Mumbai, Maharashtra (IN)

(72) Inventors: Vidya Ramdas, Maharashtra (IN); Rajeshkumar Maganlal Loriya, Maharashtra (IN); Moloy Banerjee, Maharashtra (IN); Pradeep Rangrao Patil, Maharashtra (IN); Advait Arun Joshi, Maharashtra (IN); Laxmikant Shamlal Datrange, Maharashtra (IN); Deepak Sahebrao Walke, Maharashtra (IN); Talha Hussain Khan, Maharashtra (IN); Amit Kumar Das, Maharashtra (IN); Ganesh Navinchandra Gote, Maharashtra (IN); Vaibhav Madhukar Kalhapure, Maharashtra (IN); Venkata P. Palle, Maharashtra (IN); Rajender Kumar Kamboj, Maharashtra (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 0 days.

(21) Appl. No.: 15/757,103

(22) PCT Filed: Sep. 3, 2016

(86) PCT No.: PCT/IB2016/055291
§ 371 (c)(1),
(2) Date: Mar. 2, 2018

(87) PCT Pub. No.: WO2017/037682
PCT Pub. Date: Mar. 9, 2017

(65) Prior Publication Data
US 2018/0186777 A1     Jul. 5, 2018

(30) Foreign Application Priority Data

Sep. 4, 2015 (IN) .......................... 3420/MUM/2015
Mar. 31, 2016 (IN) ............................. 201621011342

(51) Int. Cl.
| | |
|---|---|
| *C07D 405/12* | (2006.01) |
| *C07D 405/14* | (2006.01) |
| *C07D 413/14* | (2006.01) |
| *C07D 417/14* | (2006.01) |
| *A61P 29/00* | (2006.01) |

(52) U.S. Cl.
CPC ............ *C07D 405/12* (2013.01); *A61P 29/00* (2018.01); *C07D 405/14* (2013.01); *C07D 413/14* (2013.01); *C07D 417/14* (2013.01)

(58) Field of Classification Search
CPC .. C07D 405/12; C07D 405/14; C07D 413/14; C07D 417/14; A61P 29/00
See application file for complete search history.

(56) References Cited

U.S. PATENT DOCUMENTS

2007/0105820 A1*  5/2007  Chafeev ............... C07D 209/34
                                                                   514/80
2017/0137415 A1*  5/2017  Ramdas ............... C07D 417/12

FOREIGN PATENT DOCUMENTS

| WO | 2006/110917 A2 | 10/2006 |
|---|---|---|
| WO | 2007/109324 A2 | 9/2007 |
| WO | 2008/046049 A1 | 4/2008 |
| WO | 2008/046084 A2 | 4/2008 |
| WO | 2008/046087 A2 | 4/2008 |
| WO | 2008/060789 A2 | 5/2008 |
| WO | 2009/012242 A2 | 1/2009 |
| WO | 2010/035166 A1 | 4/2010 |
| WO | 2010/045197 A1 | 4/2010 |
| WO | 2010/045251 A2 | 4/2010 |

(Continued)

OTHER PUBLICATIONS

England and Rawson, "Isoform-selective voltage-gated Na+ channel modulators as next-generation analgesics", Future Med. Chem., 2, 775-790 (2010).

(Continued)

*Primary Examiner* — Alexander R Pagano
(74) *Attorney, Agent, or Firm* — Merchant & Gould P.C.

(57) ABSTRACT

The present invention relates to sulfonamide compounds Formula (I) wherein the substituents are as described herein, and their use in a medicine for the treatment of diseases, disorders associated with the inhibition of Voltage-gated sodium channels (VGSC) particularly $Na_v1.7$. It further relates to the compounds herein and their pharmaceutically acceptable salts thereof, pharmaceutical compositions thereof useful in treating diseases, disorders, syndromes and/or conditions associated with the inhibition of Voltage-gated sodium channels (VGSC) particularly $Na_v1.7$. The invention also relates to process for the preparation of the compounds of the invention.

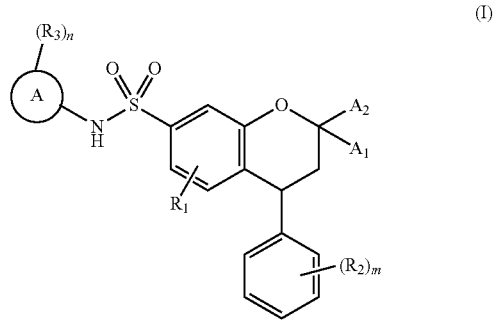

21 Claims, No Drawings

(56) References Cited

FOREIGN PATENT DOCUMENTS

| | | |
|---|---|---|
| WO | 2010/053998 A1 | 5/2010 |
| WO | 2010/078307 A1 | 7/2010 |
| WO | 2010/151595 A1 | 12/2010 |
| WO | 2010/151597 A1 | 12/2010 |
| WO | 2011/002708 A1 | 1/2011 |
| WO | 2011/026240 A1 | 3/2011 |
| WO | 2011/056985 A2 | 5/2011 |
| WO | 2011/058766 A1 | 5/2011 |
| WO | 2011/088201 A1 | 7/2011 |
| WO | 2011/103196 A1 | 8/2011 |
| WO | 2011/140425 A1 | 11/2011 |
| WO | 2013/122897 A1 | 8/2013 |
| WO | 2015/151001 A1 | 10/2015 |

OTHER PUBLICATIONS

Hoyt et al., "3-Amino-1,5-benzodiazepinones: Potent, state-dependent sodium channel blockers with anti-epileptic activity", Bioorganic & Medicinal Chemistry Letters, 18, 1963-1966 (2008).

Chowdhury et al., "Discovery of XEN907, a spirooxindole blocker of Nav1.7 for the treatment of pain", Bioorganic & Medicinal Chemistry Letters, 21, 3676-681 (2011).

Toledo-Aral et al., "Identification of PN1, a predominant voltage-dependent sodium channel expressed principally in peripheral neurons", Proc. Natl. Acad. Sci., USA, 94, 1527-1532 (1997).

Klugbauer et al., "Structure and functional expression of a new member of the tetrodotoxin-sensitive voltage-activated sodium channel family from human neuroendocrine cells", EMBO J., 14, 1084-90 (1995).

Fraser et al., "Voltage-Gated Sodium Channel Expression and Potentiation of Human Breast Cancer Metastasis", Clin. Cancer Res., 11, 5381-5389 (2005).

Roger et al., "Voltage-Gated Sodium Channels: New Targets in Cancer Therapy?" Current Pharmaceutical Design, 12, 3681-3695 (2006).

Diss et al, "A potential novel marker for human prostate cancer: voltage-gated sodium channel expression in vivo", Prostate Cancer and Prostatic Diseases, 8, 266-273 (2005).

International Search Report and Written Opinion from International Application No. PCT/IB2016/055291, dated Nov. 22, 2016, 8 pages.

* cited by examiner

SULFONAMIDE COMPOUNDS AS VOLTAGE-GATED SODIUM CHANNEL MODULATORS

RELATED APPLICATIONS

This application is a National Stage Application of International Patent Application No. PCT/IB2016/055291, filed Sep. 3, 2016, which claims the benefit of Indian Provisional Patent Application No. 3420/MUM/2015 filed on Sep. 4, 2015 and Indian Provisional Patent Application No. 201621011342 filed on Mar. 31, 2016 and which applications are incorporated herein by reference. To the extent appropriate, a claim of priority is made to each of the above disclosed applications.

FIELD OF THE INVENTION

The invention relates to sulfonamide compounds their pharmaceutically acceptable salts thereof and pharmaceutical compositions for the treatment, management, and/or lessening severity of diseases, disorders, syndromes or conditions which are associated with the voltage-gated sodium channels (VGSC). The invention also relates to processes for the preparation of compounds of the invention and methods of treating, managing and/or lessening the severity of the diseases disorders, syndromes or conditions associated with voltage-gated sodium channels (VGSC).

BACKGROUND OF THE INVENTION

Voltage-gated sodium channels play a crucial role in maintaining a specific membrane potential (intra- and extracellular ionic environments) across the mammalian cell membrane. The intracellular concentration of $Na^+$ is kept low relative to the extracellular by active sodium pumps that eject three $Na^+$ ions for every two $K^+$ ions taken in. This generates a negative membrane potential (since more positive charge is pumped out and less taken in) and maintains the Na+ concentration of 6 and 140 mM in the intra and extracellular milieu. On opening of the voltage-gated sodium channels (VGSC), $Na^+$ rushes in and leads to depolarization of the membrane because of the associated positive charge. The entry of $Na^+$ via VGSC's occurs in cells of the heart, central and peripheral nervous system and is essential to initiate the firing of an action potential.

VGSCs consist of a pore-forming alpha subunit and a stabilizing beta subunit, 9 isoforms of the alpha subunit have been identified till date ($Na_V1.1$ to $Na_V1.9$). All nine members of the family have >50% identity in the amino acid sequence in the extracellular and transmembrane domain. The channels have also been further classified based on their sensitivity to the puffer fish toxin (tetrodotoxin, TTX). Channels $Na_V1.8$, $Na_V1.9$ and $Na_V1.5$ are TTX resistant (TTX-R) whereas the remaining channels are sensitive to TTX (TTX-S). (England and Rawson. *Future Med. Chem.* (2010), 2, 775-790). However, $Na_V1.7$ gene is prominently responsible to cause to pain.

Loss of function mutations in the human $Na_V1.7$ gene lead to congenital insensitivity to pain which was observed for the first time in certain Pakistani families. Affected individuals displayed painless burns, fractures, and injuries of the lips and tongue. The patients did not have any autonomic or motor abnormalities, and reportedly had normal tear formation, sweating ability, reflexes, and intelligence. This genetic evidence clearly indicates that gain or loss of $Na_V1.7$ function can lead to exacerbation or loss of pain sensation respectively. Thus, it may be possible to treat chronic pain by pharmacologically blocking $Na_V1.7$. Moreover, $Na_V1.7$ has also been implicated in epilepsy. Small molecule $Na_V1.7$ blockers showed efficacy in in vivo epilepsy models. It has therefore been proposed that selective $Na_V1.7$ blockers may lead to therapeutic benefit in epilepsy (Hoyt et al. *Bioorganic & Medicinal Chemistry Letters* (2008), 18, 1963-1966).

Genetic evidence stems from the human gain of function as well as loss of function mutations that lead to inherited pain disorders and insensitivity to pain respectively. Non selective VGSC blockers have been shown to alleviate pain in animal models as well as in humans (e.g., Carbamazepine). Ralfinamide, another non-selective sodium channel blocker, is also being developed for the treatment of neuropathic pain.

Voltage-gated sodium channels are implicated in various diseases and disease conditions, including but not limited to chronic pain, visceral pain, arrhythmia, multiple sclerosis, epilepsy and related disorders as well as cancer. Thus, small molecules targeting one or more of the relevant VGSCs is likely to alleviate the suffering from these conditions.

International publication numbers WO 2006/110917, WO 2007/109324, WO 2008/046049, WO 2008/046084, WO 2008/046087, WO 2008/060789, WO 2009/012242, WO 2010/035166, WO 2010/045197, WO 2010/045251, WO 2010/053998, WO 2010/078307, WO2010/151595, WO2010/151597, WO 2011/002708, WO 2011/026240, WO 2011/103196, WO 2011/056985, WO 2011/058766, WO 2011/088201, WO2011/140425, WO 2015/151001, WO 2013/122897 and *Bioorganic & Medicinal Chemistry Letters* (2011), 21, 3676-681 disclose compounds related to voltage-gated sodium channel (VGSC) modulators for the treatment of various diseases mediated by VGSC modulation.

SUMMARY OF THE INVENTION

In accordance with one aspect, the invention provides compounds having the structure of Formula (I),

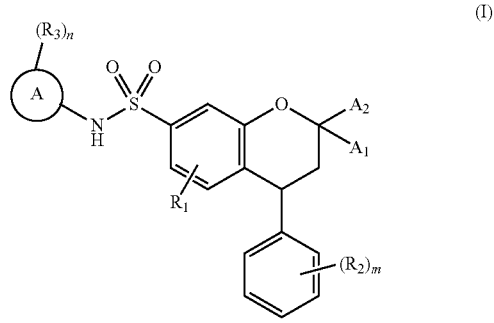

(I)

wherein, $A_1$ and $A_2$ are independently hydrogen or substituted or unsubstituted $(C_1-C_6)$alkyl; or $A_1$ and $A_2$, together with the carbon atom to which they are attached, form a substituted or unsubstituted 3- to 6-membered cycloalkyl ring or 4- to 6-membered heterocyclic ring;

$R_1$ is selected from the group consisting of hydrogen, halogen, cyano, substituted or unsubstituted $(C_1-C_6)$alkyl and substituted or unsubstituted $(C_1-C_6)$alkoxy;

$R_2$, which may be same or different at each occurrence, is independently selected from the group consisting of halogen, cyano, substituted or unsubstituted ($C_1$-$C_6$)alkyl, ($C_1$-$C_6$)haloalkyl, —($CH_2$)$_{0-2}$—S(O)$_2$-alkyl, —O—$R_6$, substituted or unsubstituted alkoxyalkyl, substituted or unsubstituted ($C_3$-$C_5$)cycloalkyl, substituted or unsubstituted ($C_6$-$C_{10}$)aryl, substituted or unsubstituted 5- to 6-membered monocyclic heteroaryl, substituted or unsubstituted 4- to 6-membered monocyclic heterocyclyl, —C(O)OH, —C(O)O-alkyl and —C(O)NR$_4$R$_5$;

ring A is monocyclic six membered heteroaryl containing 1- to 3-nitrogen atoms in the ring;

$R_3$, which may be same or different at each occurrence, is independently selected from the group consisting of halogen, cyano, substituted or unsubstituted ($C_1$-$C_6$)alkyl and substituted or unsubstituted ($C_1$-$C_6$)alkoxy;

$R_4$ and $R_5$ are independently selected from hydrogen or substituted or unsubstituted ($C_1$-$C_6$)alkyl; or $R_4$ and $R_5$ together with the nitrogen atom to which they are attached, form substituted or unsubstituted 5- to 6-membered heterocylic ring;

$R_6$ is selected from the group consisting of hydrogen, substituted or unsubstituted ($C_1$-$C_6$)alkyl, ($C_1$-$C_6$)haloalkyl, substituted or unsubstituted alkoxyalkyl, substituted or unsubstituted ($C_3$-$C_5$)cycloalkyl, substituted or unsubstituted ($C_6$-$C_{10}$)aryl, substituted or unsubstituted 5- to 6-membered monocyclic heteroaryl and substituted or unsubstituted 4- to 6-membered monocyclic heterocyclyl;

'm' is an integer ranging from 0 to 3, both inclusive;

'n' is an integer ranging from 0 to 3, both inclusive;

wherein the substituents for substituted or unsubstituted alkyl, substituted or unsubstituted alkoxy, substituted or unsubstituted cycloalkyl, substituted or unsubstituted aryl, substituted or unsubstituted heteroaryl, substituted or unsubstituted heterocyclyl, substituted or unsubstituted heterocyclic ring, substituted or unsubstituted alkoxyalkyl are one or more same or different and independently selected from the group consisting of hydroxy, halogen, carboxy, cyano, nitro, oxo (=O), ($C_1$-$C_6$)alkyl, ($C_1$-$C_6$)haloalkyl, hydroxy ($C_1$-$C_6$)alkyl, alkoxyalkyl, ($C_2$-$C_6$)alkenyl, ($C_2$-$C_6$)alkynyl, ($C_6$-$C_{10}$)aryl, arylalkyl, ($C_3$-$C_5$)cycloalkyl, cycloalkylalkyl, 5 to 10 membered heteroaryl, 4 to 10 membered heterocyclic ring, 3 to 10 membered heterocyclylalkyl, heteroarylalkyl, —C(O)OR$_x$, —C(O)R$_y$, —C(S)R$_y$, —C(O)NR$_x$R$_z$, —NR$_x$C(O)NR$_x$R$_z$, —N(R$_x$)S(O)$_2$R$_y$, —NR$_x$R$_z$, —NR$_x$C(O)R$_y$, —NR$_x$C(S)R$_y$, —NR$_x$C(S)NR$_x$R$_z$, —S(O)$_2$NR$_x$R$_z$, —OR$_x$, —OC(O)R$_y$, —C(R$_a$R$_b$)$_{1-3}$C(O)OR$_x$, —C(R$_a$R$_b$)$_{1-3}$C(O)NR$_x$R$_z$, —OC(R$_a$R$_b$)$_{2-3}$—OR$_x$, —OC(R$_a$R$_b$)$_{2-3}$—NR$_x$R$_z$, —OC(R$_a$R$_b$)$_{2-3}$—S(O)$_{0-2}$R$_y$, —C(R$_a$R$_b$)$_{1-3}$—NR$_x$R$_z$, —C(R$_a$R$_b$)$_{1-3}$—S(O)$_{0-2}$R$_y$, —OC(R$_a$R$_b$)$_{1-3}$—C(O)NR$_x$R$_z$, —OC(R$_a$R$_b$)$_{1-3}$—C(O)OR$_x$, and —S(O)$_{0-2}$R$_y$;

each of R$_x$ is selected from the group consisting hydrogen, ($C_1$-$C_6$)alkyl, ($C_1$-$C_6$)haloalkyl, ($C_2$-$C_6$)alkenyl, ($C_2$-$C_6$)alkynyl, ($C_6$-$C_{10}$)aryl, arylalkyl, ($C_3$-$C_5$)cycloalkyl, ($C_3$-$C_5$)cycloalkenyl, 5 to 10 membered heteroaryl, heterocyclic ring, heterocyclylalkyl and heteroarylalkyl;

each of R$_y$ is selected from the group consisting ($C_1$-$C_6$) alkyl, ($C_1$-$C_6$)haloalkyl, ($C_2$-$C_6$)alkenyl, ($C_2$-$C_6$)alkynyl, ($C_6$-$C_{10}$)aryl, arylalkyl, ($C_3$-$C_5$)cycloalkyl, ($C_3$-$C_5$)cycloalkenyl, 5 to 10 membered heteroaryl, heterocyclic ring, heterocyclylalkyl and heteroarylalkyl;

each of R$_z$ is selected from the group consisting hydrogen, ($C_1$-$C_6$)alkyl, ($C_1$-$C_6$)haloalkyl, ($C_2$-$C_6$)alkenyl, ($C_2$-$C_6$)alkynyl, ($C_6$-$C_{10}$)aryl, arylalkyl, ($C_3$-$C_5$)cycloalkyl, ($C_3$-$C_5$)cycloalkenyl, 5 to 10 membered heteroaryl, heterocyclic ring, heterocyclylalkyl and heteroarylalkyl; or R$_x$ and R$_z$ together with the nitrogen atom to which they are attached form a substituted or unsubstituted, saturated or unsaturated 4- to 8-membered cyclic ring, wherein the unsaturated cyclic ring may have one or two double bonds; and each of R$_a$ and R$_b$ are independently selected from the group consisting of hydrogen, halogen and substituted or unsubstituted ($C_1$-$C_6$)alkyl;

or N-oxides thereof or a pharmaceutically acceptable salt thereof or stereoisomer thereof.

In accordance with one aspect, the invention provides compounds having the structure of Formula (I),

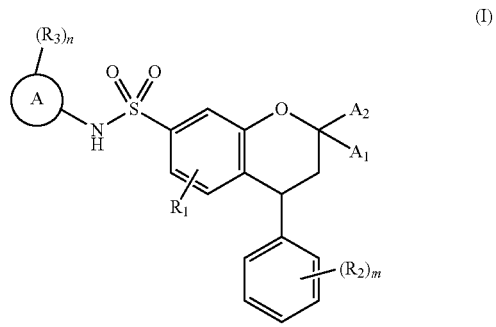

(I)

wherein, $A_1$ and $A_2$ are independently hydrogen or substituted or unsubstituted alkyl; or $A_1$ and $A_2$, together with the carbon atom to which they are attached, form a substituted or unsubstituted 3 to 6 membered cycloalkyl ring or 4-6 membered heterocyclyl ring;

$R_1$ is selected from hydrogen, halogen, cyano, substituted or unsubstituted alkyl and substituted or unsubstituted alkoxy;

$R_2$, which may be same or different at each occurrence, is independently selected from halogen, cyano, substituted or unsubstituted alkyl, haloalkyl, —S(O)$_2$-alkyl, substituted or unsubstituted alkoxy, substituted or unsubstituted alkoxyalkyl, substituted or unsubstituted cycloalkyl, substituted or unsubstituted aryl, substituted or unsubstituted monocyclic heteroaryl, substituted or unsubstituted monocyclic heterocyclyl, —C(O)OH, —C(O)O-alkyl and —C(O)NR$_4$R$_5$;

ring A is monocyclic 6-membered heteroaryl containing 1- to 3-nitrogen atoms in the ring;

$R_3$ is selected from halogen, cyano, substituted or unsubstituted alkyl and substituted or unsubstituted alkoxy;

$R_4$ and $R_5$ are independently selected from hydrogen or substituted or unsubstituted alkyl; or $R_4$ and $R_5$ together with the nitrogen atom to which they are attached, form substituted or unsubstituted 5 to 6 membered heterocylic ring;

'm' is an integer ranging from 0 to 3, both inclusive;

'n' is an integer ranging from 0 to 3, both inclusive;

wherein the substituents for substituted or unsubstituted alkyl, substituted or unsubstituted alkoxy, substituted or unsubstituted cycloalkyl, substituted or unsubstituted aryl, substituted or unsubstituted heteroaryl, substituted or unsubstituted heterocyclyl, substituted or unsubstituted alkoxyalkyl, substituted or unsubstituted haloalkyl are one or more same or different and independently selected from the group consisting of hydroxy, halogen, carboxy, cyano, nitro, oxo (=O), alkyl, haloalkyl, hydroxyalkyl, alkoxyalkyl, alkenyl, alkynyl, aryl, arylalkyl, cycloalkyl, cycloalkylalkyl, heteroaryl, heterocyclic ring, heterocyclylalkyl, heteroarylalkyl, —C(O)OR$_x$, —C(O)R$_y$, —C(S)R$_y$, —C(O)NR$_x$R$_z$, —NR$_x$C(O)NR$_x$R$_z$, —N(R$_x$)S(O)$_2$R$_y$, —NR$_x$R$_z$, —NR$_x$C(O)R$_y$, —NR$_x$C(S)R$_y$, —NR$_x$C(S)NR$_x$R$_z$, —S(O)$_2$NR$_x$R$_z$, —OR$_x$, —OC(O)R$_y$, —C(R$_a$R$_b$)$_{1-3}$C(O)OR$_x$, —C(R$_a$R$_b$)$_{1-3}$C(O)NR$_x$R$_z$, —OC(R$_a$R$_b$)$_{2-3}$—OR$_x$, —OC(R$_a$R$_b$)$_{2-3}$—NR$_x$R$_z$, —OC(R$_a$R$_b$)$_{2-3}$—S(O)$_{0-2}$R$_y$, —C(R$_a$R$_b$)$_{1-3}$—NR$_x$R$_z$, —C(R$_a$R$_b$)$_{1-3}$—S(O)$_{0-2}$R$_y$, —OC(R$_a$R$_b$)$_{1-3}$—C(O)NR$_x$R$_z$, —OC(R$_a$R$_b$)$_{1-3}$—C(O)OR$_x$, and —S(O)$_{0-2}$R$_y$;

R$_x$ is selected from hydrogen, alkyl, haloalkyl, alkenyl, alkynyl, aryl, arylalkyl, cycloalkyl, cycloalkenyl, heteroaryl, heterocyclic ring, heterocyclylalkyl and heteroarylalkyl;

R$_y$ is selected from alkyl, haloalkyl, alkenyl, alkynyl, aryl, arylalkyl, cycloalkyl, cycloalkenyl, heteroaryl, heterocyclic ring, heterocyclylalkyl and heteroarylalkyl;

R$_z$ is selected from hydrogen, alkyl, haloalkyl, alkenyl, alkynyl, aryl, arylalkyl, cycloalkyl, cycloalkenyl, heteroaryl, heterocyclic ring, heterocyclylalkyl and heteroarylalkyl; or R$_x$ and R$_z$ together with the nitrogen atom to which they are attached form a substituted or unsubstituted, saturated or unsaturated 4 to 8 membered cyclic ring, wherein the unsaturated cyclic ring may have one or two double bonds; and each of R$_a$ and R$_b$ are independently selected from the group consisting of hydrogen, halogen and substituted or unsubstituted alkyl;

or a pharmaceutically acceptable salt thereof.

In accordance with one aspect, the invention provides compounds having the structure of Formula (I), wherein, A$_1$ and A$_2$ are independently hydrogen or substituted or unsubstituted alkyl; or A$_1$ and A$_2$, together with the carbon atom to which they are attached, form a substituted or unsubstituted 3- to 6-membered cycloalkyl ring or 4- to 6-membered heterocyclic ring;

R$_1$ is selected from the group consisting of hydrogen, halogen, cyano, substituted or unsubstituted alkyl and substituted or unsubstituted alkoxy;

R$_2$, which may be same or different at each occurrence, is independently selected from the group consisting of halogen, cyano, substituted or unsubstituted alkyl, haloalkyl, —(CH$_2$)$_{0-2}$—S(O)$_2$-alkyl, substituted or unsubstituted alkoxy, substituted or unsubstituted alkoxyalkyl, substituted or unsubstituted cycloalkyl, substituted or unsubstituted aryl, substituted or unsubstituted 5- to 6-membered monocyclic heteroaryl, substituted or unsubstituted 4- to 6-membered monocyclic heterocyclyl, —C(O)OH, —C(O)O-alkyl and —C(O)NR$_4$R$_5$;

ring A is monocyclic six membered heteroaryl containing 1- to 3-nitrogen atoms in the ring;

R$_3$, which may be same or different at each occurrence, is independently selected from the group consisting of halogen, cyano, substituted or unsubstituted alkyl and substituted or unsubstituted alkoxy;

R$_4$ and R$_5$ are independently selected individually from hydrogen or substituted or unsubstituted alkyl; or R$_4$ and R$_5$ together with the nitrogen atom to which they are attached, form substituted or unsubstituted 5- to 6-membered heterocylic ring;

'm' is an integer ranging from 0 to 3, both inclusive;

'n' is an integer ranging from 0 to 3, both inclusive;

wherein the substituents for substituted or unsubstituted alkyl, substituted or unsubstituted alkoxy, substituted or unsubstituted cycloalkyl, substituted or unsubstituted aryl, substituted or unsubstituted heteroaryl, substituted or unsubstituted heterocyclyl, substituted or unsubstituted heterocyclic ring, substituted or unsubstituted alkoxyalkyl are one or more same or different and independently selected from the group consisting of hydroxy, halogen, carboxy, cyano, nitro, oxo (=O), alkyl, haloalkyl, hydroxyalkyl, alkoxyalkyl, alkenyl, alkynyl, aryl, arylalkyl, cycloalkyl, cycloalkylalkyl, heteroaryl, heterocyclic ring, heterocylylalkyl, heteroarylalkyl, —C(O)OR$_x$, —C(O)R$_y$, —C(S)R$_y$, —C(O)NR$_x$R$_z$, —NR$_x$C(O)NR$_x$R$_z$, —N(R$_x$)S(O)$_2$R$_y$, —NR$_x$R$_z$, —NR$_x$C(O)R$_y$, —NR$_x$C(S)R$_y$, —NR$_x$C(S)NR$_x$R$_z$, —S(O)$_2$NR$_x$R$_z$, —OR$_x$, —OC(O)R$_y$, —C(R$_a$R$_b$)$_{1-3}$C(O)OR$_x$, —C(R$_a$R$_b$)$_{1-3}$C(O)NR$_x$R$_z$, —OC(R$_a$R$_b$)$_{2-3}$—OR$_x$, —OC(R$_a$R$_b$)$_{2-3}$—NR$_x$R$_z$, —OC(R$_a$R$_b$)$_{2-3}$—S(O)$_{0-2}$R$_y$, —C(R$_a$R$_b$)$_{1-3}$—NR$_x$R$_z$, —C(R$_a$R$_b$)$_{1-3}$—S(O)$_{0-2}$R$_y$, —OC(R$_a$R$_b$)$_{1-3}$—C(O)NR$_x$R$_z$, —OC(R$_a$R$_b$)$_{1-3}$—C(O)OR$_x$, and —S(O)$_{0-2}$R$_y$;

R$_x$ is selected from the group consisting hydrogen, alkyl, haloalkyl, alkenyl, alkynyl, aryl, arylalkyl, cycloalkyl, cycloalkenyl, heteroaryl, heterocyclic ring, heterocyclylalkyl and heteroarylalkyl;

R$_y$ is selected from the group consisting alkyl, haloalkyl, alkenyl, alkynyl, aryl, arylalkyl, cycloalkyl, cycloalkenyl, heteroaryl, heterocyclic ring, heterocyclylalkyl and heteroarylalkyl;

R$_z$ is selected from the group consisting hydrogen, alkyl, haloalkyl, alkenyl, alkynyl, aryl, arylalkyl, cycloalkyl, cycloalkenyl, heteroaryl, heterocyclic ring, heterocyclylalkyl and heteroarylalkyl; or R$_x$ and R$_z$ together with the nitrogen atom to which they are attached form a substituted or unsubstituted, saturated or unsaturated 4- to 8-membered cyclic ring, wherein the unsaturated cyclic ring may have one or two double bonds; and each of R$_a$ and R$_b$ are independently selected individually from the group consisting of hydrogen, halogen and substituted or unsubstituted alkyl;

or a pharmaceutically acceptable salt thereof.

The details of one or more embodiments of the invention set forth in the below are only illustrative in nature and not intended to limit the scope of the invention. Other features, objects and advantages of the inventions will be apparent from the description and claims.

According to one embodiment, the invention provides compounds having the structure of Formula (II)

or N-oxides thereof or a pharmaceutically acceptable salt thereof or stereoisomer thereof;

wherein, ring A is monocyclic six membered heteroaryl containing 1- to 2-nitrogen atoms in the ring;

$A_1$ and $A_2$ are independently hydrogen or substituted or unsubstituted $(C_1$-$C_6)$alkyl;

$R_{2a}$ is selected from halogen, cyano, substituted or unsubstituted $(C_1$-$C_6)$alkyl, $(C_1$-$C_6)$haloalkyl, —$(CH_2)_{0-2}$—$S(O)_2$-alkyl, —O—$R_6$, substituted or unsubstituted alkoxyalkyl, $(C_3$-$C_5)$cycloalkyl, substituted or unsubstituted $(C_6$-$C_{10})$aryl, substituted or unsubstituted 5- to 6-membered monocyclic heteroaryl, substituted or unsubstituted 4- to 6-membered monocyclic heterocyclyl, —C(O)OH, —C(O)O-alkyl and —C(O)NR$_4$R$_5$ where R$_4$ and R$_5$ are hydrogen or $(C_1$-$C_6)$alkyl;

$R_6$ is selected from the group consisting of hydrogen, substituted or unsubstituted $(C_1$-$C_6)$alkyl, $(C_1$-$C_6)$haloalkyl, substituted or unsubstituted alkoxyalkyl, substituted or unsubstituted $(C_3$-$C_5)$cycloalkyl, substituted or unsubstituted $(C_6$-$C_{10})$aryl, substituted or unsubstituted 5- to 6-membered monocyclic heteroaryl, and substituted or unsubstituted 4- to 6-membered monocyclic heterocyclyl;

$R_1$, $R_2$, $R_3$ and 'n' are as defined herein above.

According to another embodiment, the invention provides compounds having the structure of Formula (III)

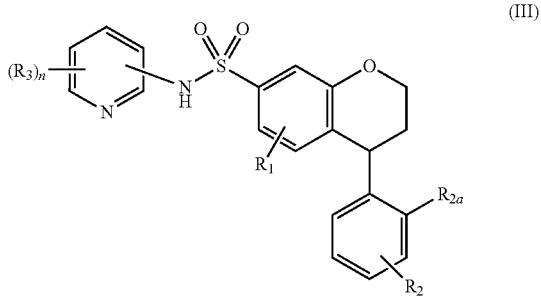

(III)

or N-oxides thereof or a pharmaceutically acceptable salt thereof or stereoisomer thereof;

wherein, $R_{2a}$ is selected from halogen, cyano, substituted or unsubstituted $(C_1$-$C_6)$alkyl, $(C_1$-$C_6)$haloalkyl, —$(CH_2)_{0-2}$—$S(O)_2$-alkyl, —O—$R_6$, substituted or unsubstituted alkoxyalkyl, $(C_3$-$C_5)$cycloalkyl, substituted or unsubstituted $(C_6$-$C_{12})$aryl, substituted or unsubstituted 5- to 6-membered monocyclic heteroaryl, substituted or unsubstituted 4- to 6-membered monocyclic heterocyclyl, —C(O)OH, —C(O)O-alkyl and —C(O)NR$_4$R$_5$ where R$_4$ and R$_5$ are hydrogen or $(C_1$-$C_6)$alkyl;

$R_6$ is selected from the group consisting of hydrogen, substituted or unsubstituted $(C_1$-$C_6)$alkyl, $(C_1$-$C_6)$haloalkyl, substituted or unsubstituted alkoxyalkyl, $(C_3$-$C_5)$cycloalkyl, substituted or unsubstituted $(C_6$-$C_{12})$aryl, substituted or unsubstituted 5- to 6-membered monocyclic heteroaryl, and substituted or unsubstituted 4- to 6-membered monocyclic heterocyclyl;

$R_1$, $R_2$, $R_3$ and 'n' are as defined herein above.

In one embodiment there are provided compounds of Formula (III) wherein $R_1$ is hydrogen, halogen or $(C_1$-$C_6)$alkyl;

$R_2$ is selected from halogen, cyano, $(C_1$-$C_6)$alkyl, $(C_1$-$C_6)$haloalkyl, —O—$R_6$, alkoxyalkyl and $(C_3$-$C_5)$cycloalkyl; $R_6$ is selected hydrogen, $(C_1$-$C_6)$alkyl, $(C_1$-$C_6)$haloalkyl and alkoxy alkyl;

$R_3$ is halogen, cyano, substituted or unsubstituted $(C_1$-$C_6)$alkyl and substituted or unsubstituted $(C_1$-$C_6)$alkoxy; 'n' is 0 or 1.

According to another embodiment, the invention provides compounds having the structure of Formula (IV)

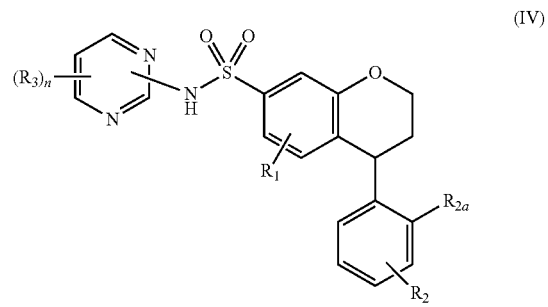

(IV)

or N-oxides thereof or a pharmaceutically acceptable salt thereof or stereoisomer thereof;

wherein, $R_{2a}$ is selected from halogen, cyano, substituted or unsubstituted $(C_1$-$C_6)$alkyl, $(C_1$-$C_6)$haloalkyl, —$(CH_2)_{0-2}$—$S(O)_2$-alkyl, —O—$R_6$, substituted or unsubstituted alkoxyalkyl, $(C_3$-$C_5)$cycloalkyl, substituted or unsubstituted $(C_6$-$C_{12})$aryl, substituted or unsubstituted 5- to 6-membered monocyclic heteroaryl, substituted or unsubstituted 4- to 6-membered monocyclic heterocyclyl, —C(O)OH, —C(O)O-alkyl and —C(O)NR$_4$R$_5$ where R$_4$ and R$_5$ are hydrogen or $(C_1$-$C_6)$alkyl;

$R_6$ is selected from the group consisting of hydrogen, substituted or unsubstituted $(C_1$-$C_6)$alkyl, $(C_1$-$C_6)$haloalkyl, substituted or unsubstituted alkoxyalkyl, $(C_3$-$C_5)$cycloalkyl, substituted or unsubstituted $(C_6$-$C_{12})$aryl, substituted or unsubstituted 5- to 6-membered monocyclic heteroaryl, and substituted or unsubstituted 4- to 6-membered monocyclic heterocyclyl;

$R_1$, $R_2$, $R_3$ and 'n' are as defined herein above.

In one embodiment there are provided compounds of Formula (IV) wherein $R_1$ is hydrogen, halogen or $(C_1$-$C_6)$alkyl;

$R_2$ is selected from halogen, cyano, $(C_1$-$C_6)$alkyl, $(C_1$-$C_6)$haloalkyl, —O—$R_6$, alkoxyalkyl and $(C_3$-$C_5)$cycloalkyl; $R_6$ is selected hydrogen, $(C_1$-$C_6)$alkyl, $(C_1$-$C_6)$haloalkyl and alkoxy alkyl;

$R_3$ is halogen, cyano, substituted or unsubstituted $(C_1$-$C_6)$alkyl and substituted or unsubstituted $(C_1$-$C_6)$alkoxy; 'n' is 0 or 1.

According to another embodiment, the invention provides compounds having the structure of Formula (V)

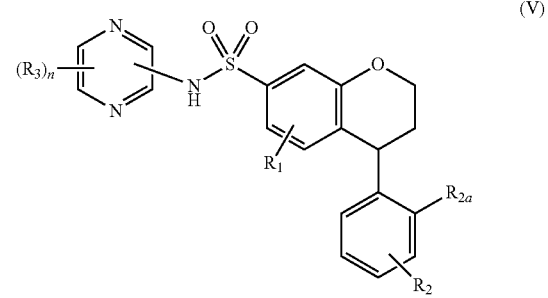

(V)

or N-oxides thereof or a pharmaceutically acceptable salt thereof or stereoisomer thereof;

wherein, $R_{2a}$ is selected from halogen, cyano, substituted or unsubstituted $(C_1-C_6)$alkyl, $(C_1-C_6)$haloalkyl, —$(CH_2)_{0-2}$—$S(O)_2$-alkyl, —O—$R_6$, substituted or unsubstituted alkoxyalkyl, $(C_3-C_5)$cycloalkyl, substituted or unsubstituted $(C_6-C_{12})$aryl, substituted or unsubstituted 5- to 6-membered monocyclic heteroaryl, substituted or unsubstituted 4- to 6-membered monocyclic heterocyclyl, —C(O)OH, —C(O)O-alkyl and —C(O)$NR_4R_5$ where $R_4$ and $R_5$ are hydrogen or $(C_1-C_6)$alkyl;

$R_6$ is selected from the group consisting of hydrogen, substituted or unsubstituted $(C_1-C_6)$alkyl, $(C_1-C_6)$haloalkyl, substituted or unsubstituted alkoxyalkyl, $(C_3-C_5)$cycloalkyl, substituted or unsubstituted $(C_6-C_{12})$aryl, substituted or unsubstituted 5- to 6-membered monocyclic heteroaryl, and substituted or unsubstituted 4- to 6-membered monocyclic heterocyclyl;

$R_1$, $R_2$, $R_3$ and 'n' are as defined herein above.

In one embodiment there are provided compounds of Formula (V), wherein $R_1$ is hydrogen, halogen or $(C_1-C_6)$alkyl;

$R_2$ is selected from halogen, cyano, $(C_1-C_6)$alkyl, $(C_1-C_6)$haloalkyl, —O—$R_6$, alkoxyalkyl and $(C-C_8)$cycloalkyl; $R_6$ is selected hydrogen, $(C_1-C_6)$alkyl, $(C_1-C_6)$haloalkyl and alkoxy alkyl;

$R_3$ is halogen, cyano, substituted or unsubstituted $(C_1-C_6)$alkyl and substituted or unsubstituted $(C_1-C_6)$alkoxy; 'n' is 0 or 1.

According to another embodiment, the invention provides compounds having the structure of Formula (VI)

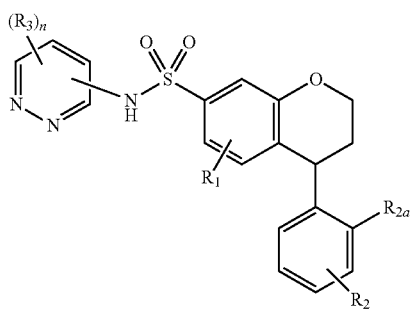

(VI)

or N-oxides thereof or a pharmaceutically acceptable salt thereof or stereoisomer thereof;

wherein, $R_{2a}$ is selected from halogen, cyano, substituted or unsubstituted $(C_1-C_6)$alkyl, $(C_1-C_6)$haloalkyl, —$(CH_2)_{0-2}$—$S(O)_2$-alkyl, —O—$R_6$, substituted or unsubstituted alkoxyalkyl, $(C_3-C_5)$cycloalkyl, substituted or unsubstituted $(C_6-C_{12})$aryl, substituted or unsubstituted 5- to 6-membered monocyclic heteroaryl, substituted or unsubstituted 4- to 6-membered monocyclic heterocyclyl, —C(O)OH, —C(O)O-alkyl and —C(O)$NR_4R_5$ where $R_4$ and $R_5$ are hydrogen or $(C_1-C_6)$alkyl;

$R_6$ is selected from the group consisting of hydrogen, substituted or unsubstituted $(C_1-C_6)$alkyl, $(C_1-C_6)$haloalkyl, substituted or unsubstituted alkoxyalkyl, substituted or unsubstituted $(C_3-C_5)$cycloalkyl, substituted or unsubstituted $(C_6-C_{12})$aryl, substituted or unsubstituted 5- to 6-membered monocyclic heteroaryl, and substituted or unsubstituted 4- to 6-membered monocyclic heterocyclyl;

$R_1$, $R_2$, $R_3$ and 'n' are as defined herein above.

In one embodiment there are provided compounds of Formula (VI), wherein $R_1$ is hydrogen, halogen or $(C_1-C_6)$alkyl;

$R_2$ is selected from halogen, cyano, $(C_1-C_6)$alkyl, $(C_1-C_6)$haloalkyl, —O—$R_6$, alkoxyalkyl and $(C_3-C_5)$cycloalkyl; $R_6$ is selected hydrogen, $(C_1-C_6)$alkyl, $(C_1-C_6)$haloalkyl and alkoxy alkyl;

$R_3$ is halogen, cyano, substituted or unsubstituted $(C_1-C_6)$alkyl and substituted or unsubstituted $(C_1-C_6)$alkoxy; 'n' is 0 or 1.

According to another embodiment, the invention provides compounds having the structure of Formula (VII) and (VIII)

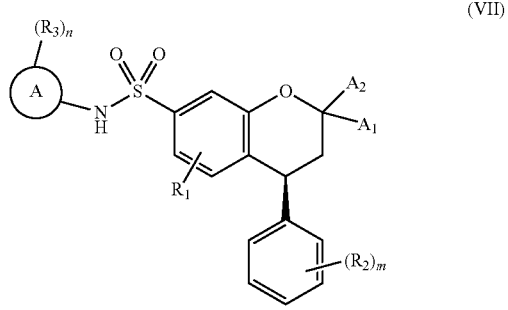

(VII)

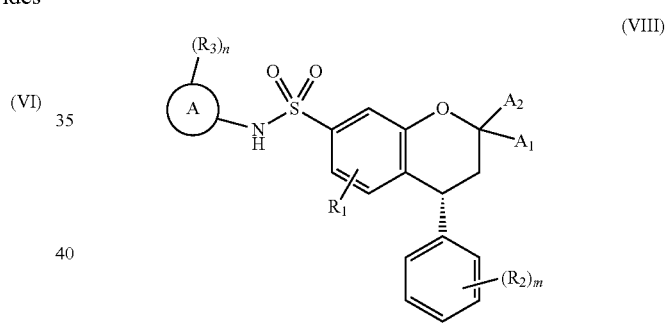

(VIII)

or a pharmaceutically acceptable salt thereof;

wherein, ring A, $A_1$, $A_2$, $R_1$, $R_2$, $R_3$, 'm' and 'n' are as defined herein above.

According to another embodiment, the invention provides compounds having the structure of Formula (IIa) and (IIb)

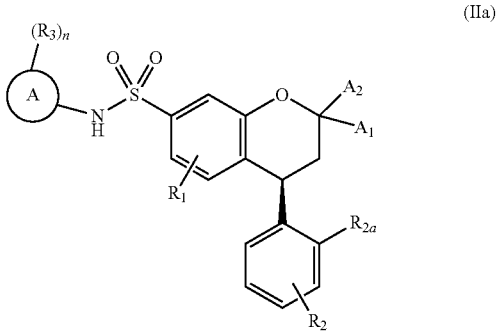

(IIa)

-continued

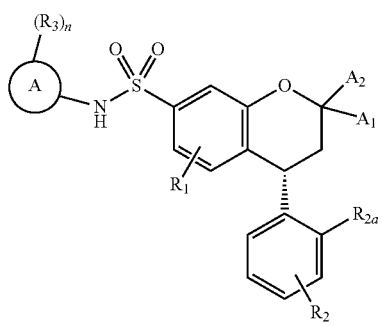
(IIb)

or a pharmaceutically acceptable salt thereof;
wherein,
ring A, $A_1$, $A_2$, $R_1$, $R_2$, $R_{2a}$, $R_3$ and 'n' are as defined herein above.

According to certain embodiments ring A is selected from

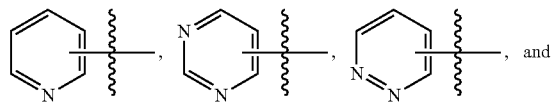

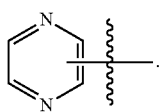

According to certain embodiments $R_3$ is halogen, cyano, $(C_1-C_6)$alkyl and $(C_1-C_6)$alkoxy; and 'n' is 0 or 1.

According to certain embodiments $A_1$ and $A_2$ are independently hydrogen or $(C_1-C_6)$alkyl.

According to certain embodiments $A_1$ and $A_2$ together with the carbon atom to which they are attached, form a 3- to 6-membered cycloalkyl ring.

According to certain embodiments $R_1$ is hydrogen, halogen or $(C_1-C_6)$alkyl;

According to certain embodiments $R_2$ is selected from halogen, cyano, substituted or unsubstituted $(C_1-C_6)$alkyl, $(C_1-C_6)$haloalkyl, —$(CH_2)_{0-2}$—$S(O)_2$-alkyl, —O—$R_6$, substituted or unsubstituted alkoxyalkyl, $(C_3-C_{68})$cycloalkyl, substituted or unsubstituted $(C_6-C_{12})$aryl (e.g. phenyl), substituted or unsubstituted 5- to 6-membered monocyclic heteroaryl (e.g pyridyl, pyrazolyl, triazolyl, thiazolyl, oxazolyl), substituted or unsubstituted 4- to 6-membered monocyclic heterocyclyl (e.g. pyrrolidinone, oxazolidinone, morpholine, morpholinone, thiomorpholine 1,1-dioxide, tetrahydropyran), —C(O)OH, —C(O)O-alkyl and —C(O)NR$_4$R$_5$ where R$_4$ and R$_5$ are hydrogen or $(C_1-C_6)$alkyl; R$_6$ is selected from the group consisting of hydrogen, substituted or unsubstituted $(C_1-C_6)$alkyl, $(C_1-C_6)$haloalkyl, substituted or unsubstituted alkoxyalkyl, $(C_3-C_5)$cycloalkyl, substituted or unsubstituted $(C_6-C_{12})$aryl, substituted or unsubstituted 5- to 6-membered monocyclic heteroaryl, and substituted or unsubstituted 4- to 6-membered monocyclic heterocyclyl; and 'm' is 0, 1 or 2.

In certain embodiments $R_{2a}$ is selected from halogen, substituted or unsubstituted $(C_1-C_6)$alkyl, $(C_1-C_6)$haloalkyl, $(CH_2)_{0-2}$—$S(O)_2$-alkyl, —O—$R_6$, substituted or unsubstituted alkoxyalkyl, substituted or unsubstituted $(C_6-C_{12})$aryl, substituted or unsubstituted 5- to 6-membered monocyclic heteroaryl, or substituted or unsubstituted 4- to 6-membered monocyclic heterocyclyl; where $R_6$ is selected from the group consisting of hydrogen, substituted or unsubstituted $(C_1-C_6)$alkyl, $(C_1-C_6)$haloalkyl, substituted or unsubstituted alkoxyalkyl, $(C_3-C_5)$cycloalkyl, substituted or unsubstituted $(C_6-C_{12})$aryl, substituted or unsubstituted 5- to 6-membered monocyclic heteroaryl, and substituted or unsubstituted 4- to 6-membered monocyclic heterocyclyl; preferably, $R_{2a}$ is pyridyl, pyrazolyl, phenyl, triazolyl, thiazolyl, oxazolyl, pyrolidinone, oxazolidinone, pyrolidinone, morpholine, morpholinone, thiomorpholine1,1-dioxide, tetrahydropyran or —$(CH_2)_2SO_2CH_3$ and $R_2$ is halogen, —OR$_6$ or $(C_1-C_6)$ haloalkyl, preferably —CF$_3$.

Compounds of the invention include, for example, compounds of the Formula (I) or pharmaceutically acceptable salts thereof, wherein, unless otherwise stated, each of ring A, $R_1$, $R_2$, $R_3$, 'm', 'n', $A_1$ and $A_2$ has any of the meanings defined hereinbefore or independently in any of paragraphs (1) to (7):

wherein,

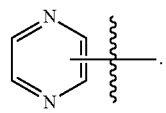

1) ring A is selected from N

2) $R_1$ is hydrogen, halogen or $(C_1-C_6)$alkyl.

3) $R_2$ is selected from halogen, cyano, substituted or unsubstituted $(C_1-C_6)$alkyl, $(C_1-C_6)$haloalkyl, —$(CH_2)_{0-2}$—$S(O)_2$-alkyl, —O—$R_6$, substituted or unsubstituted alkoxyalkyl, $(C_3-C_5)$cycloalkyl, substituted or unsubstituted $(C_6-C_{12})$aryl, substituted or unsubstituted 5- to 6-membered monocyclic heteroaryl, substituted or unsubstituted 4- to 6-membered monocyclic heterocyclyl, —C(O)OH, —C(O)O-alkyl and —C(O)NR$_4$R$_5$ where R$_4$ and R$_5$ are hydrogen or $(C_1-C_6)$alkyl; and R$_6$ is selected from the group consisting of hydrogen, substituted or unsubstituted $(C_1-C_6)$alkyl, $(C_1-C_6)$haloalkyl, substituted or unsubstituted alkoxyalkyl, $(C_3-C_5)$cycloalkyl, substituted or unsubstituted $(C_6-C_{12})$aryl, substituted or unsubstituted 5- to 6-membered monocyclic heteroaryl, and substituted or unsubstituted 4- to 6-membered monocyclic heterocyclyl.

4) $R_3$ is halogen, cyano, substituted or unsubstituted $(C_1-C_6)$alkyl and substituted or unsubstituted $(C_1-C_6)$alkoxy.

5) 'm' is an integer ranging from 0 to 3, both inclusive.

6) 'n' is an integer ranging from 0 to 2, both inclusive.

7) $A_1$ and $A_2$ are independently hydrogen or substituted or unsubstituted $(C_1-C_6)$alkyl; or $A_1$ and $A_2$, together with the carbon atom to which they are attached, form a 3- to 6-membered cycloalkyl.

According to another embodiment, there are provided compounds having the structure of Formula (II)

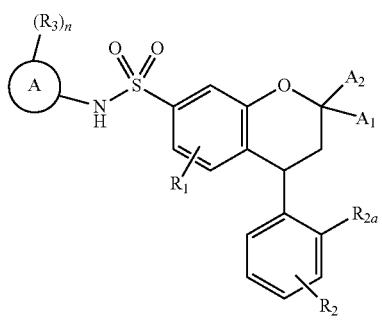

(II)

wherein $A_1$ and $A_2$ are hydrogen; $R_1$ is hydrogen; ring A is monocyclic six membered heteroaryl containing 1- to 2-nitrogen atoms in the ring

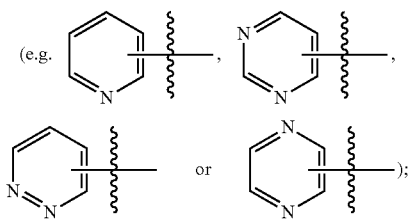

$R_2$ is halogen, $(C_1-C_6)$haloalkyl (e.g. $CF_3$) or —O—$R_6$; $R_{2a}$ is halogen, substituted or unsubstituted $(C_1-C_6)$alkyl, —$(CH_2)_{0-2}$—$S(O)_2$-alkyl, —O—$R_6$, substituted or unsubstituted alkoxyalkyl, substituted or unsubstituted $(C_6-C_{10})$ aryl

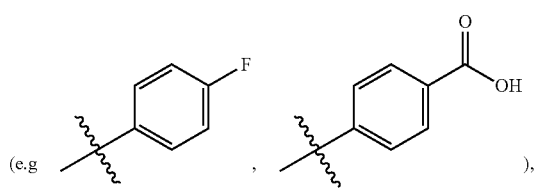 [SMILES: *c1ccc(F)cc1 ; *c1ccc(C(=O)O)cc1]

substituted or unsubstituted 5- to 6-membered monocyclic heteroaryl

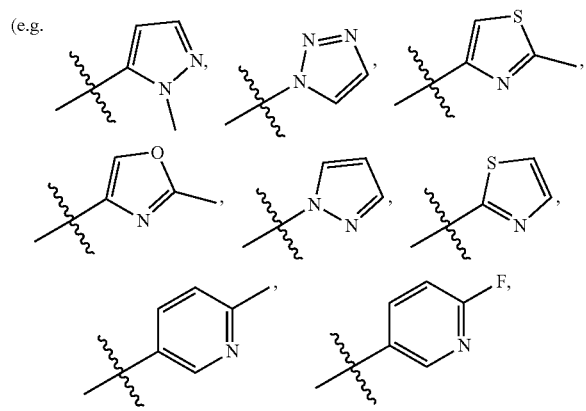

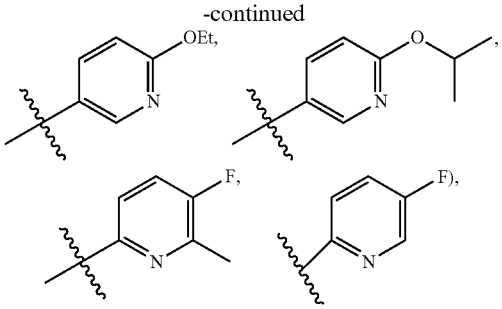

substituted or unsubstituted 4- to 6-membered monocyclic heterocyclyl

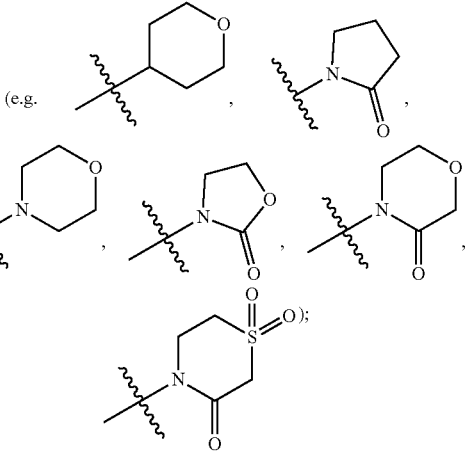

where $R_6$ is substituted or unsubstituted $(C_1-C_6)$alkyl, substituted or unsubstituted alkoxyalkyl and substituted or unsubstituted 4- to 6-membered monocyclic heterocyclyl (e.g.

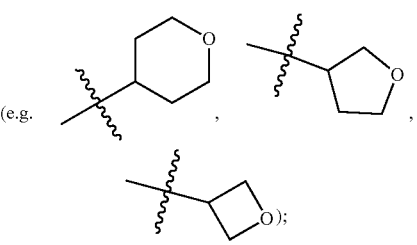

$R_3$ is halogen, substituted or unsubstituted $(C_1-C_6)$alkyl and substituted or unsubstituted $(C_1-C_6)$alkoxy; and 'n' is 0 or 1.

It should be understood that the Formula (I) to (VI) structurally encompasses all tautomers, stereoisomers, enantiomers and diastereomers, including isotopes wherever applicable and pharmaceutically acceptable salts that may be contemplated from the chemical structures generally described herein.

Below Examples 1 to 245 are representative compounds, which are only illustrative in nature and are not intended to limit the scope of the invention:

(S)—N-(6-Fluoropyridin-2-yl)-4-(2-(1-methyl-1H-pyrazol-5-yl)-4-(trifluoromethyl)phenyl)chroman-7-sulfonamide;

(R)—N-(6-Fluoropyridin-2-yl)-4-(2-(1-methyl-1H-pyrazol-5-yl)-4-(trifluoromethyl)phenyl)chroman-7-sulfonamide;

(S&R)—N-(4-Fluoropyridin-2-yl)-4-(2-(1-methyl-1H-pyrazol-5-yl)-4-(trifluoromethyl)phenyl)chroman-7-sulfonamide;
(S&R)—N-(5-Fluoropyridin-2-yl)-4-(2-(1-methyl-1H-pyrazol-5-yl)-4-(trifluoromethyl)phenyl)chroman-7-sulfonamide;
(S&R)—N-(5-Fluoropyrimidin-2-yl)-4-(2-(1-methyl-1H-pyrazol-5-yl)-4-(trifluoromethyl)phenyl)chroman-7-sulfonamide;
(S&R)-4-(2-(1-Methyl-1H-pyrazol-5-yl)-4-(trifluoromethyl)phenyl)-N-(pyrimidin-4-yl)chroman-7-sulfonamide;
(S&R)-4-(2-(1-Methyl-1H-pyrazol-5-yl)-4-(trifluoromethyl)phenyl)-N-(pyrazin-2-yl)chromane-7-sulfonamide;
(S&R)-4-(2-(1-Methyl-1H-pyrazol-5-yl)-4-(trifluoromethyl)phenyl)-N-(pyridazin-3-yl)chromane-7-sulfonamide;
(S&R)-4-(2-(1-Methyl-1H-pyrazol-5-yl)-4-(trifluoromethyl)phenyl)-N-(pyrimidin-2-yl)chromane-7-sulfonamide;
(S&R)—N-(3-Fluoropyridin-2-yl)-4-(2-(1-methyl-1H-pyrazol-5-yl)-4-(trifluoromethyl)phenyl)chromane-7-sulfonamide;
(S&R)-4-(2-(1-Methyl-1H-pyrazol-5-yl)-4-(trifluoromethyl)phenyl)-N-(6-methylpyridin-2-yl)chroman-7-sulfonamide;
(S&R)-4-(2-(1-Methyl-1H-pyrazol-5-yl)-4-(trifluoromethyl)phenyl)-N-(5-methylpyridin-2-yl)chroman-7-sulfonamide;
(S&R)-4-(2-(1-Methyl-1H-pyrazol-5-yl)-4-(trifluoromethyl)phenyl)-N-(4-methylpyridin-2-yl)chroman-7-sulfonamide;
(S&R)—N-(6-Isopropoxypyridin-2-yl)-4-(2-(1-methyl-1H-pyrazol-5-yl)-4-(trifluoromethyl)phenyl)chroman-7-sulfonamide;
(S&R)—N-(2-Fluoropyridin-3-yl)-4-(2-(1-methyl-1H-pyrazol-5-yl)-4-(trifluoromethyl)phenyl)chroman-7-sulfonamide;
(S&R)-4-(2-(1-Methyl-1H-pyrazol-5-yl)-4-(trifluoromethyl)phenyl)-N-(4-methylpyrimidin-2-yl)chroman-7-sulfonamide;
(S&R)-4-(4-Chloro-2-(1-methyl-1H-pyrazol-5-yl)phenyl)-N-(6-fluoropyridin-2-yl)chroman-7-sulfonamide;
(S&R)—N-(6-Fluoropyridin-2-yl)-4-(4-isopropoxy-2-(1-methyl-1H-pyrazol-5-yl)phenyl)chroman-7-sulfonamide;
(S&R)-4-(2-(6-Fluoropyridin-3-yl)-4-(trifluoromethyl)phenyl)-N-(pyrimidin-2-yl)chromane-7-sulfonamide;
(S&R)-4-(2-(6-Fluoropyridin-3-yl)-4-(trifluoromethyl)phenyl)-N-(5-fluoropyrimidin-2-yl)chromane-7-sulfonamide;
(S&R)-4-(2-(6-Fluoropyridin-3-yl)-4-(trifluoromethyl)phenyl)-N-(pyrimidin-4-yl)chromane-7-sulfonamide;
(S&R)-4-(2-(6-Fluoropyridin-3-yl)-4-(trifluoromethyl)phenyl)-N-(pyridazin-3-yl)chromane-7-sulfonamide;
(S&R)-4-(4'-Fluoro-5-(trifluoromethyl)-[1,1'-biphenyl]-2-yl)-N-(pyrimidin-2-yl)chromane-7-sulfonamide;
(S&R)-4-(4'-Fluoro-5-(trifluoromethyl)-[1,1'-biphenyl]-2-yl)-N-(5-fluoropyrimidin-2-yl) chromane-7-sulfonamide;
(S&R)-4-(4'-Fluoro-5-(trifluoromethyl)-[1,1'-biphenyl]-2-yl)-N-(pyrimidin-4-yl)chromane-7-sulfonamide;
(S&R)-4-(4'-Fluoro-5-(trifluoromethyl)-[1,1'-biphenyl]-2-yl)-N-(6-fluoropyridin-2-yl)chromane-7-sulfonamide;
(S&R)-4-(2-(1H-1,2,3-Triazol-1-yl)-4-(trifluoromethyl)phenyl)-N-(pyrimidin-2-yl)chromane-7-sulfonamide;
(S&R)-4-(2-(1H-1,2,3-Triazol-1-yl)-4-(trifluoromethyl)phenyl)-N-(pyridazin-3-yl)chromane-7-sulfonamide;
(S&R)-4-(2-(1H-1,2,3-Triazol-1-yl)-4-(trifluoromethyl)phenyl)-N-(5-fluoro pyrimidin-2-yl)chromane-7-sulfonamide;
(S&R)-4-(2-(1H-1,2,3-Triazol-1-yl)-4-(trifluoromethyl)phenyl)-N-(pyrimidin-4-yl)chromane-7-sulfonamide;
(S&R)-4-(2-(1H-1,2,3-Triazol-1-yl)-4-(trifluoromethyl)phenyl)-N-(6-fluoropyridin-2-yl)chromane-7-sulfonamide;
(S&R)—N-(6-Fluoropyridin-2-yl)-4-(2-(2-methylthiazol-4-yl)-4-(trifluoro methyl)phenyl)chroman-7-sulfonamide;
(S&R)-4-(2-(2-Methylthiazol-4-yl)-4-(trifluoromethyl)phenyl)-N-(pyrimidin-2-yl)chroman-7-sulfonamide;
(S&R)—N-(5-Fluoropyrimidin-2-yl)-4-(2-(2-methylthiazol-4-yl)-4-(trifluoromethyl)phenyl)chroman-7-sulfonamide;
(S&R)-4-(2-(2-Methylthiazol-4-yl)-4-(trifluoromethyl)phenyl)-N-(pyrimidin-4-yl)chroman-7-sulfonamide;
(S&R)-4-(2-(2-Methylthiazol-4-yl)-4-(trifluoromethyl)phenyl)-N-(pyridazin-3-yl)chroman-7-sulfonamide;
(S&R)—N-(5-Fluoropyrimidin-2-yl)-4-(2-(2-methyloxazol-4-yl)-4-(trifluoromethyl)phenyl)chroman-7-sulfonamide;
(S&R)—N-(6-Fluoropyridin-2-yl)-4-(2-(2-methyloxazol-4-yl)-4-(trifluoromethyl)phenyl)chroman-7-sulfonamide;
(S&R)-4-(2-(2-Methyloxazol-4-yl)-4-(trifluoromethyl)phenyl)-N-(pyrimidin-2-yl)chroman-7-sulfonamide;
(S&R)-4-(2-(2-Methyloxazol-4-yl)-4-(trifluoromethyl)phenyl)-N-(pyrimidin-4-yl)chroman-7-sulfonamide;
(S&R)-4-(2-(2-Methyloxazol-4-yl)-4-(trifluoromethyl)phenyl)-N-(pyridazin-3-yl)chroman-7-sulfonamide;
(S&R)—N-(6-Fluoropyridin-2-yl)-4-(2-(2-(methylsulfonyl)ethyl)-4-(trifluoromethyl)phenyl)chroman-7-sulfonamide;
(S&R)-4-(2-(2-(Methylsulfonyl)ethyl)-4-(trifluoromethyl)phenyl)-N-(pyrimidin-2-yl)chroman-7-sulfonamide;
(S&R)—N-(5-Fluoropyrimidin-2-yl)-4-(2-(2-(methyl sulfonyl)ethyl)-4-(trifluoromethyl)phenyl)chroman-7-sulfonamide;
(S&R)-4-(2-(2-(Methylsulfonyl)ethyl)-4-(trifluoromethyl)phenyl)-N-(pyrimidin-4-yl)chroman-7-sulfonamide;
(S&R)-4-(2-(1H-Pyrazol-1-yl)-4-(trifluoromethyl)phenyl)-N-(6-fluoropyridin-2-yl)chroman-7-sulfonamide;
(S&R)—N-(5-Fluoropyrimidin-2-yl)-4-(2-(thiazol-2-yl)-4-(trifluoromethyl)phenyl)chroman-7-sulfonamide;
(R/S)—N-(Pyrimidin-2-yl)-4-(2-(thiazol-2-yl)-4-(trifluoromethyl)phenyl)chroman-7-sulfonamide;
(R/S)—N-(Pyrimidin-4-yl)-4-(2-(thiazol-2-yl)-4-(trifluoromethyl)phenyl)chroman-7-sulfonamide;
(R/S)—N-(Pyridazin-3-yl)-4-(2-(thiazol-2-yl)-4-(trifluoromethyl)phenyl)chroman-7-sulfonamide;
(R/S)—N-(6-Fluoropyridin-2-yl)-4-(2-(thiazol-2-yl)-4-(trifluoromethyl)phenyl)chroman-7-sulfonamide;
(S&R)-4-(2-(6-Isopropoxypyridin-3-yl)-4-(trifluoromethyl)phenyl)-N-(pyrimidin-2-yl)chroman-7-sulfonamide;
(S&R)—N-(5-Fluoropyrimidin-2-yl)-4-(2-(6-isopropoxypyridin-3-yl)-4-(trifluoromethyl)phenyl)chroman-7-sulfonamide;
(S&R)-4-(2-(6-Ethoxypyridin-3-yl)-4-(trifluoromethyl)phenyl)-N-(5-fluoropyrimidin-2-yl)chroman-7-sulfonamide;
(R/S)-4-(2-(6-Ethoxypyridin-3-yl)-4-(trifluoromethyl)phenyl)-N-(pyrimidin-2-yl)chroman-7-sulfonamide;
(S/R)-4-(2-Chloro-4-(trifluoromethyl)phenyl)-N-(pyrimidin-2-yl)chroman-7-sulfonamide;
(S/R)-4-(2-Chloro-4-(trifluoromethyl)phenyl)-N-(5-fluoropyrimidin-2-yl)chroman-7-sulfonamide;
(S/R)-4-(2-Chloro-4-(trifluoromethyl)phenyl)-N-(pyrimidin-4-yl)chroman-7-sulfonamide;

(S/R)-4-(2-Chloro-4-(trifluoromethyl)phenyl)-N-(pyridazin-3-yl)chroman-7-sulfonamide;
(S/R)-4-(2-Chloro-4-(trifluoromethyl)phenyl)-N-(6-fluoropyridin-2-yl)chroman-7-sulfonamide;
(S&R)—N-(Pyrimidin-2-yl)-4-(2-(tetrahydro-2H-pyran-4-yl)-4-(trifluoromethyl)phenyl)chroman-7-sulfonamide;
(S&R)—N-(6-Fluoropyridin-2-yl)-4-(2-(2-oxopyrrolidin-1-yl)-4-(trifluoromethyl)phenyl)chroman-7-sulfonamide;
(S&R)—N-(5-Fluoropyrimidin-2-yl)-4-(2-(2-oxopyrrolidin-1-yl)-4-(trifluoromethyl)phenyl)chroman-7-sulfonamide;
(R/S)-4-(2-(2-Oxopyrrolidin-1-yl)-4-(trifluoromethyl)phenyl)-N-(pyrimidin-2-yl)chroman-7-sulfonamide;
(R/S)-4-(2-(2-Oxopyrrolidin-1-yl)-4-(trifluoromethyl)phenyl)-N-(pyrimidin-4-yl)chroman-7-sulfonamide;
(R/S)-4-(2-(2-Oxopyrrolidin-1-yl)-4-(trifluoromethyl)phenyl)-N-(pyridazin-3-yl)chromane-7-sulfonamide;
(S&R)-4-(2-Morpholino-4-(trifluoromethyl)phenyl)-N-(pyrimidin-2-yl)chroman-7-sulfonamide;
(S/R)—N-(5-Fluoropyrimidin-2-yl)-4-(2-morpholino-4-(trifluoromethyl)phenyl)chroman-7-sulfonamide;
(R/S)-4-(2-Morpholino-4-(trifluoromethyl)phenyl)-N-(pyrimidin-4-yl)chroman-7-sulfonamide;
(R/S)-4-(2-Morpholino-4-(trifluoromethyl)phenyl)-N-(pyridazin-3-yl)chroman-7-sulfonamide;
(R/S)—N-(6-Fluoropyridin-2-yl)-4-(2-morpholino-4-(trifluoromethyl)phenyl)chroman-7-sulfonamide;
(S&R)-4-(2-(2-Methoxyethoxy)-4-(trifluoromethyl)phenyl)-N-(pyrimidin-2-yl)chroman-7-sulfonamide;
(R/S)—N-(5-Fluoropyrimidin-2-yl)-4-(2-(2-methoxyethoxy)-4-(trifluoromethyl)phenyl)chroman-7-sulfonamide;
(R/S)-4-(2-(2-Methoxyethoxy)-4-(trifluoromethyl)phenyl)-N-(pyrimidin-4-yl)chroman-7-sulfonamide;
(R/S)-4-(2-(2-Methoxyethoxy)-4-(trifluoromethyl)phenyl)-N-(pyridazin-3-yl)chroman-7-sulfonamide;
(R/S)—N-(6-Fluoropyridin-2-yl)-4-(2-(2-methoxyethoxy)-4-(trifluoromethyl)phenyl)chroman-7-sulfonamide;
(S&R)-4-(2-(3-Methoxypropoxy)-4-(trifluoromethyl)phenyl)-N-(pyrimidin-2-yl)chroman-7-sulfonamide;
(R/S)—N-(5-Fluoropyrimidin-2-yl)-4-(2-(3-methoxypropoxy)-4-(trifluoromethyl)phenyl)chroman-7-sulfonamide;
(R/S)-4-(2-(3-Methoxypropoxy)-4-(trifluoromethyl)phenyl)-N-(pyridazin-3-yl)chroman-7-sulfonamide;
(R/S)—N-(6-Fluoropyridin-2-yl)-4-(2-(3-methoxypropoxy)-4-(trifluoromethyl)phenyl)chroman-7-sulfonamide;
(R/S)-4-(2-(2-Methoxyethyl)-4-(trifluoromethyl)phenyl)-N-(pyrimidin-2-yl)chroman-7-sulfonamide;
(R/S)—N-(5-Fluoropyrimidin-2-yl)-4-(2-(2-methoxyethyl)-4-(trifluoromethyl)phenyl)chroman-7-sulfonamide;
(R/S)—N-(6-Fluoropyridin-2-yl)-4-(2-(2-methoxyethyl)-4-(trifluoromethyl)phenyl)chroman-7-sulfonamide;
(R/S)-4-(2-(2-Methoxyethyl)-4-(trifluoromethyl)phenyl)-N-(pyrimidin-4-yl)chroman-7-sulfonamide;
(R/S)-4-(2-(2-Methoxyethyl)-4-(trifluoromethyl)phenyl)-N-(pyridazin-3-yl)chroman-7-sulfonamide;
(S&R)-4-(2-(3-Methoxypropyl)-4-(trifluoromethyl)phenyl)-N-(pyrimidin-2-yl)chroman-7-sulfonamide;
(R/S)—N-(5-Fluoropyrimidin-2-yl)-4-(2-(3-methoxypropyl)-4-(trifluoromethyl)phenyl)chroman-7-sulfonamide;
(R/S)-4-(2-(3-Methoxypropyl)-4-(trifluoromethyl)phenyl)-N-(pyrimidin-4-yl)chroman-7-sulfonamide;
(R/S)-4-(2-(3-Methoxypropyl)-4-(trifluoromethyl)phenyl)-N-(pyridazin-3-yl)chroman-7-sulfonamide;
(R/S)—N-(6-Fluoropyridin-2-yl)-4-(2-(3-methoxypropyl)-4-(trifluoromethyl)phenyl)chroman-7-sulfonamide;
(S&R)-4-(2-(4-Methoxybutyl)-4-(trifluoromethyl)phenyl)-N-(pyrimidin-2-yl)chroman-7-sulfonamide;
(R/S)—N-(5-Fluoropyrimidin-2-yl)-4-(2-(4-methoxybutyl)-4-(trifluoromethyl)phenyl)chroman-7-sulfonamide;
(R/S)-4-(2-(4-Methoxybutyl)-4-(trifluoromethyl)phenyl)-N-(pyrimidin-4-yl)chroman-7-sulfonamide;
(R/S)-4-(2-(4-Methoxybutyl)-4-(trifluoromethyl)phenyl)-N-(pyridazin-3-yl)chroman-7-sulfonamide;
(S&R)—N-(6-Fluoropyridin-2-yl)-4-(2-(4-methoxybutyl)-4-(trifluoromethyl)phenyl)chroman-7-sulfonamide;
(R/S)-4-(2-(2-Fluoroethyl)-4-(trifluoromethyl)phenyl)-N-(pyrimidin-2-yl)chroman-7-sulfonamide;
(R/S)-4-(2-(2-Fluoroethyl)-4-(trifluoromethyl)phenyl)-N-(5-fluoro pyrimidin-2-yl)chroman-7-sulfonamide;
(R/S)-4-(2-(2-Fluoroethyl)-4-(trifluoromethyl)phenyl)-N-(pyrimidin-4-yl)chroman-7-sulfonamide;
(R/S)-4-(2-(2-Fluoroethyl)-4-(trifluoromethyl)phenyl)-N-(pyridazin-3-yl)chroman-7-sulfonamide;
(R/S)-4-(2-(2-Fluoroethyl)-4-(trifluoromethyl)phenyl)-N-(6-fluoropyridin-2-yl)chroman-7-sulfonamide;
(R/S)-4-(2-(3-Fluoropropyl)-4-(trifluoromethyl)phenyl)-N-(pyrimidin-2-yl)chroman-7-sulfonamide;
(R/S)-4-(2-(3-Fluoropropyl)-4-(trifluoromethyl)phenyl)-N-(5-fluoropyrimidin-2-yl)chroman-7-sulfonamide;
(R/S)-4-(2-(3-Fluoropropyl)-4-(trifluoromethyl)phenyl)-N-(pyrimidin-4-yl)chroman-7-sulfonamide;
(R/S)-4-(2-(3-Fluoropropyl)-4-(trifluoromethyl)phenyl)-N-(pyridazin-3-yl)chroman-7-sulfonamide;
(R/S)-4-(2-(3-Fluoropropyl)-4-(trifluoromethyl)phenyl)-N-(6-fluoropyridin-2-yl)chroman-7-sulfonamide;
(R/S)-4-(2-(4-Fluorobutyl)-4-(trifluoromethyl)phenyl)-N-(pyrimidin-2-yl)chroman-7-sulfonamide;
(R/S)-4-(2-(4-Fluorobutyl)-4-(trifluoromethyl)phenyl)-N-(5-fluoropyrimidin-2-yl)chroman-7-sulfonamide;
(R/S)-4-(2-(4-Fluorobutyl)-4-(trifluoromethyl)phenyl)-N-(pyrimidin-4-yl)chroman-7-sulfonamide;
(R/S)-4-(2-(4-Fluorobutyl)-4-(trifluoromethyl)phenyl)-N-(pyridazin-3-yl)chroman-7-sulfonamide;
(R/S)-4-(2-(4-Fluorobutyl)-4-(trifluoromethyl)phenyl)-N-(6-fluoropyridin-2-yl)chroman-7-sulfonamide;
(R&S)—N-(Pyrimidin-2-yl)-4-(2-((tetrahydro-2H-pyran-4-yl)oxy)-4-(trifluoromethyl)phenyl)chroman-7-sulfonamide;
(R&S)—N-(5-Fluoropyrimidin-2-yl)-4-(2-((tetrahydro-2H-pyran-4-yl)oxy)-4-(trifluoromethyl)phenyl)chroman-7-sulfonamide;
(R&S)—N-(Pyrimidin-4-yl)-4-(2-((tetrahydro-2H-pyran-4-yl)oxy)-4-(trifluoromethyl)phenyl)chroman-7-sulfonamide;
(R&S)—N-(Pyridazin-3-yl)-4-(2-((tetrahydro-2H-pyran-4-yl)oxy)-4-(trifluoromethyl)phenyl)chroman-7-sulfonamide;
(R&S)—N-(6-Fluoropyridin-2-yl)-4-(2-((tetrahydro-2H-pyran-4-yl)oxy)-4-(trifluoromethyl)phenyl)chroman-7-sulfonamide;
(R&S)—N-(Pyrimidin-2-yl)-4-(2-(((S)-tetrahydrofuran-3-yl)oxy)-4-(trifluoromethyl)phenyl)chroman-7-sulfonamide;
(R&S)—N-(6-Fluoropyridin-2-yl)-4-(2-(((S)-tetrahydrofuran-3-yl)oxy)-4-(trifluoromethyl)phenyl)chroman-7-sulfonamide;
(S/R)—N-(5-Fluoropyrimidin-2-yl)-4-(2-(((S)-tetrahydrofuran-3-yl)oxy)-4-(trifluoromethyl)phenyl)chroman-7-sulfonamide;

(S/R)—N-(Pyrimidin-4-yl)-4-(2-(((S)-tetrahydrofuran-3-yl) oxy)-4-(trifluoromethyl)phenyl)chroman-7-sulfonamide;
(S/R)—N-(Pyridazin-3-yl)-4-(2-(((S)-tetrahydrofuran-3-yl) oxy)-4-(trifluoromethyl)phenyl)chroman-7-sulfonamide;
(S&R)—N-(Pyrimidin-2-yl)-4-(2-(((R)-tetrahydrofuran-3-yl)oxy)-4-(trifluoromethyl)phenyl)chroman-7-sulfonamide;
(S&R)-2'-(7-(N-(Pyrimidin-2-yl)sulfamoyl)chroman-4-yl)-5'-(trifluoromethyl)-[1,1'-biphenyl]-4-carboxylic acid;
(S&R)-2'-(7-(N-(5-Fluoropyrimidin-2-yl)sulfamoyl)chroman-4-yl)-5-(trifluoromethyl)-[1,1'-biphenyl]-4-carboxylic acid;
(R/S)-2'-(7-(N-(Pyridazin-3-yl)sulfamoyl)chroman-4-yl)-5'-(trifluoromethyl)-[1,1'-biphenyl]-4-carboxylic acid;
(R/S)-2'-(7-(N-(6-Fluoropyridin-2-yl)sulfamoyl)chroman-4-yl)-5'-(trifluoromethyl)-[1,1'-biphenyl]-4-carboxylic acid;
(S&R)-4-(2-(5-Fluoropyridin-2-yl)-4-(trifluoromethyl)phenyl)-N-(pyrimidin-2-yl)chroman-7-sulfonamide;
(S&R)-4-(2-(5-Fluoropyridin-2-yl)-4-(trifluoromethyl)phenyl)-N-(5-fluoropyrimidin-2-yl)chroman-7-sulfonamide;
(S&R)-4-(2-(5-Fluoropyridin-2-yl)-4-(trifluoromethyl)phenyl)-N-(pyrimidin-4-yl)chroman-7-sulfonamide;
(S&R)-4-(2-(5-Fluoropyridin-2-yl)-4-(trifluoromethyl)phenyl)-N-(pyridazin-3-yl)chroman-7-sulfonamide;
(S)-4-(2-(6-Methylpyridin-3-yl)-4-(trifluoromethyl)phenyl)-N-(pyrimidin-2-yl)chroman-7-sulfonamide;
(R)-4-(2-(6-Methylpyridin-3-yl)-4-(trifluoromethyl)phenyl)-N-(pyrimidin-2-yl)chroman-7-sulfonamide;
(R/S)—N-(5-Fluoropyrimidin-2-yl)-4-(2-(6-methylpyridin-3-yl)-4-(trifluoromethyl)phenyl)chroman-7-sulfonamide;
(R/S)-4-(2-(6-Methylpyridin-3-yl)-4-(trifluoromethyl)phenyl)-N-(pyrimidin-4-yl)chroman-7-sulfonamide;
(R/S)-4-(2-(6-Methylpyridin-3-yl)-4-(trifluoromethyl)phenyl)-N-(pyridazin-3-yl)chroman-7-sulfonamide;
(R/S)—N-(6-Fluoropyridin-2-yl)-4-(2-(6-methylpyridin-3-yl)-4-(trifluoromethyl)phenyl)chroman-7-sulfonamide;
(R/S)-4-(2-(2-Oxooxazolidin-3-yl)-4-(trifluoromethyl)phenyl)-N-(pyrimidin-2-yl)chroman-7-sulfonamide;
(R/S)—N-(5-Fluoropyrimidin-2-yl)-4-(2-(2-oxooxazolidin-3-yl)-4-(trifluoromethyl)phenyl)chroman-7-sulfonamide;
(R/S)-4-(2-(2-Oxooxazolidin-3-yl)-4-(trifluoromethyl)phenyl)-N-(pyridazin-3-yl)chroman-7-sulfonamide;
(R/S)—N-(6-Fluoropyridin-2-yl)-4-(2-(2-oxooxazolidin-3-yl)-4-(trifluoromethyl)phenyl)chromane-7-sulfonamide;
(R/S)-4-(2-(3,3-Difluoropropyl)-4-(trifluoromethyl)phenyl)-N-(pyrimidin-2-yl)chroman-7-sulfonamide;
(R/S)-4-(2-(3,3-Difluoropropyl)-4-(trifluoromethyl)phenyl)-N-(5-fluoropyrimidin-2-yl)chroman-7-sulfonamide;
(R/S)-4-(2-(3,3-Difluoropropyl)-4-(trifluoromethyl)phenyl)-N-(pyrimidin-4-yl)chroman-7-sulfonamide;
(R/S)-4-(2-(3,3-Difluoropropyl)-4-(trifluoromethyl)phenyl)-N-(pyridazin-3-yl)chroman-7-sulfonamide;
(R/S)-4-(2-(3,3-Difluoropropyl)-4-(trifluoromethyl)phenyl)-N-(6-fluoropyridin-2-yl)chromane-7-sulfonamide;
(R&S)-4-(2-(Oxetan-3-yloxy)-4-(trifluoromethyl)phenyl)-N-(pyrimidin-2-yl)chroman-7-sulfonamide;
(S/R)—N-(5-Fluoropyrimidin-2-yl)-4-(2-(oxetan-3-yloxy)-4-(trifluoromethyl)phenyl)chroman-7-sulfonamide;
(S/R)—N-(6-Fluoropyridin-2-yl)-4-(2-(oxetan-3-yloxy)-4-(trifluoromethyl)phenyl)chromane-7-sulfonamide;
(S&R)-4-(2-(3-Fluoropropoxy)-4-(trifluoromethyl)phenyl)-N-(pyrimidin-2-yl)chroman-7-sulfonamide;
(R/S)-4-(2-(5-Fluoro-6-methylpyridin-2-yl)-4-(trifluoromethyl)phenyl)-N-(pyrimidin-2-yl)chroman-7-sulfonamide;
(R/S)-4-(2-(5-Fluoro-6-methylpyridin-2-yl)-4-(trifluoromethyl)phenyl)-N-(5-fluoropyrimidin-2-yl)chroman-7-sulfonamide;
(R/S)-4-(2-(5-Fluoro-6-methylpyridin-2-yl)-4-(trifluoromethyl)phenyl)-N-(pyridazin-3-yl)chroman-7-sulfonamide;
(R/S)-4-(2-(5-Fluoro-6-methylpyridin-2-yl)-4-(trifluoromethyl)phenyl)-N-(6-fluoropyridin-2-yl)chroman-7-sulfonamide;
(S&R)-4-(2-Methoxy-4-(trifluoromethyl)phenyl)-N-(pyrimidin-2-yl)chroman-7-sulfonamide;
(S&R)—N-(6-Fluoropyridin-2-yl)-4-(2-methoxy-4-(trifluoromethyl)phenyl)chroman-7-sulfonamide;
(S&R)-4-(2-(3-Oxomorpholino)-4-(trifluoromethyl)phenyl)-N-(pyrimidin-2-yl)chroman-7-sulfonamide;
(S&R)-4-(2-(1,1-Dioxidothiomorpholino)-4-(trifluoromethyl)phenyl)-N-(pyrimidin-2-yl)chroman-7-sulfonamide;
(R/S)-4-(2-(1,1-Dioxidothiomorpholino)-4-(trifluoromethyl)phenyl)-N-(5-fluoropyrimidin-2-yl)chroman-7-sulfonamide;
(R/S)-4-(2-(1,1-Dioxidothiomorpholino)-4-(trifluoromethyl)phenyl)-N-(6-fluoropyridin-2-yl)chroman-7-sulfonamide;
(R/S)-4-(2-(1,1-Dioxidothiomorpholino)-4-(trifluoromethyl)phenyl)-N-(pyridazin-3-yl)chroman-7-sulfonamide;
(R/S)-4-(2-(1,1-Dioxidothiomorpholino)-4-(trifluoromethyl)phenyl)-N-(pyrimidin-4-yl)chromane-7-sulfonamide;
(S&R)-4-(2-propyl-4-(trifluoromethyl)phenyl)-N-(pyrimidin-2-yl)chroman-7-sulfonamide;
(S&R)—N-(5-fluoropyrimidin-2-yl)-4-(2-propyl-4-(trifluoromethyl)phenyl)chroman-7-sulfonamide;
(S&R)-4-(2-propyl-4-(trifluoromethyl)phenyl)-N-(pyridazin-3-yl)chroman-7-sulfonamide; and
(S&R)—N-(6-fluoropyridin-2-yl)-4-(2-propyl-4-(trifluoromethyl)phenyl)chroman-7-sulfonamide or racemate thereof, N-oxide thereof or a pharmaceutically acceptable salt thereof.

In another embodiment, the invention provides a compound of Formulae (I) to (VI) wherein the compound is in free base form.

In another embodiment, the invention provides a compound of Formulae (I) to (VI) wherein the compound is pharmaceutically acceptable salt.

In another embodiment, the invention provides compounds of Formulae (I) to (VI) structurally encompass stereoisomers including enantiomers or diastereomers.

In another embodiment, the invention provides a compound of Formulae (I) to (VI) wherein the compound is racemic mixture containing 'R' isomer and 'S' isomer.

In another embodiment, the invention provides a compound of Formulae (I) to (VI) wherein the compound is 'R' isomer.

In another embodiment, the invention provides a compound of Formulae (I) to (VI) wherein the compound is 'S' isomer.

In another aspect of the invention, there is provided a compound of Formulae (I) to (VI) or a pharmaceutically acceptable salt thereof for use as a medicament.

In another aspect of the invention, there is provided a compound of Formulae (I) to (VI), or a pharmaceutically acceptable salt thereof, for use in treating the diseases, disorders, syndromes or conditions associated with VGSC particularly Nav1.7.

In another aspect, the invention provides a pharmaceutical composition comprising at least one compound of Formulae (I) to (VI), or a pharmaceutically acceptable salt thereof and at least one pharmaceutically acceptable excipient.

In another aspect, the invention provides a pharmaceutical composition comprising a compound of Formulae (I) to (VI), or a pharmaceutically acceptable salt thereof, for use in treating, the diseases disorders, syndromes or conditions associated with VGSC particularly Na$_v$1.7 in a subject, in need thereof by administering to the subject, one or more compounds described herein in a therapeutically effective amount to cause modulation of such receptor.

In another aspect, the invention provides a pharmaceutical composition comprising a compound of Formulae (I) to (VI), or a pharmaceutically acceptable salt thereof, N-oxide thereof, or a pharmaceutically acceptable stereoisomer thereof, together with a pharmaceutically acceptable excipient.

In another aspect of the invention, there is provided use of a compound of Formulae (I) to (VI), or a pharmaceutically acceptable salt thereof, for the manufacture of a medicament for treating, the diseases, disorders, syndromes or conditions associated with VGSC.

In another aspect, there are provided process for the preparation of compounds of Formula (Ia):

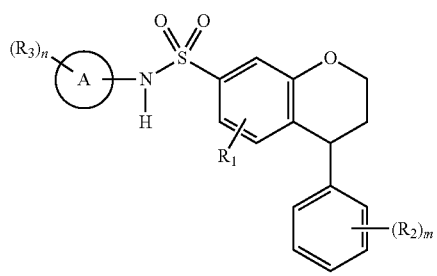

(Ia)

wherein ring A, R$_1$, R$_2$, R$_3$, 'm' and 'n' are as defined herein above;
the process comprising the steps of:
  a) reacting a compound of formula (2) with NCS followed by pentafluorophenol gives the pentafluoro ester of formula (7)

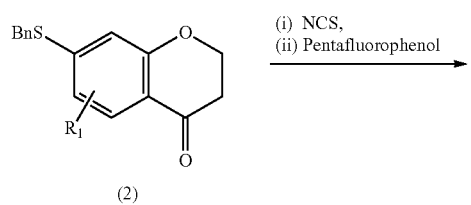

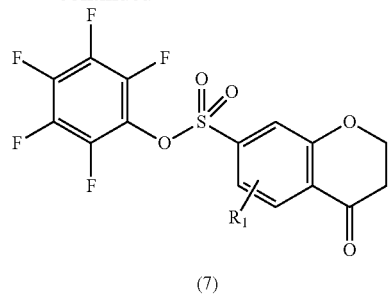

(7)

b) reacting a compound of formula (7) with p-tosyl hydrazine to give the hydrazone compound of formula (8)

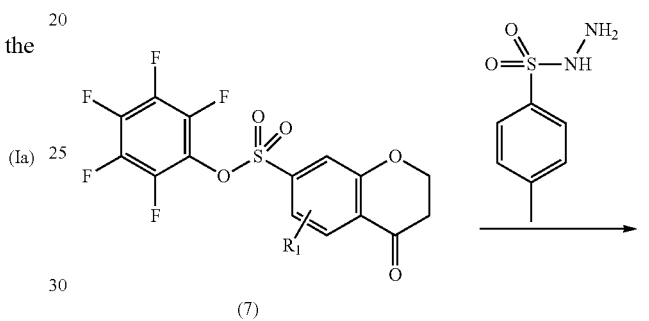

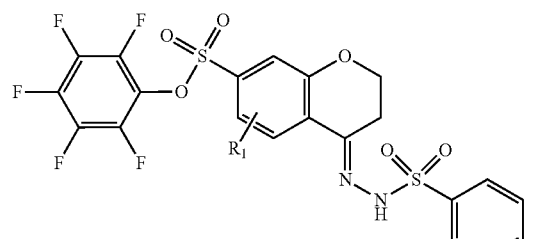

(8)

c) coupling of a compound of formula (8) with compound of formula (4) in presence of suitable Pd catalyst to give compound of formula (6) which can also be prepared from compound of formula (5) by reacting with sulfuryl chloride or NCS or dichlorohydantoin followed by pentafluorophenol

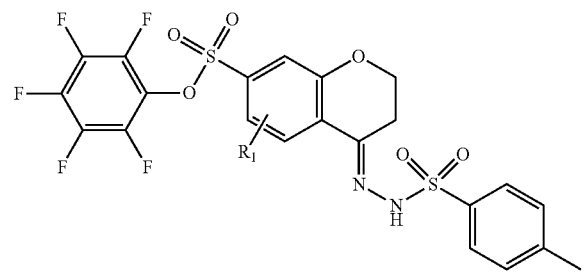

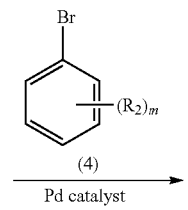

(8)

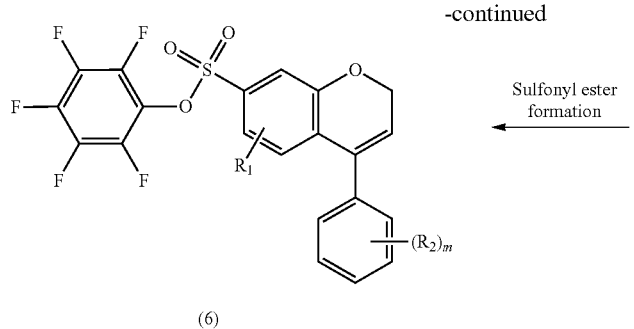

(6)

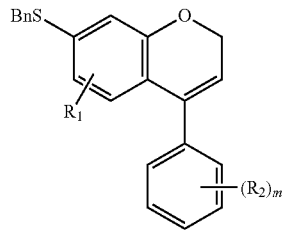

(5)

d) reducing a compound of formula (6) using Pd/C to give compound of formula (9)

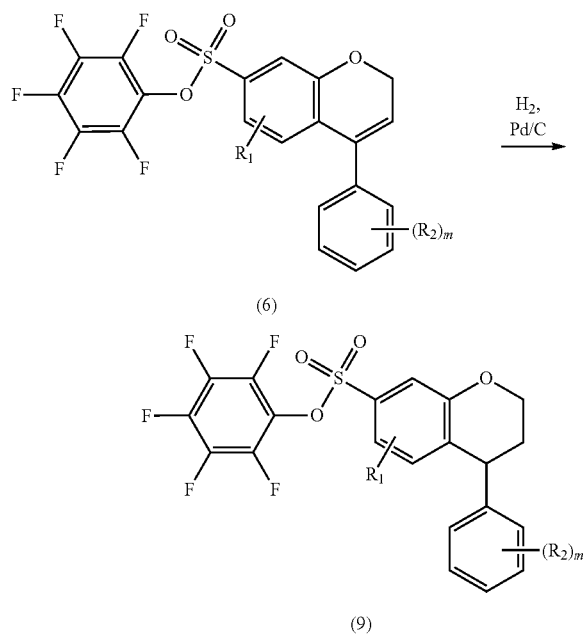

e) coupling of compound of formula (9) with amine of formula (10) to give compound of formula (Ia)

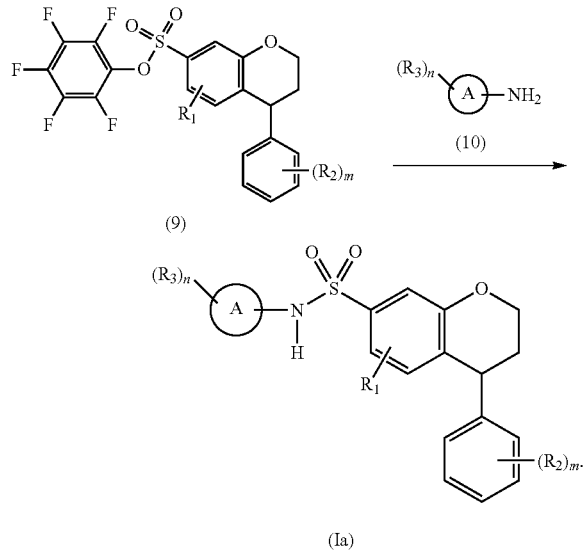

DETAILED DESCRIPTION OF THE INVENTION

Definitions and Abbreviations:

Unless otherwise stated, the following terms used in the specification and claims have the meanings given below.

For purposes of interpreting the specification, the following definitions will apply and whenever appropriate, terms used in the singular will also include the plural and vice versa.

The terms "halogen" or "halo" means fluorine, chlorine, bromine or iodine.

Unless otherwise stated, in the present application "oxo" means C(=O) group. Such an oxo group may be a part of either a cycle or a chain in the compounds of the present invention.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, e.g., methyl, ethyl, n-propyl, 1-methylethyl (isopropyl), n-butyl, n-pentyl, 1,1-dimethylethyl (t-butyl) and the like. Unless set forth or recited to the contrary, all alkyl groups described or claimed herein may be straight chain or branched.

The term "alkenyl" refers to a hydrocarbon radical containing from 2 to 10 carbon atoms and including at least one carbon-carbon double bond. Non-limiting examples of alkenyl groups include ethenyl, 1-propenyl, 2-propenyl (allyl), iso-propenyl, 2-methyl-1-propenyl, 1-butenyl, 2-butenyl and the like. Unless set forth or recited to the contrary, all alkenyl groups described or claimed herein may be straight chain or branched.

The term "alkynyl" refers to a hydrocarbon radical containing 2 to 10 carbon atoms and including at least one carbon-carbon triple bond. Non-limiting examples of alkynyl groups include ethynyl, propynyl, butynyl and the like. Unless set forth or recited to the contrary, all alkynyl groups described or claimed herein may be straight chain or branched.

The term "alkoxy" denotes an alkyl group attached via an oxygen linkage to the rest of the molecule. Representative examples of such groups are —OCH$_3$ and —OC$_2$H$_5$. Unless set forth or recited to the contrary, all alkoxy groups described or claimed herein may be straight chain or branched.

The term "alkoxyalkyl" refers to an alkoxy group as defined above directly bonded to an alkyl group as defined above, e.g., —CH$_2$—O—CH$_3$, —CH$_2$—O—CH$_2$CH$_3$, —CH$_2$CH$_2$—O—CH$_3$ and the like.

The term "hydroxyalkyl" refers to an alkyl group, as defined above that is substituted by one or more hydroxy groups. Preferably, the hydroxyalkyl is monohydroxyalkyl or dihydroxyalkyl. Non-limiting examples of a hydroxyalkyl include 2-hydroxyethyl, 3-hydroxypropyl, 2-hydroxypropyl, and the like.

The term "haloalkyl" refers to an alkyl group as defined above that is substituted by one or more halogen atoms as defined above. Preferably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Preferably, a polyhaloalkyl is substituted with up to 12 halogen atoms. Non-limiting examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms. Unless set forth or recited to the contrary, all haloalkyl groups described or claimed herein may be straight chain or branched.

The term "cycloalkyl" refers to a non-aromatic mono or multicyclic ring system having 3 to 12 carbon atoms, such as cyclopropyl, cyclobutyl, cyclopentyl, cyclohexyl and the like. Examples of multicyclic cycloalkyl groups include, but are not limited to, perhydronapthyl, adamantyl and norbornyl groups, bridged cyclic groups or spirobicyclic groups, e.g., spiro(4,4)non-2-yl and the like.

The term "cycloalkenyl" refers to a non-aromatic mono or multicyclic ring system having 3 to 12 carbon atoms and including at least one carbon-carbon double bond, such as cyclopentenyl, cyclohexenyl, cycloheptenyl and the like.

The term "cycloalkylalkyl" refers to a cycloalkyl group as defined above, directly bonded to an alkyl group as defined above, e.g., cyclopropylmethyl, cyclobutylmethyl, cyclopentylmethyl, cyclohexylmethyl, cyclohexylethyl, etc.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like.

The term "arylalkyl" refers to an aryl group as defined above directly bonded to an alkyl group as defined above, e.g., —$CH_2C_6H_5$ and —$C_2H_4C_6H_5$.

A "4 to 8" membered cyclic ring" as used herein refers to a monocyclic or bicyclic heteroaryl or heterocyclic ring systems.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(s) and one or two carbon atoms(s) in the heterocyclic ring or heterocyclyl may be interrupted with —$CF_2$—, —$C(O)$—, —$S(O)$—, $S(O)_2$, —$C(\!=\!N\text{-alkyl})$-, or —$C(\!=\!N\text{-cy-cloalkyl})$, etc. In addition heterocyclic ring may also be fused with aromatic ring. Non-limiting examples of heterocyclic rings include azetidinyl, benzopyranyl, chromanyl, decahydroisoquinolyl, indolinyl, isoindolinyl, isochromanyl, isothiazolidinyl, isoxazolidinyl, morpholinyl, oxazolidinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl, tetrahydropyranyl, thiazolinyl, thiazolidinyl, thiamorpholinyl, thiamorpholinyl sulfoxide, thiamorpholinyl sulfone indoline, benzodioxole, tetrahydroquinoline, tetrahydrobenzopyran and the like. The heterocyclic ring may be attached to the main structure at any heteroatom or carbon atom that results in the creation of a stable structure.

The term "heteroaryl" unless otherwise specified, refers to a substituted or unsubstituted 5- to 14-membered aromatic heterocyclic ring with one or more heteroatom(s) independently selected from N, O or S. In addition the nitrogen atom in a heteroaryl ring is optionally quaternized to form corresponding N-oxide. The heteroaryl may be a mono-, bi- or tricyclic ring system. The heteroaryl ring may be attached to the main structure at any heteroatom or carbon atom that results in the creation of a stable structure. Non-limiting examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure.

The term "heteroarylalkyl" refers to a heteroaryl ring radical directly bonded to an alkyl group. The heteroarylalkyl radical may be attached to the main structure at any carbon atom in the alkyl group that results in the creation of a stable structure.

The compounds of the present invention may have one or more chiral centers. The absolute stereochemistry at each chiral center may be 'R' or 'S'. The compounds of the invention include all diastereomers and enantiomers and mixtures thereof. Unless specifically mentioned otherwise, reference to one stereoisomer applies to any of the possible stereoisomers. Whenever the stereoisomeric composition is unspecified, it is to be understood that all possible stereoisomers are included.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers. 'or1' mentioned in the structures herein refers to single stereoisomer that is assigned to be either R isomer or S isomer.

The term "treating" or "treatment" of a state, disease, disorder, condition or syndrome includes: (a) preventing or delaying the appearance of clinical symptoms of the state, disease, disorder, condition or syndrome developing in a subject that may be afflicted with or predisposed to the state, disease, disorder, condition or syndrome but does not yet experience or display clinical or subclinical symptoms of the state, disease, disorder, condition or syndrome; (b) inhibiting the state, disease, disorder, condition or syndrome, i.e., arresting or reducing the development of the disease or at least one clinical or subclinical symptom thereof; c) lessening the severity of a disease disorder or condition or at least one of its clinical or subclinical symptoms thereof; and/or (d) relieving the disease, i.e., causing regression of the state, disorder or condition or at least one of its clinical or subclinical symptoms.

The term "modulate" or "modulating" or "modulation" refers to a decrease or inhibition in the amount, quality, or effect of a particular activity, function or molecule; by way of illustration that antagonists of a voltage-gated sodium channels are modulators of VGSC. Any such modulation, whether it is partial or complete inhibition or prevention of ion flux, is sometimes referred to herein as "blocking" and corresponding compounds as "blockers". For example, the compounds of invention are useful as modulators of the NaV1.7. In general, the compounds of the invention modulates the activity of a sodium channel downwards, inhibits the voltage-dependent activity of the sodium channel, and/or reduces or prevents sodium ion flux across a cell membrane by preventing sodium channel activity such as ion flux.

The term "subject" includes mammals, preferably humans and other animals, such as domestic animals; e.g., household pets including cats and dogs.

A "therapeutically effective amount" refers to the amount of a compound that, when administered to a subject in need thereof, is sufficient to cause a desired effect. The "therapeutically effective amount" will vary depending on the compound, the disease and its severity, age, weight, physical condition and responsiveness of the subject to be treated.

Pharmaceutically Acceptable Salts:

The compounds of the invention may form salts with acid or base. The compounds of invention may be sufficiently basic or acidic to form stable nontoxic acid or base salts, administration of the compound as a pharmaceutically acceptable salt may be appropriate. Non-limiting examples of pharmaceutically acceptable salts are inorganic, organic acid addition salts formed by addition of acids including hydrochloride salts. Non-limiting examples of pharmaceutically acceptable salts are inorganic, organic base addition salts formed by addition of bases. The compounds of the invention may also form salts with amino acids. Pharmaceutically acceptable salts may be obtained using standard procedures well known in the art, for example by reacting a sufficiently basic compound such as an amine with a suitable acid affording a physiologically acceptable anion.

With respect to the overall compounds described by the Formula (I), the invention extends to these stereoisomeric forms and to mixtures thereof. To the extent prior art teaches synthesis or separation of particular stereoisomers, the different stereoisomeric forms of the invention may be separated from one another by a method known in the art, or a given isomer may be obtained by stereospecific or asymmetric synthesis or chiral HPLC (high performance liquid chromatography. Tautomeric forms and mixtures of compounds described herein are also contemplated.

Compound Screening:

The screening of compounds of the invention for VGSC modulatory activity can be achieved by using various in vitro and in vivo protocols. Some of the methods include measuring current (electrophysiology), estimating membrane potential (using membrane potential dyes or voltage specific dye pairs), measuring ion flux (e.g., Sodium or Guanidium), measuring second messenger and transcription factor levels, measuring sodium concentration or by Rubidium efflux assay. These assays can be performed in tissue slices or cell lines that endogenously express sodium channels (e.g. ND7/23, SHSY-5Y). Alternatively, one can also use cell lines stably expressing the NaV of interest (e.g., stable cell lines generated in HEK293 cells or CHO cells).

Pharmaceutical Compositions:

The invention relates to pharmaceutical compositions containing the compound of Formula (I). In particular, the pharmaceutical compositions contain a therapeutically effective amount of at least one compound of Formula (I) and at least one pharmaceutically acceptable excipient (such as a carrier or diluent). Preferably, the pharmaceutical compositions include the compound(s) described herein in an amount sufficient to modulate the ion flux through a voltage-dependent sodium channel to treat sodium channel mediated diseases such as pain when administered to a subject.

The compound of the invention may be incorporated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes a pharmaceutical agent that does not itself induce the production of antibodies harmful to the individual receiving the composition, and which may be administered without undue toxicity.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, salicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be administered in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral Formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Liquid Formulations include, but are not limited to, syrups, emulsions, soft gelatin and sterile injectable liquids, such as aqueous or non-aqueous liquid suspensions or solutions. For parenteral application, particularly suitable are injectable solutions or suspensions Formulation.

Liquid Formulations include, but are not limited to, syrups, emulsions, suspensions, solutions, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

For administration to human patients, the total daily dose of the compounds of the invention depends, of course, on the mode of administration. For example, oral administration may require a higher total daily dose, than an intravenous (direct into blood). The quantity of active component in a unit dose preparation may be varied or adjusted from 0.1 mg to 10000 mg, more typically 1.0 mg to 1000 mg, and most typically 10 mg to 500 mg, according to the potency of the active component or mode of administration.

Suitable doses of the compounds for use in treating the diseases disorders, syndromes and conditions described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects for the patient. For example, the daily dosage of the Sodium channel modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the invention.

Methods of Treatment:

In one aspect, the invention are provided compounds and pharmaceutical compositions that are useful in the treatment of diseases, disorders, syndromes and/or conditions modulated by NaV channel. The invention further provides a method of treating a disease, condition and/or disorder modulated by NaV channel in a subject in need thereof by administering to the subject a therapeutically effective amount of a compound or a pharmaceutical composition of the invention.

One aspect of the invention provides methods for decreasing ion flow through voltage-gated sodium channels in a cell, comprising contacting a cell containing the target ion channels with a compound, associated to voltage-dependent gated ion channel, described herein.

In another aspect of the invention, the methods are also useful for the diagnosis of conditions that can be treated by acting on ion flux through voltage-dependent gated ion channel, for determining if a patient will be responsible to therapeutic agents.

In still another aspect of the invention provides a method for the treatment of a disorder or condition through modulating a voltage-gated sodium channel. In this method, a subject in need of such treatment is administered an effective amount of a compound described herein and/or according to Formulae (I) to (VI) described herein.

The compound of Formulae (I) to (VI), being a voltage-dependent gated sodium channel modulator, is potentially useful in the treating, managing and/or lessening of diseases, disorders, syndromes or conditions including but not limited to pain, erythromyalgia, neurological disorders, cardiovascular conditions, neuromuscular conditions, multiple sclerosis, cancer, pruritus, benign prostatic hyperplasia (BPH) and the like.

Pain includes, but is not limited to, acute pain, musculoskeletal pain, post-operative pain, chronic pain, persistent pain, peripherally mediated pain, centrally mediated pain.

The compounds, compositions and methods of the invention are of particular use in treating, managing and/or lessening of pain including inflammatory, neuropathic, nociceptive and idiopathic pain.

The compounds, compositions and methods of the invention are of particular use in treating, managing and/or lessening of pain including but not limited to postoperative pain, arthritis pain, osteoarthritis pain, pain associated with cancer including chemotherapy pain, neuropathic pain secondary to metastatic inflammation, neuralgic, orofacial pain, burn pain, somatic pain, dental pain, sciatica pain, intestinal obstruction pain, visceral pain, colicky pain, myofascial pain, trauma pain, labour pain, trigeminal neuralgia, glossopharyngeal neuralgia, adiposis dolorosa, acute herpetic and postherpetic neuralgia, diabetic neuropathy, causalgia, brachial plexus avulsion, occipital neuralgia, reflex sympathetic dystrophy, fibromyalgia, gout, phantom limb pain, pain following stroke, thalamic lesions, radiculopathy, chronic headache, migraine pain, familial hemiplegic migraine, conditions associated with cephalic pain, sinus headache, tension headache, cardiac pain arising from an ischemic myocardium, pain following stroke, neuropathy secondary to metastatic inflammation, pain due to connective tissue damage, and other forms of neuralgic, neuropathic, and idiopathic pain syndromes.

Idiopathic pain is pain of unknown origin, for example, phantom limb pain. Neuropathic pain is generally caused by injury or infection of the peripheral sensory nerves generally it includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies.

The compounds of the invention may be useful for treating certain types of inflammatory disease such as pancreatitis, which includes acute pancreatitis and chronic pancreatitis, is characterized by recurring or persistent abdominal pain with or without steatorrhea or diabetes mellitus, hereditary pancreatitis, pancreatic dysfunction. And it may also useful for treating the pain associated with pancreatitis and its related disorders.

The compounds of the invention may be useful for treating cardiovascular conditions such as arrhythmias, atrial fibrillation and ventricular fibrillation.

Na$_V$1.7 was first cloned from the pheochromocytoma PC12 cell line (Toledo-Aral, J. J., et al. *Proc. Natl. Acad. Sci. USA* (1997), 94, 1527-1532). Its presence at high levels in the growth cones of small-diameter neurons suggested that it could play a role in the transmission of nociceptive information. Although this has been challenged by experts in the field as Na$_V$1.7 is also expressed in neuroendocrine cells associated with the autonomic system (Klugbauer, N., et al. *EMBO J* (1995), 14, 1084-90) and as such has been implicated in autonomic processes. The compounds of the invention may be useful for treating Crohns disease, multiple sclerosis (MS) and pain associated with multiple sclerosis (MS), amyotrophic lateral sclerosis (ALS), disseminated sclerosis, motor failure, ataxia, tremor, muscle weakness, and dystonia. Epilepsy and cardiac arrhythmias are often targets of sodium channel blockers. Recent evidence from animal models suggests that sodium channel blockers may also be useful for neuroprotection under ischemic conditions caused by stroke or neural trauma and in patients with multiple sclerosis (MS).

The compounds of the invention may be useful for treating certain type of cancers for example prostate cancer, breast cancer, ovarian cancer, testicular cancer, thyroid neoplasia. The VGSC's are reported to have been expressed in prostate and breast cancer cells. Na$_V$1.5 has been identified in breast cancer cells and the enhanced expression of this isoform was associated with strong metastatic potential in vitro and breast cancer progression in vivo. (Fraser et al. *Clin. Cancer Res.* (2005), 11, 5381-5389). Expression of Na$_V$1.7 is upregulated ~20 fold in prostate cancer. Moreover, the expression correlates with high metastatic potential in vitro. (*Current Pharmaceutical Design* (2006), 12, 3681-3695; *Prostate Cancer and Prostatic Diseases* (2005), 8, 266-273).

The compounds of invention may be useful in the treatment of epilepsy, partial and general tonic seizures, arrhythmias, fibromyalgia, neuroprotection under ischaemic conditions caused by stroke, glaucoma or neural trauma, neuromuscular conditions such as restless leg syndrome and muscle paralysis or tetanus.

The compounds of invention may be useful in the treatment of pruritus and related diseases such as psoriatic pruritus, itch due to hemodialysis, aguagenic pruritus, itching caused by skin disorders, allergic itch, insect bite itch, itch caused by hypersensitivity such as dry skin, acne, eczema, psoriasis or injury, itch caused by vulvar vestibulitis and the similar itch.

The compounds of the invention may be useful in treating the symptoms associated with BPH (benign prostate hyperplasia) including but not limited to acute urinary retention and urinary tract infection.

It is to be understood that the invention encompasses any of the compounds of Formulae (I) to (VI) or pharmaceutically acceptable salts thereof for use in the treatment of any of the conditions disclosed herein.

It is to be understood that the invention encompasses the use of any of the compounds of Formulae (I) to (VI), or pharmaceutically acceptable salts thereof for the manufacture of a medicament for the treatment of any of the conditions disclosed herein.

GENERAL METHODS OF PREPARATION

The compounds described herein may be prepared by techniques known in the art. In addition, the compounds described herein may be prepared by following the reaction sequence as depicted in Scheme-1 to Scheme-3. Further, in the following schemes, where specific bases, acids, reagents, solvents, coupling agents, etc. are mentioned, it is understood that other bases, acids, reagents, solvents, coupling agents etc., known in the art may also be used and are therefore included within the scope of the present invention. Variations in reaction conditions, for example, temperature and/or duration of the reaction, which may be used as known in the art, are also within the scope of the present invention. All the isomers of the compounds described in these schemes, unless otherwise specified, are also encompassed within the scope of this invention. The absolute stereochemistry of the compounds is assigned using vibrational circular dichroism (VCD) spectra.

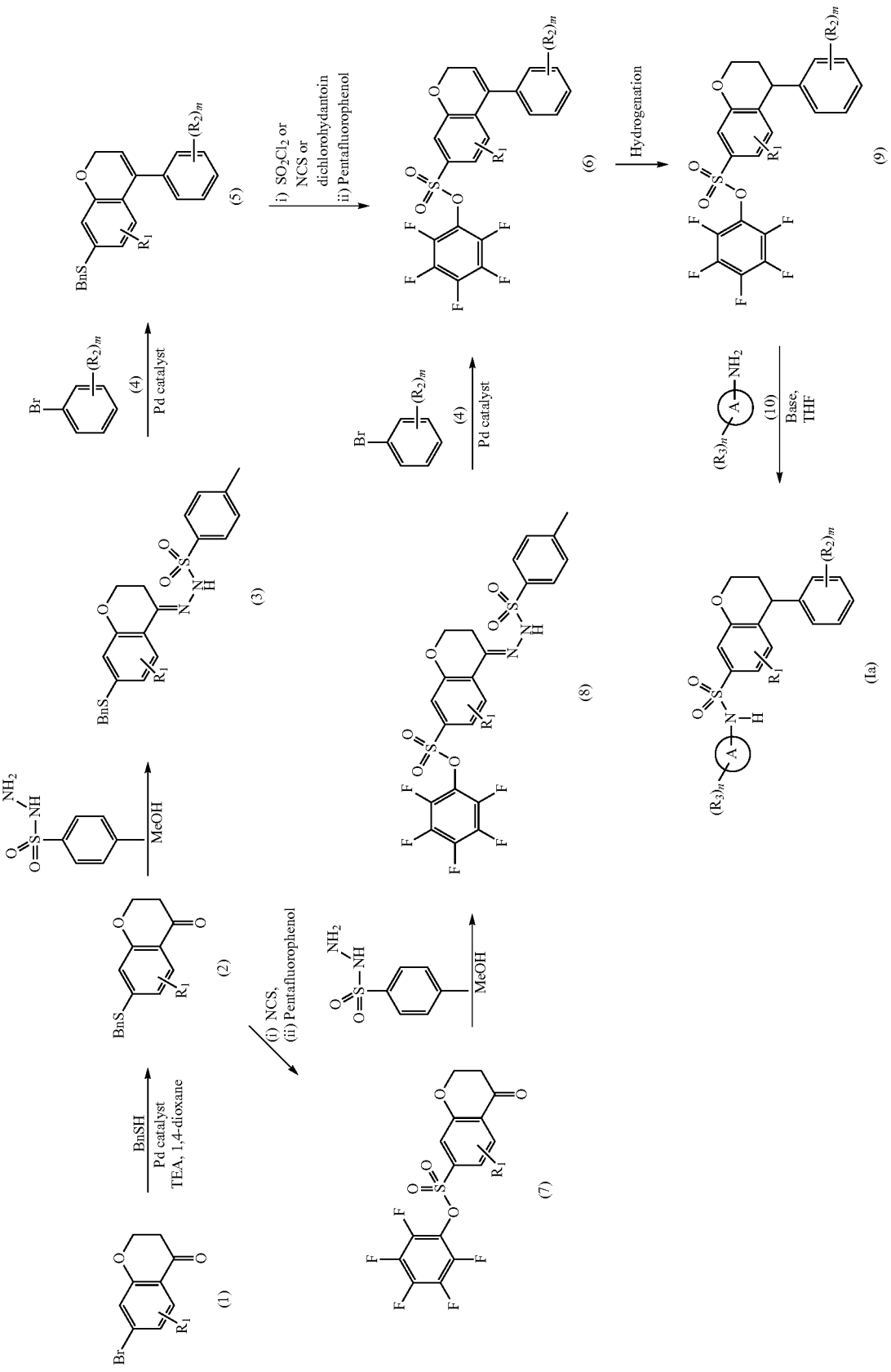

Compound of formula (1) reacts with benzyl thiol in the presence of Pd catalyst to give the compound of formula (2). The keto compound of formula (2) reacts with the p-tosyl hydrazine in MeOH to give the hydrazone compound of formula (3) which reacts with halo derivative of formula (4) in the presence of Pd catalyst and base to give compound of formula (5). The compound of formula (5) reacts with sulfuryl chloride or NCS (N-Chlorosuccinimide) or dichlorohydantoin using suitable solvent to give sulfonyl chloride which on treatment with pentafluorophenol in the presence of organic base like TEA gives the pentafluoro ester of formula (6).

Alternatively, the compound of Formula (6) can also be prepared by reacting compound of formula (2) with NCS using suitable solvents to give sulfonyl chloride which on treatment with pentafluorophenol in the presence of organic base like TEA gives the pentafluoro ester of formula (7). The compound of formula (7) reacts with p-tosyl hydrazine in MeOH to give the hydrazone compound of formula (8) which further reacts with halo derivative of formula (4) in the presence of Pd catalyst and base to give compound of formula (6).

Finally compound of formula (6) undergoes reduction reaction using $H_2$, Pd/C to give the compound of formula (9). The reduction of olefin can also be achieved enantioselectively using compound of formula (9). The reduction of olefin can also be achieved enantioselectively using chiral ligands/catalysts which are known in the literature to obtain stereo selective product. The compound of formula (9) then reacts with the amine of formula (10) in the presence of base like LiHMDS in suitable solvent to give compound of formula (Ia).

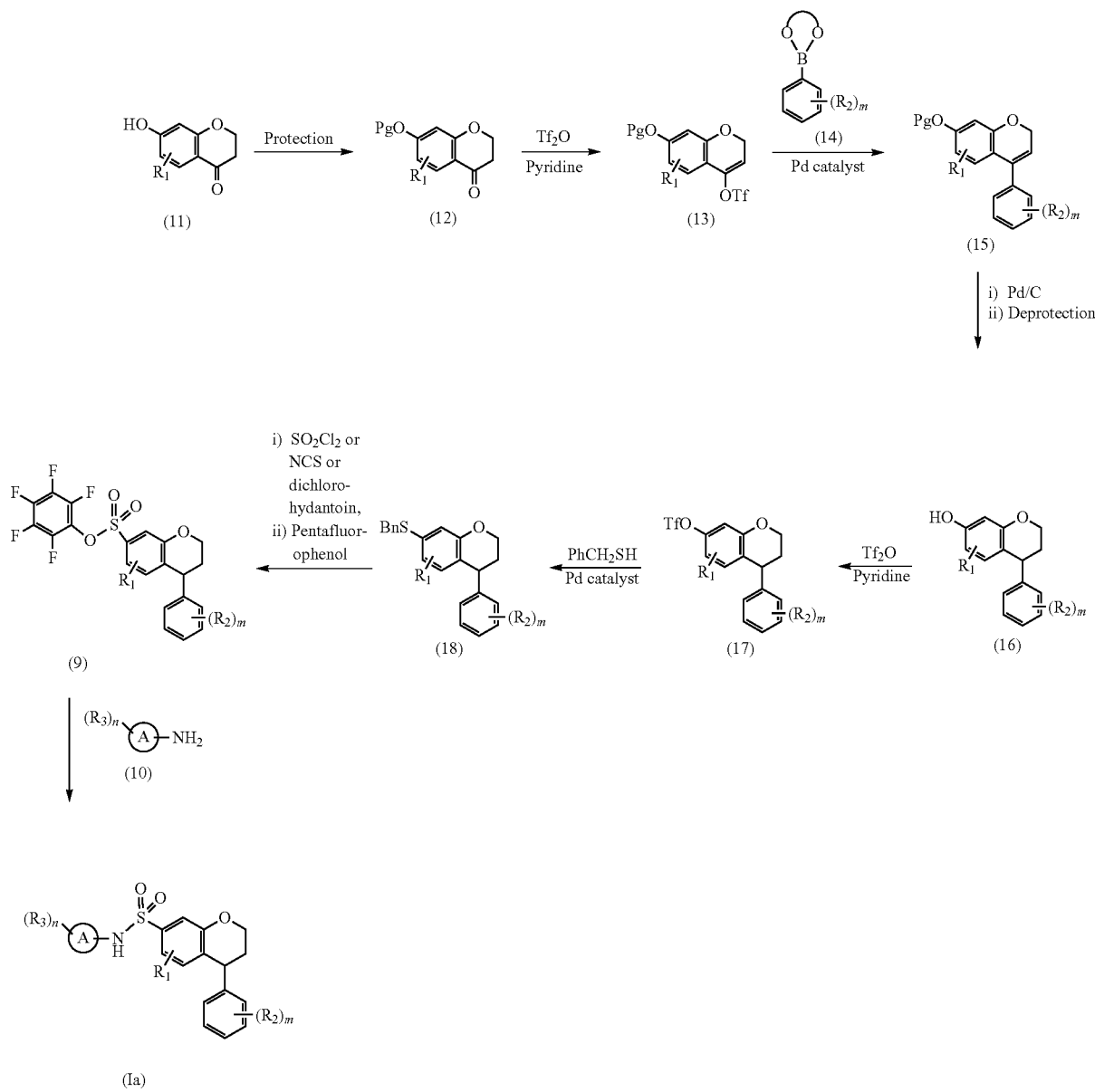

General scheme-2

The hydroxy group in compound of formula (11) can be protected with suitable protecting group like TBDMS to give the compound of formula (12), which further reacts with triflating agents like triflic anhydride or 1,1,1-trifluoro-N-phenyl-N-((trifluoromethyl)sulfonyl)methane sulfonamide in the presence of a base like pyridine to give compound of formula (13). The compound of formula (13) undergoes Suzuki coupling reaction in presence of boronic acid or boronic ester of formula (14) followed by reduction and deprotection of hydroxyl group to give the compound of formula (16). The compound of formula (16) reacts with suitable triflating agents in the presence of base to give compound of formula (17) which further reacts with benzyl mercaptan in the presence of Pd catalyst and solvent like 1,4-dioxane to give the compound of formula (18). The compound of formula (18) reacts with sulfuryl chloride or dichlorohydantoin or NCS and water: acetic acid in suitable solvent to give sulfonyl chloride which on treatment with pentafluorophenol in the presence of organic base like TEA to give the pentafluoro ester of formula (9). The compound of formula (9) reacts with compound of formula (10) in the presence of a suitable base such as LiHMDS in suitable solvent like THF to give the compound of formula (Ia).

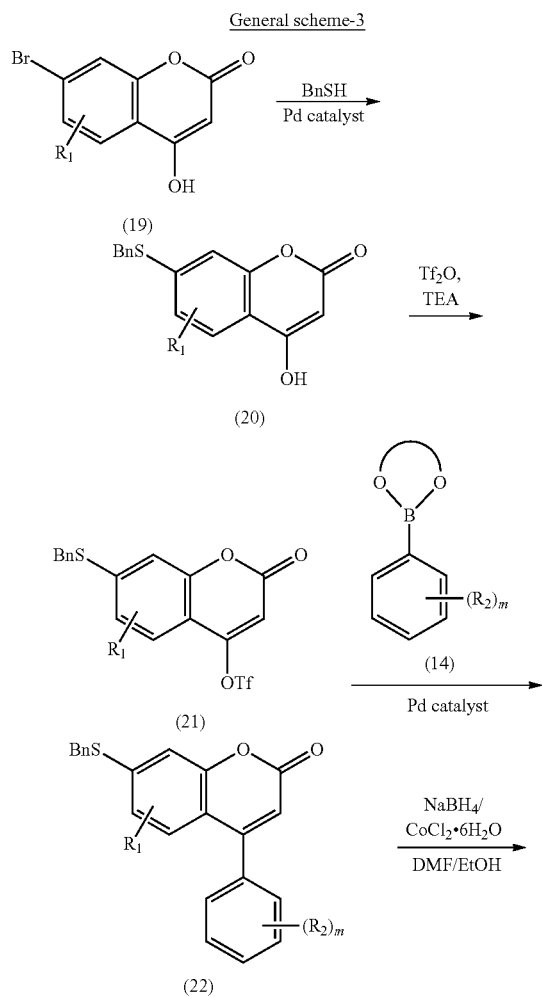

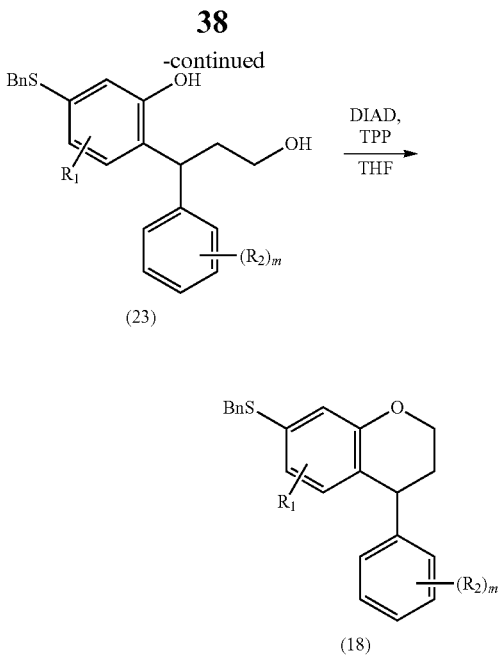

Substituted coumarin of formula (19) reacts with benzyl thiol in the presence of Pd catalyst gives the compound of formula (20). The hydroxyl compound of formula (20) reacts with triflic anhydride in the presence of suitable base like TEA to give the triflate compound of formula (21) which further reacts with boronic acid or boronic ester of formula (14) under Suzuki coupling condition gives the compound of formula (22). The compound of formula (22) can be converted to diol of formula (23) using reagents like $NaBH_4/CoCl_2.6H_2O$ which can further cyclize to give the compound of formula (18). The compound of formula (18) can be converted to compound of formula (Ia) as described in general scheme-2.

EXPERIMENTAL

The invention is further illustrated by the following examples which are provided merely to be exemplary of the invention and do not limit the scope of the invention. The examples set forth below demonstrate the synthetic procedures for the preparation of the representative compounds. Certain modifications and equivalents will be apparent to those skilled in the art and are intended to be included within the scope of the invention.

Unless otherwise stated, work-up implies the following operations: distribution of the reaction mixture between the organic and aqueous phase, separation of layers, drying the organic layer over sodium sulfate, filtration and evaporation of the organic solvent. Purification, unless otherwise mentioned, implies purification by silica gel chromatographic techniques, generally using ethyl acetate/petroleum ether mixture of a suitable polarity as the mobile phase.

INTERMEDIATES

Intermediate-1: N-(7-(Benzylthio)chroman-4-ylidene)-4-methylbenzenesulfono Hydrazide

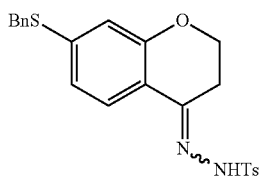

Step-1: 7-(Benzylthio)chroman-4-one

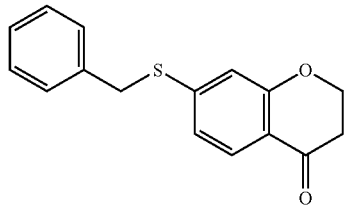 [SMILES: O=C1CCOc2cc(SCc3ccccc3)ccc21]

7-bromochroman-4-one (390 g, 1.718 mol) was dissolved in 1,4-dioxane (4500 ml) and the solution was purged with nitrogen and then added Pd$_2$(dba)$_3$ (39.3 g, 0.0429 mol), Hunig's Base (600 ml, 3.435 mol) and benzyl mercaptan (193 ml, 1.632 mol). The reaction mixture was heated to 80° C. maintained for 1 h. After completion of reaction as indicated by TLC, the compound was extracted with ethyl acetate and washed with water. The ethyl acetate layer was then dried over Na$_2$SO$_4$ and evaporated under vacuum. The crude product was purified by column chromatography to obtain title compound as a pale yellow solid (279 g, 60%). $^1$H NMR (400 MHz, Chloroform-d) δ 7.78 (d, J=8.3 Hz, 1H), 7.49-7.23 (m, 5H), 6.90 (dd, J=8.3, 1.8 Hz, 1H), 6.85-6.75 (m, 1H), 4.52 (m, 2H), 4.20 (s, 2H), 2.78 (m, 2H).

Step-2: N-(7-(Benzylthio)chroman-4-ylidene)-4-methylbenzenesulfonohydrazide

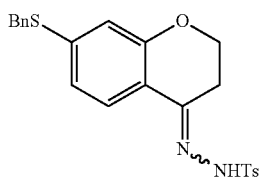

7-(Benzylthio)chroman-4-one (100 g, 0.370 mol) and 4-methylbenzenesulfonohydrazide (76 g, 0.407 mol) was added into MeOH (2.5 lit.) and the mixture was heated at 80° C. for overnight. The reaction mixture was then cooled in an ice salt bath for 1 h and then the pale yellow solid was filtered and was washed with ethanol. The solid product was then triturated with hexane and dried under vacuum to obtain title compound (153 g, 94%). LCMS(ESI): m/z 439.09 (M+H)$^+$; $^1$H NMR (400 MHz, Chloroform-d) δ 7.91 (d, J=8.1 Hz, 2H), 7.82 (d, J=8.4 Hz, 1H), 7.38-7.29 (m, 7H), 6.86 (dd, J=8.4, 1.9 Hz, 1H), 6.77 (d, J=1.8 Hz, 1H), 4.25-4.18 (m, 2H), 4.16 (s, 2H), 2.75 (t, J=6.1 Hz, 2H), 2.44 (s, 3H).

Intermediate-2: 5-(2-bromo-5-(trifluoromethyl)phenyl)-1-methyl-1H-pyrazole

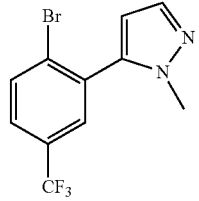 [SMILES: Cn1nccc1-c1cc(C(F)(F)F)ccc1Br]

Step-1: N-(2-bromo-4-(trifluoromethyl)phenyl)acetamide

Acetyl chloride (32.6 ml, 458 mmol) was added to drop wise to a solution of 2-bromo-4-(trifluoromethyl)aniline (50 g, 208 mmol) in ethyl acetate (250 ml). After the addition, the reaction mixture was heated at 60° C. for 45 min. The solution was cooled to room temperature and the reaction mixture was poured into ice cold NaHCO$_3$ solution and the product was extracted with ethyl acetate. The organic layer was dried over Na$_2$SO$_4$ and evaporated to obtain the product as a white solid. 1H NMR (400 MHz, Chloroform-d) δ 8.56 (d, J=8.7 Hz, 1H), 7.82 (d, J=2.1 Hz, 1H), 7.77 (s, 1H), 7.59 (dd, J=8.7, 2.1 Hz, 1H), 2.30 (s, 3H).

Step-2: N-(2-(1-methyl-1H-pyrazol-5-yl)-4-(trifluoromethyl)phenyl)acetamide A mixture of 1,4-dioxane (500 ml) and water (50 ml) was degassed and potassium phosphate (78 g, 369 mmol), N-(2-bromo-4-(trifluoromethyl)phenyl)acetamide (52 g, 184 mmol), 1-methyl-5-(4,4,5,5-tetramethyl-1,3,2-dioxaborolan-2-yl)-1H-pyrazole (38.4 g, 184 mmol) and PdCl$_2$(dppf)-CH$_2$Cl$_2$Adduct (15.06 g, 18.44 mmol) was added and the reaction mixture was refluxed for 1 h. The reaction mixture was poured into water and extracted with ethyl acetate. The combined organic layer was washed with water, dried over Na$_2$SO$_4$ and evaporated under vacuum to obtain title compound (52 g, 100%). LCMS (ESI): m/z 283.40 (M+H)+.

Step-3: 2-(1-methyl-1H-pyrazol-5-yl)-4-(trifluoromethyl)aniline

N-(2-(1-methyl-1H-pyrazol-5-yl)-4-(trifluoromethyl) phenyl)acetamide (132 g, 466 mmol) was dissolved in a mixture of MeOH (600 ml)/water (200 ml) and KOH (78 g, 1398 mmol) was added and the reaction mixture was heated at 70° C. for 6 h. The reaction mixture was then acidified with conc HCl to pH 2 and the aq. layer was washed with ethyl acetate. The aqueous layer was then basified and the product was then extracted with ethyl acetate. The organic layer was dried over Na$_2$SO$_4$ and concentrated to obtain the title compound (112 g, 100%). LCMS (ESI): m/z 241.95 (M+H)+.

Step-4: 5-(2-bromo-5-(trifluoromethyl)phenyl)-1-methyl-1H-pyrazole 2-(1-methyl-1H-pyrazol-5-yl)-4-(trifluoromethyl)aniline (110 g, 456 mmol) was dissolved in acetonitrile (3 lit) and copper(II) bromide (50.9 g, 228 mmol) was added to it. The reaction mixture was heated at 70° C. and tert-butyl nitrite (90 ml, 684 mmol) was added to it drop wise. After the addition, the reaction was continued for 3 h then poured into ice cold brine solution and extracted with ethyl acetate. The organic layer was dried over $Na_2SO_4$ and concentrated and the crude purified by column chromatography to obtain the product as a yellow solid (84 g, 60%). 1H NMR (400 MHz, Chloroform-d) δ 7.87 (d, J=8.1 Hz, 1H), 7.70-7.53 (m, 3H), 6.34 (d, J=1.9 Hz, 1H), 3.76 (s, 3H).

Intermediate-3: Perfluorophenyl 4-(2-(1-methyl-1H-pyrazol-5-yl)-4-(trifluoromethyl)phenyl)chroman-7-sulfonate

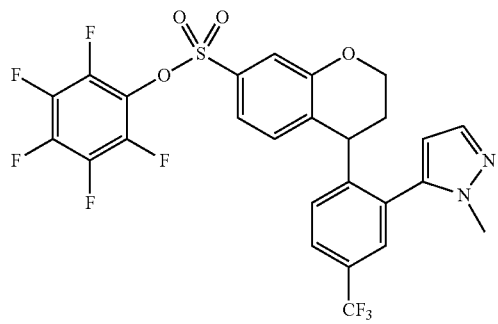 [SMILES: Cn1nccc1-c1cc(C(F)(F)F)ccc1C1CCOc2cc(S(=O)(=O)Oc3c(F)c(F)c(F)c(F)c3F)ccc21]

Step-1: 5-(2-(7-(Benzylthio)-2H-chromen-4-yl)-5-(trifluoromethyl)phenyl)-1-methyl-1H-pyrazole

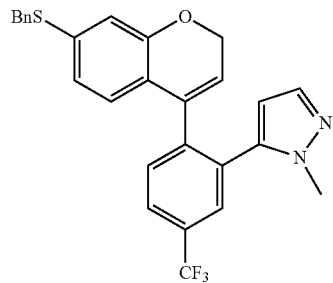

A mixture of 1,4-dioxane (2400 ml) and water (400 ml) was degassed for 30 min with $N_2$ after which Intermediate-2 (84 g, 0.275 mol), Intermediate-1 (121 g, 0.275 mol), sodium carbonate (73 g, 0.688 mol) and $PdCl_2$(dppf)-DCM adduct (22.48 g, 0.0275 mol) were added and the reaction mixture was refluxed for 5 h. The compound was extracted with ethyl acetate, dried over $Na_2SO_4$ and evaporated under vacuum. The crude was purified by column chromatography to obtain title compound as an off white solid (100 g, 76%). LCMS(ESI): m/z 479.09 (M+H)$^+$; $^1$H NMR (400 MHz, Chloroform-d) δ 7.74 (d, J=8.0 Hz, 1H), 7.67 (s, 1H), 7.51 (d, J=8.1 Hz, 1H), 7.40 (d, J=1.9 Hz, 1H), 7.36-7.30 (m, 4H), 7.28 (s, 1H), 6.79 (d, J=1.8 Hz, 1H), 6.70 (dd, J=8.1, 1.9 Hz, 1H), 6.56 (d, J=8.1 Hz, 1H), 6.16 (d, J=1.9 Hz, 1H), 5.50 (t, J=3.9 Hz, 1H), 4.71 (d, J=3.9 Hz, 2H), 4.13 (s, 2H), 3.65 (s, 3H).

Step-2: Perfluorophenyl 4-(2-(1-methyl-1H-pyrazol-5-yl)-4-(trifluoromethyl)phenyl)-2H-chromene-7-sulfonate

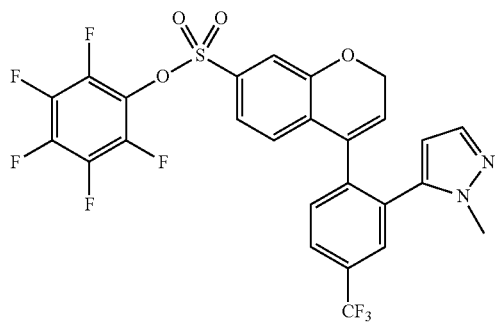 [SMILES: Cn1nccc1-c1cc(C(F)(F)F)ccc1C1=CCOc2cc(S(=O)(=O)Oc3c(F)c(F)c(F)c(F)c3F)ccc21]

5-(2-(7-(benzylthio)-2H-chromen-4-yl)-5-(trifluoromethyl)phenyl)-1-methyl-1H-pyrazole (100 g, 199 mmol) was dissolved in DCM (1500 ml) and acetic acid (45.5 ml) followed by water (14.31 ml) and the solution was cooled to −5° C. and sulfuryl chloride (48.4 ml, 0.596 mol) was added drop wise. After the addition, the reaction was stirred for 1 h. TLC showed formation of sulfonyl chloride. The reaction mixture was washed with water and the DCM layer was dried over $Na_2SO_4$ and concentrated. The crude sulfonyl chloride product was diluted with 500 mL of DCM and added slowly to a stirred solution of 2,3,4,5,6-pentafluorophenol (54.8 g, 0.298 mol) and triethylamine (138 ml, 0.993 mol) in DCM at −5° C. The reaction mixture was stirred for 1 h after which it was washed with water and the DCM layer was dried over $Na_2SO_4$ and concentrated. The crude product was purified by column chromatography to obtain title compound as a pale yellow solid (85 g, 71%). LCMS(ESI): m/z 603.03 (M+H)$^+$; $^1$H NMR (400 MHz, Chloroform-d) δ 7.82 (dd, J=8.1, 1.9 Hz, 1H), 7.72 (d, J=1.9 Hz, 1H), 7.56 (d, J=8.0 Hz, 1H), 7.44-7.31 (m, 3H), 6.83 (d, J=8.1 Hz, 1H), 6.13 (d, J=1.9 Hz, 1H), 5.84 (t, J=3.8 Hz, 1H), 4.92 (d, J=3.8 Hz, 2H), 3.70 (s, 3H).

Step-3: Perfluorophenyl 4-(2-(1-methyl-1H-pyrazol-5-yl)-4-(trifluoromethyl)phenyl)chroman-7-sulfonate Ethyl acetate (1000 ml) was degassed and perfluorophenyl 4-(2-(1-methyl-1H-pyrazol-5-yl)-4-(trifluoromethyl)phenyl)-2H-chromene-7-sulfonate (85 g, 0.141 mol) was dissolved in it. The solution was put in a Parr shaker and 10% Pd—C (67.6 g, 0.0635 mol) was added and the mixture was hydrogenated at 50 psi for 4 h. After completion of reaction, the reaction mixture was filtered through a pad of celite and the pad was washed with ethyl acetate. The filtrate was concentrated and the crude was purified by column chromatography to obtain the product as a pale yellow solid (80 g, 94%). LCMS(ESI): m/z 604.08 (M+H)$^+$; $^1$H NMR (400 MHz, Chloroform-d) δ 7.69 (dd, J=8.3, 2.0 Hz, 1H), 7.63 (dd, J=5.1, 1.9 Hz, 2H), 7.50 (d, J=2.0 Hz, 1H), 7.38 (dd, J=8.2, 2.0 Hz, 1H), 7.16 (d, J=8.2 Hz, 1H), 6.96-6.88 (m, 1H), 6.36 (d, J=1.9 Hz, 1H), 4.39-4.30 (m, 1H), 4.27 (t, J=7.5 Hz, 1H), 4.21-4.16 (m, 1H), 3.81 (s, 3H), 2.24-2.14 (m, 1H), 2.07-1.98 (m, 1H).

Intermediate-4: Perfluorophenyl 4-(2-tosylhydrazono)chroman-7-sulfonate

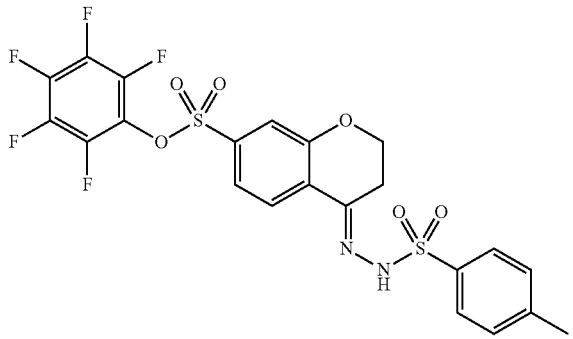 [SMILES: Cc1ccc(S(=O)(=O)N/N=C2\CCOc3cc(S(=O)(=O)Oc4c(F)c(F)c(F)c(F)c4F)ccc32)cc1]

Step-1: Perfluorophenyl 4-oxochroman-7-sulfonate

To a suspension of 7-(benzylthio)chroman-4-one (37 g, 137 mmol) in acetic acid (200 ml) and water (50 ml) was added N-chlorosuccinimide (NCS) (54.8 g, 411 mmol) in two portion. Stirred for 45 min. Reaction mixture was diluted with ether: water and extracted with ether. The combined organic layer was washed with water, brine, dried over $Na_2SO_4$ and evaporated to dryness under reduced pressure. This sulfonyl chloride intermediate taken in DCM (dichloromethane) and charged into the stirring solution of 2,3,4,5,6-pentafluorophenol (35.3 g, 192 mmol) and triethanolamine (TEA) (114 ml, 821 mmol) in DCM (200 ml) at 0° C. Stirred for 45 min then quenched with water and extracted with DCM. The combined organic layer was dried over $Na_2SO_4$ and evaporated under vacuum. The crude was purified by column chromatography (25% ethyl acetate/petroleum ether) to obtain off-white solid (35 g, 65%). $^1$H NMR (400 MHz, DMSO-d6) δ 8.06 (d, J=8.2 Hz, 1H), 7.71 (d, J=1.8 Hz, 1H), 7.65 (dd, J=8.2, 1.9 Hz, 1H), 4.70 (t, J=6.5 Hz, 2H), 2.95 (t, J=6.4 Hz, 2H).

Step-2: Perfluorophenyl 4-(2-tosylhydrazono)chroman-7-sulfonate

A mixture of perfluorophenyl 4-oxochroman-7-sulfonate (34 g, 86 mmol) and 4-methylbenzenesulfonohydrazide (16.06 g, 86 mmol) was heated in MeOH (200 ml) at 65° C. maintained for 16 h. After completion of reaction as indicated by TLC, reaction mixture was evaporated to minimize the MeOH and then filtered the solid and washed with MeOH to obtain title compound as pale yellow solid (35 g, 72%). $^1$H NMR (400 MHz, DMSO-d6) δ 11.08 (s, 1H), 8.03 (d, J=8.4 Hz, 1H), 7.85 (d, 2H), 7.55 (dd, J=8.5, 2.0 Hz, 1H), 7.49 (d, J=2.0 Hz, 1H), 7.43 (d, J=8.1 Hz, 2H), 4.32 (t, J=6.2 Hz, 2H), 2.82 (t, J=6.2 Hz, 2H), 2.39 (s, 3H).

Intermediate-5: 5-(2-Bromo-5-(trifluoromethyl)phenyl)-2-fluoropyridine

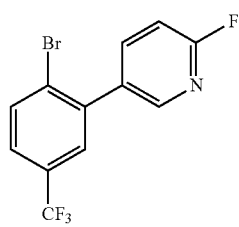 [SMILES: Fc1ccc(-c2cc(C(F)(F)F)ccc2Br)cn1]

Step 1

A mixture of toluene (780 ml), water (520 ml) and EtOH (260 ml) was degassed by bubbling a stream of nitrogen and 2-bromo-4-(trifluoromethyl)aniline (118 g, 492 mmol), (6-fluoropyridin-3-yl)boronic acid (90 g, 639 mmol), sodium carbonate (182 g, 1721 mmol) and $Pd(Ph_3P)_4$ (56.8 g, 49.2 mmol) was added to it and the mixture was refluxed for 8 h. After completion of reaction as indicated by TLC, the reaction mixture was diluted with ethyl acetate. The ethyl acetate layer was washed with brine, dried, concentrated and the crude 2-(6-fluoropyridin-3-yl)-4-(trifluoromethyl) aniline was used for the further reaction. LCMS: m/z 257.09 $(M+H)^+$.

Step-2

2-(6-Fluoropyridin-3-yl)-4-(trifluoromethyl)aniline (126 g, 492 mmol) was dissolved in acetonitrile (1500 ml)) and cupric bromide (65.9 g, 295 mmol) was added to it. The reaction mixture was heated at 65° C. and tert-butyl nitrite (97 ml, 738 mmol) was added to it drop wise. After the addition, the reaction was continued for 1 h and then cooled. The reaction mixture was then passed through a celite bed and the filtrate was concentrated and the crude purified on column to obtain the product as a white solid (115 g, 73%). $^1$H NMR (400 MHz, Chloroform-d) δ 8.30 (d, J=2.5 Hz, 1H), 7.91 (dd, J=8.1, 2.6 Hz, 1H), 7.89-7.84 (m, 1H), 7.59 (d, J=2.2 Hz, 1H), 7.55 (dd, J=8.3, 2.3 Hz, 1H), 7.07 (dd, J=8.5, 2.9 Hz, 1H).

Intermediate-6: Perfluorophenyl 4-(2-(6-fluoropyridin-3-yl)-4-(trifluoromethyl)phenyl)chromane-7-sulfonate

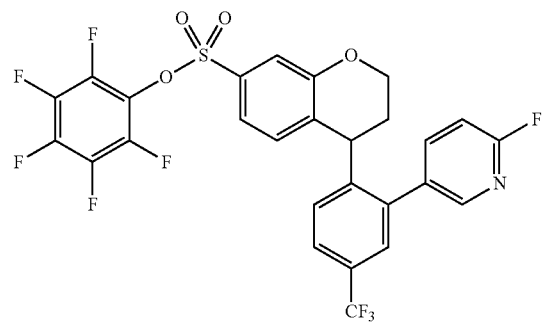

Step-1: Perfluorophenyl 4-(2-(6-fluoropyridin-3-yl)-4-(trifluoromethyl)phenyl)-2H-chromene-7-sulfonate A mixture of 1,4-dioxane (200 ml) and water (33 ml) was degassed by bubbling a stream of nitrogen and Intermediate-4 (22.85 g, 40.6 mmol), Intermediate-5 (10 g, 31.2 mmol), sodium carbonate (8.28 g, 78 mmol) and $PdCl_2$ (dppf)-$CH_2Cl_2$ (2.55 g, 3.12 mmol) was added and the mixture was heated to 100° C. maintained for 45 min. After completion of the reaction, the mixture was diluted with ethyl acetate and washed with brine. The ethyl acetate layer was dried over $Na_2SO_4$ and concentrated. The crude product was purified by column chromatography to obtain the title compound as a white solid (10 g, 52%). LCMS: m/z 618.03 $(M+H)^+$; $^1$H NMR (400 MHz, Chloroform-d) δ 8.22 (d, J=2.5 Hz, 1H), 7.80 (dd, J=7.9, 1.8 Hz, 1H), 7.76-7.66 (m, 2H), 7.55 (d, J=7.9 Hz, 1H), 7.32 (dd, J=13.2, 1.9 Hz, 2H), 6.89 (dd, J=8.5, 2.9 Hz, 1H), 6.75 (d, J=8.1 Hz, 1H), 5.95 (t, J=3.7 Hz, 1H), 4.98-4.92 (m, 2H).

Step-2: Perfluorophenyl 4-(2-(6-fluoropyridin-3-yl)-4-(trifluoromethyl)phenyl)chromane-7-sulfonate To a solution of perfluorophenyl 4-(2-(6-fluoropyridin-3-yl)-4-(trifluoromethyl)phenyl)-2H-chromene-7-sulfonate (28 g, 45.3 mmol) in degassed ethyl acetate (150 ml), 10% Pd—C (12.06 g, 11.34 mmol) was added and the mixture was stirred under 50 psi hydrogen pressure in a Parr shaker at room temperature for 16 h, then catalyst was filtered through a pad of celite and the filtrate was concentrated and the crude passed through a column to obtain the title compound as a white solid (26 g, 90%). LCMS: m/z 620.10 (M+H)+; 1H NMR (400 MHz, Chloroform-d) δ 8.30 (d, J=2.5 Hz, 1H), 7.85 (td, J=7.9, 2.5 Hz, 1H), 7.66 (dd, J=8.2, 2.0 Hz, 1H), 7.58 (d, J=2.0 Hz, 1H), 7.50 (d, J=2.0 Hz, 1H), 7.38 (dd, J=8.2, 2.0 Hz, 1H), 7.18-7.09 (m, 2H), 6.94 (dd, J=8.1, 1.0 Hz, 1H), 4.42-4.28 (m, 2H), 4.20-4.10 (m, 1H), 2.25-2.07 (m, 2H).

Intermediate-7: 5-(2-bromo-5-isopropoxyphenyl)-1-methyl-1H-pyrazole

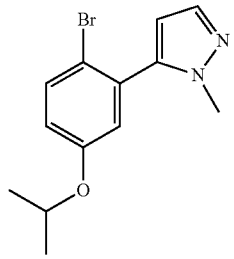 [SMILES: CC(C)Oc1ccc(Br)c(-c2ccnn2C)c1]

Step-1: 1-bromo-2-iodo-4-isopropoxybenzene

A mixture of 4-bromo-3-iodophenol (7.2 g, 24.09 mmol) and Cs2CO3 (9.81 g, 30.1 mmol) in acetonitrile (25 ml) was stirred for 10 min, after which 2-bromopropane (6.78 g, 72.3 mmol) and KI (0.40 g, 2.409 mmol) was added and heated at 50° C. for overnight. The volatiles were concentrated and the residue was diluted with ethyl acetate and washed with water. The ethyl acetate layer was concentrated and the crude was purified by column chromatography to obtain the title compound as colorless oil (4 g, 48%). 1H NMR (400 MHz, Chloroform-d) δ 7.47 (d, J=8.8 Hz, 1H), 7.40 (d, J=2.8 Hz, 1H), 6.76 (dd, J=8.9, 2.8 Hz, 1H), 4.50 (p, J=6.1 Hz, 1H), 1.34 (d, J=6.0 Hz, 6H).

Step-2: 5-(2-bromo-5-isopropoxyphenyl)-1-methyl-1H-pyrazole

DMF (15 ml) was degassed and 1-bromo-2-iodo-4-isopropoxybenzene (2 g, 5.87 mmol), 1-methyl-5-(4,4,5,5-tetramethyl-1,3,2-dioxaborolan-2-yl)-1H-pyrazole (1.22 g, 5.87 mmol), potassium phosphate (2.49 g, 11.73 mmol) and PdCl2(dppf)-DCM adduct (0.24 g, 0.293 mmol) was added and the mixture was heated at 80° C. for 3 h. The reaction mixture was cooled and quenched with water and extracted with ethyl acetate. The ethyl acetate layer was dried and conc. The crude was purified by column chromatography to obtain the product as a viscous oil (0.7 g, 40%). 1H NMR (400 MHz, Chloroform-d) δ 7.60-7.52 (m, 2H), 6.91-6.83 (m, 2H), 6.28 (d, J=1.8 Hz, 1H), 4.54 (h, J=6.1 Hz, 1H), 3.75 (s, 3H), 1.37 (d, J=6.1 Hz, 6H).

Intermediate-8: Perfluorophenyl 4-(4-isopropoxy-2-(1-methyl-1H-pyrazol-5-yl)phenyl)chroman-7-sulfonate

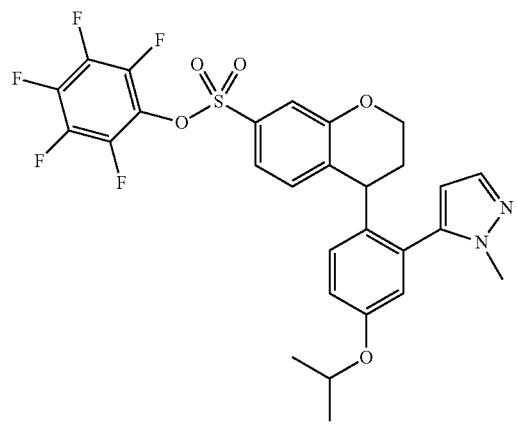 [SMILES: CC(C)Oc1ccc(C2CCOc3cc(S(=O)(=O)Oc4c(F)c(F)c(F)c(F)c4F)ccc32)c(-c2ccnn2C)c1]

The title compound was prepared by following similar procedure as described in Intermediate-6 using Intermediate-4 and Intermediate-7. 1H NMR (400 MHz, Chloroform-d) δ 7.59 (d, J=1.8 Hz, 1H), 7.46 (d, J=1.9 Hz, 1H), 7.35 (dd, J=8.2, 2.0 Hz, 1H), 7.02-6.79 (m, 4H), 6.29 (d, J=1.9 Hz, 1H), 4.56 (h, J=6.0 Hz, 1H), 4.37-4.28 (m, 1H), 4.21-4.06 (m, 2H), 3.81 (s, 3H), 2.17-1.97 (m, 2H), 1.38 (d, J=6.1 Hz, 6H).

Intermediate-9: 4'-Fluoro-2-iodo-5-(trifluoromethyl)-1,1'-biphenyl

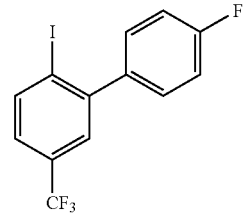 [SMILES: Fc1ccc(-c2cc(C(F)(F)F)ccc2I)cc1]

Step 1: 4'-Fluoro-5-(trifluoromethyl)-[1,1'-biphenyl]-2-amine

The title compound was prepared by following the similar procedure as described in step-1 of Intermediate-5 using 2-bromo-4-(trifluoromethyl)aniline and 4-fluorophenyl boronic acid. LCMS: m/z 255.16 (M)+; 1H NMR (400 MHz, Chloroform-d) δ 7.47-7.39 (m, 3H), 7.36 (d, J=2.2 Hz, 1H), 7.22-7.15 (m, 2H), 6.81 (d, J=8.4 Hz, 1H), 4.10 (brs, 2H).

Step 2: 4'-Fluoro-2-iodo-5-(trifluoromethyl)-1,1'-biphenyl

4'-Fluoro-5-(trifluoromethyl)-[1,1'-biphenyl]-2-amine (1.5 g, 5.88 mmol) was dissolved in acetonitrile (20 ml) and 4-methylbenzenesulfonic acid (3.04 g, 17.63 mmol) was added to get the precipitation. This was dissolved by the addition of 5 ml of water, and the solution cooled in an ice bath. A mixture of sodium nitrite (0.811 g, 11.75 mmol) and potassium iodide (2.44 g, 14.69 mmol) was dissolved in 20 ml water and added drop wise to the solution of the amine. The color of the solution turned brown and after 1 h, TLC showed completion of reaction. The reaction was quenched by the addition of dilute solution of sodium thiosulfate and extracted with ethyl acetate. The ethyl acetate layer was dried and concentrated to obtain the crude which was purified to obtain the title compound as oil (1.75 g, 81%). LCMS: m/z 365.98 (M)+; $^1$H NMR (400 MHz, Chloroform-d) δ 8.11 (d, J=8.3 Hz, 1H), 7.54 (d, J=2.2 Hz, 1H), 7.37-7.29 (m, 3H), 7.17 (t, J=8.7 Hz, 2H).

Intermediate-10: Perfluorophenyl 4-(4'-fluoro-5-(trifluoromethyl)-[1,1'-biphenyl]-2-yl)chromane-7-sulfonate

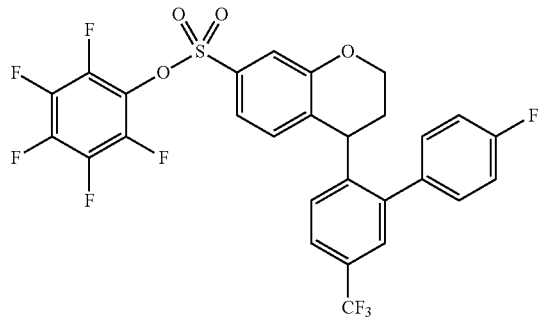 [SMILES: O=S(=O)(Oc1c(F)c(F)c(F)c(F)c1F)c1ccc2c(c1)OCCC2c1ccc(C(F)(F)F)cc1-c1ccc(F)cc1]

The title compound was prepared by following the similar procedure as described in Intermediate-6 using Intermediate-4 and Intermediate-9.

$^1$H NMR (400 MHz, Chloroform-d) δ 7.61-7.55 (m, 2H), 7.49 (d, J=2.0 Hz, 1H), 7.39-7.34 (m, 3H), 7.21 (t, J=8.4 Hz, 2H), 7.08 (d, J=8.1 Hz, 1H), 6.96 (d, J=8.2 Hz, 1H), 4.45-4.40 (m, 1H), 4.39-4.31 (m, 1H), 4.18-4.14 (m, 1H), 2.20-2.07 (m, 2H).

Intermediate-11: 1-(2-Iodo-5-(trifluoromethyl)phenyl)-1H-1,2,3-triazole

Step-1: 2-Azido-1-iodo-4-(trifluoromethyl)benzene

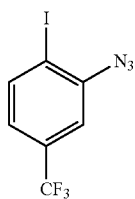

2-Iodo-5-(trifluoromethyl)aniline (13 g, 45.3 mmol) was dissolved in a mixture of water (100 ml) and acetonitrile (50 ml) into which HCl (34.4 ml, 1132 mmol) was added. The solution was cooled to −5° C. and a solution of sodium nitrite (4.69 g, 67.9 mmol) in water was added slowly. The solution was stirred at that temperature for 30 min after which a solution of sodium azide (4.42 g, 67.9 mmol) was added to this mixture. The solution was warmed to room temperature over another 30 min and the reaction mixture was extracted with ethyl acetate and the ethyl acetate layer dried and concentrated to obtain the product as viscous dark oil (14 g, 99%). $^1$H NMR (400 MHz, Chloroform-d) δ 7.95 (d, J=8.2 Hz, 1H), 7.35 (s, 1H), 7.14 (d, J=8.2 Hz, 1H).

Step-2: 1-(2-Iodo-5-(trifluoromethyl)phenyl)-4-(trimethylsilyl)-1H-1,2,3-triazole

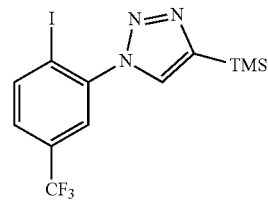 [SMILES: C[Si](C)(C)c1cn(-c2cc(C(F)(F)F)ccc2I)nn1]

2-Azido-1-iodo-4-(trifluoromethyl)benzene (7.2 g, 23.00 mmol), ethynyltrimethylsilane (2.26 g, 23.00 mmol), sodium 2-((S)-1,2-dihydroxyethyl)-4-hydroxy-5-oxo-2,5-dihydrofuran-3-olate (1.82 g, 9.20 mmol), potassium carbonate (6.36 g, 46.0 mmol) was dissolved in a mixture of t-butanol (50 ml) and water (50 ml) and copper(II) sulfate penthydrate (1.15 g, 4.60 mmol) was added to it. The ppt was observed and the reaction mixture was stirred for 16 h after which it was dissolved in ethyl acetate and washed with water. The ethyl acetate layer was dried and concentrated and the crude purified on column to obtain the product as a pale brown solid (4 g, 42%). LCMS: m/z 412.16 (M+H)$^+$; $^1$H NMR (400 MHz, Chloroform-d) δ 8.18 (d, J=8.3 Hz, 1H), 7.89 (s, 1H), 7.72 (d, J=2.1 Hz, 1H), 7.50 (dd, J=8.3, 2.1 Hz, 1H), 0.43 (s, 9H).

Step-3: 1-(2-Iodo-5-(trifluoromethyl)phenyl)-1H-1,2,3-triazole

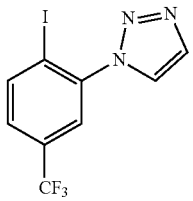 [SMILES: FC(F)(F)c1ccc(I)c(-n2ccnn2)c1]

1-(2-Iodo-5-(trifluoromethyl)phenyl)-4-(trimethylsilyl)-1H-1,2,3-triazole (8 g, 19.45 mmol) was dissolved in ethyl acetate (80 ml), and a solution of 8% HCl (70 ml, 19.45 mmol) was added to it. The reaction mixture was heated to 50° C. maintained for 5 h and then diluted with ethyl acetate. The organic phase was washed with water, brine, dried over Na$_2$SO$_4$ and concentrated. The crude was purified by column chromatography to obtain 1-(2-iodo-5-(trifluoromethyl)phenyl)-1H-1,2,3-triazole (6 g, 91%). LCMS: m/z 339.84 (M+H)$^+$; $^1$H NMR (400 MHz, Chloroform-d) δ 8.20 (d, J=8.3 Hz, 1H), 7.96 (dd, J=13.5, 1.2 Hz, 2H), 7.74 (d, J=2.1 Hz, 1H), 7.53 (dd, J=8.3, 2.1 Hz, 1H).

Intermediate-12: Perfluorophenyl 4-(2-(1H-1,2,3-triazol-1-yl)-4-(trifluoromethyl)phenyl)chromane-7-sulfonate

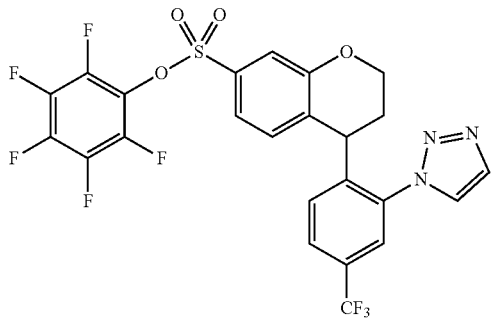 [SMILES: O=S(=O)(Oc1c(F)c(F)c(F)c(F)c1F)c1ccc2c(c1)OCCC2c1ccc(C(F)(F)F)cc1-n1ccnn1]

The title compound was prepared by following the similar procedure as described in Intermediate-3 using Intermediate-1 and Intermediate-11. LCMS: m/z 592.20 (M+H)$^+$; $^1$H NMR (400 MHz, Chloroform-d) δ 7.97 (d, J=15.9 Hz, 2H), 7.77 (d, J=8.3 Hz, 1H), 7.68 (s, 1H), 7.51 (d, J=2.0 Hz, 1H), 7.38 (dd, J=8.2, 2.0 Hz, 1H), 7.26 (d, J=8.2 Hz, 1H), 7.00 (d, J=8.2 Hz, 1H), 4.40-4.25 (m, 2H), 4.25-4.17 (m, 1H), 2.50-2.37 (m, 1H), 2.23-2.09 (m, 1H).

Intermediate-13: 4-(2-Bromo-5-(trifluoromethyl)phenyl)-2-methylthiazole

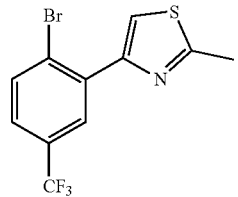

Step-1: 2-Bromo-1-(2-bromo-5-(trifluoromethyl)phenyl)ethanone

To a solution of 1-(2-Bromo-5-(trifluoromethyl)phenyl)ethanone (5 g, 18.72 mmol) in DCM (100 ml), pyridinium tribromide (7.32 g, 20.60 mmol) was added and the mixture was stirred at room temperature for 1 h. After completion of reaction, reaction mixture was poured into water and extracted with DCM. The combined organic layer was dried over Na$_2$SO$_4$ and concentrated. The crude was purified by column chromatography to obtain the product as off white solid. $^1$H NMR (400 MHz, Chloroform-d) δ 7.81 (d, J=8.4 Hz, 1H), 7.73 (d, J=2.2 Hz, 1H), 7.63 (dd, J=8.4, 2.2 Hz, 1H), 4.52 (s, 2H).

Step-2: 4-(2-Bromo-5-(trifluoromethyl)phenyl)-2-methylthiazole

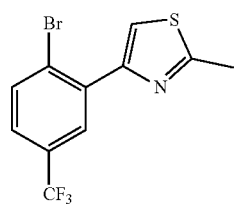 [SMILES: Cc1nc(-c2cc(C(F)(F)F)ccc2Br)cs1]

To a solution of 2-Bromo-1-(2-bromo-5-(trifluoromethyl)phenyl)ethanone (2 g, 5.78 mmol) in EtOH (20 ml), thioacetamide (0.43 g, 5.78 mmol) was added and the solution was heated in a sealed tube for 12 h at 80° C. The solution was cooled and concentrated under vacuum. The reaction mixture was extracted with ethyl acetate, washed with water, dried over Na$_2$SO$_4$ and concentrated under vacuum. The crude was purified by column chromatography to obtain the product as a red oil (1.8 g, 99%). $^1$H NMR (400 MHz, Chloroform-d) δ 8.11 (d, J=2.3 Hz, 1H), 7.82 (d, J=8.4 Hz, 1H), 7.70 (s, 1H), 7.45 (dd, J=8.4, 2.3 Hz, 1H), 2.82 (s, 3H).

Intermediate-14: Perfluorophenyl 4-(2-(2-methylthiazol-4-yl)-4-(trifluoromethyl)phenyl)chroman-7-sulfonate

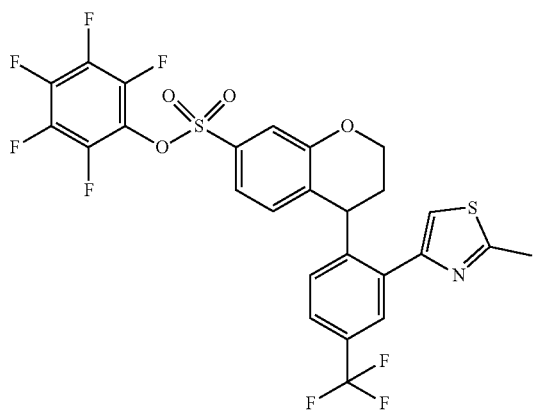

The title compound was prepared by following the similar procedure as described in Intermediate-6 using Intermediate-4 and Intermediate-13. LCMS(ESI): m/z 622.00 (M+H)$^+$; $^1$H NMR (400 MHz, Chloroform-d) δ 7.77 (d, J=2.0 Hz, 1H), 7.57 (dd, J=7.9, 2.0 Hz, 1H), 7.50 (d, J=2.0 Hz, 1H), 7.36 (dd, J=8.2, 2.0 Hz, 1H), 7.28 (s, 1H), 7.07 (d, J=8.2 Hz, 2H), 4.92 (t, J=7.0 Hz, 1H), 4.39-4.29 (m, 1H), 4.27-4.19 (m, 1H), 2.81 (s, 3H), 2.43-2.32 (m, 1H), 2.20-2.11 (m, 1H).

Intermediate-15: 4-(2-Bromo-5-(trifluoromethyl)phenyl)-2-methyloxazole

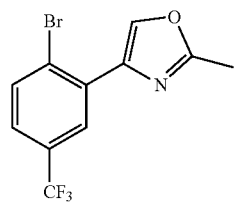

2-Bromo-1-(2-bromo-5-(trifluoromethyl)phenyl)ethanone (1 g, 2.89 mmol) was dissolved in N,N-Dimethylformamide (6 ml) in a 20 ml microwave vial and acetamide (0.43 g, 7.23 mmol) was added to the solution. It was heated at 150° C. under microwave irradiation for 1.5 h. The reaction mixture was diluted with ether and washed with water. The ether layer was dried over Na$_2$SO$_4$ and concentrated. The crude was purified by column chromatography to obtain title compound (0.67 g, 76%). $^1$H NMR (400 MHz, Chloroform-d) δ 8.42 (s, 1H), 8.35 (d, J=2.3 Hz, 1H), 7.78 (d, J=8.4 Hz, 1H), 7.41 (dd, J=8.4, 2.2 Hz, 1H), 2.57 (s, 3H).

Intermediate-16: Perfluorophenyl 4-(2-(2-methyloxazol-4-yl)-4-(trifluoromethyl)phenyl)chroman-7-sulfonate

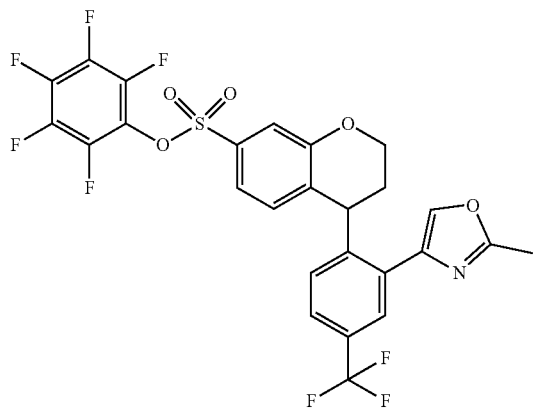 [SMILES: Cc1nc(-c2cc(C(F)(F)F)ccc2C2CCOc3cc(S(=O)(=O)Oc4c(F)c(F)c(F)c(F)c4F)ccc32)co1]

The title compound was prepared by following the similar procedure as described in Intermediate-6 using Intermediate-4 and Intermediate-15. LCMS (ESI): m/z 606.11 (M+H)⁺.

Intermediate-17: 1-Bromo-2-(2-(methylsulfonyl)ethyl)-4-(trifluoromethyl)benzene

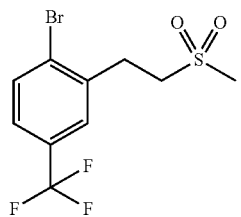 [SMILES: CS(=O)(=O)CCc1cc(C(F)(F)F)ccc1Br]

Step-1: 2-Bromo-5-(trifluoromethyl)phenethyl 4-methylbenzenesulfonate

To a solution of 2-(2-bromo-5-(trifluoromethyl)phenyl)ethanol (5 g, 18.58 mmol) (Synthesise as described in *JACS*, 2011, vol. 133(20), 7916-7925) in DCM (50 ml) was added Ts-Cl (3.9 g, 20.44 mmol), 4-dimethylaminopyridine (DMAP) (0.227 g, 1.858 mmol) and TEA (5.70 ml, 40.9 mmol) at room temperature and stirred for 2 h. After completion of reaction as indicated by TLC, reaction mass was poured into water and extracted with DCM. The organic layer was dried over Na₂SO₄ and evaporated under reduced pressure. The crude product was purified by column chromatography to obtain 2-bromo-5-(trifluoromethyl) phenethyl-4-methylbenzenesulfonate (6 g, 76%). ¹H NMR (400 MHz, Chloroform-d) δ 7.69 (d, J=8.3 Hz, 2H), 7.61 (d, J=8.3 Hz, 1H), 7.41 (d, J=2.3 Hz, 1H), 7.35 (dd, J=8.4, 2.2 Hz, 1H), 7.28 (d, J=8.2 Hz, 2H), 4.32 (t, J=6.6 Hz, 2H), 3.17 (t, J=6.6 Hz, 2H), 2.45 (s, 3H).

Step-2: 1-Bromo-2-(2-(methylsulfonyl)ethyl)-4-(trifluoromethyl)benzene

To a solution of 2-Bromo-5-(trifluoromethyl)phenethyl 4-methylbenzenesulfonate (9 g, 21.26 mmol), in ethanol (100 ml) was added sodium methanethiolate (1.78 g, 25.5 mmol) at room temperature for 2 h, after which oxone (65.4 g, 106 mmol) followed by water (30 ml) was added to the reaction mixture. The reaction mixture was stirred for 12 h at 25° C., then poured into water and extracted with ethyl acetate. The combined organic layers were washed with brine, dried over anhydrous Na₂SO₄, filtered and concentrated under vacuum. The crude product was purified by column chromatography to obtain 1-bromo-2-(2-(methylsulfonyl)ethyl)-4-(trifluoromethyl)benzene as white solid (6 g, 85%) ¹H NMR (400 MHz, Chloroform-d) δ 7.74 (d, J=8.3 Hz, 1H), 7.59 (d, J=2.3 Hz, 1H), 7.44 (dd, J=8.4, 2.1 Hz, 1H), 3.36 (s, 4H), 2.99 (s, 3H).

Intermediate-18: Perfluorophenyl 4-(2-(2-(methylsulfonyl)ethyl)-4-(trifluoromethyl)phenyl)chroman-7-sulfonate

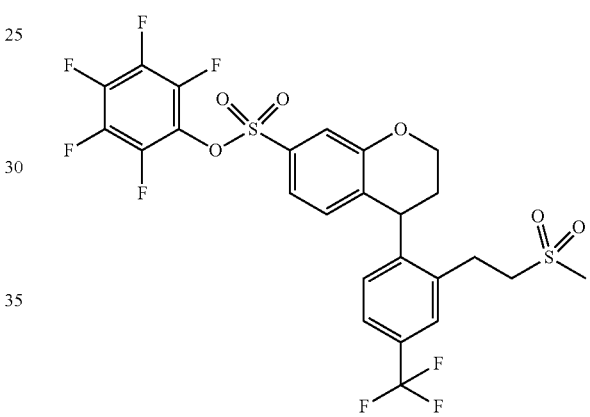

The title compound was prepared by following the similar procedure as described in Intermediate-6 using Intermediate-4 and Intermediate-17. ¹H NMR (400 MHz, Chloroform-d) δ 7.57-7.47 (m, 3H), 7.39 (dd, J=8.1, 1.9 Hz, 1H), 7.02-6.91 (m, 2H), 4.68-4.61 (m, 1H), 4.41-4.26 (m, 2H), 3.49-3.31 (m, 4H), 3.01 (s, 3H), 2.48-2.36 (m, 1H), 2.17-2.08 (m, 1H).

Intermediate-19: 1-(2-Iodo-5-(trifluoromethyl)phenyl)-1H-pyrazole

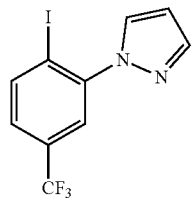 [SMILES: FC(F)(F)c1ccc(I)c(-n2cccn2)c1]

Step-1: 2-(1H-Pyrazol-1-yl)-4-(trifluoromethyl)aniline

2-Bromo-4-(trifluoromethyl)aniline (3.5 g, 14.58 mmol), 1H-pyrazole (1.98 g, 29.2 mmol), N1,N2-dimethylethane- 1,2-diamine (0.78 ml, 7.29 mmol), cesium carbonate (10.45 g, 32.1 mmol) was added to degassed 1,4-dioxane (15 ml) in a sealed tube and copper(i) iodide (0.55 g, 2.92 mmol) was added. The tube was sealed and heated at 120° C. for 72 h. After the solution was cooled, the mixture was passed through a pad of celite and the filtrate was extracted with ethyl acetate. The ethyl acetate layer was washed with brine, dried over $Na_2SO_4$ and concentrated. The crude was purified by column chromatography to obtain the product as off white solid (2.7 g, 83%). LCMS (ESI): m/z 228.39 (M+H)+.

Step-2: 1-(2-Iodo-5-(trifluoromethyl)phenyl)-1H-pyrazole 2-(1H-Pyrazol-1-yl)-4-(trifluoromethyl)aniline (2.74 g, 12.06 mmol) was dissolved into acetonitrile (30 ml) and water (15 ml) followed by the addition of 4-methylbenzenesulfonic acid (8.31 g, 48.2 mmol). Potassium iodide (5.01 g, 30.2 mmol) and sodium nitrite (1.664 g, 24.12 mmol) in water was added to the reaction mixture slowly at −5° C. Reaction mixture was stirred for another 1.5 h at −5° C. then quenched by addition of water and extracted with ethyl acetate. The combined organic layer was washed with brine, dried over $Na_2SO_4$ and conc. under reduced pressure. The crude product was purified by chromatography (3% ethyl acetate/petroleum ether) to obtain title compound (3.5 g, 87%). $^1$H NMR (400 MHz, Chloroform-d) δ 8.13 (d, J=8.3 Hz, 1H), 7.83-7.78 (m, 2H), 7.70 (d, J=2.1 Hz, 1H), 7.41 (dd, J=8.3, 2.1 Hz, 1H), 6.53 (t, J=2.1 Hz, 1H).

Intermediate-20: Perfluorophenyl 4-(2-(1H-pyrazol-1-yl)-4-(trifluoromethyl)phenyl)chroman-7-sulfonate

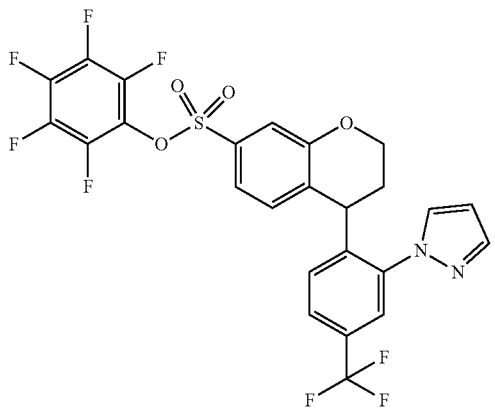 [SMILES: O=S(=O)(Oc1c(F)c(F)c(F)c(F)c1F)c1ccc2c(c1)OCCC2c1ccc(C(F)(F)F)cc1-n1cccn1]

Step-1: N'-(7-(Benzyloxy) chroman-4-ylidene)-4-methylbenzenesulfonohydrazide

To a stirred solution of 7-(benzyloxy)chroman-4-one (1 g, 3.93 mmol) in methanol (30 ml), 4-methylbenzenesulfonohydrazide (0.81 g, 4.33 mmol), was added and reaction was stirred for 12 h at 75° C. After completion of reaction as indicated by TLC, reaction mixture was concentrated under vacuum and purified by column chromatography to obtain title compound as a pale yellow solid (1.3 g, 78%). LCMS (ESI): m/z 422.884 (M+H)+.

Step-2: 1-(2-(7-(Benzyloxy)-2H-chromen-4-yl)-5-(trifluoromethyl)phenyl)-1H-pyrazole

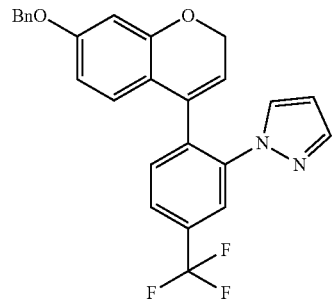 [SMILES: FC(F)(F)c1ccc(C2=CCOc3cc(OCc4ccccc4)ccc32)c(-n2cccn2)c1]

A solution of Intermediate-19 (1.2 g, 3.55 mmol), N'-(7-(benzyloxy)chroman-4-ylidene)-4-methylbenzenesulfono hydrazide (Step-1) (1.5 g, 3.55 mmol) in 1,4-dioxane (50 ml): water (10 ml) was purged with nitrogen then $Na_2CO_3$ (0.941 g, 8.87 mmol) and $PdCl_2(dppf)$-DCM adduct (0.290 g, 0.355 mmol) was added and reaction was stirred for 12 h at 110° C. After completion of reaction, it was poured in to water and extracted with ethyl acetate. Organic layer was dried over $Na_2SO_4$ and concentrated under vacuum. The crude was purified by column chromatography to obtain title compound as pale yellow oil (0.4 g, 25%). LCMS (ESI): m/z 448.54 (M+H)+.

Step-3: 4-(2-(1H-Pyrazol-1-yl)-4-(trifluoromethyl)phenyl)chroman-7-ol

To the stirred solution of 1-(2-(7-(Benzyloxy)-2H-chromen-4-yl)-5-(trifluoromethyl)phenyl)-1H-pyrazole (0.70 g, 1.561 mmol) in ethyl acetate (20 ml), 10% Pd—C (0.17 g, 0.156 mmol) was added and reaction mixture was stirred under hydrogen balloon at room temperature for 12 h. After completion of reaction, it was filtered through celite bed, the filtrate was concentrated under vacuum and purified by column chromatography to obtain title compound (0.4 g, 71%). LCMS (ESI): m/z 361.26 (M+H)+.

Step-4: 4-(2-(1H-Pyrazol-1-yl)-4-(trifluoromethyl)phenyl)chroman-7-yl trifluoromethane sulfonate A solution of 4-(2-(1H-pyrazol-1-yl)-4-(trifluoromethyl)phenyl)chroman-7-ol (0.40 g, 1.11 mmol) and 2,6-lutidine (0.26 ml, 2.22 mmol) in DCM (15 ml) was cooled to −30° C. trifluoromethylsulfonic anhydride (0.28 ml, 1.67 mmol) was added drop wise to the reaction mixture and stirred allowing it to come at room temperature for 1 h. Reaction mixture was quenched with cold water and extracted with ethyl acetate. Combined organic layer was dried over $Na_2SO_4$ and concentrated under vacuum. The crude was purified by column chromatography to obtain title compound (0.32, 58%). LCMS (ESI): m/z 493.17 (M+H)+.

Step-5: 1-(2-(7-(Benzylthio)chroman-4-yl)-5-(trifluoromethyl)phenyl)-1H-pyrazole 4-(2-(1H-pyrazol-1-yl)-4-(trifluoromethyl)phenyl)chroman-7-yl trifluoromethanesulfonate (0.32 g, 0.650 mmol) was dissolved in 1,4-dioxane (10 ml) and the solution was degassed by passing nitrogen. Xantphos (0.019 g, 0.032 mmol), $Pd_2(dba)_3$ (0.015 g, 0.016 mmol), Hunig's Base (0.227 ml, 1.300 mmol) and benzyl mercaptan (0.077 ml, 0.650 mmol) was added into the reaction mass and heated at 100° C. for 18 h. After completion of reaction, reaction mixture was poured into water and extracted with ethyl acetate. The ethyl acetate layer was dried and concentrated. The crude was purified by column chromatography to obtain title compound (0.30 g, 97%). LCMS (ESI): m/z 467.09 (M+H)$^+$.

Step-6: Perfluorophenyl 4-(2-(1H-pyrazol-1-yl)-4-(trifluoromethyl)phenyl)chroman-7-sulfonate To an ice-cold solution of 1-(2-(7-(benzylthio)chroman-4-yl)-5-(trifluoromethyl)phenyl)-1H-pyrazole (0.35 g, 0.750 mmol) in DCM (10 ml) was added acetic acid (0.215 ml, 3.75 mmol), water (0.068 ml, 3.75 mmol) followed by sulfuryl chloride (0.183 ml, 2.251 mmol). The reaction mixture was stirred at same temperature for 15 min then diluted with DCM: water and extracted with DCM. The combined organic layer was dried over $Na_2SO_4$, and concentrated under vacuum. This crude product was taken in DCM and added drop wise to a solution of 2,3,4,5,6-pentafluorophenol (0.207 g, 1.125 mmol) and TEA (0.837 ml, 6.00 mmol) in DCM (5 mL) at 0-5° C. Stirred for 30 min at room temperature then the reaction mixture was diluted with DCM:water, extracted with DCM. The organic layer was dried over $Na_2SO_4$, and concentrated to dryness, the crude was purified by column chromatography to obtain title compound (0.27 g, 61%). LCMS (ESI): m/z 591.01 (M+H)$^+$.

Intermediate-21: 2-(2-bromo-5-(trifluoromethyl)phenyl)thiazole

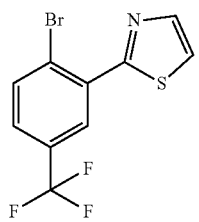

Step-1: 2-(thiazol-2-yl)-4-(trifluoromethyl)aniline

A mixture of Water (Volume: 10 ml) and 1,4-Dioxane (30 ml) was degassed and 2-(4,4,5,5-tetramethyl-1,3,2-dioxaborolan-2-yl)-4-(trifluoromethyl)aniline (2.9 g, 10.10 mmol), 2-bromothiazole (1.09 ml, 12.12 mmol), sodium carbonate (4.28 g, 40.4 mmol) and $PdCl_2(dppf)$-DCM adduct (0.825 g, 1.010 mmol) was added and the mixture refluxed overnight. The mixture was cooled and water was added followed by extraction with ethyl acetate. The EA layer was dried and concentrated and the product purified on column chromatography (1.9 g, 77%). LCMS (ESI): m/z 244.89 (M+H)$^+$.

Step-2: 2-(2-bromo-5-(trifluoromethyl)phenyl)thiazole

To a solution of 2-(thiazol-2-yl)-4-(trifluoromethyl)aniline (1.9 g, 7.78 mmol) and Cu(II)Br (0.956 g, 4.28 mmol) in acetonitrile (20 ml), tert-butylnitrite (1.110 ml, 9.34 mmol) was added drop wise at 60° C. and stirred for 30 min. After completion of reaction as indicated by TLC, Reaction mixture was poured into water and extract with ethyl acetate. The organic layer was dried over $Na_2SO_4$, and concentrated under vacuum. The crude product was purified by column chromatography to obtain title compound (1.4 g, 58%). $^1$H NMR (400 MHz, Chloroform-d) δ 8.43 (d, J=2.3 Hz, 1H), 8.04 (d, J=3.2 Hz, 1H), 7.88 (d, J=8.4 Hz, 1H), 7.59 (d, J=3.3 Hz, 1H), 7.54 (dd, J=8.4, 2.3 Hz, 1H).

Intermediate-22a/22b: (R&S)-perfluorophenyl 4-(2-(thiazol-2-yl)-4-(trifluoromethyl)phenyl)chroman-7-sulfonate

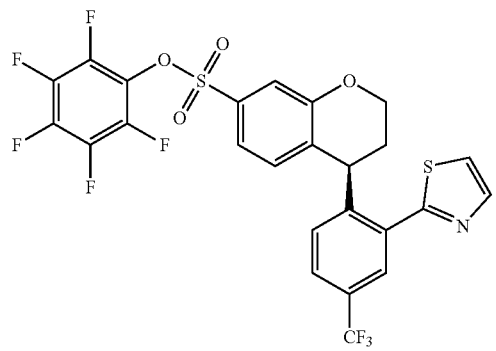

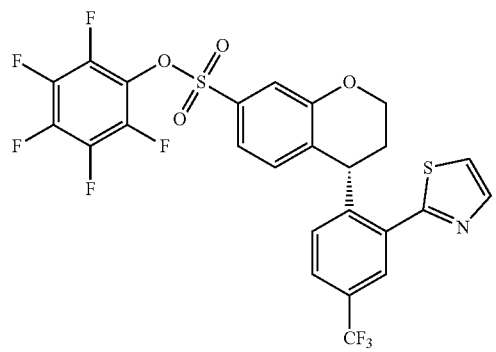

The title compound was prepared by following the similar procedure as described in Intermediate-6 using Intermediate-4 and Intermediate-21. LCMS (ESI): m/z 607.96 (M+H)$^+$.

Further the enantiomers were separated using chiral preparative HPLC (Column: ChiralPak IA; Mobile phase: A=(Hexane+0.1% DEA), B=(IPA), A:B=80:20, to afford isomer-1 and isomer-2. These isomers were obtained at retention time 5.86 min (Intermediate-22a) and retention time 6.52 min (Intermediate-22b).

Intermediate-23: 5-(2-bromo-5-(trifluoromethyl)phenyl)-2-isopropoxypyridine

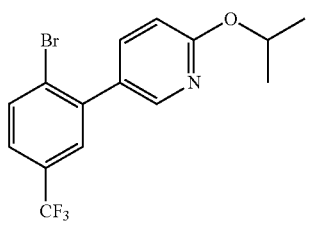 [SMILES: CC(C)Oc1ccc(-c2cc(C(F)(F)F)ccc2Br)cn1]

Step-1: 5-Bromo-2-isopropoxypyridine

In a 2-Propanol (100 ml) NaH (2.73 g, 68.2 mmol) was added slowly then the mixture was heated at 80° C. for 1 h. 5-bromo-2-fluoropyridine (5 g, 28.4 mmol) was added and the resultant mixture was heated at 80° C. for further 15 h. Reaction was monitored by TLC. The solvent was evaporated under vacuum, water was added in the residue and extracted with ethyl acetate. The combined organic layer was washed with water, brine, dried over $Na_2SO_4$ and concentrated under vacuum to obtain title compound as an oil (5 g, 81%). $^1$H NMR (400 MHz, Chloroform-d) δ 8.20 (d, J=3.2 Hz, 1H), 7.64 (d, J=8.7 Hz, 1H), 6.62 (dd, J=8.7, 2.6 Hz, 1H), 5.26 (Quint, J=6.6 Hz, 1H), 1.41-1.32 (d, 6H).

Step-2: 2-Isopropoxy-5-(4,4,5,5-tetramethyl-1,3,2-dioxaborolan-2-yl)pyridine A stirred suspension of 5-bromo-2-isopropoxypyridine (5 g, 23.14 mmol), potassium acetate (5.68 g, 57.9 mmol) and 4,4,4',4',5,5,5',5'-octamethyl-2,2'-bi(1,3,2-dioxaborolane) (8.81 g, 34.7 mmol) in 1,4-dioxane (50 ml) was degassed using nitrogen for 20 min. $PdCl_2$(dppf)-DCM adduct (1.89 g, 2.314 mmol) was added and reaction mixture was heated at 110° C. for 1 h. Water was added to the reaction mixture and it was extracted with ethyl acetate. The combined organic layer was washed with water, brine, dried over $Na_2SO_4$ and concentrated under vacuum. The crude was purified by column chromatography title compound as oil (5 g, 82% yield). $^1$H NMR (400 MHz, Chloroform-d) δ 8.54 (s, 1H), 7.92 (d, J=8.3 Hz, 1H), 6.76-6.46 (m, 1H), 5.45-5.25 (m, 1H), 1.37 (d, J=2.4 Hz, 6H), 1.28 (s, 12H).

Step-3: 2-(6-isopropoxypyridin-3-yl)-4-(trifluoromethyl)aniline

A mixture of toluene (30 ml)/water (20 ml)/EtOH (10.00 ml) was degassed and 2-bromo-4-(trifluoromethyl)aniline (4 g, 16.67 mmol), 2-isopropoxy-5-(4,4,5,5-tetramethyl-1,3,2-dioxaborolan-2-yl)pyridine (5.7 g, 21.66 mmol), sodium carbonate (6.18 g, 58.3 mmol) and Pd(Ph$_3$P)$_4$ (1.93 g, 1.67 mmol) was added and the mixture was refluxed for 4 h. TLC shown completion of reaction. The reaction mixture was diluted with ethyl acetate, washed with brine, dried over Na2SO4 and concentrated under vacuum. The crude product was purified by column chromatography to obtain title compound as an oil (3.30 g, 66.8%). $^1$H NMR (400 MHz, Chloroform-d) δ 8.27 (s, 1H), 7.76 (d, J=8.5 Hz, 1H), 7.43 (d, J=8.5 Hz, 1H), 7.34 (s, 1H), 6.91-6.81 (m, 2H), 5.41 (quint, J=6.4 Hz, 1H), 1.44 (d, 6H).

Step-4: 5-(2-bromo-5-(trifluoromethyl)phenyl)-2-isopropoxypyridine

The title compound was prepared by following similar procedure as described in Intermediate-21 (Step-2) using step-3 intermediate. $^1$H NMR (400 MHz, Chloroform-d) δ 8.21 (s, 1H), 7.83 (d, J=8.3 Hz, 1H), 7.68 (dd, J=8.6, 2.4 Hz, 1H), 7.58 (d, J=2.3 Hz, 1H), 7.49 (d, J=8.3 Hz, 1H), 6.79 (d, J=8.6 Hz, 1H), 5.39 (quint, J=6.2 Hz, 1H), 1.42 (d, J=6.1 Hz, 6H).

Intermediate-24: Perfluorophenyl 4-(2-(6-isopropoxypyridin-3-yl)-4-(trifluoromethyl)phenyl)chroman-7-sulfonate

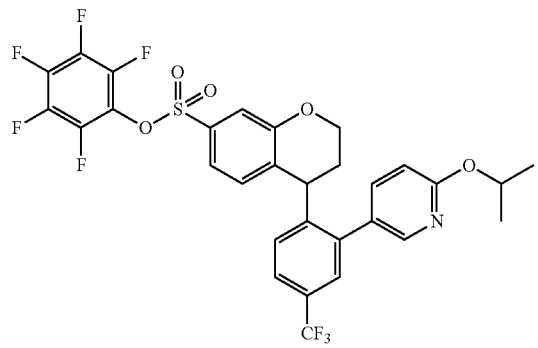 [SMILES: CC(C)Oc1ccc(-c2cc(C(F)(F)F)ccc2C2CCOc3cc(S(=O)(=O)Oc4c(F)c(F)c(F)c(F)c4F)ccc32)cn1]

The title compound was prepared by following the similar procedure as described in Intermediate-6 using Intermediate-4 and Intermediate-23. LCMS (ESI): m/z 659.46 (M+H)$^+$.

Intermediate-25: 5-(2-bromo-5-(trifluoromethyl)phenyl)-2-ethoxypyridine

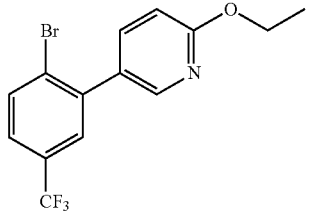 [SMILES: CCOc1ccc(-c2cc(C(F)(F)F)ccc2Br)cn1]

The title compound was prepared by following similar procedure as shown in Intermediate-23. $^1$H NMR (400 MHz, Chloroform-d) δ 8.21 (s, 1H), 7.83 (d, J=8.4 Hz, 1H), 7.68 (d, J=8.5 Hz, 1H), 7.58 (s, 1H), 7.49 (d, J=8.1 Hz, 1H), 6.83 (d, J=8.6 Hz, 1H), 4.44 (q, 2H), 1.46 (t, J=7.1, 2.5 Hz, 3H).

Intermediate-26: perfluorophenyl 4-(2-(6-ethoxypyridin-3-yl)-4-(trifluoromethyl)phenyl)chroman-7-sulfonate

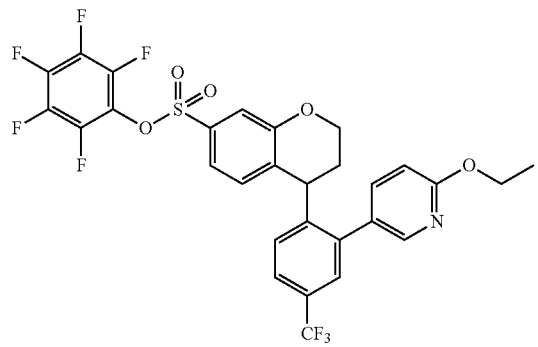

The title compound was prepared by following the similar procedure as described in Intermediate-6 using Intermediate-4 and Intermediate-25. LCMS (ESI): m/z 646.11 (M+H)$^+$.

Intermediate-27a/27b: (R&S)-Perfluorophenyl-4-(2-chloro-4-(trifluoromethyl)phenyl)chromane-7-sulfonate

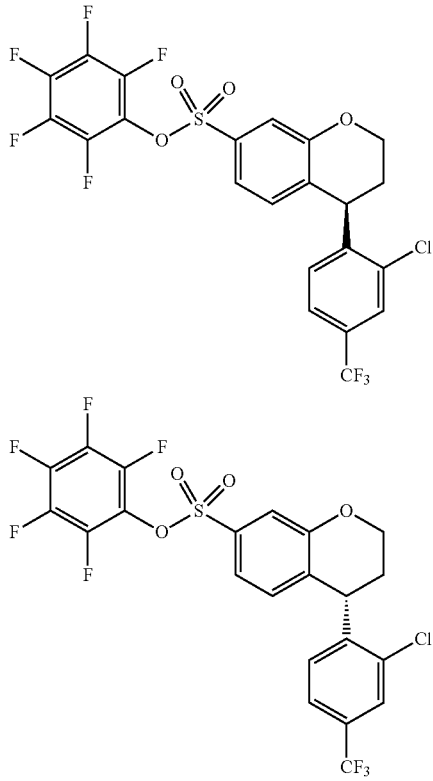

A solution of Intermediate-4 (5 g, 8.89 mmol) in 1,4-dioxane (30 ml) and water (6 ml) was purged with $N_2$ and then added into 1-bromo-2-chloro-4-(trifluoromethyl)benzene (2.77 g, 10.67 mmol), $PdCl_2$(dppf)-DCM adduct (0.73 g, 0.889 mmol) and $Na_2CO_3$ (2.35 g, 22.22 mmol). The reaction mixture was heated and maintained for 1.5 hr at 90° C. After the completion of reaction as indicated by TLC, reaction mixture was cooled and diluted with ethyl acetate. The combined organic layer was washed with brine, dried over $Na_2SO_4$ and evaporated to dryness under reduced pressure. Flash column chromatography (15% ethyl acetate/petroleum ether) to obtain pale yellow oil, which further added into ethyl acetate (30 ml) and in 10% Pd/C (0.946 g, 8.89 mmol) and stirred overnight under $H_2$ balloon pressure. After the completion of reaction as indicated by TLC, reaction mixture was filtered through celite and filtrate was evaporated to dryness to obtain title compound as off white solid (2.5 g, 50%). $^1$H NMR (400 MHz, Chloroform-d) δ 7.77-7.74 (m, 1H), 7.55 (d, J=2.0 Hz, 1H), 7.48 (dt, J=8.1, 1.2 Hz, 1H), 7.42 (dd, J=8.2, 2.0 Hz, 1H), 7.06 (dd, J=8.1, 0.9 Hz, 1H), 6.96 (d, J=8.1 Hz, 1H), 4.82 (t, J=6.1 Hz, 1H), 4.37-4.20 (m, 2H), 2.49-2.38 (m, 1H), 2.25-2.14 (m, 1H).

Further the enantiomers were separated using chiral preparative HPLC (Column: ChiralPak IA; Mobile phase: A=(Hexane+0.1% DEA), B=IPA, A:B=90:10 to afford isomer 1 and isomer 2. These isomers were obtained at retention time: 5.59 min (Intermediate-27a) and retention time: 6.20 min (Intermediate-27b).

Intermediate-28: 4-(2-bromo-5-(trifluoromethyl)phenyl)-3,6-dihydro-2H-pyran

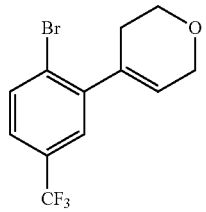 [SMILES: FC(F)(F)c1ccc(Br)c(C2=CCOCC2)c1]

Step-1: 4-(2-bromo-5-(trifluoromethyl)phenyl)tetrahydro-2H-pyran-4-ol

To a solution of 1-bromo-2-iodo-4-(trifluoromethyl)benzene (2 g, 5.70 mmol) in 10 ml dry THF was slowly added isopropylmagnesium chloride (2.85 ml, 2M solution, 5.70 mmol) at −10° C. and reaction mixture was stirred for next 30 min. Then the solution of dihydro-2H-pyran-4(3H)-one (0.63 g, 6.27 mmol) in 10 ml THF was added to the reaction mixture and stirred further for 1.5 h. After completion of reaction as indicated by TLC, reaction mixture was quenched by adding saturated $NH_4Cl$ solution and partitioned between ethyl acetate and water. The organic phase was washed with brine, dried over $Na_2SO_4$ and concentrated under vacuum. The crude was purified by column chromatography to obtain title compound (0.55 g, 29%).

Step-2: 4-(2-bromo-5-(trifluoromethyl)phenyl)-3,6-dihydro-2H-pyran

To a solution of 4-(2-bromo-5-(trifluoromethyl)phenyl)tetrahydro-2H-pyran-4-ol (1 g, 3.08 mmol) in toluene (50 ml) was added p-toluenesulfonic acid monohydrate (0.29 g, 1.54 mmol) and reaction mixture was refluxed for 7 h. The solvent was removed under vacuum and the crude residue was purified by column chromatography to obtain title compound (0.75, 79%). $^1$H NMR (400 MHz, Chloroform-d) δ 7.71 (d, J=8.3 Hz, 1H), 7.48-7.37 (m, 2H), 5.78 (t, J=2.3 Hz, 1H), 4.34 (q, J=2.8 Hz, 2H), 3.96 (t, J=5.3 Hz, 2H), 2.47 (tq, J=5.0, 2.4 Hz, 2H).

Intermediate-29: Perfluorophenyl 4-(2-(tetrahydro-2H-pyran-4-yl)-4-(trifluoromethyl)phenyl)chromane-7-sulfonate

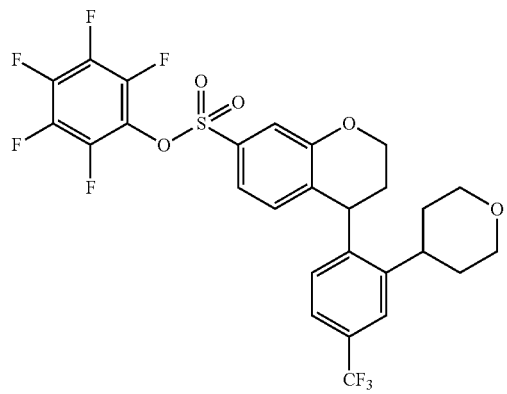 [SMILES: O=S(=O)(Oc1c(F)c(F)c(F)c(F)c1F)c1ccc2c(c1)OCCC2c1ccc(C(F)(F)F)cc1C1CCOCC1]

The title compound was prepared by following the similar procedure as described in Intermediate-6 using Intermediate-4 and Intermediate-28. LCMS (ESI): m/z 609.05 (M+H)$^+$.

Intermediate-30: 1-(2-Bromo-5-(trifluoromethyl)phenyl)pyrrolidin-2-one

Step-1: N-(2-Bromo-5-(trifluoromethyl)phenyl)-4-hydroxybutanamide

2-Bromo-5-(trifluoromethyl)aniline (2 g, 8.33 mmol) was dissolved in DCM (25 ml) and trimethyl aluminum (5.83 ml, 11.67 mmol) was added slowly to it. After the addition the solution was stirred for 15 min after which dihydrofuran-2 (3H)-one (0.897 ml, 11.67 mmol) was added to it and the reaction mixture stirred at room temperature overnight. The reaction was quenched by the slow addition of 1N HCl and extracted with ethyl acetate. The ethyl acetate layer was dried and conc. and the crude purified on column to obtain the product as a white solid (1.8 g, 66%) $^1$H NMR (400 MHz, Chloroform-d) δ 8.74 (d, J=2.3 Hz, 1H), 7.92 (s, 1H), 7.68 (d, J=8.4 Hz, 1H), 7.25 (dd, J=8.4, 2.2 Hz, 1H), 3.81 (q, J=5.5 Hz, 2H), 2.66 (t, J=7.0 Hz, 2H), 2.06-1.98 (m, 2H).

Step-2: 1-(2-Bromo-5-(trifluoromethyl)phenyl)pyrrolidin-2-one

N-(2-Bromo-5-(trifluoromethyl)phenyl)-4-hydroxybutanamide (1.36 g, 4.17 mmol) was dissolved in DCM (60 ml) and triphenylphosphine (1.31 g, 5.00 mmol) was added to it. Diethyl azodicarboxylate (DEAD) (0.792 ml, 5.00 mmol) was added to this solution drop wise (color disappears) and the reaction mixture was allowed to stir at room temperature overnight. The volatiles were then conc. and the crude purified by column chromatography to obtain the product as a white solid (1 g, 78%). $^1$H NMR (400 MHz, Chloroform-d) δ 7.82 (d, J=8.4 Hz, 1H), 7.57 (d, J=2.2 Hz, 1H), 7.48 (dd, J=8.4, 2.1 Hz, 1H), 3.83 (t, J=7.0 Hz, 2H), 2.63 (t, J=8.1 Hz, 2H), 2.37-2.23 (m, 2H).

Intermediate-31a/31b: (R&S)-Perfluorophenyl 4-(2-(2-oxopyrrolidin-1-yl)-4-(trifluoromethyl)phenyl)chroman-7-sulfonate

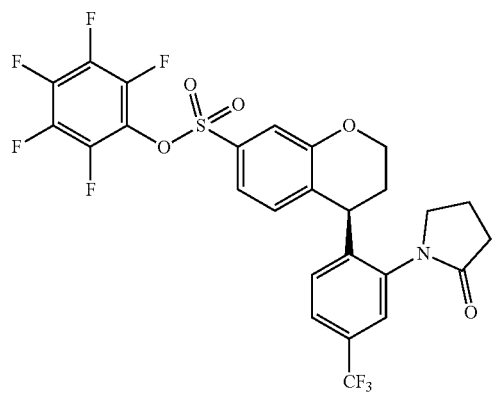

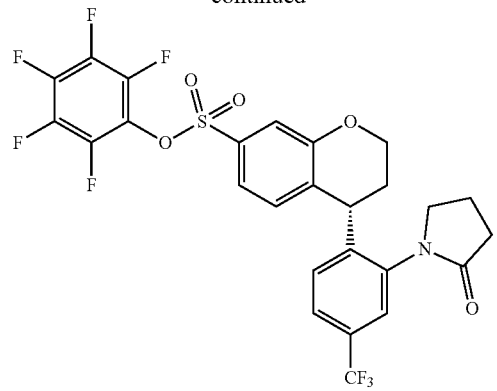

The title compound was prepared by following the similar procedure as described in Intermediate-6 using Intermediate-4 and Intermediate-30. $^1$H NMR (400 MHz, Chloroform-d) δ 7.59-7.47 (m, 3H), 7.40-7.26 (m, 2H), 7.08 (d, J=8.2 Hz, 1H), 4.51-4.22 (m, 3H), 4.00-3.81 (m, 2H), 2.67 (t, J=8.1 Hz, 2H), 2.42-2.28 (m, 2H), 2.22-1.85 (m, 2H).

Further the enantiomers were separated using chiral preparative HPLC (Column: ChiralPak IC; Mobile phase: A=(Hexane+0.1% DEA), B=(IPA:DCM=1:1), A:B=70:30, to afford isomer-1 and isomer-2. These isomers were obtained at retention time 5.89 min (Intermediate-31a) and retention time 6.71 min (Intermediate-31b).

Intermediate-32: 4-(2-bromo-5-(trifluoromethyl)phenyl)morpholine

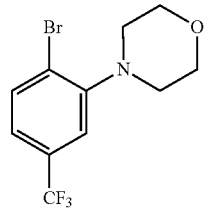 [SMILES: FC(F)(F)c1ccc(Br)c(N2CCOCC2)c1]

Step-1: 4-(2-nitro-5-(trifluoromethyl)phenyl)morpholine

To a solution of 2-fluoro-1-nitro-4-(trifluoromethyl)benzene (7 g, 33.5 mmol) and morpholine (3.79 g, 43.5 mmol) in DMF (70 ml) was added K$_2$CO$_3$ (11.57 g, 84 mmol) and stirred for 4 h at 120° C. Reaction mixture was diluted with ethyl acetate and washed with water. The organic phase was washed with brine, dried over Na$_2$SO$_4$ and concentrated to obtain title compound (8.9 g, 96%). $^1$H NMR (400 MHz, Chloroform-d) δ 7.86 (d, J=8.4 Hz, 1H), 7.40-7.26 (m, 2H), 3.87 (t, 4H), 3.13 (t, 4H).

Step-2: 2-morpholino-4-(trifluoromethyl)aniline

To a solution of 4-(2-nitro-5-(trifluoromethyl)phenyl)morpholine (7.5 g, 27.2 mmol) in MeOH (100 ml) was added 10% Pd—C (2.89 g, 27.2 mmol) and reaction mixture was stirred for 3 h under H$_2$ atmosphere. Reaction was monitored by TLC. Reaction mixture was filtered through celite pad and filtrate was washed with ethyl acetate. The combined filtrate was concentrated under vacuum to obtain title compound (6.6 g, 99%). LCMS (ESI): m/z 246.22 (M+1)$^+$.

Step-3: 4-(2-bromo-5-(trifluoromethyl)phenyl)morpholine

The title compound was prepared by following similar procedure as described for Intermediate-21 (Step-2), using 2-morpholino-4-(trifluoromethyl)aniline. LCMS (ESI): m/z 310.34 & 312.34 (M+1)+.

Intermediate-33a/33b: (R&S)-Perfluorophenyl 4-(2-morpholino-4-(trifluoromethyl)phenyl)chroman-7-sulfonate mmol) and $Cs_2CO_3$ (20.28 g, 62.2 mmol) in acetonitrile (10 ml) was heated to 80° C. for 16 h. The reaction was quenched by the addition of water and the reaction mixture was extracted with ethyl acetate. The ethyl acetate layer was dried over $Na_2SO_4$ and concentrated under vacuum. The crude was purified by column chromatography to obtain the product as white gummy liquid (6 g, 97%).

Intermediate-35a/35b: (R&S)-perfluorophenyl 4-(2-(2-methoxyethoxy)-4-(trifluoromethyl)phenyl)chroman-7-sulfonate

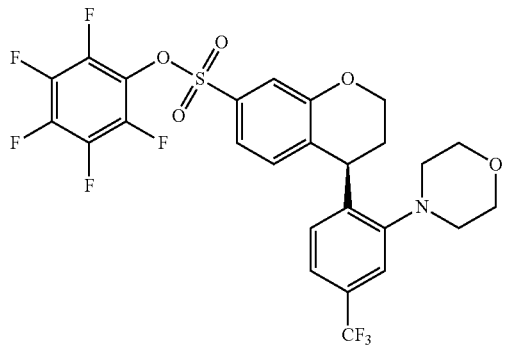

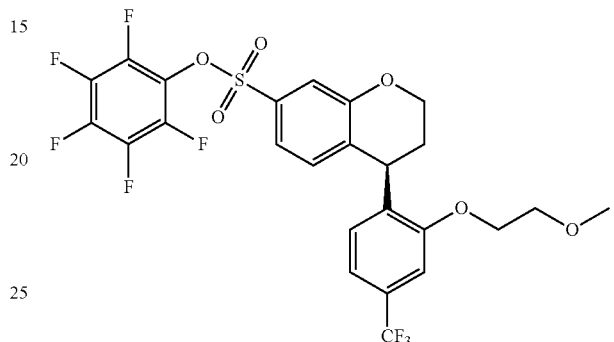

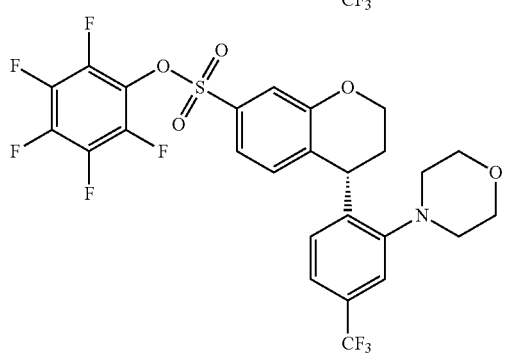

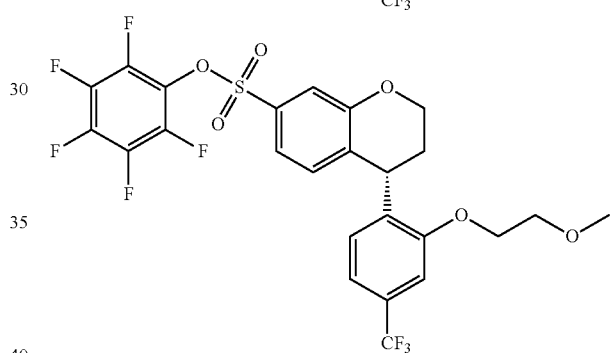

The title compounds were prepared by following the similar procedure as described in Step-1 and Step-2 of Intermediate-6 using Intermediate-4 and Intermediate-32. LCMS (ESI): m/z 610.0 (M+H)+.

Further the enantiomers were separated using chiral preparative HPLC (Column: ChiralPak IC; Mobile phase: A=(Hexane+0.1% DEA), B=(IPA:MeOH=1:1), A:B=90:10, to afford isomer-1 and isomer-2. These isomers were obtained at retention time 7.85 min (Intermediate-33a) and retention time 9.07 min (Intermediate-33b).

Intermediate-34: 1-bromo-2-(2-methoxyethoxy)-4-(trifluoromethyl)benzene

The title compounds were prepared by following the similar procedure as described Step-1 and Step-2 of Intermediate-6 using Intermediate-4 and Intermediate-34. LCMS (ESI): m/z 621.04 (M+Na)+.

Further the enantiomers were separated using chiral preparative HPLC (Column: ChiralPak IA; Mobile phase: A=(Hexane+0.1% DEA), B=(IPA:DCM=1:1), A:B=90:10, to afford isomer-1 and isomer-2. These isomers were obtained at retention time 5.69 min (Intermediate-35a) and retention time 6.34 min (Intermediate-35b).

Intermediate-36: 2-bromo-1-(3-methoxypropoxy)-4-(trifluoromethyl)benzene

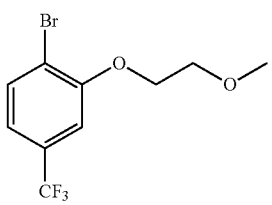 [SMILES: COCCOc1cc(C(F)(F)F)ccc1Br]

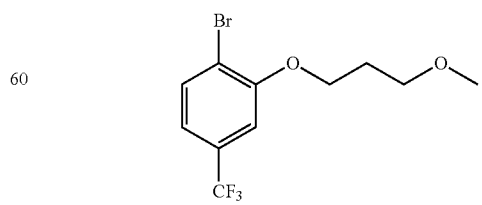

A solution of 2-bromo-5-(trifluoromethyl)phenol (5 g, 20.75 mmol), 1-bromo-2-methoxyethane (5.77 g, 41.5

A mixture of 2-bromo-5-(trifluoromethyl)phenol (2 g, 8.30 mmol), 3-bromopropan-1-ol (1.73 g, 12.45 mmol) and Cs₂CO₃ (13.52 g, 41.5 mmol) in acetonitrile (10 ml) was heated at 80° C. for 16 h. The reaction mixture was quenched by the addition of water and the reaction mixture was extracted with ethyl acetate. The ethyl acetate layer was dried over Na₂SO₄ and concentrated under vacuum. The crude product was purified by column chromatography to obtain 3-(2-bromo-4-(trifluoromethyl)phenoxy)propan-1-ol as white gummy liquid (2 g, 81%).

NaH (0.401 g, 10.03 mmol) was added in DMF (10 ml) at 0° C. and then added 3-(2-bromo-4-(trifluoromethyl)phenoxy)propan-1-ol (1 g, 3.34 mmol) and stirred for 10 min. Methyl iodide (0.475 g, 3.34 mmol) was added to the reaction mixture and stirred further 16 h. The reaction mixture was poured into water and extracted with ethyl acetate. The ethyl acetate layer was dried over Na₂SO₄ and concentrated under reduced pressure and the crude purified by column chromatography to obtain the product as white gummy liquid. ¹H NMR (400 MHz, Chloroform-d) δ 7.67 (d, J=8.1 Hz, 1H), 7.24-7.07 (m, 2H), 4.19 (t, J=6.1 Hz, 2H), 3.64 (t, J=6.0 Hz, 2H), 3.39 (s, 3H), 2.15 (quintet, J=6.1 Hz, 2H).

Intermediate-37a/37b: (R&S)-Perfluorophenyl 4-(2-(3-methoxypropoxy)-4-(trifluoromethyl)phenyl)chroman-7-sulfonate

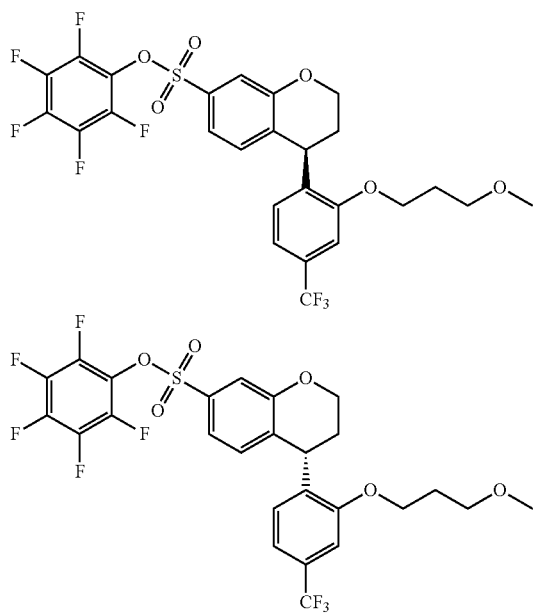

The title compounds were prepared by following the similar procedure as described in Step-1 and Step-2 of Intermediate-6 using Intermediate-4 and Intermediate-36. LCMS(ESI): m/z 613.02 (M+H)⁺.

Further the enantiomers were separated using chiral preparative HPLC (Column: ChiralPak IA; Mobile phase: A=(Hexane+0.1% TFA), B=(IPA), A:B=90:10, to afford isomer-1 and isomer-2. These isomers were obtained at retention time 6.12 min (Intermediate-37a) and retention time 6.92 min (Intermediate-37b).

Intermediate-38: 1-bromo-2-(2-methoxyethyl)-4-(trifluoromethyl)benzene

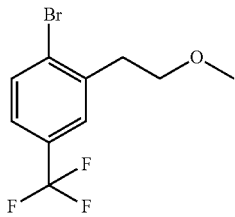

Step-1: 2-(2-bromo-5-(trifluoromethyl)phenyl)ethanol

To a suspension of (methoxymethyl)triphenylphosphonium chloride (13.55 g, 39.5 mmol) in THF (70 ml) was added potassium tert-butoxide (4.43 g, 39.5 mmol) under nitrogen and stirred for 1 h at 0° C., then 2-bromo-5-(trifluoromethyl)benzaldehyde (5 g, 19.76 mmol) in THF (10 ml) was added to the reaction mixture and allowed to stir at room temperature for 3 h. Reaction mixture was quenched with water, extracted with ethyl acetate, dried over Na₂SO₄ and concentrated under vacuum. The crude was purified by column chromatography and then taken it in THF and heated with 5N HCl for 2.5 h at 70° C. It was then neutralized with bicarbonate solution and extracted with diethyl ether. The combined organic layer was dried over Na₂SO₄ and evaporated to give the crude compound and this was taken in MeOH (40 ml) and NaBH₄ (0.673 g, 17.79 mmol) was added and maintained for 1 h. The solvent was evaporated under reduced pressure and reaction mixture was quenched with water. The product was extracted with ethyl acetate and combined organic layers washed with water, brine, dried over Na₂SO₄ and concentrated under vacuum. The crude was purified to obtain title compound as oil. (3.5 g, 66%). LCMS (ESI): m/z 268.06 & 270.08 (M+H)⁺.

Step-2: 1-bromo-2-(2-methoxyethyl)-4-(trifluoromethyl)benzene

To a suspension of NaH (0.580 g, 14.49 mmol) in THF (30 ml) at 0° C., a solution of 2-(2-bromo-5-(trifluoromethyl)phenyl)ethanol (3 g, 11.15 mmol) in THF was added drop wise and stirred for 10 min. Iodomethane (1.394 ml, 22.30 mmol) was added to the reaction mixture and stirred further 45 min. After completion of reaction as indicated by TLC, The reaction mixture was quenched by addition of water and extracted with ethyl acetate. Organic layer combined and washed with brine, dried over sodium sulfate and concentrated under vacuum.

The crude was purified by column chromatography to obtain title compound (1.8 g, 57%).

¹H NMR (400 MHz, Chloroform-d) δ 7.69 (d, J=8.3 Hz, 1H), 7.58-7.52 (m, 1H), 7.36 (dd, J=8.4, 2.2 Hz, 1H), 3.66 (t, J=6.8 Hz, 2H), 3.39 (s, 3H), 3.10 (t, J=6.8 Hz, 2H).

Intermediate-39a/39b: (S&R)-perfluorophenyl 4-(2-(2-methoxyethyl)-4-(trifluoromethyl)phenyl)chroman-7-sulfonate

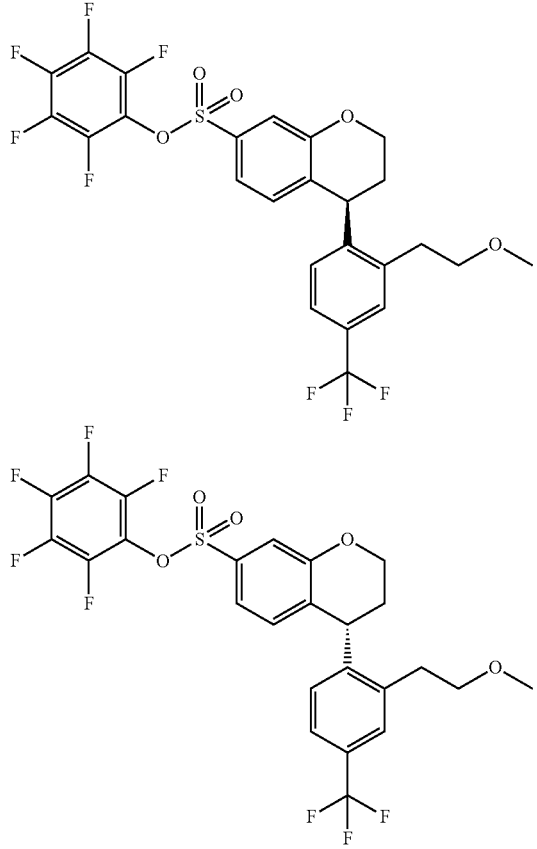

The title compounds were prepared by following the similar procedure as described in Step-1 and Step-2 of Intermediate-6 using Intermediate-4 and Intermediate-38.

Further the enantiomers were separated using chiral preparative HPLC (Column: ChiralPak IA; Mobile phase: A=(Hexane+0.1% DEA), B=(IPA), A:B=90:10, to afford isomer-1 and isomer-2. These isomers were obtained at retention time 6.56 min (Intermediate-39a) and retention time 7.91 min (Intermediate-39b).

LCMS (ESI): m/z 605.05 (M+Na)$^+$. $^1$H NMR (400 MHz, Chloroform-d) δ 7.57-7.54 (m, 1H), 7.52 (d, J=2.0 Hz, 1H), 7.42 (dd, J=8.3, 2.0 Hz, 1H), 7.36 (dd, J=8.2, 2.0 Hz, 1H), 6.98 (dd, J=8.2, 0.9 Hz, 1H), 6.91 (d, J=8.2 Hz, 1H), 4.73 (t, J=6.9 Hz, 1H), 4.39-4.27 (m, 2H), 3.78-3.64 (m, 2H), 3.37 (s, 3H), 3.22-3.11 (m, 1H), 3.06-2.96 (m, 1H), 2.41-2.32 (m, 1H), 2.15-2.05 (m, 1H).

Intermediate-40: 1-bromo-2-(3-methoxyprop-1-yn-1-yl)-4-(trifluoromethyl)benzene

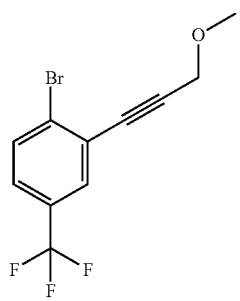 [SMILES: COCC#Cc1cc(C(F)(F)F)ccc1Br]

Step-1: 3-(2-bromo-5-(trifluoromethyl)phenyl)prop-2-yn-1-ol

The title compound was prepared by following similar procedure as shown in Intermediate-48 (Step-1) using 1-bromo-2-iodo-4-(trifluoromethyl)benzene and prop-2-yn-1-ol. $^1$H NMR (400 MHz, Chloroform-d) δ 7.78-7.71 (m, 2H), 7.44 (dd, J=8.5, 2.2 Hz, 1H), 4.59 (s, 2H).

Step-2: 1-bromo-2-(3-methoxyprop-1-yn-1-yl)-4-(trifluoromethyl)benzene

To a solution of 3-(2-bromo-5-(trifluoromethyl)phenyl)prop-2-yn-1-ol (2.7 g, 9.68 mmol) in dry THF (50 ml) was added NaH (0.43 g, 10.64 mmol) at 0° C. and stirred for another 15 min then added MeI (0.907 ml, 14.51 mmol). Reaction mixture was stirred for additional 30 min at room temperature. After completion of reaction, reaction mixture was poured into aqueous NH$_4$C$_1$ solution and extracted with ethyl acetate. The organic phase was washed with 1N HCl, brine, dried over Na$_2$SO$_4$ and concentrated to obtain title compound (2.5 g, 88%). $^1$H NMR (400 MHz, Chloroform-d) δ 7.79-7.70 (m, 2H), 7.48-7.39 (m, 1H), 4.41 (s, 2H), 3.52 (s, 3H).

Intermediate-41a/41b: (S&R)Perfluorophenyl 4-(2-(3-methoxypropyl)-4-(trifluoromethyl)phenyl)chroman-7-sulfonate

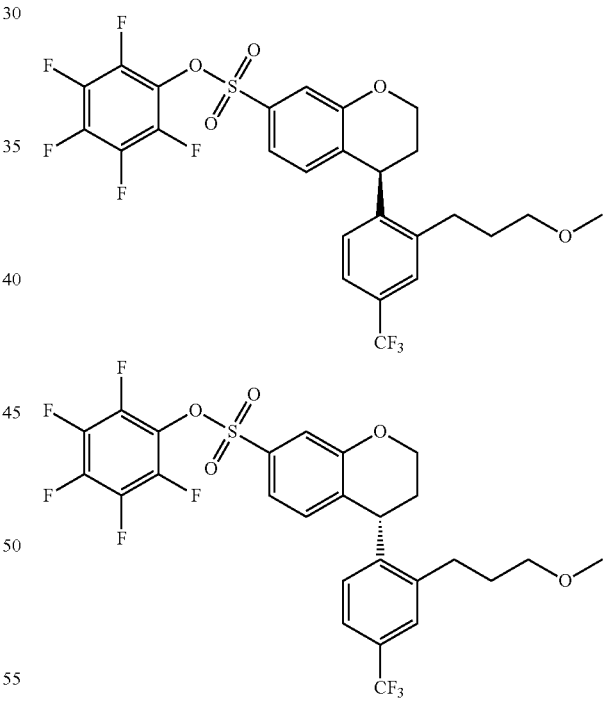

The title compounds were prepared by following the similar procedure as described in Intermediate-6 using Intermediate-4 and Intermediate-40. LCMS(ESI): m/z 597.03 (M+H)$^+$.

Further the enantiomers were separated using chiral preparative HPLC (Column: ChiralPak IA; Mobile phase: A=(Hexane+0.1% DEA), B=(IPA), A:B=95:5, to afford isomer-1 and isomer-2. These isomers were obtained at retention time 7.09 min (Intermediate-41a) and retention time 8.69 min (Intermediate-41b).

Intermediate-42: 1-bromo-2-(4-methoxybut-1-yn-1-yl)-4-(trifluoromethyl)benzene

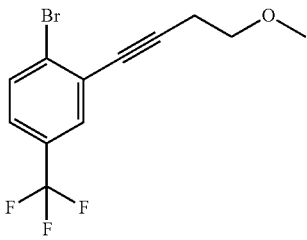 [SMILES: COCCC#Cc1cc(C(F)(F)F)ccc1Br]

The title compound was prepared by following similar procedure as described for Intermediate-40 using 1-bromo-2-iodo-4-(trifluoromethyl)benzene and but-3-yn-1-ol. LCMS (ESI): m/z 306.93 & 308.93 (M+1)$^+$.

Intermediate-43a/43b: (R&S)Perfluorophenyl 4-(2-(4-methoxybutyl)-4-(trifluoromethyl)phenyl)chroman-7-sulfonate

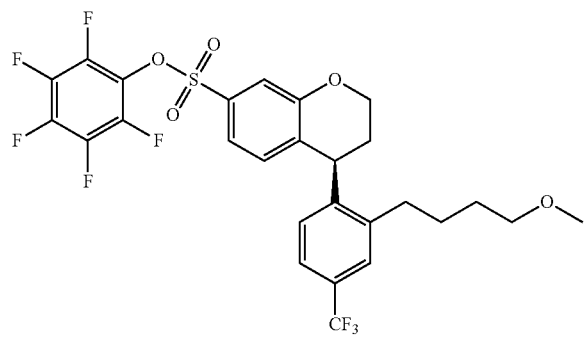

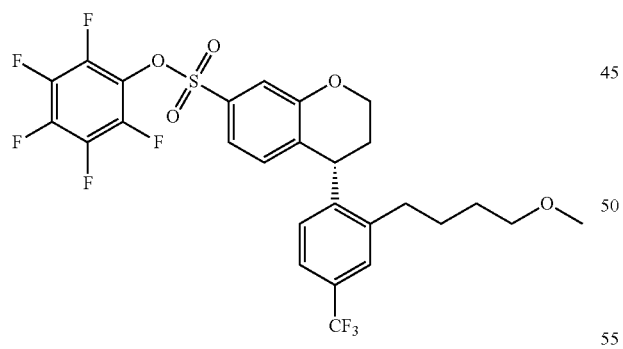

The title compounds were prepared by following the similar procedure as described in Intermediate-6 using Intermediate-4 and Intermediate-42. LCMS (ESI): m/z 611.13 (M+H)$^+$.

Further the enantiomers were separated using chiral preparative HPLC (Column: ChiralPak IA; Mobile phase: A=(Hexane+0.1% DEA), B=(IPA), A:B=90:10, to afford isomer-1 and isomer-2. These isomers were obtained at retention time 5.63 min (Intermediate-43a) and retention time 6.83 min (Intermediate-43b).

Intermediate-44: 1-bromo-2-(2-fluoroethyl)-4-(trifluoromethyl)benzene

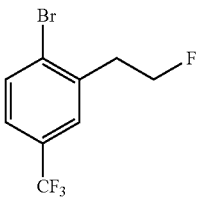 [SMILES: FCCc1cc(C(F)(F)F)ccc1Br]

Step-1: 2-(2-bromo-5-(trifluoromethyl)phenyl)ethanol

To a suspension of (methoxymethyl)triphenylphosphonium chloride (13.55 g, 39.5 mmol) in THF (70 ml) was added potassium tert-butoxide (4.43 g, 39.5 mmol) under nitrogen and stirred for 1 h at 0° C., then 2-bromo-5-(trifluoromethyl)benzaldehyde (5 g, 19.76 mmol) in THF (10 ml) was added to the reaction mixture and allowed to stir at room temperature for 3 h. Reaction mixture was quenched with water, extracted with ethyl acetate, dried over Na$_2$SO$_4$ and concentrated under vacuum. The crude was purified by column chromatography and then taken it in THF and heated with 5N HCl for 2.5 h at 70° C. It was then neutralized with bicarbonate solution and extracted with diethyl ether. The combined organic layer was dried over Na$_2$SO$_4$ and evaporated to dryness to give the crude compound. Which was taken in MeOH (40 ml) and NaBH$_4$ (0.673 g, 17.79 mmol) was added and the resultant mixture was stirred for 1 h. The solvent was evaporated under reduced pressure and reaction mixture was quenched with water.

The product was extracted with ethyl acetate and combined organic layers washed with water, brine, dried over Na$_2$SO$_4$ and concentrated under vacuum. The crude was purified to obtain title compound as oil. (3.5 g, 66%). LCMS (ESI): m/z 268.06 & 270.08 (M+H)$^+$.

Step-2: 1-bromo-2-(2-fluoroethyl)-4-(trifluoromethyl)benzene

To stirred solution of 2-(2-bromo-5-(trifluoromethyl)phenyl)ethanol (3.5 g, 13.01 mmol) in DCM (50 ml) DAST (4.30 ml, 32.5 mmol) was added at 0° C., then reaction mixture was allowed to warm to room temperature & stirred at for 16 h. After completion of reaction as indicated by TLC, reaction mixture was quenched with sat NaHCO$_3$ solution and then extracted with DCM. The organic layer was evaporated under vacuum and the crude was purified by column chromatography to obtain title compound as oil (2.10 g, 59). $^1$H NMR (400 MHz, Chloroform-d) δ 7.72 (d, J=8.4 Hz, 1H), 7.58 (d, J=2.2 Hz, 1H), 7.40 (dd, J=8.4, 2.2 Hz, 1H), 4.77 (t, J=6.2 Hz, 1H), 4.66 (t, J=6.2 Hz, 1H), 3.28 (t, J=6.2 Hz, 1H), 3.22 (t, J=6.2 Hz, 1H).

Intermediate-45a/45b: (S&R)-Perfluorophenyl 4-(2-(2-fluoroethyl)-4-(trifluoromethyl)phenyl)chroman-7-sulfonate

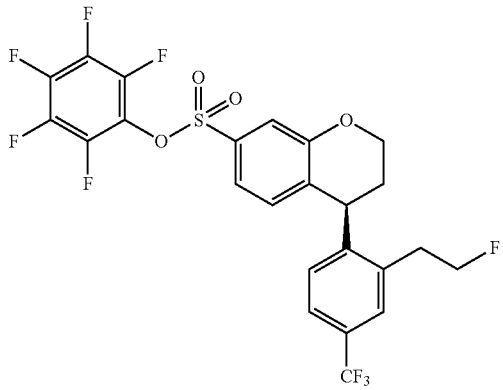

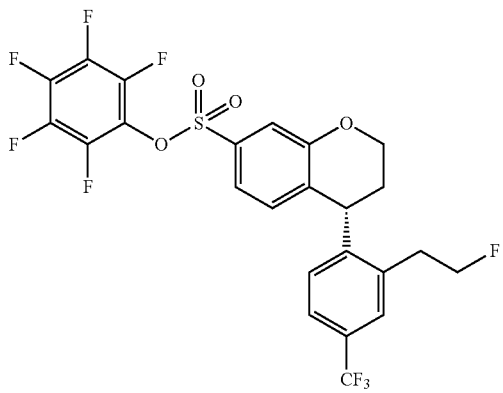

The title compounds were prepared by following similar procedure as described in Intermediate-6 using Intermediate-4 and Intermediate-44.

Further the enantiomers were separated using chiral preparative HPLC (Column: ChiralPak IA; Mobile phase: A=(Hexane+0.1% TFA), B=(IPA), A:B=80:20, to afford isomer-1 and isomer-2. These isomers were obtained at retention time 6.36 min (Intermediate-45a) and retention time 7.47 min (Intermediate-45b).

$^1$H NMR (400 MHz, Chloroform-d) δ 7.61-7.42 (m, 3H), 7.36 (d, J=8.1 Hz, 1H), 6.96 (dd, J=8.3, 2.8 Hz, 2H), 4.90-4.57 (m, 3H), 4.40-4.25 (m, 2H), 3.37-3.08 (m, 2H), 2.47-2.30 (m, 1H), 2.21-2.08 (m, 1H).

Intermediate-46: 1-bromo-2-(3-fluoropropyl)-4-(trifluoromethyl)benzene

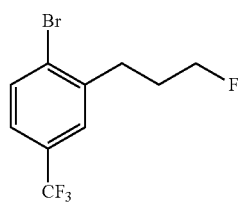 [SMILES: FCCCc1cc(C(F)(F)F)ccc1Br]

Step-1: Ethyl 3-(2-bromo-5-(trifluoromethyl)phenyl)acrylate

Ethyl 2-(diethoxyphosphoryl)acetate (1.53 g, 6.82 mmol) was added to a suspension of NaH (0.31 g, 7.71 mmol) in THF (20 ml) at room temperature. After stirring for an hour, a solution of 2-bromo-5-(trifluoromethyl)benzaldehyde (1.5 g, 5.93 mmol) in THF was added to the reaction mixture followed by stirring for another 1 h. After completion of reaction as indicated by TLC, reaction mixture was poured into water and extracted with ethyl acetate. The combined organic layer was washed with saturated sodium chloride solution and dried over $Na_2SO_4$. The solvent was removed under vacuum and the residue was purified by column chromatography to obtain title compound (0.9 g, 47%). LCMS (ESI): m/z 323.01 (M+)+.

Step-2: ethyl 3-(2-bromo-5-(trifluoromethyl)phenyl)propanoate

To a stirred solution of ethyl 3-(2-bromo-5-(trifluoromethyl)phenyl)acrylate (0.9 g, 2.79 mmol) in THF (5 ml) and water (5 ml) was added 4-methylbenzenesulfonohydrazide (1.04 g, 5.57 mmol) and sodium acetate (0.69 g, 8.36 mmol). The reaction mixture was refluxed for 16 h. After completion of reaction; water was added to the reaction mixture and extracted with ethyl acetate. Combined organic layer was washed with brine, dried over $Na_2SO_4$ and concentrated under vacuum. This was purified by column chromatography to obtain title compound as a colorless oil (0.8 g, 88%). LCMS (ESI): m/z 325.03 (M+)+.

Step-3: 3-(2-bromo-5-(trifluoromethyl)phenyl)propan-1-ol

To a solution of ethyl 3-(2-bromo-5-(trifluoromethyl)phenyl)propanoate (0.8 g, 2.461 mmol) in toluene (10 ml) was added DIBAL-H (7.38 ml, 1 molar, 7.38 mmol) at −78° C. drop wise. The reaction mixture was allowed to warm to room temperature over 30 min. then quenched with saturated solution of sodium sulfate and the product was extracted with ethyl acetate. The combined organic layer was washed with brine, dried over $Na_2SO_4$ and concentrated under vacuum. The crude product was purified by column chromatography (0.65, 93%). LCMS (ESI): m/z 284.06 (M+)+.

Step-4: 1-bromo-2-(3-fluoropropyl)-4-(trifluoromethyl)benzene

To a solution of 3-(2-bromo-5-(trifluoromethyl)phenyl) propan-1-ol (0.65 g, 2.296 mmol) in DCM (7 ml) was added DAST (0.455 ml, 3.44 mmol) drop wise. The reaction was allowed to stir at room temperature over 16 h. The reaction mixture was quenched with saturated solution of sodium bicarbonate and the product was extracted with ethyl acetate. The combined organic layer was washed with brine, dried over $Na_2SO_4$ and concentrated under vacuum. The crude product was purified by column chromatography (0.6 g, 92%). $^1$H NMR (400 MHz, Chloroform-d) δ 7.70 (d, J=8.3 Hz, 1H), 7.51 (s, 1H), 7.36 (d, J=8.4 Hz, 1H), 4.59 (t, J=5.8 Hz, 1H), 4.47 (t, J=5.8 Hz, 1H), 3.01-2.92 (m, 2H), 2.16-1.97 (m, 2H).

Intermediate-47a/47b: Perfluorophenyl (S&R)-4-(2-(3-fluoropropyl)-4-(trifluoromethyl)phenyl)chromane-7-sulfonate

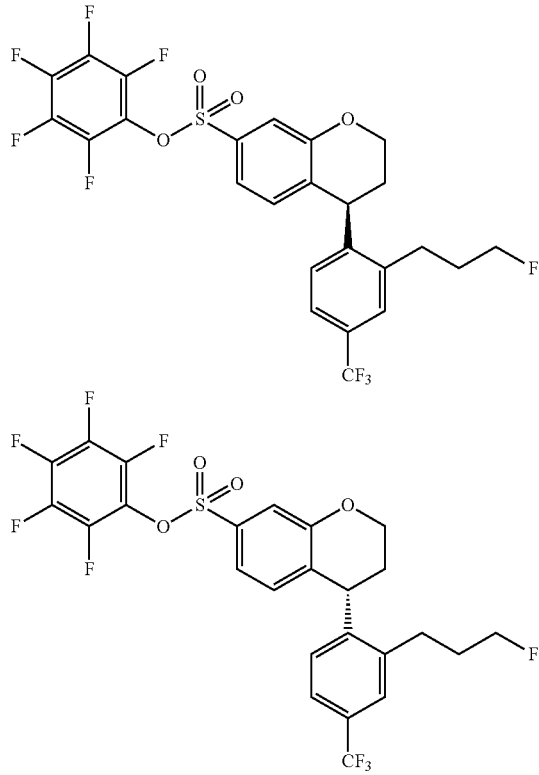

The title compound was prepared by following similar procedure as described in Intermediate-6 using Intermediate-4 and Intermediate-46.
Further the enantiomers were separated using chiral preparative HPLC (Column: ChiralPak IA; Mobile phase: A=(Hexane+0.1% TFA), B=IPA, A:B=80:20 to afford isomer 1 and isomer 2. These isomers were obtained at retention time: 5.58 min (Intermediate-47a) and retention time: 6.51 min (Intermediate-47b).
LCMS(ESI): m/z 607.06 (M+Na)$^+$; $^1$H NMR (400 MHz, DMSO-d$_6$) δ 7.67 (d, J=2.0 Hz, 1H), 7.50 (dd, J=8.2, 2.0 Hz, 1H), 7.45 (d, J=2.0 Hz, 1H), 7.39 (dd, J=8.2, 2.1 Hz, 1H), 7.00 (d, J=8.2 Hz, 2H), 4.73 (t, J=7.0 Hz, 1H), 4.60 (t, J=5.9 Hz, 1H), 4.49 (t, J=5.9 Hz, 1H), 4.41-4.26 (m, 2H), 3.01-2.82 (m, 2H), 2.37-2.27 (m, 1H), 2.12-2.01 (m, 3H).

Intermediate-48: 1-bromo-2-(4-fluorobut-1-yn-1-yl)-4-(trifluoromethyl)benzene

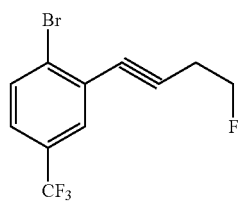 [SMILES: FCCC#Cc1cc(C(F)(F)F)ccc1Br]

Step-1: 4-(2-bromo-5-(trifluoromethyl)phenyl)but-3-yn-1-ol

To the N$_2$ purged solution of TEA (10 ml) and DMF (10 ml) was added but-3-yn-1-ol (0.75 g, 10.69 mmol), 1-bromo-2-iodo-4-(trifluoromethyl)benzene (2.5 g, 7.12 mmol), copper(I) iodide (0.27 g, 1.425 mmol), bis(triphenylphosphine)palladium(II) chloride (0.50 g, 0.712 mmol) at room temperature and stirred further for 15 min. After completion of reaction as indicated by TLC, reaction mass was poured in to water and extracted with ethyl acetate. The combined organic layer was dried over Na$_2$SO$_4$, conc under reduced pressure and purified by column chromatography to obtain title compound (1.4 g, 67%). LCMS (ESI): m/z 292.96 (M+H)$^+$.

Step-2: 1-bromo-2-(4-fluorobut-1-yn-1-yl)-4-(trifluoromethyl)benzene

To a solution of 4-(2-bromo-5-(trifluoromethyl)phenyl)but-3-yn-1-ol (1.4 g, 4.78 mmol) in dichloromethane (10 ml) was added DAST (1.58 ml, 11.94 mmol) drop wise at 0° C. The reaction was allowed to stir at room temperature over 16 h. The reaction mixture was quenched with saturated solution of sodium bicarbonate and the product was extracted with ethyl acetate. The combined organic layer was washed with brine, dried over Na$_2$SO$_4$ and concentrated under vacuum. The crude product was purified by column chromatography to obtain title compound (1 g, 70%). $^1$H NMR (400 MHz, Chloroform-d) δ 7.76-7.69 (m, 2H), 7.44-7.37 (m, 1H), 4.72 (t, J=6.6 Hz, 1H), 4.60 (t, J=6.6 Hz, 1H), 2.94 (dt, J=19.9, 6.6 Hz, 2H).

Intermediate-49a/49b: (R&S)-Perfluorophenyl 4-(2-(4-fluorobutyl)-4-(trifluoromethyl)phenyl)chroman-7-sulfonate

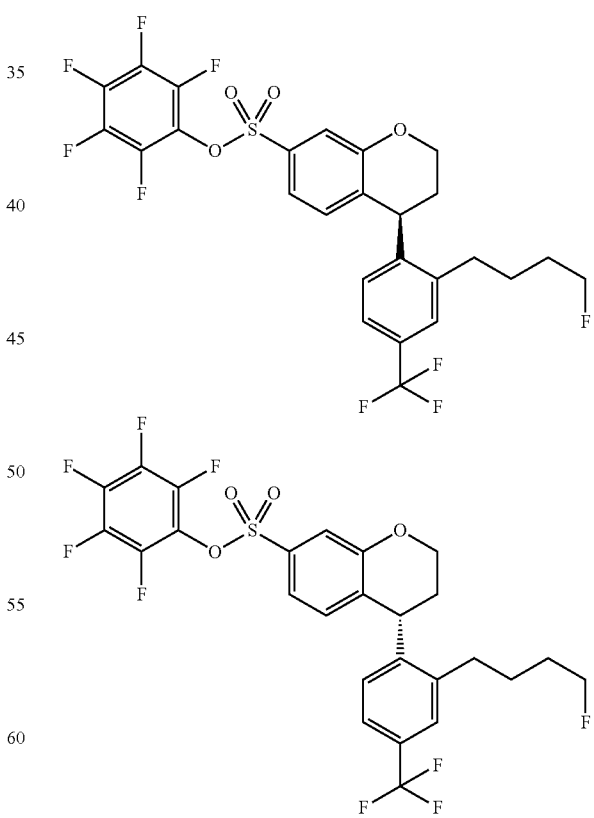

The title compound was prepared by following similar procedure as described in Intermediate-6 using Intermediate-4 and Intermediate-48.

Further the enantiomers were separated using chiral preparative HPLC (Column: ChiralPak IA; Mobile phase: A=(Hexane+0.1% TFA), B=IPA, A:B=80:20 to afford isomer 1 and isomer 2. These isomers were obtained at retention time: 5.64 min (Intermediate-49a) and retention time: 6.76 min (Intermediate-49b).

¹H NMR (400 MHz, Chloroform-d) δ 7.53 (s, 2H), 7.42 (d, J=8.5 Hz, 1H), 7.36 (d, J=8.2 Hz, 1H), 6.93 (d, J=8.2 Hz, 2H), 4.63-4.53 (m, 2H), 4.52-4.47 (m, 1H), 4.40-4.32 (m, 2H), 2.95-2.79 (m, 2H), 2.42-2.32 (m, 1H), 2.18-2.09 (m, 1H), 1.93-1.81 (m, 4H).

Intermediate-50: 4-(2-bromo-5-(trifluoromethyl)phenoxy)tetrahydro-2H-pyran

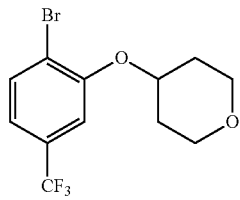 [SMILES: FC(F)(F)c1ccc(Br)c(OC2CCOCC2)c1]

To a solution of tetrahydro-2H-pyran-4-ol (2 g, 19.58 mmol) and 2-bromo-5-(trifluoromethyl)phenol (3.78 g, 15.67 mmol) in THF (100 ml) was added triphenylphosphine (6.16 g, 23.50 mmol) followed by DIAD (4.57 ml, 23.50 mmol) at 0° C. then allowed to stir the reaction mixture at room temperature. After completion of reaction as indicated by TLC, reaction mixture was evaporated under vacuum and purified by column chromatography to obtain title compound (3.5 g, 55%). ¹H NMR (400 MHz, Chloroform-d) δ 7.70 (d, J=8.3 Hz, 1H), 7.21-7.11 (m, 2H), 4.72-4.62 (m, 1H), 4.04 (ddd, J=11.3, 7.5, 3.5 Hz, 2H), 3.72-3.62 (m, 2H), 2.13-2.01 (m, 2H), 1.96-1.83 (m, 2H).

Intermediate-51: Perfluorophenyl 4-(2-((tetrahydro-2H-pyran-4-yl)oxy)-4-(trifluoromethyl)phenyl)chroman-7-sulfonate

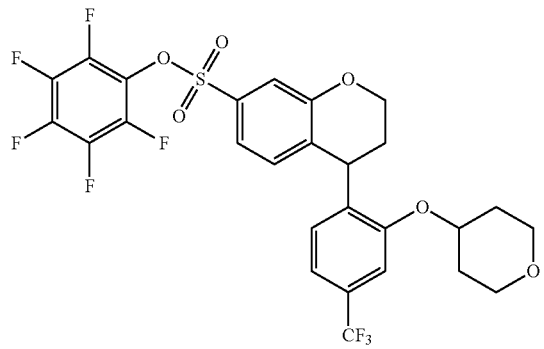

The title compound was prepared by following similar procedure as described for Intermediate-6 using Intermediate-4 and Intermediate-50. ¹H NMR (400 MHz, Chloroform-d) δ 7.52 (d, J=2.0 Hz, 1H), 7.39 (dd, J=8.1, 2.0 Hz, 1H), 7.18 (d, J=8.0 Hz, 1H), 7.12 (s, 1H), 7.05 (d, J=8.2 Hz, 1H), 6.95 (d, J=7.9 Hz, 1H), 4.69-4.60 (m, 2H), 4.34-4.20 (m, 2H), 4.01-3.85 (m, 2H), 3.72-3.59 (m, 2H), 2.36-2.21 (m, 2H), 2.17-1.79 (m, 4H).

Intermediate-52: (S)-3-(2-bromo-4-(trifluoromethyl)phenoxy)tetrahydrofuran

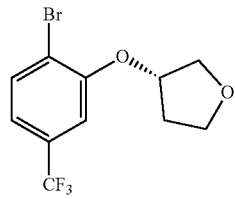 [SMILES: FC(F)(F)c1ccc(Br)c(O[C@H]2CCOC2)c1]

The title compound was prepared similarly as shown in Intermediate-50 using 2-bromo-5-(trifluoromethyl)phenol and (R)-tetrahydrofuran-3-ol. LCMS (ESI): m/z 310.00 & 311.88 (M+H)⁺.

Intermediate-53a/53b: (R&S)-perfluorophenyl 4-(2-(((S)-tetrahydrofuran-3-yl)oxy)-4 (trifluoromethyl)phenyl)chroman-7-sulfonate

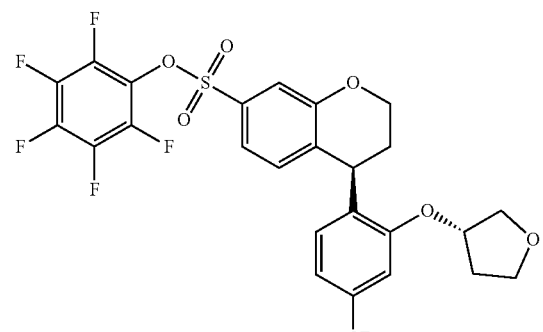

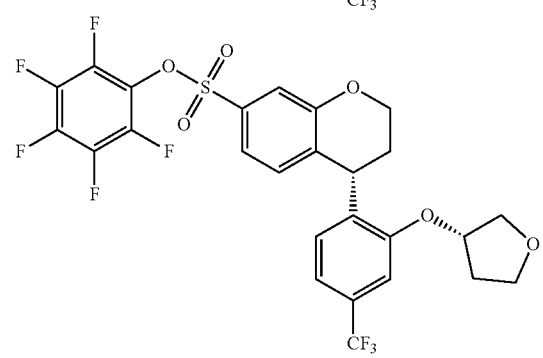

The title compound was prepared by following similar procedure as described for Intermediate-6 using Intermediate-4 and Intermediate-52. LCMS (ESI): m/z 633.07 (M+Na)⁺;

Further the enantiomers were separated using chiral preparative HPLC (Column: ChiralPak IA; Mobile phase: A=(Hexane+0.1% DEA), B=IPA, A:B=90:10, to afford isomer-1 and isomer-2. These isomers were obtained at retention time 7.76 min (Intermediate-53a) and retention time 9.38 min (Intermediate-53b).

Intermediate-54: (R)-3-(2-bromo-4-(trifluoromethyl)phenoxy)tetrahydrofuran

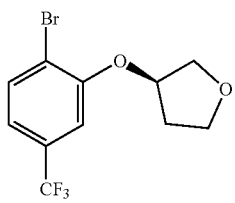 [SMILES: FC(F)(F)c1ccc(Br)c(O[C@@H]2CCOC2)c1]

The title compound was prepared similarly as shown in Intermediate-50 using 2-bromo-5-(trifluoromethyl)phenol and (S)-tetrahydrofuran-3-ol. LCMS (ESI): m/z 309.93 & 312.01 (M+H).

Intermediate-55: Perfluorophenyl 4-(2-(((R)-tetrahydrofuran-3-yl)oxy)-4-(trifluoromethyl)phenyl)chroman-7-sulfonate

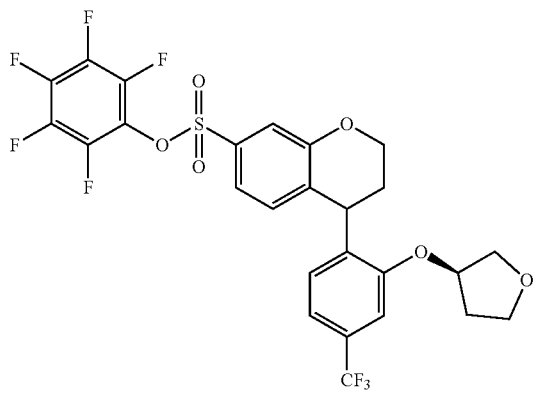 [SMILES: O=S(=O)(Oc1c(F)c(F)c(F)c(F)c1F)c1ccc2c(c1)OCCC2c1ccc(C(F)(F)F)cc1O[C@@H]1CCOC1]

The title compound was prepared by following similar procedure as described for Intermediate-6 using Intermediate-4 and Intermediate-54. $^1$H NMR (400 MHz, Chloroform-d) δ 7.52 (d, J=2.1 Hz, 1H), 7.43-7.35 (m, 1H), 7.20 (d, J=8.1 Hz, 1H), 7.09-7.02 (m, 2H), 6.92 (dd, J=22.4, 8.1 Hz, 1H), 5.13-5.01 (m, 1H), 4.69-4.56 (m, 1H), 4.32-4.16 (m, 2H), 4.10-3.81 (m, 4H), 2.41-1.99 (m, 4H).

Intermediate-56: tert-butyl 2'-bromo-5'-(trifluoromethyl)-[1,1'-biphenyl]-4-carboxylate

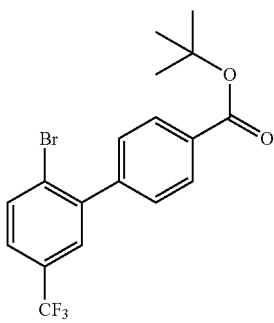 [SMILES: CC(C)(C)OC(=O)c1ccc(-c2cc(C(F)(F)F)ccc2Br)cc1]

Step-1: tert-butyl 4-bromobenzoate

To a solution of 4-bromobenzoic acid (10 g, 49.7 mmol) in Chloroform (150 ml), 2-methylpropan-2-ol (18.44 g, 249 mmol), EDC.HCl (23.84 g, 124 mmol), followed by DMAP (15.19 g, 124 mmol) was added and stirred for 18 h at room temperature. After completion of reaction as indicated by TLC, the mixture was poured into water and extracted with DCM. The organic layer was collected and dried over sodium sulphate, finally evaporated and purified by column chromatography (7 g, 55%). $^1$H NMR (400 MHz, Chloroform-d) δ 7.87 (d, 2H), 7.57 (d, 2H), 1.61 (s, 9H).

Step-2: tert-butyl 4-(4,4,5,5-tetramethyl-1,3,2-dioxaborolan-2-yl)benzoate

The title compound was prepared by following similar procedure as described in Intermediate-23, Step-2 using tert-butyl 4-bromobenzoate and 4,4,4',4',5,5,5',5'-octamethyl-2,2'-bi(1,3,2-dioxa borolane)
$^1$H NMR (400 MHz, Chloroform-d) δ 7.98 (d, 2H), 7.86 (d, J=8.0 Hz, 2H), 1.62 (s, 9H), 1.38 (s, 12H).

Step-3: tert-butyl 2'-amino-5'-(trifluoromethyl)-[1,1'-biphenyl]-4-carboxylate

A solution of 2-bromo-4-(trifluoromethyl)aniline (5 g, 20.83 mmol), tert-butyl 4-(4,4,5,5-tetramethyl-1,3,2-dioxaborolan-2-yl)benzoate (6.34 g, 20.83 mmol), and sodium carbonate (5.52 g, 52.1 mmol) in toluene (30 ml)/water (20 ml)/Ethanol (10 ml), N$_2$ was purged for 10 min. then Tetrakistriphenyl phosphinePd (0) (2.407 g, 2.083 mmol) was charged and stirred at 95° C. for 4 h. After completion of reaction as indicated by TLC, the mixture was poured into water and extracted with ethyl acetate. The organic layer was collected and dried over sodium sulphate, finally evaporated and purified by column chromatography (4.5 g, 64%). LCMS (ESI): m/z 338.10 (M+H)$^+$.

Step-4: tert-butyl 2'-bromo-5'-(trifluoromethyl)-[1,1'-biphenyl]-4-carboxylate

To a solution of tert-butyl 2'-amino-5'-(trifluoromethyl)-[1,1'-biphenyl]-4-carboxylate (4.5 g, 13.34 mmol) in acetonitrile (60 ml), copper(II) bromide (1.64 g, 7.34 mmol) was added followed by tert-butyl nitrite (2.4 ml, 20.01 mmol) was added dropwise and reaction was heated for 45 min at 65° C. Reaction was monitored by TLC. After completion the mixture was added to water and extracted with ethyl acetate. The organic layer was collected and dried over sodium sulphate, finally evaporated to get crude which was purified by column.
$^1$H NMR (400 MHz, Chloroform-d) δ 8.13-8.07 (m, 2H), 7.84 (d, J=8.3 Hz, 1H), 7.58 (d, J=2.2 Hz, 1H), 7.54-7.45 (m, 3H), 1.65 (s, 9H).

Intermediate-57a/57b: (R&S)-tert-butyl 2'-(7-((perfluorophenoxy)sulfonyl)chroman-4-yl)-5'-(trifluoromethyl)-[1,1'-biphenyl]-4-carboxylate

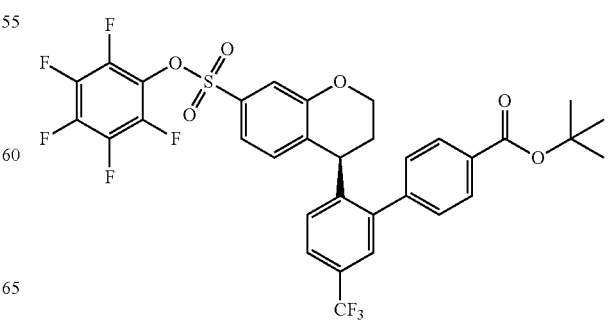

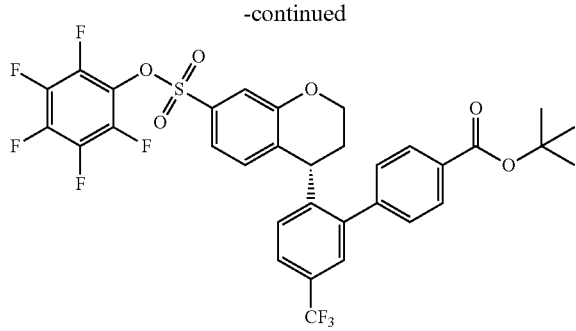

The title compound was prepared by following the similar procedure as described in Intermediate-6 using Intermediate-4 and Intermediate-56. LCMS (ESI): m/z 723.08 (M+H)⁺.

Further the enantiomers were separated using chiral preparative HPLC (Column: ChiralPak IA; Mobile phase: A=(Hexane), B=(IPA:DCM=1:1), A:B=75:25, to afford isomer-1 and isomer-2. These isomers were obtained at retention time 3.99 min (Intermediate-57a) and retention time 6.10 min (Intermediate-57b).

Intermediate-58: 2-(2-bromo-5-(trifluoromethyl) phenyl)-5-fluoropyridine 1-oxide

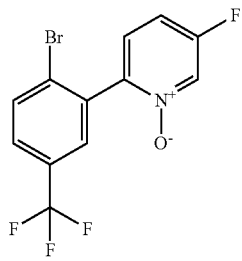 [SMILES: [O-][n+]1cc(F)ccc1-c1cc(C(F)(F)F)ccc1Br]

Step-1: 2-(4,4,5,5-tetramethyl-1,3,2-dioxaborolan-2-yl)-4-(trifluoromethyl)aniline

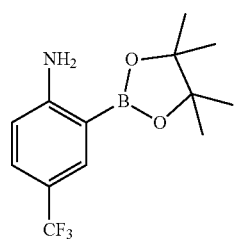 [SMILES: CC1(C)OB(c2cc(C(F)(F)F)ccc2N)OC1(C)C]

A stirred suspension of 2-bromo-4-(trifluoromethyl)aniline (50 g, 208 mmol), 4,4,4',4',5,5,5',5'-octamethyl-2,2'-bi(1,3,2-dioxaborolane) (79 g, 312 mmol) and potassium acetate (53.2 g, 542 mmol) in 1,4-dioxane (150 ml) was degassed for 20 min and then PdCl$_2$(dppf)-DCM adduct (17.01 g, 20.83 mmol) was added to the reaction mixture and heated for 5 h at 95° C. After completion of reaction as indicated by TLC, Reaction mixture was filtered through celite bed and residue was washed with ethyl acetate. The filtrate was evaporated and the crude was purified by column chromatography to obtain title compound as off white solid (35 g, 58%). ¹H NMR (400 MHz, Chloroform-d) δ 7.91-7.85 (m, 1H), 7.44 (dd, J=8.6, 2.3 Hz, 1H), 6.64 (d, J=8.5 Hz, 1H), 1.37 (s, 12H).

Step-2: 2-(5-fluoropyridin-2-yl)-4-(trifluoromethyl) aniline

Nitrogen was purged containing 2-(4,4,5,5-tetramethyl-1,3,2-dioxaborolan-2-yl)-4-(trifluoromethyl)aniline (1.5 g, 5.22 mmol), 2-bromo-5-fluoropyridine (1.01 g, 5.75 mmol) in 1,4-dioxane (15 ml), water (3 ml) for 10 minutes. After which PdCl$_2$(dppf)DCM complex (0.382 g, 0.522 mmol) and sodium carbonate (1.38 g, 13.06 mmol) were added and heated at 90° C. for 18 h. After completion of reaction as indicated by TLC, reaction mixture was cooled to room temperature and concentrated under vacuum. The crude brown solid was purified by column chromatography to obtain title compound (1.2 g, 90%). LCMS (ESI): m/z 256.10 (M+H)⁺.

Step-3: 2-(2-bromo-5-(trifluoromethyl)phenyl)-5-fluoropyridine

To a stirred solution of 2-(5-fluoropyridin-2-yl)-4-(trifluoromethyl)aniline (0.70 g, 2.73 mmol) in acetonitrile (25 ml), copper(II) bromide (0.3 g, 1.639 mmol) was added and heated reaction mixture at 60° C. After 5 min tert-butylnitrite (0.31 ml, 4.10 mmol) was added drop wise and stirred further 1 h. After completion of reaction as indicated by TLC, reaction mixture was poured into water and extracted with ethyl acetate. The combined organic layer was collected and washed with water, dried over Na$_2$SO$_4$ and evaporated under vacuum. The crude was purified by column chromatography to obtain title compound (0.55 g, 62%). ¹H NMR (400 MHz, Chloroform-d) δ 8.62 (d, J=2.9 Hz, 1H), 7.87-7.79 (m, 2H), 7.69 (dd, J=8.7, 4.3 Hz, 1H), 7.55 (td, J=8.6, 2.7 Hz, 2H).

Step-4: 2-(2-bromo-5-(trifluoromethyl)phenyl)-5-fluoropyridine 1-oxide

To a stirred solution of 2-(2-bromo-5-(trifluoromethyl) phenyl)-5-fluoropyridine (0.50 g, 1.56 mmol) in CHCl$_3$ (10 ml), m-CPBA (0.59 g, 3.44 mmol) was added and reaction mixture was heated at 45° C. for 4 h. After completion of reaction, reaction mixture was conc. under vacuum. The crude was purified by column chromatography to obtain title compound (0.40 g, 76%). LCMS (ESI): m/z 336.03 & 337.78 (M+H)⁺.

Intermediate-59: Perfluorophenyl 4-(2-(5-fluoropyridin-2-yl)-4-(trifluoromethyl)phenyl)chroman-7-sulfonate

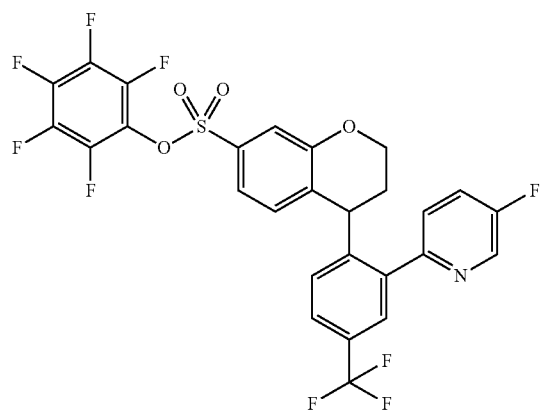 [SMILES: O=S(=O)(Oc1c(F)c(F)c(F)c(F)c1F)c1ccc2c(c1)OCCC2c1ccc(C(F)(F)F)cc1-c1ccc(F)cn1]

The title compound was prepared by following the similar procedure as described in Intermediate-6 using Intermediate-4 and Intermediate-58. LCMS (ESI): m/z 620.02 (M+H)+.

Intermediate-60: (R&S)-perfluorophenyl 4-(2-bromo-4-(trifluoromethyl)phenyl)chroman-7-sulfonate

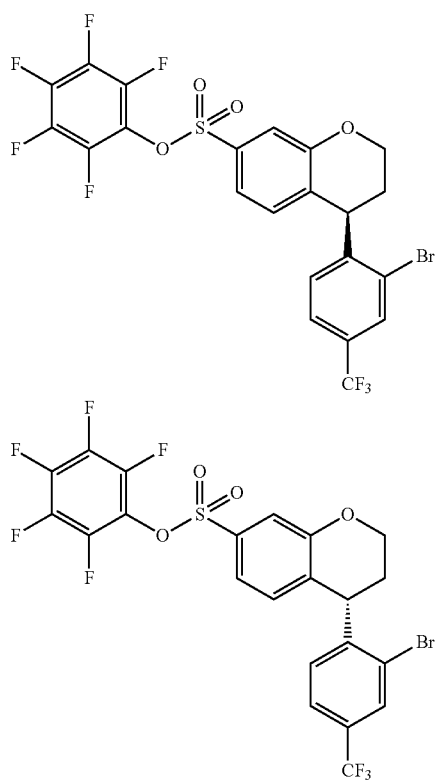

Step-1: Perfluorophenyl 4-(2-nitro-4-(trifluoromethyl)phenyl)-2H-chromene-7-sulfonate

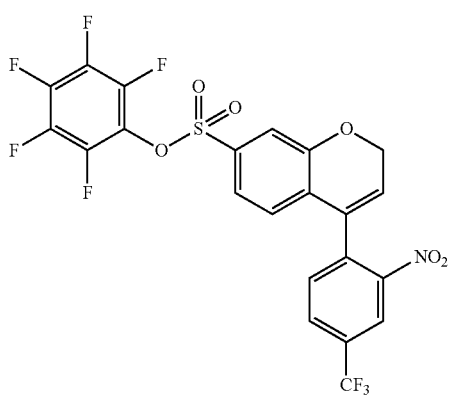 [SMILES: O=[N+]([O-])c1cc(C(F)(F)F)ccc1C1=CCOc2cc(S(=O)(=O)Oc3c(F)c(F)c(F)c(F)c3F)ccc21]

A stirred suspension of 1-bromo-2-nitro-4-(trifluoromethyl)benzene (10 g, 37.0 mmol), perfluorophenyl 4-(2-tosylhydrazono)chroman-7-sulfonate (22.92 g, 40.7 mmol) and Na$_2$CO$_3$ (11.78 g, 111 mmol) in 1,4-Dioxane (210 ml)/Water (35 ml) was degassed using nitrogen for 20 min. then PdCl$_2$(dppf)-CH$_2$Cl$_2$ adduct (3.02 g, 3.70 mmol) was added and reaction was heated at 100° C. for 1 h. After completion of reaction as indicated by TLC, reaction mixture was poured into water and extracted with ethyl acetate. The combined organic layer was washed with water, brine dried over Na$_2$SO$_4$ and concentrated under vacuum. The crude product was purified by column chromatography to obtain title compound as yellow thick mass (14.0 g, 66%). LCMS(ESI): m/z 590.00 (M+H)+; $^1$H NMR (400 MHz, Chloroform-d) δ 8.42-8.38 (m, 1H), 8.04-7.98 (m, 1H), 7.62 (d, J=7.9 Hz, 1H), 7.49 (d, J=1.9 Hz, 1H), 7.38 (dd, J=8.1, 2.0 Hz, 1H), 6.72 (d, J=8.1 Hz, 1H), 5.99 (t, J=3.7 Hz, 1H), 5.15-5.02 (m, 2H).

Step-2: Perfluorophenyl 4-(2-amino-4-(trifluoromethyl)phenyl)chroman-7-sulfonate

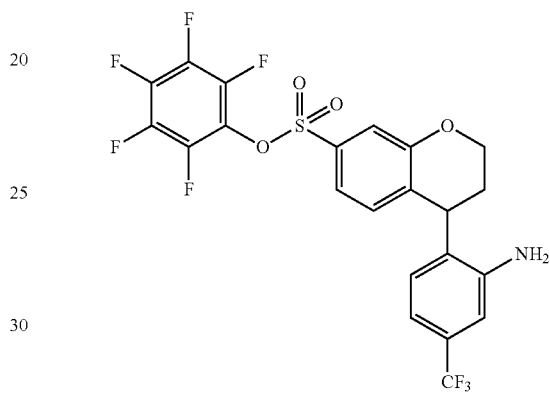

A stirred suspension of perfluorophenyl 4-(2-nitro-4-(trifluoromethyl)phenyl)-2H-chromene-7-sulfonate (14 g, 24.68 mmol) and 10% Pd—C (13.13 g, 123 mmol) in ethyl acetate (150 ml) was kept under hydrogen balloon gas pressure for 48 h. After completion of reaction as indicated by LCMS, reaction mixture was filtered through celite bed and concentrated under vacuum. The crude was purified by column chromatography to obtain title compound (11.50 g, 86%). LCMS(ESI): m/z 540.01 (M+H)+; $^1$H NMR (400 MHz, DMSO-d$_6$) δ 7.46-7.39 (m, 2H), 7.17 (d, J=7.9 Hz, 1H), 7.03 (d, J=1.9 Hz, 1H), 6.73 (dd, J=8.2, 1.9 Hz, 1H), 6.58 (d, J=8.0 Hz, 1H), 5.75 (brs, 2H), 4.54 (t, J=5.6 Hz, 1H), 4.33-4.23 (m, 1H), 4.15-4.06 (m, 1H), 2.24-2.17 (m, 1H), 2.06-1.97 (m, 1H).

Step-3: (S/R)-perfluorophenyl 4-(2-bromo-4-(trifluoromethyl)phenyl)chroman-7-sulfonate

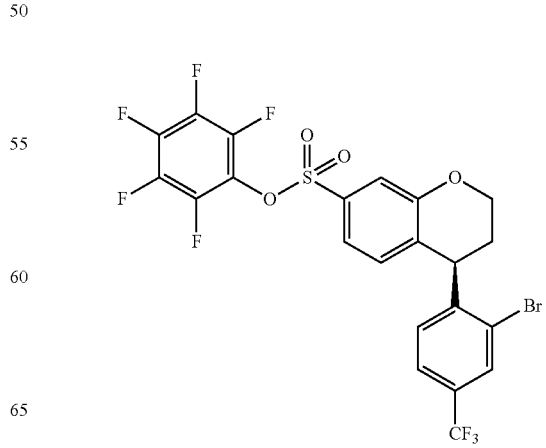

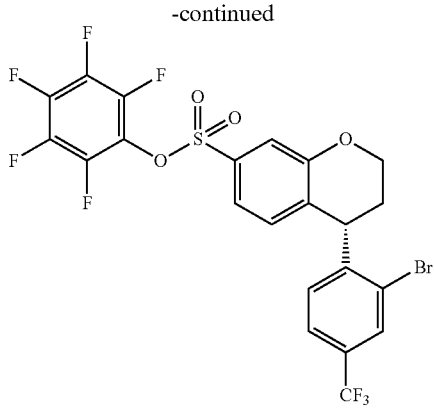

To a stirred suspension of Cu(II)Br (1.86 g, 8.34 mmol) and perfluorophenyl 4-(2-amino-4-(trifluoromethyl)phenyl)chroman-7-sulfonate (9 g, 16.69 mmol) in acetonitrile (90 ml) was added tert-butyl nitrite (3.76 ml, 25.03 mmol) at 70° C. This was stirred for 1 h at 70° C. After completion of reaction as indicated by TLC, Saturated solution of ammonium chloride was added to the reaction mixture and extracted with ethyl acetate. The combined organic layer was washed with brine, dried over Na$_2$SO$_4$ and concentrated under vacuum. The crude was purified by column chromatography to obtain title compound as a mixture of isomers (3.2 g, 32%).

Further the enantiomers were separated using chiral preparative HPLC (Column: ChiralPak IA; Mobile phase: A=(Hexane+0.1% DEA), B=(IPA), A:B=90:10, to afford isomer-1 and isomer-2. These isomers were obtained at retention time 6.75 (Intermediate-60a) min and retention time 7.81 (Intermediate-60b) min.

Intermediate-61: (R/S)-perfluorophenyl 4-(2-(6-methylpyridin-3-yl)-4-(trifluoromethyl)phenyl)chroman-7-sulfonate

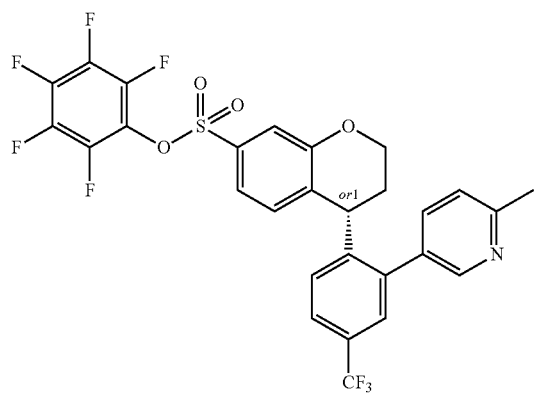

A stirred suspension of Intermediate-60b (0.70 g, 1.160 mmol), 2-methyl-5-(4,4,5,5-tetramethyl-1,3,2-dioxaborolan-2-yl)pyridine (0.64 g, 2.90 mmol) and Na$_2$CO$_3$ (0.25 g, 2.321 mmol) in 1,4-dioxane (10 ml)/water (1.0 ml) was degassed for 15 min using nitrogen then PdCl$_2$(dppf)-CH$_2$Cl$_2$ adduct (0.095 g, 0.116 mmol) was added and heated at 100° C. for 2 h. After completion of reaction as indicated by TLC, reaction mixture was poured into water and extracted with ethyl acetate. The combined organic layer was washed with water, brine dried over Na$_2$SO$_4$ and concentrated under vacuum. The crude product was purified by column chromatography to obtain title compound (0.65 g, 91%). LCMS (ESI): m/z 516.11 (M+H)$^+$;

Intermediate-62: 3-(2-iodo-5-(trifluoromethyl)phenyl)oxazolidin-2-one

Step-1: 3-(2-amino-5-(trifluoromethyl)phenyl)oxazolidin-2-one

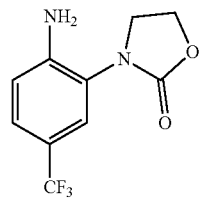 [SMILES: Nc1ccc(C(F)(F)F)cc1N1CCOC1=O]

2-bromo-4-(trifluoromethyl)aniline (4 g, 16.67 mmol), oxazolidin-2-one (3.63 g, 41.7 mmol), N1,N2-dimethylethane-1,2-diamine (0.88 g, 10.00 mmol), cesium carbonate (13.57 g, 41.7 mmol) and copper(I) iodide (1.27 g, 6.67 mmol) was added to degassed 1,4-dioxane (20 ml) and heated reaction mixture in sealed tube at 110° C. for 12 h. After the solution was cooled, the mixture was passed through a pad of celite and the filtrate was extracted with ethyl acetate. The ethyl acetate layer was washed with brine, dried over Na$_2$SO$_4$ and conc. The crude was purified by column chromatography to obtain title compound (1.2 g, 29%). LCMS (ESI): m/z 246.99 (M+H)$^+$.

Step-2: 3-(2-iodo-5-(trifluoromethyl)phenyl)oxazolidin-2-one

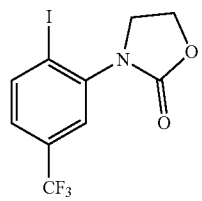 [SMILES: O=C1OCCN1c1cc(C(F)(F)F)ccc1I]

3-(2-amino-5-(trifluoromethyl)phenyl)oxazolidin-2-one (1.2 g, 4.87 mmol) was dissolved into acetonitrile (20 ml) & water (5 ml) followed by the addition of 4-methylbenzenesulfonic acid (3.36 g, 19.50 mmol) into it. KI (2.02 g, 12.19 mmol) and sodium nitrate (0.82 g, 9.75 mmol) in water (5 ml) was added to the reaction mixture slowly at −5 to 0° C. Reaction mixture was stirred at −5 to 0° C. for 1.5 h then quenched by addition of water and extracted with ethyl acetate. The combined organic layer was washed with brine, dried over Na$_2$SO$_4$ and concentrated. The crude was purified by column chromatography to obtain title compound. $^1$H NMR (400 MHz, Chloroform-d) δ 8.09 (d, J=8.2 Hz, 1H), 7.64 (d, J=2.1 Hz, 1H), 7.36 (dd, J=8.2, 2.1 Hz, 1H), 4.62 (t, J=7.9 Hz, 2H), 4.07 (t, J=7.9 Hz, 2H).

Intermediate-63a/63b: (R&S)-Perfluorophenyl 4-(2-(2-oxooxazolidin-3-yl)-4-(trifluoromethyl)phenyl)chroman-7-sulfonate

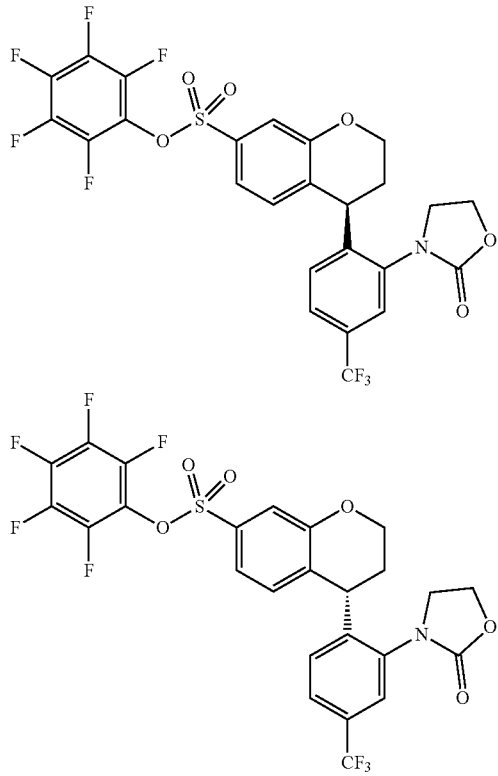

The title compound was prepared by following the similar procedure as described in Intermediate-6 using Intermediate-4 and Intermediate-62. LCMS (ESI): m/z 610.10 (M+H)$^+$.

Further the enantiomers were separated using chiral preparative HPLC (Column: ChiralPak IA; Mobile phase: A=(Hexane+0.1% TFA), B=(IPA), A:B=65:35, to afford isomer-1 and isomer-2. These isomers were obtained at retention time 5.59 min (Intermediate-63a) and retention time 6.51 min Intermediate-63b).

Intermediate-64: 1-bromo-2-(3,3-difluoropropyl)-4-(trifluoromethyl)benzene

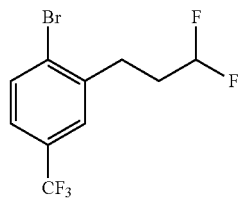

Step-1: 3-(2-bromo-5-(trifluoromethyl)phenyl)propanal

To a solution of ethyl 3-(2-bromo-5-(trifluoromethyl)phenyl)propanoate (1 g, 3.08 mmol) in toluene (10 ml), DIBAL-H (9.23 ml, 1M solution, 9.23 mmol) was added at −78° C. and stirred for 30 min. Reaction was monitored by TLC. After completion, the mixture was added to 2(N) HCl and extracted with ethyl acetate. The organic layer was collected and dried over Na$_2$SO$_4$, finally evaporated to get crude which was purified by column chromatography to obtain title compound (0.7 g, 81%). $^1$H NMR (400 MHz, Chloroform-d) δ 9.87 (s, 1H), 7.69 (dd, J=8.4, 4.6 Hz, 1H), 7.56-7.49 (m, 1H), 7.37 (dd, J=8.3, 2.2 Hz, 1H), 3.14 (t, J=7.5 Hz, 2H), 2.87 (t, 2H).

Step-2: 1-Bromo-2-(3,3-difluoropropyl)-4-(trifluoromethyl)benzene

To a solution of 3-(2-bromo-5-(trifluoromethyl)phenyl)propanal (0.7 g, 2.490 mmol) in DCM (10 ml) was added DAST (1.32 ml, 9.96 mmol) at 0° C. and reaction was allowed to warm to room temperature and stirred for 16 h. Reaction mixture was quenched slowly with sat NaHCO$_3$ and extracted with DCM. The combined organic layer was dried over Na$_2$SO$_4$ and concentrated. The crude was purified by column chromatography to obtain title compound (0.25 g, 33%). $^1$H NMR (400 MHz, Chloroform-d) δ 7.71 (d, J=8.3 Hz, 1H), 7.51 (d, J=2.2 Hz, 1H), 7.38 (dd, J=8.3, 2.2 Hz, 1H), 5.92 (tt, J=56.3, 4.2 Hz, 1H), 3.04-2.95 (m, 2H), 2.30-2.12 (m, 2H).

Intermediate-65a/65b: (R&S)-Perfluorophenyl 4-(2-(3,3-difluoropropyl)-4-(trifluoromethyl)phenyl)chroman-7-sulfonate

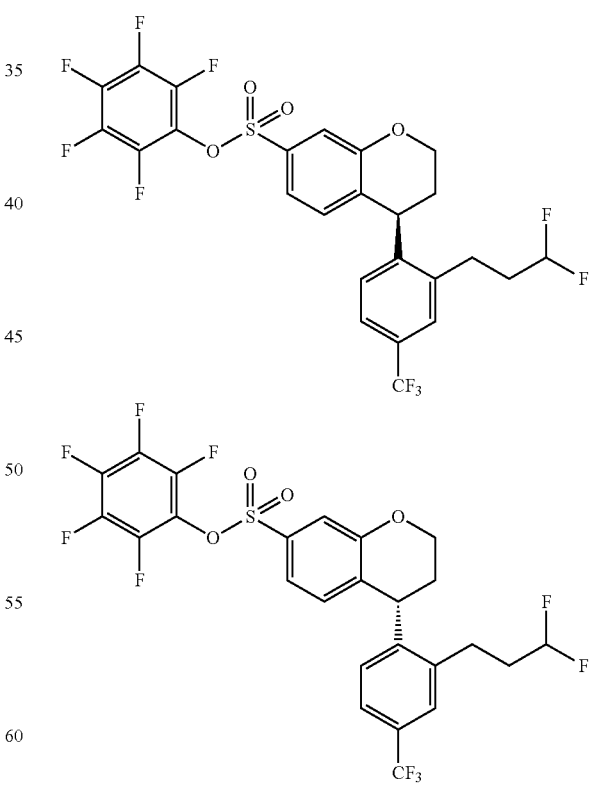

The title compound was prepared by following similar procedure as described in Intermediate-6 using Intermediate-4 and Intermediate-64. LCMS (ESI): m/z 625.09 (M+Na)$^+$;

Further the enantiomers were separated using chiral preparative HPLC (Column: ChiralPak IA; Mobile phase: A=(Hexane+0.1% TFA), B=IPA, A:B=80:20 to afford isomer 1 and isomer 2. These isomers were obtained at retention time: 5.02 min (Intermediate-65a) and retention time: 5.93 min (Intermediate-65b).

Intermediate-66:
3-(2-bromo-5-(trifluoromethyl)phenoxy)oxetane

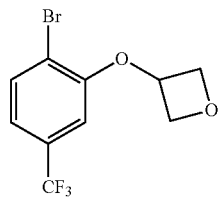

It was prepared similarly as shown in Intermediate-50 using 2-bromo-5-(trifluoromethyl)phenol and oxetan-3-ol. $^1$H NMR (400 MHz, Chloroform-d) δ 7.72 (d, J=8.2 Hz, 1H), 7.17 (dd, J=8.3, 1.9 Hz, 1H), 6.64 (d, J=1.9 Hz, 1H), 5.32 quintet, J=5.6 Hz, 1H), 5.09-5.01 (m, 2H), 4.91-4.83 (m, 2H).

Intermediate-67a/67b: (R&S)-Perfluorophenyl 4-(2-(oxetan-3-yloxy)-4-(trifluoromethyl)phenyl)chroman-7-sulfonate

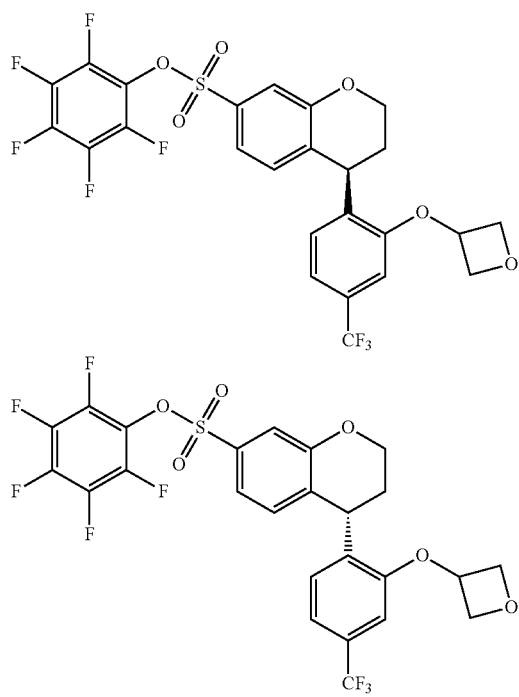

The title compound was prepared by following similar procedure as described for Intermediate-6 using Intermediate-4 and Intermediate-66. LCMS (ESI): m/z 619.03 (M+Na)$^+$;
Further the enantiomers were separated using chiral preparative HPLC (Column: ChiralPak IC; Mobile phase: A=(Hexane+0.1% DEA), B=IPA, A:B=60:40, to afford isomer-1 and isomer-2. These isomers were obtained at retention time 7.51 min (Intermediate-67a) and retention time 8.54 min (Intermediate-67b).

Intermediate-68: 2-bromo-1-(3-fluoropropoxy)-4-(trifluoromethyl)benzene

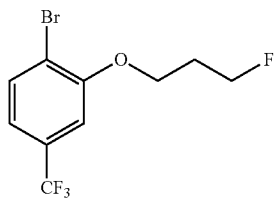 [SMILES: FCCCOc1cc(C(F)(F)F)ccc1Br]

3-(2-bromo-4-(trifluoromethyl)phenoxy)propan-1-ol (1 g, 3.34 mmol), was dissolved in DCM (10 ml) and DAST (0.701 g, 4.35 mmol) was added at 0° C. and stirred for 1 h. The reaction mixture was quenched by the addition of water and the reaction mixture was extracted with ethyl acetate. The ethyl acetate layer was dried over Na$_2$SO$_4$ and concentrated under vacuum. The crude product was purified by column chromatography to obtain the product as white gummy liquid (0.65 g, 64%). LCMS (ESI): m/z 300.05 & 302.05 (M+H)$^+$.

Intermediate-69: Perfluorophenyl 4-(2-(3-fluoropropoxy)-4-(trifluoromethyl)phenyl)chroman-7-sulfonate

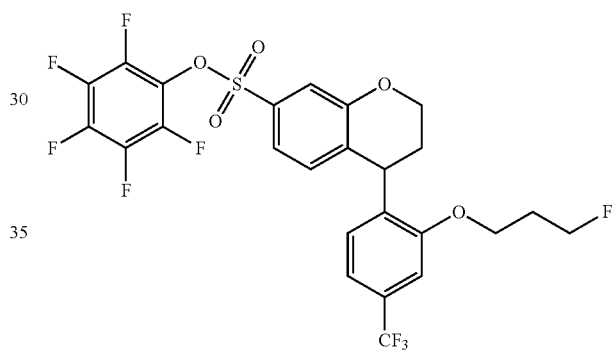

The title compound was prepared by following similar procedure as described for Intermediate-6 using Intermediate-4 and Intermediate-68. $^1$H NMR (400 MHz, Chloroform-d) δ 7.52 (d, J=2.0 Hz, 1H), 7.39 (dd, J=8.2, 2.0 Hz, 1H), 7.33-7.11 (m, 2H), 7.06 (d, J=8.1 Hz, 1H), 6.92 (d, J=7.9 Hz, 1H), 4.76-4.47 (m, 3H), 4.33-4.14 (m, 4H), 2.49-2.02 (m, 4H).

Intermediate-70: 6-(2-bromo-5-(trifluoromethyl)phenyl)-3-fluoro-2-methylpyridine

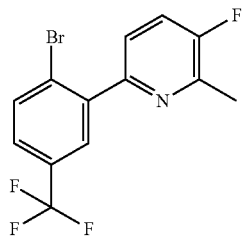 [SMILES: Cc1nc(-c2cc(C(F)(F)F)ccc2Br)ccc1F]

The title compound was prepared by following similar procedure as described in Intermediate-58 (Step-1 to 3) using 2-bromo-4-(trifluoromethyl)aniline and 6-bromo-3-fluoro-2-methylpyridine. $^1$H NMR (400 MHz, Chloroform-d) δ 7.88-7.76 (m, 2H), 7.58-7.35 (m, 3H), 2.64 (d, J=3.0 Hz, 3H).

Intermediate-71a/71b: (R&S)-Perfluorophenyl 4-(2-(5-fluoro-6-methylpyridin-2-yl)-4-(trifluoromethyl)phenyl)chroman-7-sulfonate

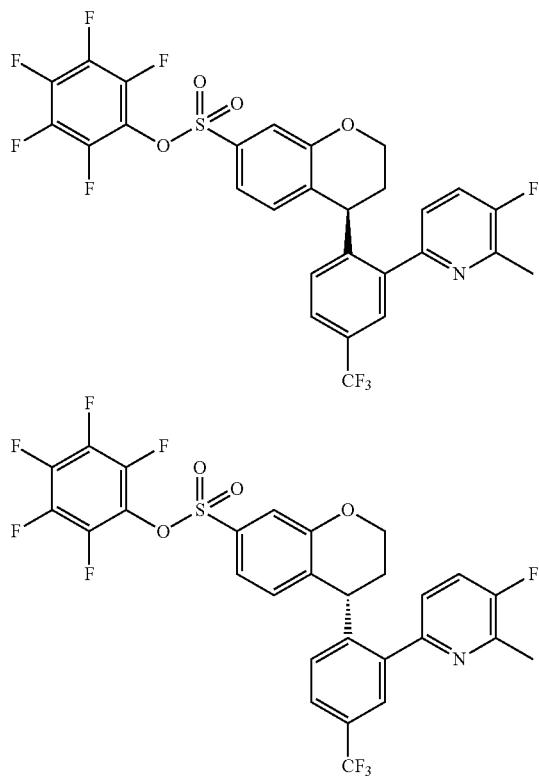

The title compound was prepared by following similar procedure as described in Intermediate-6 using Intermediate-4 and Intermediate-70.

Further the enantiomers were separated using chiral preparative HPLC (Column: ChiralPak IA; Mobile phase: A=Hexane, B=IPA, A:B=90:10, to afford isomer-1 and isomer-2. These isomers were obtained at retention time 5.33 min (Intermediate-71a) and retention time 6.82 min (Intermediate-71b).

$^1$H NMR (400 MHz, Chloroform-d) δ 7.68 (d, J=2.0 Hz, 1H), 7.61 (dd, J=8.1, 2.0 Hz, 1H), 7.53-7.46 (m, 2H), 7.41-7.32 (m, 2H), 7.16-7.03 (m, 2H), 4.70 (t, J=8.2, 6.2 Hz, 1H), 4.42-4.32 (m, 1H), 4.25-4.15 (m, 1H), 2.59 (d, J=2.9 Hz, 3H), 2.44-2.32 (m, 1H), 2.28-2.15 (m, 1H).

Intermediate-72: Perfluorophenyl 4-(2-methoxy-4-(trifluoromethyl)phenyl)chroman-7-sulfonate

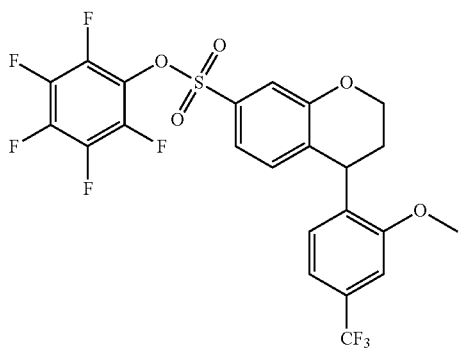 [SMILES: COc1cc(C(F)(F)F)ccc1C1CCOc2cc(S(=O)(=O)Oc3c(F)c(F)c(F)c(F)c3F)ccc21]

The title compound was prepared by following similar procedure as described in Intermediate-6 using Intermediate-4 and 1-bromo-2-methoxy-4-(trifluoromethyl)benzene.
$^1$H NMR (400 MHz, Chloroform-d) δ 7.51 (d, J=2.0 Hz, 1H), 7.38 (dd, J=8.1, 2.0 Hz, 1H), 7.22-7.12 (m, 2H), 7.05 (d, J=8.1 Hz, 1H), 6.87 (d, J=7.8 Hz, 1H), 4.68 (t, J=6.0 Hz, 1H), 4.34-4.18 (m, 2H), 3.94 (s, 3H), 2.41-2.26 (m, 1H), 2.27-2.13 (m, 1H).

Intermediate-73: 4-(2-Bromo-5-(trifluoromethyl)phenyl)morpholin-3-one

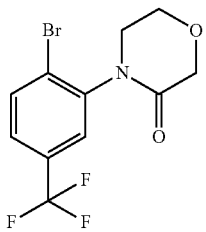 [SMILES: O=C1COCCN1c1cc(C(F)(F)F)ccc1Br]

The title compound was prepared by following similar procedure as described for Intermediate-32 using 2-fluoro-1-nitro-4-(trifluoromethyl)benzene and morpholin-3-one.
$^1$H NMR (400 MHz, Chloroform-d) δ 7.85 (d, J=8.4 Hz, 1H), 7.62-7.49 (m, 2H), 4.41 (s, 2H), 4.15-4.07 (m, 2H), 3.72 (t, J=5.0 Hz, 2H).

Intermediate-74: Perfluorophenyl 4-(2-(3-oxomorpholino)-4-(trifluoromethyl)phenyl)chroman-7-sulfonate

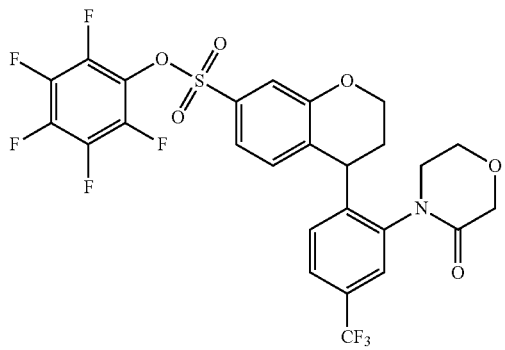 [SMILES: O=C1COCCN1c1cc(C(F)(F)F)ccc1C1CCOc2cc(S(=O)(=O)Oc3c(F)c(F)c(F)c(F)c3F)ccc21]

The title compound was prepared by following similar procedure as described in Intermediate-6 using Intermediate-4 and Intermediate-73. LCMS (ESI): m/z 624.06 (M+H)$^+$.

Intermediate-75: 4-(2-bromo-5-(trifluoromethyl)phenyl)thiomorpholine 1,1-dioxide

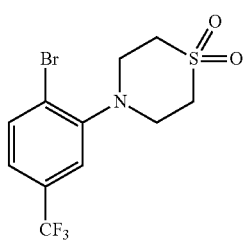 [SMILES: O=S1(=O)CCN(c2cc(C(F)(F)F)ccc2Br)CC1]

Step-1: 4-(2-nitro-5-(trifluoromethyl)phenyl)thiomorpholine

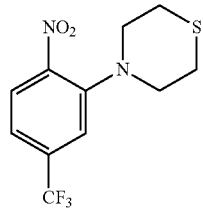

The title compound was prepared by following similar procedure as described in Intermediate-32 (Step-1) using 2-fluoro-1-nitro-4-(trifluoromethyl)benzene and thiomorpholine. LCMS (ESI): m/z 292.88 (M+H)$^+$.

Step-2: 4-(2-nitro-5-(trifluoromethyl)phenyl)thiomorpholine 1,1-dioxide

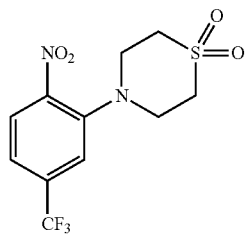

To a solution of 4-(2-nitro-5-(trifluoromethyl)phenyl)thiomorpholine (6.3 g, 21.55 mmol) in MeOH (50 ml) was added solution of OXONE (26.6 g, 86 mmol) in water (50 ml) at room temperature and stirred for 12 h. After completion of reaction, as indicated by TLC, solvent was removed and extracted with ethyl acetate. The organic phase was washed with brine, dried over $Na_2SO_4$ and concentrated to obtain title compound (5.5 g, 79%). $^1$H NMR (400 MHz, Chloroform-d) δ 7.95 (d, J=8.7 Hz, 1H), 7.60-7.49 (m, 2H), 3.71-3.54 (m, 4H), 3.34-3.18 (m, 4H).

Step-3: 4-(2-bromo-5-(trifluoromethyl)phenyl)thiomorpholine 1,1-dioxide

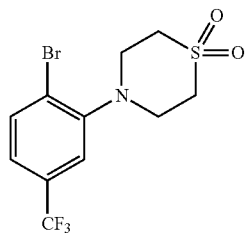 [SMILES: O=S1(=O)CCN(c2cc(C(F)(F)F)ccc2Br)CC1]

The title compound was prepared by following similar procedure as described in Intermediate-32 (Step-2&3).

$^1$H NMR (400 MHz, Chloroform-d) δ 7.75 (d, J=8.3 Hz, 1H), 7.36-7.25 (m, 2H), 3.64-3.56 (m, 4H), 3.34-3.27 (m, 4H).

Intermediate-76a/76b: (R&S)-Perfluorophenyl 4-(2-(1,1-dioxidothiomorpholino)-4-(trifluoromethyl)phenyl)chroman-7-sulfonate

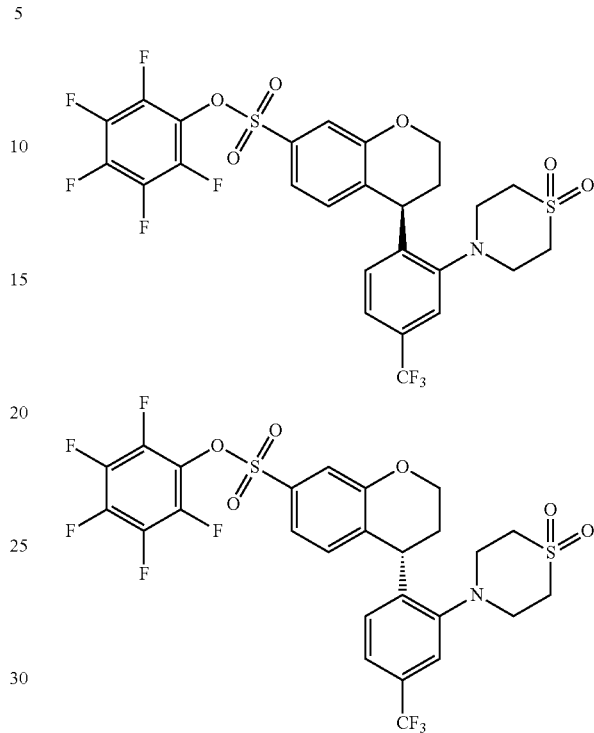

The title compounds were prepared by following similar procedure as described in Intermediate-6 using Intermediate-4 and Intermediate-75.

Further the enantiomers were separated using chiral preparative HPLC (Column: ChiralPak IC; Mobile phase: A=(Hexane+0.1% DEA), B=(IPA:DCM=1:1), A:B=30:70, to afford isomer-1 and isomer-2. These isomers were obtained at retention time 5.94 min (Intermediate-76a) and retention time 7.17 min (Intermediate-76b).

$^1$H NMR (400 MHz, Chloroform-d) δ 7.59 (s, 1H), 7.55 (d, J=1.9 Hz, 1H), 7.50-7.44 (m, 1H), 7.37 (dd, J=8.2, 1.9 Hz, 1H), 7.08 (d, J=8.2 Hz, 1H), 6.87 (d, J=8.2 Hz, 1H), 4.77 (d, J=7.6 Hz, 1H), 4.46-4.26 (m, 2H), 3.65-3.34 (m, 4H), 3.31-3.08 (m, 4H), 2.41-2.12 (m, 2H).

Intermediate-77: (4-chloro-2-(1-methyl-1H-pyrazol-5-yl)phenyl)boronic acid

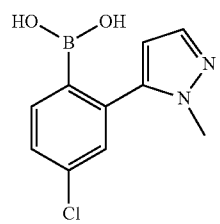 [SMILES: Cn1nccc1-c1cc(Cl)ccc1B(O)O]

Step-1: 4-chloro-2-(1-methyl-1H-pyrazol-5-yl)aniline

A solution of N-(2-bromo-4-chlorophenyl)acetamide (6 g, 24.14 mmol) and 1-methyl-5-(4,4,5,5-tetramethyl-1,3,2-dioxaborolan-2-yl)-1H-pyrazol (7.54 g, 36.2 mmol) in 1,4-dioxane (80 ml):water (15 ml) was purged with nitrogen for 5 min. after which potassium phosphate (12.81 g, 60.4 mmol) and PdCl$_2$(dppf).DCM adduct (1.76 g, 2.414 mmol) was added and reaction was stirred for 4 h at 100° C. Reaction was monitored by TLC. After completion, the reaction mixture was poured in to water and extracted with ethyl acetate. The organic layer was collected and dried over Na$_2$SO$_4$, finally evaporated to get crude which was heated with 60 ml conc. HCl for hydrolysis. After completion as shown by TLC the mixture was evaporated to dryness. The crude material was dissolved in water and basified with saturated sodium carbonate. The layer was extracted with ethyl acetate. The organic layer was collected and washed with brine, dried over Na$_2$SO$_4$ and evaporated. The crude was purified by column chromatography to obtain title compound (2.5 g, 50%). LCMS (ESI): m/z 249.91 (M+H)$^+$.

Step-2: 5-(2-bromo-5-chlorophenyl)-1-methyl-1H-pyrazole

The title compound was prepared by following similar procedure as described for Intermediate-5 (Step-2)$^1$H NMR (400 MHz, Chloroform-d) δ 7.64 (d, J=8.5 Hz, 1H), 7.57 (d, J=2.0 Hz, 1H), 7.42-7.28 (m, 2H), 6.30 (d, J=1.9 Hz, 1H), 3.75 (s, 3H).

Step-3: (4-chloro-2-(1-methyl-1H-pyrazol-5-yl)phenyl)boronic acid 5-(2-bromo-5-chlorophenyl)-1-methyl-1H-pyrazole (3 g, 11.05 mmol) and triisopropyl borate (3.08 ml, 13.26 mmol) was dissolved in diethyl ether (25 ml) and the solution was cooled to −78° C. n-BuLi (8.29 ml, 1.6 M, 13.26 mmol) was added to this mixture drop wise. Following the addition, the cooling bath was removed after 30 min, and the mixture was warmed to room temperature. An aq. 2N NaOH solution (20 ml, 40 mmol) was added, and the resulting mixture was stirred vigorously for 1 h. The mixture was diluted with water and diethyl ether. The layers were separated, and the ethereal layer was extracted with water. The combined aqueous layer was acidified with 3N aq. HCl and was extracted with ethyl acetate. The combined organic extracts were dried over Na$_2$SO$_4$, and concentrated to obtain the product as a pale yellow fluffy solid (1.5 g, 63%). $^1$H NMR (400 MHz, Chloroform-d) δ 7.95 (d, J=8.2 Hz, 1H), 7.61-7.38 (m, 3H), 6.36 (d, J=10.5 Hz, 1H), 3.47 (s, 3H).

Intermediate-78: 2-allyl-1-bromo-4-(trifluoromethyl)benzene

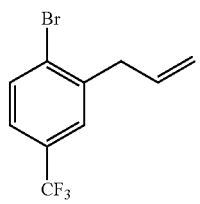

It was prepared from 2-allyl-4-(trifluoromethyl)aniline (*Org Lett*, 2012, 14(12), 3048-3051) by following similar procedure as described in Intermediate-21 (Step-2). $^1$H NMR (400 MHz, Chloroform-d) δ 7.81-7.66 (m, 1H), 7.50 (d, J=2.3 Hz, 1H), 7.48-7.32 (m, 1H), 5.98 (ddt, J=16.8, 10.1, 6.5 Hz, 1H), 5.21 (dq, J=10.1, 1.5 Hz, 1H), 5.14 (dq, J=17.1, 1.7 Hz, 1H), 3.69-3.49 (m, 2H).

Intermediate-79: Perfluorophenyl 4-(2-propyl-4-(trifluoromethyl)phenyl)chroman-7-sulfonate

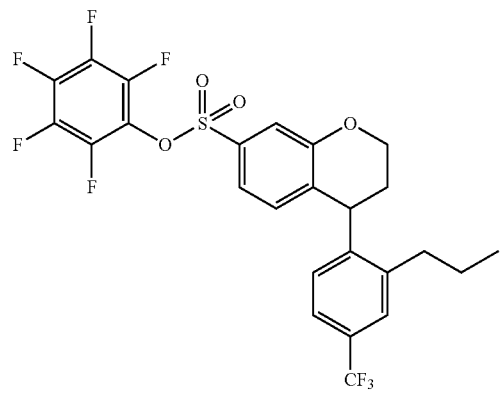 [SMILES: CCCc1cc(C(F)(F)F)ccc1C1CCOc2cc(S(=O)(=O)Oc3c(F)c(F)c(F)c(F)c3F)ccc21]

The title compound was prepared by following similar procedure as described in Intermediate-6 using Intermediate-4 and Intermediate-78. $^1$H NMR (400 MHz, Chloroform-d) δ 7.55-7.50 (m, 2H), 7.44-7.32 (m, 2H), 6.98-6.88 (m, 2H), 4.57 (t, J=6.9 Hz, 1H), 4.42-4.27 (m, 2H), 2.89-2.68 (m, 2H), 2.42-2.32 (m, 1H), 2.22-2.05 (m, 1H), 1.83-1.67 (m, 2H), 1.08 (t, J=7.3 Hz, 3H).

EXAMPLES

Example-1 and 2: (S)—N-(6-Fluoropyridin-2-yl)-4-(2-(1-methyl-1H-pyrazol-5-yl)-4-(trifluoromethyl)phenyl)chroman-7-sulfonamide and (R)—N-(6-Fluoropyridin-2-yl)-4-(2-(1-methyl-1H-pyrazol-5-yl)-4-(trifluoromethyl)phenyl)chroman-7-sulfonamide

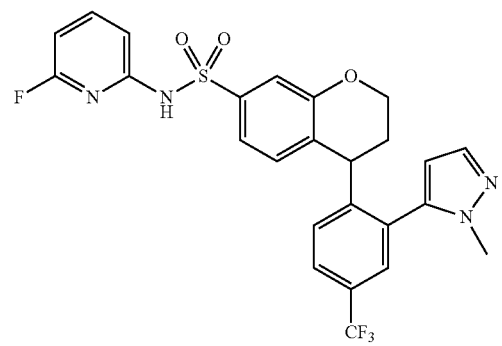 [SMILES: Cn1nccc1-c1cc(C(F)(F)F)ccc1C1CCOc2cc(S(=O)(=O)Nc3cccc(F)n3)ccc21]

6-Fluoropyridin-2-amine (0.11 g, 0.993 mmol) was dissolved in THF (10 ml) and lithium bis(trimethylsilyl)amide (LiHMDS) (0.943 ml, 1M in THF, 0.943 mmol) was added to it. After 10 min a solution of Intermediate-3 (0.30 g, 0.496 mmol) in THF was added and the dark red reaction mixture was allowed to stir at room temperature for 1.5 h. After completion of the reaction, it was quenched with a saturated solution of NH$_4$Cl and the reaction mixture was extracted with ethyl acetate. The ethyl acetate layer was washed with a 1N HCl solution and then dried over Na$_2$SO$_4$ and concentrated. The crude was purified by column chromatography to obtain the product as a white solid (0.25 g, 96%).

Further the enantiomers were separated using chiral preparative HPLC (Column: Chiral pak IE; Mobile phase: A=(Hexane+0.1% TFA), B=(EtOH:MeOH=1:1), A:B=50:50, to afford isomer-1 and isomer-2. These isomers were obtained at retention time: 5.42 min (Example-1) and retention time 6.25 min (Example-2) and the absolute stereochemistry was assigned to be S and R, respectively, using vibrational circular dichroism (VCD) spectra. The compound having alpha configuration provided better in vitro activity against $Na_V1.7$.

Example-1

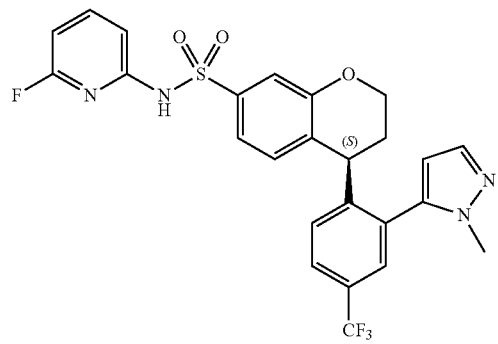

Example-2

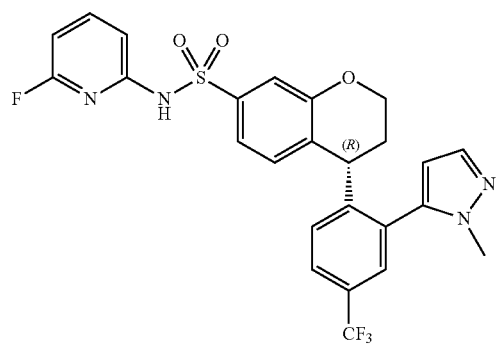

LCMS(ESI): m/z 533.07 (M+H)$^+$; $^1$H NMR (400 MHz, DMSO-d6) δ 11.39 (s, 1H), 7.86-7.74 (m, 3H), 7.52 (d, J=1.9 Hz, 1H), 7.35-7.24 (m, 3H), 6.92 (dd, J=13.6, 8.1 Hz, 2H), 6.71 (d, J=8.0 Hz, 1H), 6.42 (s, 1H), 4.30-4.15 (m, 1H), 4.19-4.08 (m, 2H), 3.69 (s, 3H), 2.18-2.08 (m, 1H), 2.02-1.90 (m, 1H).

Example-3/4: (S&R)—N-(4-Fluoropyridin-2-yl)-4-(2-(1-methyl-1H-pyrazol-5-yl)-4-(trifluoromethyl)phenyl)chroman-7-sulfonamide

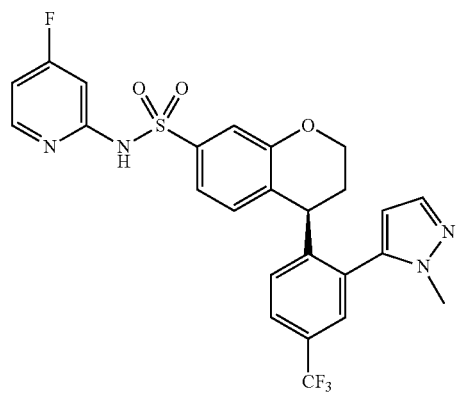

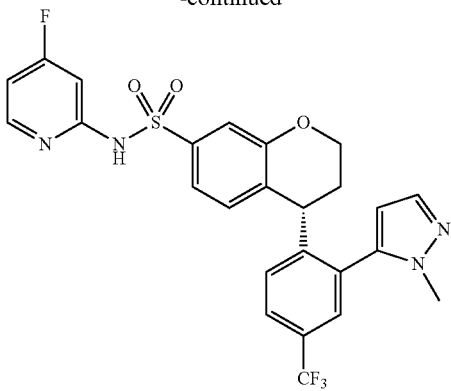

The title compounds were prepared by following the similar procedure as described in Example-1/2 using Intermediate-3 and 4-fluoropyridin-2-amine.

Further the enantiomers were separated using chiral preparative HPLC (Column: ChiralPak IA; Mobile phase: A=(Hexane+0.1% TFA), B=EtOH, A:B=50:50, to afford isomer-1 and isomer-2. These isomers were obtained at retention time: 5.90 min (Example-3) and retention time 7.61 min (Example-4).

LCMS(ESI): m/z 533.07 (M+H)$^+$; $^1$H NMR (400 MHz, DMSO-d6) δ 8.13 (s, 1H), 7.82-7.70 (m, 2H), 7.53 (d, J=1.9 Hz, 1H), 7.27 (d, J=7.3 Hz, 3H), 6.96-6.80 (m, 3H), 6.44 (s, 1H), 4.28-4.19 (m, 1H), 4.20-4.10 (m, 2H), 3.69 (s, 3H), 2.19-2.07 (m, 1H), 2.03-1.89 (m, 1H).

Example-5/6: (S&R)—N-(5-Fluoropyridin-2-yl)-4-(2-(1-methyl-1H-pyrazol-5-yl)-4-(trifluoromethyl)phenyl)chroman-7-sulfonamide

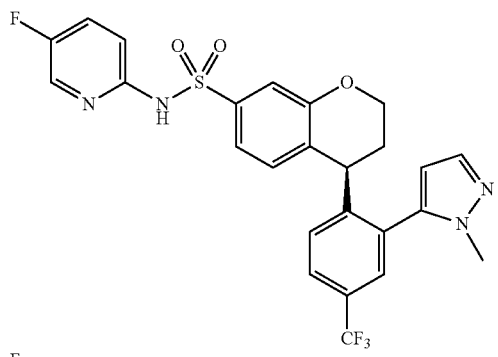

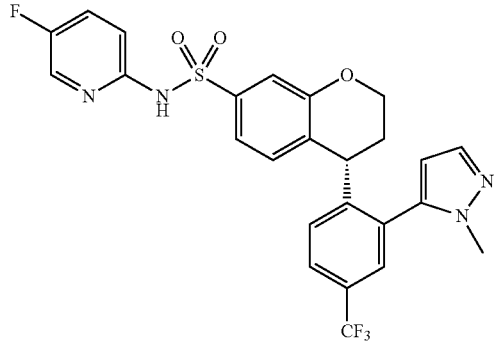

The title compounds were prepared by following the similar procedure as described in Example-1/2 using Intermediate-3 and 5-fluoropyridin-2-amine.

Further the enantiomers were separated using chiral preparative HPLC (Column: ChiralPak IA; Mobile phase: A=(Hexane+0.1% TFA), B=(EtOH:DCM=1:1), A:B=60:40, to afford isomer-1 and isomer-2. These isomers were obtained at retention time 5.83 min (Example-5) and retention time 7.07 min (Example-6).

LCMS(ESI): m/z 533.06 (M+H)+; 1H NMR (400 MHz, DMSO-d6) δ 11.13 (s, 1H), 8.21 (d, J=3.0 Hz, 1H), 7.81-7.73 (m, 2H), 7.68 (dt, J=8.6, 5.1 Hz, 1H), 7.53 (s, 1H), 7.32-7.23 (m, 3H), 7.17-7.07 (m, 1H), 6.88 (d, J=8.1 Hz, 1H), 6.42 (s, 1H), 4.27-4.18 (m, 1H), 4.18-4.10 (m, 2H), 3.69 (s, 3H), 2.17-2.07 (m, 1H), 2.04-1.91 (m, 1H).

Example-7/8: (S&R)—N-(5-Fluoropyrimidin-2-yl)-4-(2-(1-methyl-1H-pyrazol-5-yl)-4-(trifluoromethyl)phenyl)chroman-7-sulfonamide

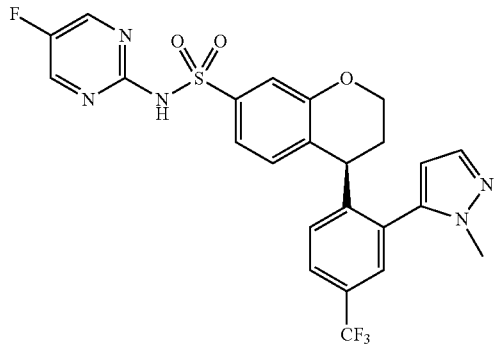

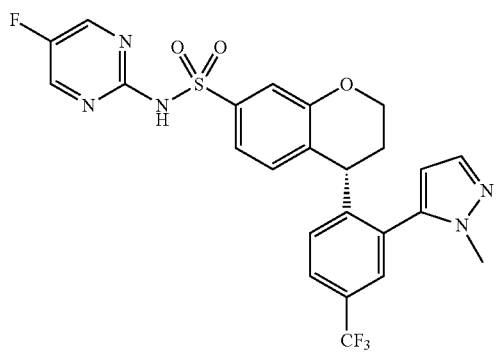

The title compounds were prepared by following the similar procedure as described in Example-1/2 using Intermediate-3 and 5-Fluoropyrimidin-2-amine.

Further the enantiomers were separated using chiral preparative HPLC (Column: ChiralPak IA; Mobile phase: A=(Hexane+0.1% TFA), B=(EtOH:DCM=1:1), A:B=60:40, to afford isomer-1 and isomer-2. These isomers were obtained at retention time 5.69 min (Example-7) and retention time 6.91 min (Example-8).

LCMS(ESI): m/z 534.07 (M+H)+; 1H NMR (400 MHz, DMSO-d6) δ 11.88 (s, 1H), 8.65 (s, 2H), 7.83-7.70 (m, 2H), 7.53 (d, J=1.8 Hz, 1H), 7.36 (d, J=7.1 Hz, 2H), 7.28 (d, J=8.2 Hz, 1H), 6.90 (d, J=8.1 Hz, 1H), 6.44 (s, 1H), 4.29-4.19 (m, 1H), 4.20-4.07 (m, 2H), 3.69 (s, 3H), 2.18-2.08 (m, 1H), 2.03-1.94 (m, 1H).

Example-9/10: (S&R)-4-(2-(1-Methyl-1H-pyrazol-5-yl)-4-(trifluoromethyl)phenyl)-N-(pyrimidin-4-yl)chroman-7-sulfonamide

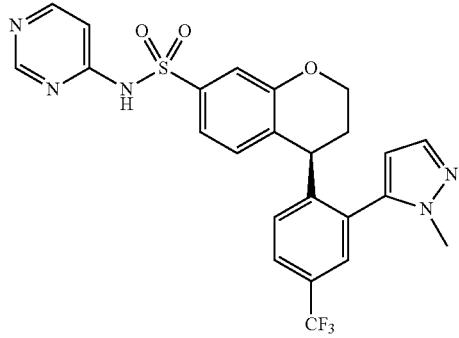

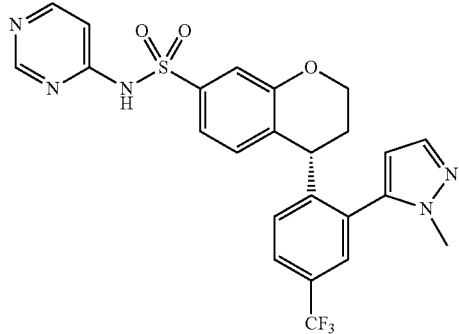

The title compounds were prepared by following the similar procedure as described in Example-1/2 using Intermediate-3 and pyrimidin-4-amine.

Further the enantiomers were separated using chiral preparative HPLC (Column: ChiralPak IA; Mobile phase: A=(Hexane+0.1% TFA), B=(EtOH:DCM=1:1), A:B=60:40, to afford isomer-1 and isomer-2. These isomers were obtained at retention time 5.40 min (Example-9) and retention time 6.68 min (Example-10).

LCMS(ESI): m/z 516.06 (M+H)+; 1H NMR (400 MHz, DMSO-d6) δ 8.65 (s, 1H), 8.36 (d, J=6.3 Hz, 1H), 7.86-7.72 (m, 2H), 7.53 (s, 1H), 7.36-7.24 (m, 3H), 7.05 (d, J=6.2 Hz, 1H), 6.88 (d, J=8.5 Hz, 1H), 6.44 (s, 1H), 4.28-4.20 (m, 1H), 4.20-4.06 (m, 2H), 3.69 (s, 3H), 2.21-2.05 (m, 1H), 2.05-1.91 (m, 1H).

Example-11/12: (S&R)-4-(2-(1-Methyl-1H-pyrazol-5-yl)-4-(trifluoromethyl)phenyl)-N-(pyrazin-2-yl)chromane-7-sulfonamide

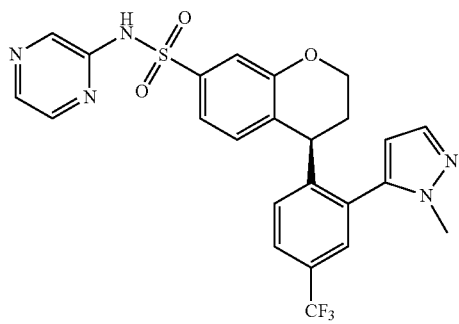

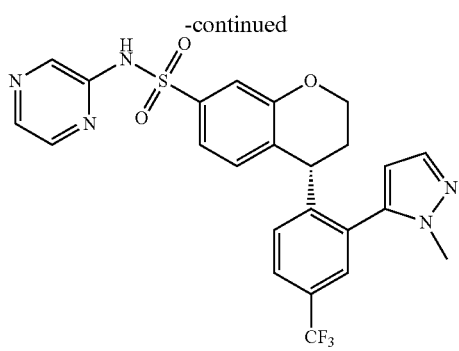

The title compounds were prepared by following the similar procedure as described in Example-1/2 using Intermediate-3 and pyrazin-2-amine.

Further the enantiomers were separated using chiral preparative HPLC (Column: ChiralPak ID; Mobile phase: A=(EtOH+0.1% TFA), B=(MeOH+0.1% TFA), A:B=90:10, to afford isomer-1 and isomer-2. These isomers were obtained at retention time 9.90 min (Example-11) and retention time 11.37 min (Example-12).

LCMS: m/z 516.04 (M+H)$^+$; $^1$H NMR (400 MHz, DMSO-d6) δ 11.59 (s, 1H), 8.33 (s, 1H), 8.22 (d, J=4.5 Hz, 2H), 7.81-7.73 (m, 2H), 7.52 (d, J=1.8 Hz, 1H), 7.33 (d, J=7.6 Hz, 2H), 7.27 (d, J=8.2 Hz, 1H), 6.89 (d, J=8.0 Hz, 1H), 6.43 (s, 1H), 4.23 (dt, J=9.6, 4.2 Hz, 1H), 4.18-4.11 (m, 2H), 3.69 (s, 3H), 2.17-2.08 (m, 1H), 2.00-1.92 (m, 1H).

Example-13/14: (S&R)-4-(2-(1-Methyl-1H-pyrazol-5-yl)-4-(trifluoromethyl)phenyl)-N-(pyridazin-3-yl)chromane-7-sulfonamide

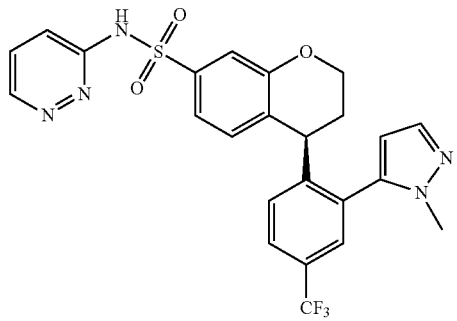

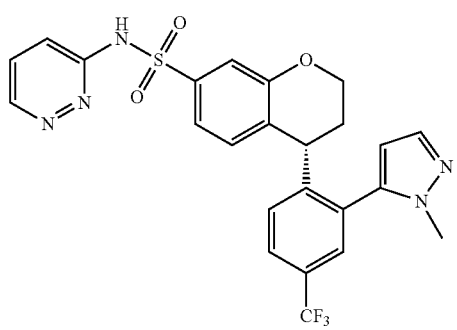

The title compounds were prepared by following the similar procedure as described in Example-1/2 using Intermediate-3 and pyridazin-3-amine.

Further the enantiomers were separated using chiral preparative HPLC (Column: ChiralPak IE; Mobile phase: A=(EtOH+0.1% TFA), B=(MeOH+0.1% TFA), A:B=50:50, to afford isomer-1 and isomer-2. These isomers were obtained at retention time 10.62 min (Example-13) and retention time 12.34 min (Example-14).

LCMS: m/z 516.19 (M+H)$^+$; $^1$H NMR (400 MHz, DMSO-d6) δ 8.34 (s, 1H), 7.83-7.71 (m, 3H), 7.66-7.59 (m, 1H), 7.54 (d, J=1.9 Hz, 1H), 7.32-7.20 (m, 3H), 6.83 (d, J=8.3 Hz, 1H), 6.46 (s, 1H), 4.26-4.18 (m, 1H), 4.16-4.09 (m, 2H), 3.70 (s, 3H), 2.14-2.10 (m, 1H), 1.98-1.90 (m, 1H).

Example-15/16: (S&R)-4-(2-(1-Methyl-1H-pyrazol-5-yl)-4-(trifluoromethyl)phenyl)-N-(pyrimidin-2-yl)chromane-7-sulfonamide

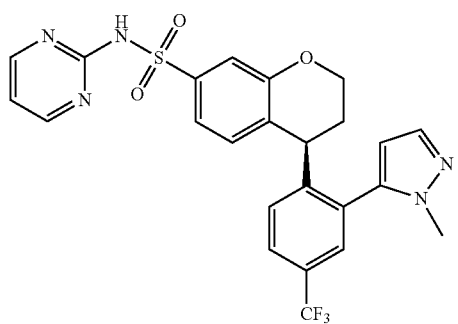

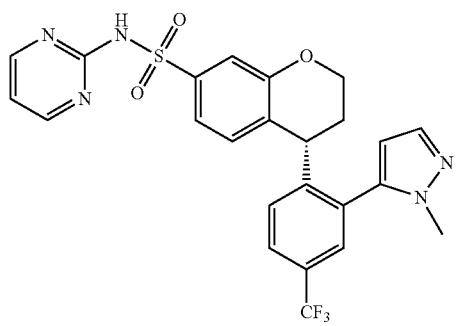

The title compounds were prepared by following the similar procedure as described in Example-1/2 using Intermediate-3 and pyrimidin-2-amine.

Further the enantiomers were separated using chiral preparative HPLC (Column: ChiralPak IA; Mobile phase: A=(Hexane+0.1% TFA), B=(EtOH:MeOH=1:1), A:B=40:60, to afford isomer-1 and isomer-2. These isomers were obtained at retention time 5.10 min (Example-15) and retention time 6.78 min (Example-16).

LCMS: m/z 516.19 (M+H)$^+$; $^1$H NMR (400 MHz, DMSO-d6) δ 11.76 (s, 1H), 8.53 (d, J=4.9 Hz, 2H), 7.82-7.73 (m, 2H), 7.53 (d, J=1.8 Hz, 1H), 7.37 (d, J=8.3 Hz, 2H), 7.28 (d, J=8.2 Hz, 1H), 7.08 (s, 1H), 6.89 (d, J=8.1 Hz, 1H), 6.44 (s, 1H), 4.28-4.20 (m, 1H), 4.20-4.08 (m, 2H), 3.70 (s, 3H), 2.19-2.07 (m, 1H), 2.02-1.91 (m, 1H).

Example-17/18: (S&R)—N-(3-Fluoropyridin-2-yl)-4-(2-(1-methyl-1H-pyrazol-5-yl)-4-(trifluoromethyl)phenyl)chromane-7-sulfonamide

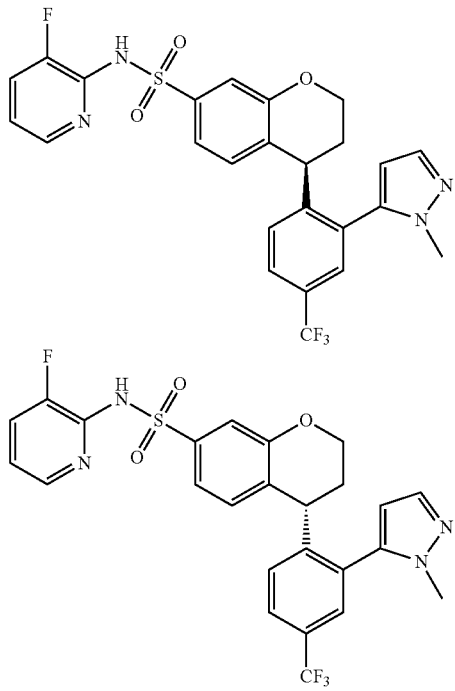

The title compounds were prepared by following the similar procedure as described in Example-1/2 using Intermediate-3 and 3-Fluoropyridin-2-amine.

Further the enantiomers were separated using chiral preparative HPLC (Column: ChiralPak IE; Mobile phase: A=(Hexane+0.1% TFA), B=(EtOH:MeOH=1:1), A:B=60:40 to afford isomer-1 and isomer-2. These isomers were obtained at retention time 8.39 min (Example-17) and retention time 9.66 min (Example-18).

LCMS: m/z 533.07 (M+H)$^+$; $^1$H NMR (400 MHz, DMSO-d6) δ 8.05-7.97 (m, 1H), 7.83-7.76 (m, 2H), 7.75-7.66 (m, 1H), 7.54 (d, J=1.8 Hz, 1H), 7.38 (s, 2H), 7.28 (d, J=8.2 Hz, 1H), 7.15-7.06 (m, 1H), 6.90 (d, J=8.1 Hz, 1H), 6.46 (s, 1H), 4.28-4.20 (m, 1H), 4.19-4.09 (m, 2H), 3.70 (s, 3H), 2.20-2.09 (m, 1H), 2.04-1.94 (m, 1H).

Example-19/20: (S&R)-4-(2-(1-methyl-1H-pyrazol-5-yl)-4-(trifluoromethyl)phenyl)-N-(6-methylpyridin-2-yl)chroman-7-sulfonamide

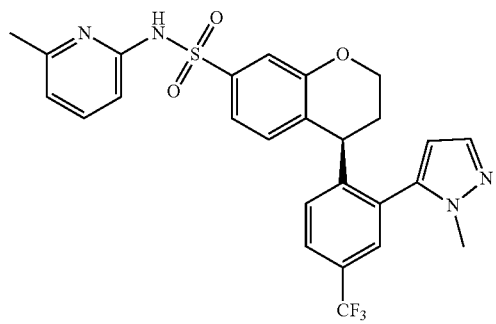

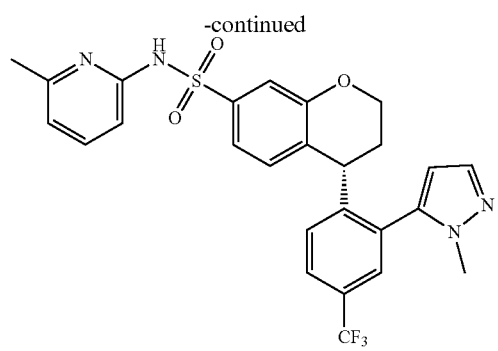

The title compounds were prepared by following the similar procedure as described in Example-1/2 using Intermediate-3 and 6-methylpyridin-2-amine.

Further the enantiomers were separated using chiral preparative HPLC (Column: ChiralPak IA; Mobile phase: A=(Hexane+0.1% TFA), B=(EtOH:MeOH=1:1), A:B=70:30, to afford isomer-1 and isomer-2. These isomers were obtained at retention time 8.10 min (Example-19) and retention time 9.29 min (Example-20).

LCMS(ESI): m/z 529.21 (M+H)$^+$; $^1$H NMR (400 MHz, Chloroform-d) δ 7.64 (d, J=8.3 Hz, 1H), 7.61-7.53 (m, 3H), 7.46 (d, J=1.8 Hz, 1H), 7.38 (dd, J=8.1, 1.9 Hz, 1H), 7.18 (d, J=8.2 Hz, 1H), 7.08 (d, J=8.7 Hz, 1H), 6.78 (d, J=8.1 Hz, 1H), 6.65 (d, J=7.3 Hz, 1H), 6.31 (d, J=1.9 Hz, 1H), 4.28-4.13 (m, 2H), 4.20-4.10 (m, 1H), 3.77 (s, 3H), 2.48 (s, 3H), 2.13-1.93 (m, 2H).

Example-21/22: (S&R)-4-(2-(1-methyl-1H-pyrazol-5-yl)-4-(trifluoromethyl)phenyl)-N-(5-methylpyridin-2-yl)chroman-7-sulfonamide

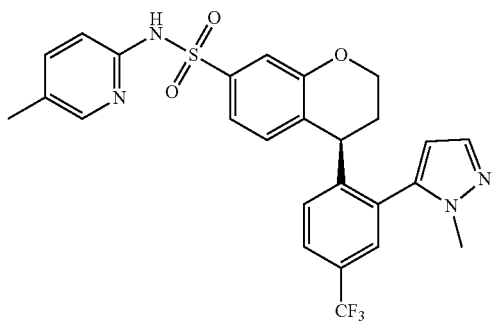

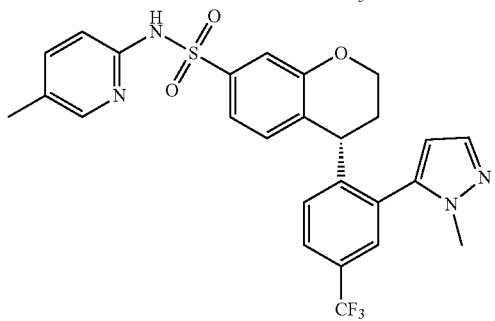

The title compounds were prepared by following the similar procedure as described in Example-1/2 using Intermediate-3 and 5-methylpyridin-2-amine.

Further the enantiomers were separated using chiral preparative HPLC (Column: ChiralPak IA; Mobile phase: A=(Hexane+0.1% TFA), B=(EtOH:MeOH=1:1), A:B=40:60, to afford isomer-1 and isomer-2. These isomers were obtained at retention time 6.16 min (Example-21) and retention time 8.91 min (Example-22).

LCMS(ESI): m/z 529.07 (M+H)⁺; ¹H NMR (400 MHz, DMSO-$d_6$) δ 7.91-7.72 (m, 3H), 7.60-7.51 (m, 2H), 7.30-7.21 (m, 3H), 7.10 (d, J=8.7 Hz, 1H), 6.84 (d, J=8.1 Hz, 1H), 6.44 (s, 1H), 4.25-4.18 (m, 1H), 4.15-4.07 (m, 2H), 3.69 (s, 3H), 2.14 (s, 3H), 2.13-2.08 (m, 1H), 1.98-1.90 (m, 1H).

Example-23/24: (S&R)-4-(2-(1-methyl-1H-pyrazol-5-yl)-4-(trifluoromethyl)phenyl)-N-(4-methylpyridin-2-yl)chroman-7-sulfonamide

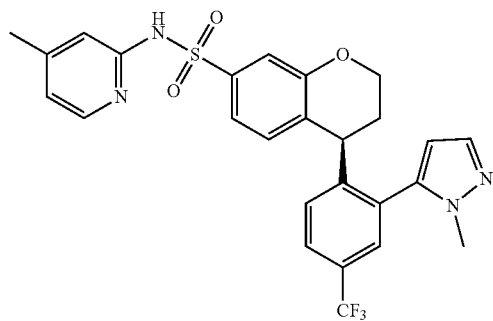

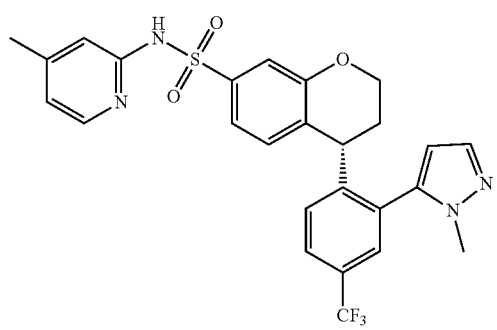

The title compounds were prepared by following the similar procedure as described in Example-1/2 using Intermediate-3 and 4-methylpyridin-2-amine.

Further the enantiomers were separated using chiral preparative HPLC (Column: ChiralPak IA; Mobile phase: A=(Hexane+0.1% TFA), B=(EtOH:MeOH=1:1), A:B=60:40, to afford isomer-1 and isomer-2. These isomers were obtained at retention time 7.26 min (Example-23) and retention time 8.32 min (Example-24).

LCMS(ESI): m/z 529.07 (M+H)⁺; ¹H NMR (400 MHz, DMSO-$d_6$) δ 7.86-7.73 (m, 3H), 7.53 (d, J=1.8 Hz, 1H), 7.30-7.21 (m, 3H), 7.04 (s, 1H), 6.83 (d, J=8.0 Hz, 1H), 6.69 (s, 1H), 6.45 (s, 1H), 4.25-4.17 (m, 1H), 4.16-4.08 (m, 2H), 3.70 (s, 3H), 2.25 (s, 3H), 2.17-1.88 (m, 2H).

Example-25/26: (S&R)—N-(6-isopropoxypyridin-2-yl)-4-(2-(1-methyl-1H-pyrazol-5-yl)-4-(trifluoromethyl)phenyl)chroman-7-sulfonamide

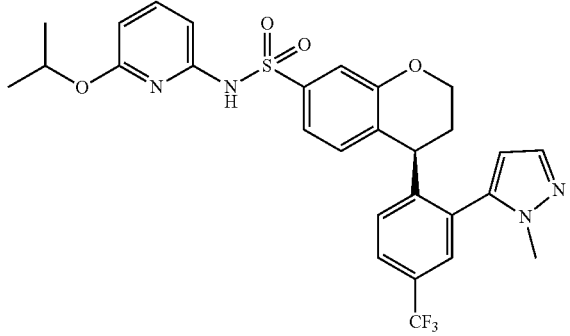

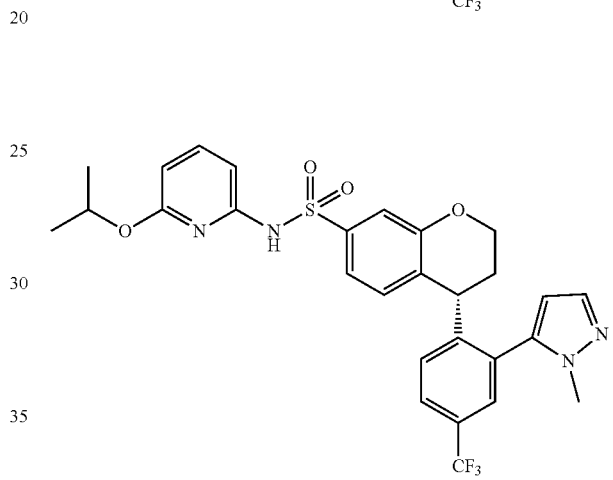

To a stirred solution N-(6-fluoropyridin-2-yl)-4-(2-(1-methyl-1H-pyrazol-5-yl)-4-(trifluoromethyl)phenyl)chroman-7-sulfonamide (racemic mixture of Example-1/2) (1 g, 1.878 mmol) in 2-Propanol (10 ml) was added KOH (0.74 g, 13.15 mmol). This was heated at 80° C. for 12 h. The solvent was evaporated from the reaction mixture and the residue was partitioned between ethyl acetate and water. The combined organic layer was washed with brine, dried over $Na_2SO_4$ and concentrated under vacuum. The crude was further purified by column chromatography to obtain mixture of isomers ((0.15 g, 15%).

Further the enantiomers were separated using chiral preparative HPLC (Column: ChiralPak IA; Mobile phase: A=(Hexane+0.1% TFA), B=(EtOH), A:B=80:20, to afford isomer-1 and isomer-2. These isomers were obtained at retention time 8.04 min (Example-25) and retention time 8.97 min (Example-26).

LCMS(ESI): m/z 573.12 (M+H)⁺; ¹H NMR (400 MHz, DMSO-$d_6$) δ 11.02 (s, 1H), 7.78 (d, J=10.2 Hz, 2H), 7.58-7.46 (m, 2H), 7.35-7.21 (m, 3H), 6.89 (d, J=8.0 Hz, 1H), 6.48-6.40 (m, 2H), 6.28 (d, J=8.1 Hz, 1H), 4.85-4.77 (m, 1H), 4.32-4.20 (m, 1H), 3.69 (s, 3H), 4.19-4.04 (m, 2H), 2.23-1.90 (m, 2H), 1.13 (d, J=6.2 Hz, 3H), 1.10 (d, J=6.1 Hz, 3H).

Example-27/28: (S&R)—N-(2-fluoropyridin-3-yl)-4-(2-(1-methyl-1H-pyrazol-5-yl)-4-(trifluoromethyl)phenyl)chroman-7-sulfonamide

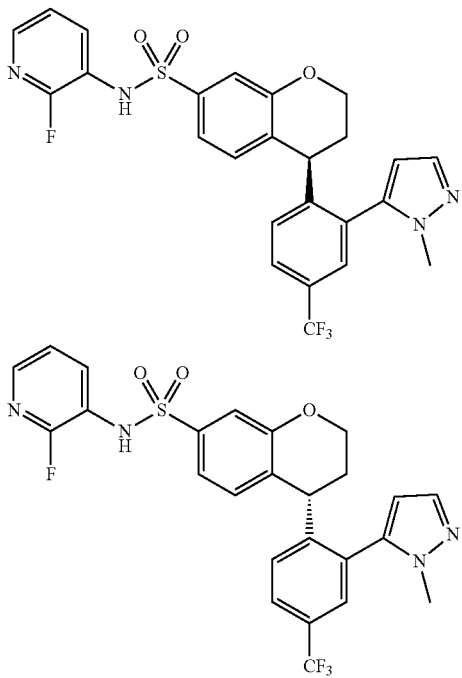

The title compounds were prepared by following the similar procedure as described in Example-1/2 using Intermediate-3 and 2-fluoropyridin-3-amine.

Further the enantiomers were separated using chiral preparative HPLC (Column: ChiralPak IA; Mobile phase: A=(Hexane+0.1% TFA), B=(EtOH:MeOH=1:1), A:B=70:30, to afford isomer-1 and isomer-2. These isomers were obtained at retention time 6.09 min (Example-27) and retention time 7.06 min (Example-28).

LCMS(ESI): m/z 533.07 (M+H)$^+$; $^1$H NMR (400 MHz, DMSO-d$_6$) δ 10.53 (s, 1H), 7.99 (d, J=4.8 Hz, 1H), 7.83-7.72 (m, 3H), 7.54 (d, J=1.8 Hz, 1H), 7.36-7.21 (m, 2H), 7.18-7.11 (m, 2H), 6.91 (d, J=7.9 Hz, 1H), 6.43 (s, 1H), 4.28-4.09 (m, 3H), 3.69 (s, 3H), 2.20-1.92 (m, 2H).

Example-29/30: (S&R)-4-(2-(1-methyl-1H-pyrazol-5-yl)-4-(trifluoromethyl)phenyl)-N-(4-methylpyrimidin-2-yl)chroman-7-sulfonamide

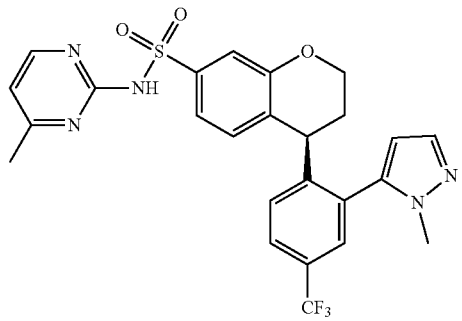

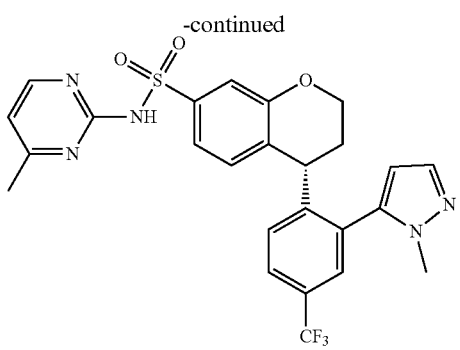

The title compounds were prepared by following the similar procedure as described in Example-1/2 using Intermediate-3 and 4-methylpyrimidin-2-amine.

Further the enantiomers were separated using chiral preparative HPLC (Column: ChiralPak IE; Mobile phase: A=(Hexane+0.1% TFA), B=(EtOH:MeOH=1:1), A:B=50:50, to afford isomer-1 and isomer-2. These isomers were obtained at retention time 9.41 min (Example-29) and retention time 11.60 min (Example-30).

LCMS(ESI): m/z 530.08 (M+H)$^+$; $^1$H NMR (400 MHz, DMSO-d$_6$) δ 8.28 (s, 1H), 7.82-7.72 (m, 2H), 7.53 (s, 1H), 7.40-7.20 (m, 3H), 6.93-6.78 (m, 2H), 6.45 (s, 1H), 4.25-4.06 (m, 3H), 3.70 (s, 3H), 2.28 (s, 3H), 2.17-1.90 (m, 2H).

Example-31/32: (S&R)-4-(4-chloro-2-(1-methyl-1H-pyrazol-5-yl)phenyl)-N-(6-fluoropyridin-2-yl)chroman-7-sulfonamide

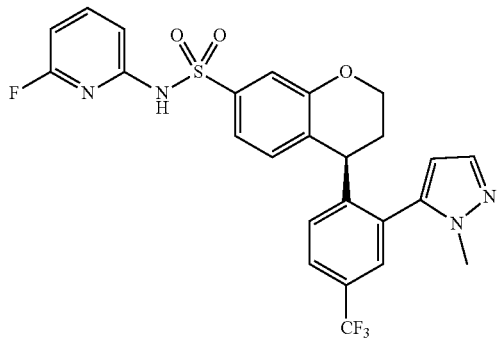

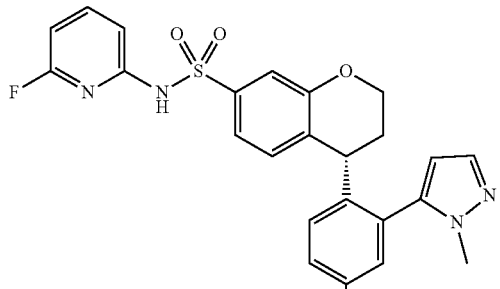

Step-1:
7-(benzylthio)-4-hydroxy-2H-chromen-2-one

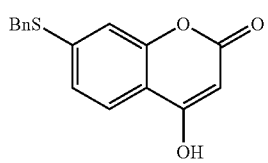

7-bromo-4-hydroxy-2H-chromen-2-one (100 g, 415 mmol) was dissolved in 1,4-dioxane (1.2 lit) and the solution was degassed by passing nitrogen and then, Xanthphos (12 g, 20.74 mmol), Pd$_2$(dba)$_3$ (9.5 g, 10.37 mmol), Hunig's base (145 ml, 830 mmol) and benzyl mercaptan (47 ml, 394 mmol) was added in a reaction mass and heated at 80° C. for 2 h. Solvent was removed under vacuum and crude reaction mixture was suspended in 50 ml of DMF and added to an ice cold water with vigorous stirring, after 15 min aqueous layer was carefully acidified till pH=5-4 and filtered off. The residue was washed with 500 ml of water and dried under vacuum. Dry residue was then suspended in 500 ml of acetone, filtered and dried under vacuum. LCMS (ESI): m/z 285.27 (M+H)$^+$.

Step-2: 7-(benzylthio)-2-oxo-2H-chromen-4-yl trifluoromethanesulfonate

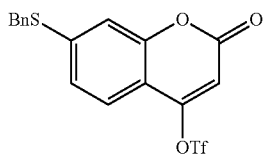

To a solution of 7-(benzylthio)-4-hydroxy-2H-chromen-2-one (Step-1) (25 g, 88 mmol) in DCM (250 ml) was added TEA (36.8 ml, 264 mmol) followed by triflic anhydride (36.9 ml, 220 mmol) dropwise at 0-5° C. and stirred under nitrogen at same temperature for 1 h. Ice cold water was added to stirred reaction mixture and diluted with DCM; organic layer was separated and washed with 2N HCl solution. Combined organic layer was dried over Na$_2$SO$_4$ and concentrated under vacuum. The crude was triturated with 100 ml of MeOH and filtered to obtain title compound (29.5 g, 81%). LCMS (ESI): m/z 416.91 (M+H)$^+$.

Step-3: 7-(benzylthio)-4-(4-chloro-2-(1-methyl-1H-pyrazol-5-yl)phenyl)-2H-chromen-2-one

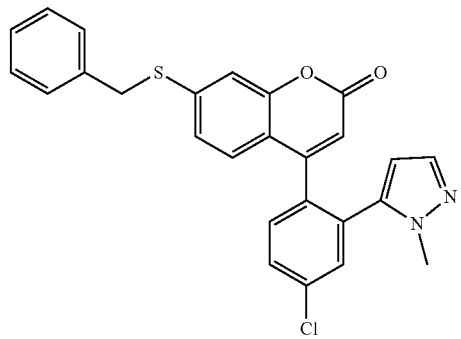 [SMILES: Cn1nccc1-c1cc(Cl)ccc1-c1cc(=O)oc2cc(SCc3ccccc3)ccc12]

A solution of 7-(benzylthio)-2-oxo-2H-chromen-4-yl trifluoromethanesulfonate (Step-2) (3.8 g, 9.13 mmol) and (4-chloro-2-(1-methyl-1H-pyrazol-5-yl)phenyl)boronic acid (2.16 g, 9.13 mmol) in 1,4-dioxane (20 ml) was purged with nitrogen after which potassium phosphate (4.84 g, 22.82 mmol) and PdCl$_2$(dppf) (0.67 g, 0.913 mmol) was added. The reaction mixture was stirred for 1 h at 80° C. After completion of reaction as indicated by TLC, the mixture was poured into water and extracted with ethyl acetate. The organic layer was collected and dried over Na$_2$SO$_4$, and evaporated. The crude was purified by column chromatography to obtain title compound (2.6 g, 62%). $^1$H NMR (400 MHz, Chloroform-d) δ 7.59 (dd, J=8.2, 2.2 Hz, 1H), 7.49 (d, J=2.1 Hz, 1H), 7.41-7.31 (m, 7H), 7.18 (d, J=1.8 Hz, 1H), 7.01 (dd, J=8.5, 1.9 Hz, 1H), 6.92 (d, J=8.4 Hz, 1H), 6.12 (s, 1H), 6.01 (d, J=2.0 Hz, 1H), 4.21 (d, J=7.2 Hz, 2H), 3.68 (s, 3H).

Step-4: 5-(benzylthio)-2-(1-(4-chloro-2-(1-methyl-1H-pyrazol-5-yl)phenyl)-3-hydroxypropyl)phenol

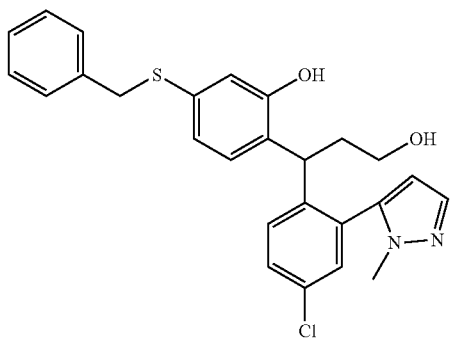 [SMILES: Cn1nccc1-c1cc(Cl)ccc1C(CCO)c1ccc(SCc2ccccc2)cc1O]

A solution of 7-(benzylthio)-4-(4-chloro-2-(1-methyl-1H-pyrazol-5-yl)phenyl)-2H-chromen-2-one (Step-3) (2.6 g, 5.66 mmol), cobalt(II)chloride hexahydrate (0.14 g, 0.566 mmol) in DMF (0.5 ml):EtOH (2 ml) stirred for 30 min at room temperature and then cooled to 0° C. NaBH$_4$ (0.86 g, 22.66 mmol) was added at 0° C. and stirred for 16 h. Reaction mixture was quenched by adding water and partitioned between ethyl acetate and water. Organic phase was washed with brine, dried over Na$_2$SO$_4$ and concentrated. The crude was purified by flash chromatography to obtain title compound (1 g, 38%). LCMS (ESI): m/z 465.23 (M+H)$^+$.

Step-5: 5-(2-(7-(benzylthio)chroman-4-yl)-5-chlorophenyl)-1-methyl-1H-pyrazole

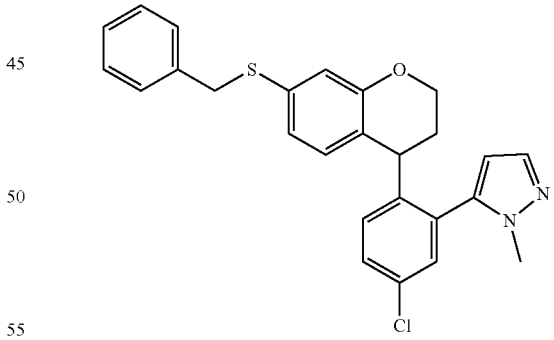

To a solution of 5-(benzylthio)-2-(1-(4-chloro-2-(1-methyl-1H-pyrazol-5-yl)phenyl)-3-hydroxypropyl)phenol (0.65 g, 1.398 mmol) in THF (15 ml), triphenylphosphine (0.55 g, 2.097 mmol) was added and cooled to 0° C. followed by DEAD (0.33 ml, 2.097 mmol) was added dropwise and stirred for 1 h. After completion the mixture was added to water and extracted with ethyl acetate. The organic layer was collected and dried over Na$_2$SO$_4$ and evaporated under vacuum. The crude was purified by column chromatography to obtain title compound (0.43 g, 68%). LCMS (ESI): m/z 447.23 (M+H)$^+$.

Step-6: Perfluorophenyl 4-(4-chloro-2-(1-methyl-1H-pyrazol-5-yl)phenyl)chroman-7-sulfonate

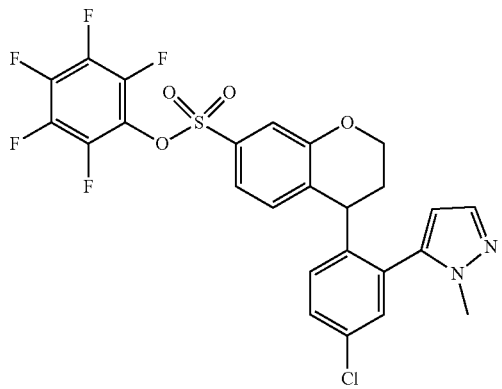 [SMILES: Cn1nccc1-c1cc(Cl)ccc1C1CCOc2cc(S(=O)(=O)Oc3c(F)c(F)c(F)c(F)c3F)ccc21]

The title compound was prepared by following similar procedure as described for Intermediate-3 (Step-2), using step-5 intermediate. LCMS (ESI): m/z 571.01 (M+H)⁺.

Step-7: (S&R)-4-(4-chloro-2-(1-methyl-1H-pyrazol-5-yl)phenyl)-N-(6-fluoropyridin-2-yl)chroman-7-sulfonamide The title compound was prepared by following the similar procedure as described in Example-1 and 2 using Step-6 intermediate and 6-fluoropyridin-2-amine.

Further the enantiomers were separated using chiral preparative HPLC (Column: ChiralPak IE; Mobile phase: A=(Hexane+0.1% TFA), B=(EtOH:MeOH=1:1), A:B=50:50, to afford isomer-1 and isomer-2. These isomers were obtained at retention time 6.24 min (Example-31) and retention time 6.96 min (Example-32).

LCMS(ESI): m/z 499.30 (M+H)⁺; ¹H NMR (400 MHz, DMSO-d₆) δ 11.38 (s, 1H), 7.91-7.83 (m, 1H), 7.51-7.44 (m, 3H), 7.36-7.28 (m, 2H), 7.08-7.03 (m, 1H), 6.97 (dd, J=8.0, 2.1 Hz, 1H), 6.90 (d, J=8.5 Hz, 1H), 6.77 (dd, J=8.0, 2.3 Hz, 1H), 6.36 (s, 1H), 4.27-4.00 (m, 3H), 3.69 (s, 3H), 2.14-1.87 (m, 2H).

Example-33/34: (S&R)—N-(6-fluoropyridin-2-yl)-4-(4-isopropoxy-2-(1-methyl-1H-pyrazol-5-yl)phenyl)chroman-7-sulfonamide

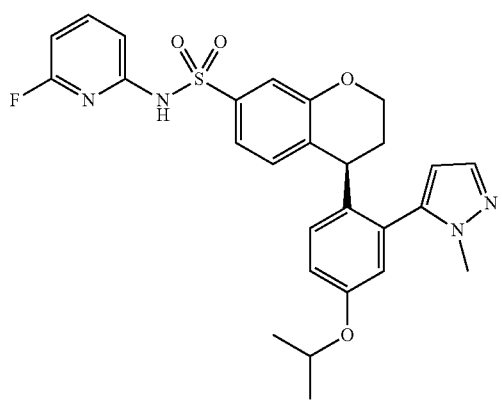

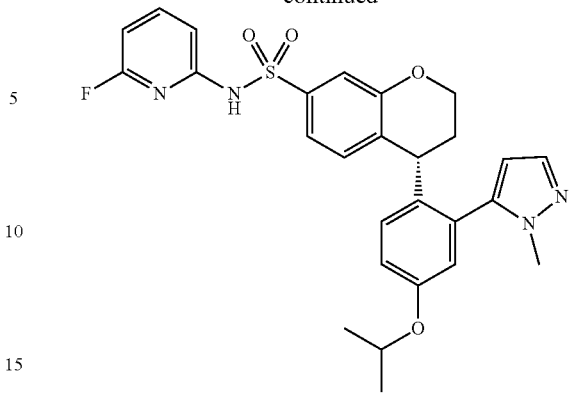

The title compounds were prepared by following the similar procedure as described in Example-1/2 using Intermediate-8 and 6-fluoropyridin-2-amine.

Further the enantiomers were separated using chiral preparative HPLC (Column: ChiralPak IE; Mobile phase: A=(Hexane+0.1% TFA), B=(EtOH:MeOH=1:1), A:B=50:50, to afford isomer-1 and isomer-2. These isomers were obtained at retention time 6.43 min (Example-33) and retention time 7.23 min (Example-34).

LCMS(ESI): m/z 523.19 (M+H)⁺; ¹H NMR (400 MHz, DMSO-d₆) δ 11.37 (s, 1H), 7.93-7.81 (m, 1H), 7.46 (d, J=1.8 Hz, 1H), 7.31 (d, J=7.0 Hz, 2H), 7.04-6.82 (m, 5H), 6.76 (dd, J=8.0, 2.4 Hz, 1H), 6.30 (s, 1H), 4.70-4.59 (m, 1H), 4.27-4.17 (m, 1H), 4.16-3.90 (m, 2H), 3.69 (s, 3H), 2.09-2.00 (m, 1H), 1.95-1.86 (m, 1H), 1.26 (d, J=6.0 Hz, 6H).

Example-35/36: (S&R)-4-(2-(6-Fluoropyridin-3-yl)-4-(trifluoromethyl)phenyl)-N-(pyrimidin-2-yl)chromane-7-sulfonamide

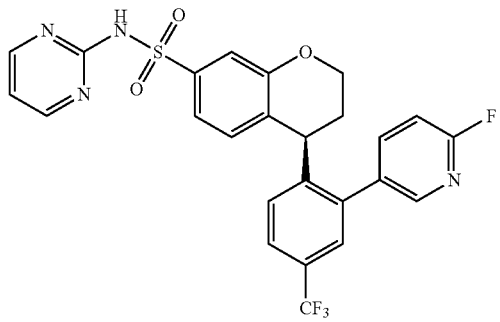

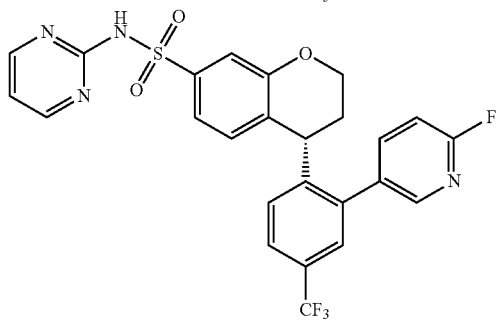

The title compounds were prepared by following the similar procedure as described in Example-1/2 using Intermediate-6 and pyrimidin-2-amine.

Further the enantiomers were separated using chiral preparative HPLC (Column: ChiralPak IE; Mobile phase: MeOH+0.1% TFA, to afford isomer-1 and isomer-2. These isomers were obtained at retention time 4.43 min (Example-35) and retention time 5.09 min (Example-36).

LCMS: m/z 531.09 (M+H)$^+$; $^1$H NMR (400 MHz, DMSO-d6) δ 11.79 (s, 1H), 8.52 (d, J=4.9 Hz, 2H), 8.38 (d, J=2.5 Hz, 1H), 8.15 (td, J=8.1, 2.5 Hz, 1H), 7.73 (dd, J=8.4, 2.0 Hz, 1H), 7.70-7.65 (m, 1H), 7.40-7.29 (m, 3H), 7.24 (d, J=8.2 Hz, 1H), 7.07 (t, J=4.9 Hz, 1H), 6.96 (d, J=8.1 Hz, 1H), 4.28-4.18 (m, 2H), 4.18-4.08 (m, 1H), 2.18-2.08 (m, 1H), 2.02-1.96 (m, 1H).

Example-37/38: (S&R)-4-(2-(6-Fluoropyridin-3-yl)-4-(trifluoromethyl)phenyl)-N-(5-fluoropyrimidin-2-yl) chromane-7-sulfonamide

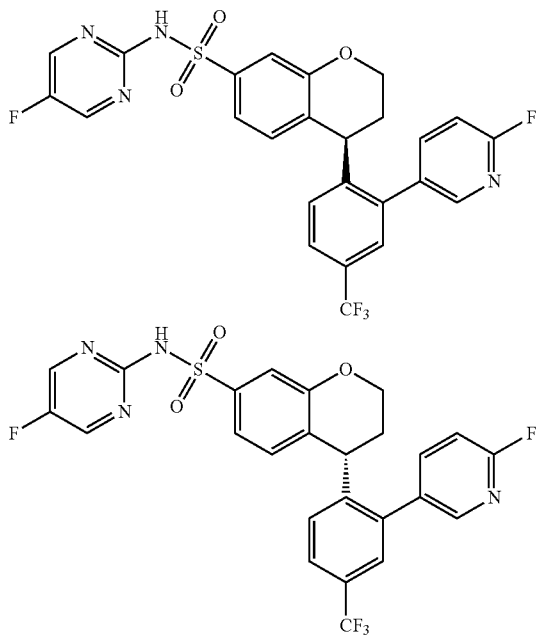

The title compounds were prepared by following the similar procedure as described in Example-1/2 using Intermediate-6 and 5-Fluoropyrimidin-2-amine.

Further the enantiomers were separated using chiral preparative HPLC (Column: ChiralPak IA; Mobile phase: A=(Hexane+0.1% TFA), B=(IPA:MeOH=1:1), A:B=50:50, to afford isomer-1 and isomer-2. These isomers were obtained at retention time 5.73 min (Example-37) and retention time 7.58 min (Example-38).

LCMS: m/z 549.08 (M+H)$^+$; $^1$H NMR (400 MHz, DMSO-d6) δ 8.48 (s, 2H), 8.38 (d, J=2.5 Hz, 1H), 8.15 (td, J=8.2, 2.5 Hz, 1H), 7.73 (dd, J=8.4, 2.0 Hz, 1H), 7.67 (d, J=2.0 Hz, 1H), 7.34-7.26 (m, 3H), 7.24 (d, J=8.2 Hz, 1H), 6.89 (d, J=8.0 Hz, 1H), 4.27-4.17 (m, 2H), 4.14-4.07 (m, 1H), 2.18-2.09 (m, 1H), 2.01-1.97 (m, 1H).

Example-39/40: (S&R)-4-(2-(6-Fluoropyridin-3-yl)-4-(trifluoromethyl)phenyl)-N-(pyrimidin-4-yl)chromane-7-sulfonamide

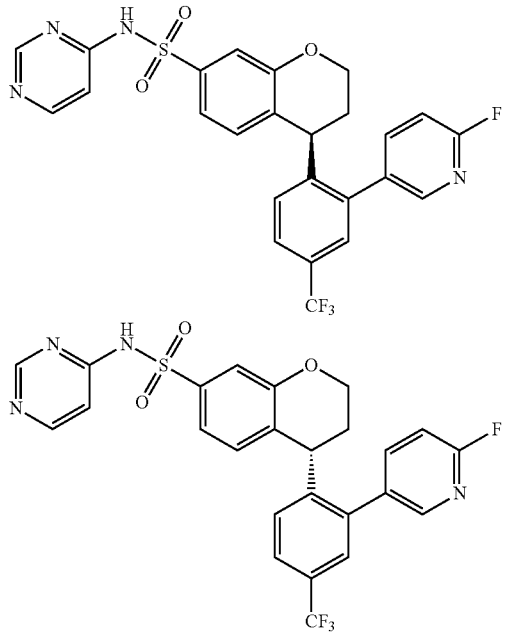

The title compounds were prepared by following the similar procedure as described in Example-1/2 using Intermediate-6 and Pyrimidin-4-amine.

Further the enantiomers were separated using chiral preparative HPLC (Column: ChiralPak IA; Mobile phase: A=(Hexane+0.1% TFA), B=(MeOH:DCM=1:1), A:B=70:30, to afford isomer-1 and isomer-2. These isomers were obtained at retention time 6.30 min (Example-39) and retention time 7.72 min (Example-40).

LCMS: m/z 530.82 (M+H)$^+$; $^1$H NMR (400 MHz, DMSO-d6) δ 8.64 (s, 1H), 8.43-8.31 (m, 2H), 8.15 (td, J=8.2, 2.5 Hz, 1H), 7.73 (dd, J=8.3, 2.1 Hz, 1H), 7.70-7.67 (m, 1H), 7.36-7.27 (m, 3H), 7.25 (d, J=8.2 Hz, 1H), 7.04 (s, 1H), 6.96 (d, J=8.6 Hz, 1H), 4.29-4.18 (m, 2H), 4.18-4.08 (m, 1H), 2.18-2.10 (m, 1H), 2.04-1.94 (m, 1H).

Example-41/42: (S&R)-4-(2-(6-Fluoropyridin-3-yl)-4-(trifluoromethyl)phenyl)-N-(pyridazin-3-yl)chromane-7-sulfonamide

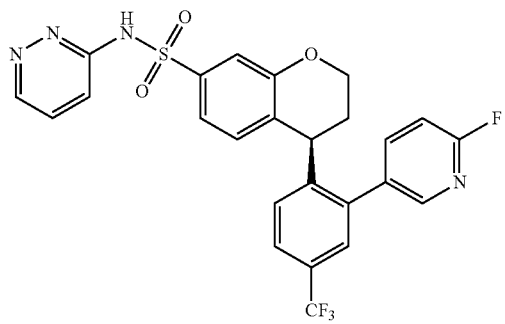

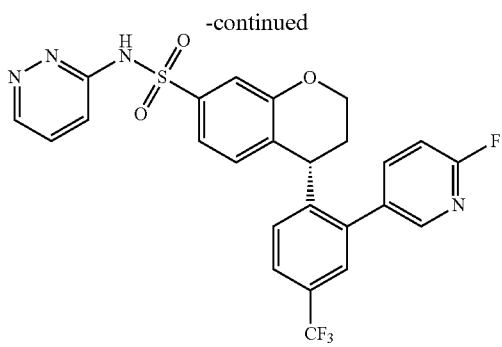

The title compounds were prepared by following the similar procedure as described in Example-1/2 using Intermediate-6 and pyridazin-3-amine.

Further the enantiomers were separated using chiral preparative HPLC (Column: ChiralPak IA; Mobile phase: A=(Hexane+0.1% TFA), B=(IPA:MeOH=1:1), A:B=50:50, to afford isomer-1 and isomer-2. These isomers were obtained at retention time 6.62 min (Example-41) and retention time 7.76 min (Example-42).

LCMS: m/z 531.02 (M+H)$^+$; $^1$H NMR (400 MHz, DMSO-d6) δ 8.38 (d, J=2.4 Hz, 1H), 8.34 (s, 1H), 8.15 (td, J=8.1, 2.5 Hz, 1H), 7.81-7.71 (m, 2H), 7.68 (d, J=2.0 Hz, 1H), 7.62 (dd, J=9.6, 4.1 Hz, 1H), 7.32 (dd, J=8.4, 2.7 Hz, 1H), 7.28-7.19 (m, 3H), 6.90 (d, J=8.5 Hz, 1H), 4.26-4.17 (m, 2H), 4.16-4.08 (m, 1H), 2.19-2.08 (m, 1H), 2.03-1.94 (m, 1H).

Example-43/44: (S&R)-4-(4'-Fluoro-5-(trifluoromethyl)-[1,1'-biphenyl]-2-yl)-N-(pyrimidin-2-yl)chromane-7-sulfonamide

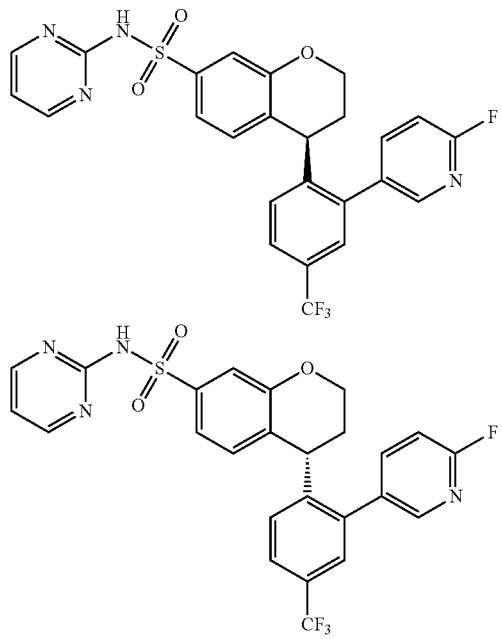

The title compounds were prepared by following the similar procedure as described in Example-1/2 using Intermediate-10 and pyrimidin-2-amine.

Further the enantiomers were separated using chiral preparative HPLC (Column: ChiralPak IE; Mobile phase: A=(Hexane+0.1% TFA), B=(MeOH:DCM=1:1), A:B=60:40, to afford isomer-1 and isomer-2. These isomers were obtained at retention time 6.91 min (Example-43) and retention time 7.81 min (Example-44).

LCMS: m/z 530.19 (M+H)$^+$; $^1$H NMR (400 MHz, DMSO-d6) δ 11.76 (s, 1H), 8.53 (d, J=4.9 Hz, 2H), 7.72-7.65 (m, 1H), 7.61-7.49 (m, 3H), 7.43-7.27 (m, 4H), 7.21 (d, J=8.2 Hz, 1H), 7.13-7.04 (m, 1H), 6.93 (d, J=8.4 Hz, 1H), 4.37-4.19 (m, 2H), 4.19-4.01 (m, 1H), 2.16-2.07 (m, 1H), 2.05-1.99 (m, 1H).

Example-45/46: (S&R)-4-(4'-Fluoro-5-(trifluoromethyl)-[1,1'-biphenyl]-2-yl)-N-(5-fluoropyrimidin-2-yl) chromane-7-sulfonamide

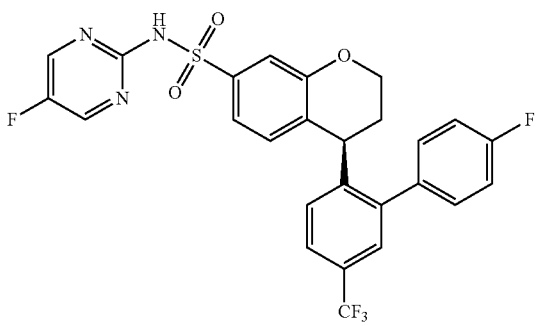

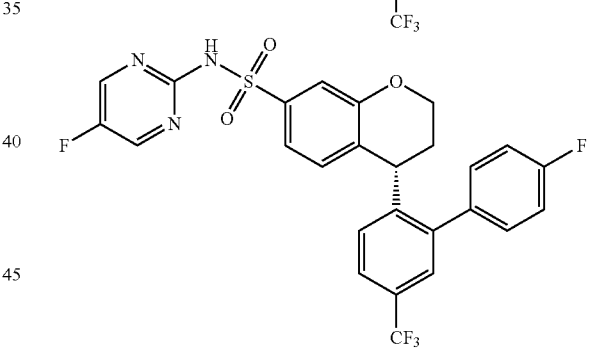

The title compounds were prepared by following the similar procedure as described in Example-1/2 using Intermediate-10 and 5-fluoropyrimidin-2-amine.

Further the enantiomers were separated using chiral preparative HPLC (Column: ChiralPak IE; Mobile phase: A=(Hexane+0.1% DEA), B=(MeOH:DCM=1:1), A:B=70:30, to afford isomer-1 and isomer-2. These isomers were obtained at retention time 6.93 min (Example-45) and retention time 8.01 min (Example-46).

LCMS: m/z 547.99 (M+H)$^+$; $^1$H NMR (400 MHz, DMSO-d6) δ 11.88 (s, 1H), 8.65 (s, 2H), 7.69 (d, J=8.2 Hz, 1H), 7.62-7.47 (m, 3H), 7.44-7.28 (m, 4H), 7.21 (d, J=8.3 Hz, 1H), 6.93 (d, J=8.4 Hz, 1H), 4.35-4.18 (m, 2H), 4.18-4.01 (m, 1H), 2.13-2.06 (m, 1H), 2.04-1.95 (m, 1H).

Example-47/48: (S&R)-4-(4'-Fluoro-5-(trifluoromethyl)-[1,1'-biphenyl]-2-yl)-N-(pyrimidin-4-yl)chromane-7-sulfonamide

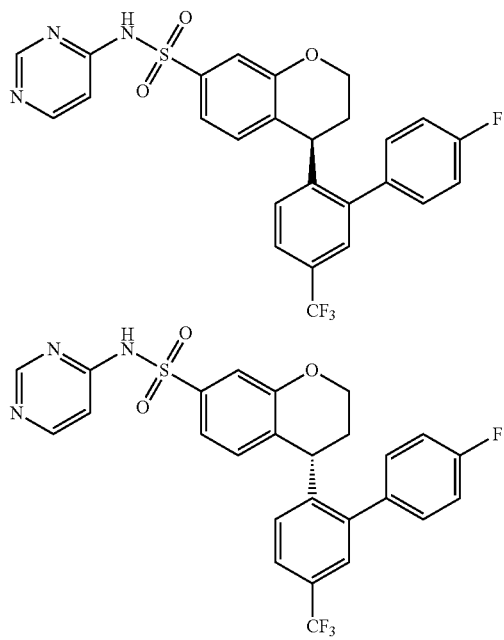

The title compounds were prepared by following the similar procedure as described in Example-1/2 using Intermediate-10 and pyrimidin-4-amine.

Further the enantiomers were separated using chiral preparative HPLC (Column: ChiralPak IE; Mobile phase: A=(Hexane+0.1% DEA), B=(MeOH:DCM=1:1), A:B=70:30, to afford isomer-1 and isomer-2. These isomers were obtained at retention time 7.83 min (Example-47) and retention time 8.97 min (Example-48).

LCMS: m/z 529.97 (M+H)+; 1H NMR (400 MHz, DMSO-d6) δ 8.65 (s, 1H), 8.37 (s, 1H), 7.69 (d, J=8.3 Hz, 1H), 7.62-7.48 (m, 3H), 7.43-7.26 (m, 4H), 7.22 (d, J=8.3 Hz, 1H), 7.05 (s, 1H), 6.92 (d, J=8.3 Hz, 1H), 4.35-4.17 (m, 2H), 4.14-4.10 (m, 1H), 2.11-2.09 (m, 1H), 2.08-1.94 (m, 1H).

Example-49/50: (S&R)-4-(4'-Fluoro-5-(trifluoromethyl)-[,1'-biphenyl]-2-yl)-N-(6-fluoropyridin-2-yl)chromane-7-sulfonamide

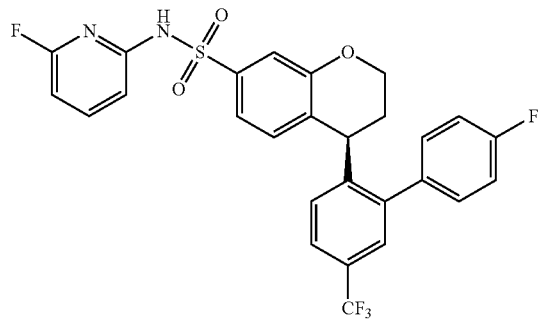

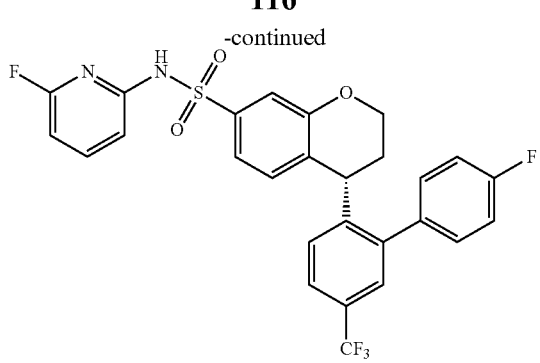

The title compounds were prepared by following the similar procedure as described in Example-1/2 using Intermediate-10 and 6-fluoropyridin-2-amine.

Further the enantiomers were separated using chiral preparative HPLC (Column: ChiralPak ID; Mobile phase: A=(Hexane+0.1% DEA), B=(MeOH:DCM=1:1), A:B=85:15, to afford isomer-1 and isomer-2. These isomers were obtained at retention time 9.22 min (Example-49) and retention time 10.00 min (Example-50).

LCMS: m/z 547.00 (M+H)+; 1H NMR (400 MHz, DMSO-d6) δ 11.38 (s, 1H), 7.87 (dd, 1H), 7.68 (d, J=8.3 Hz, 1H), 7.61-7.47 (m, 3H), 7.32 (d, J=8.6 Hz, 4H), 7.20 (d, J=8.2 Hz, 1H), 7.05-6.87 (m, 2H), 6.80-6.67 (m, 1H), 4.33-4.16 (m, 2H), 4.16-4.06 (m, 1H), 2.13-2.04 (m, 1H), 2.04-1.96 (m, 1H).

Example-51/52: (S&R)-4-(2-(1H-1,2,3-Triazol-1-yl)-4-(trifluoromethyl)phenyl)-N-(pyrimidin-2-yl)chromane-7-sulfonamide

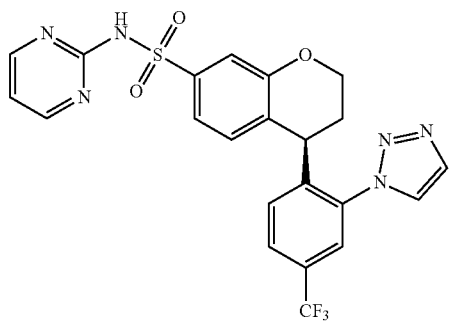

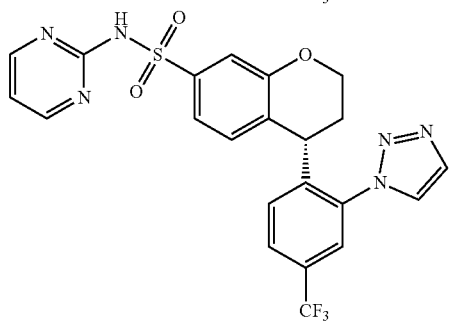

The title compounds were prepared by following the similar procedure as described in Example-1/2 using Intermediate-12 and pyrimidin-2-amine.

Further the enantiomers were separated using chiral preparative HPLC (Column: ChiralPak IA; Mobile phase: A=(Hexane+0.1% TFA), B=(IPA:MeOH=1:1), A:B=50:50 to afford isomer-1 and isomer-2. These isomers were obtained at retention time 6.04 min (Example-51) and retention time 8.32 min (Example-52).

LCMS: m/z 502.98 (M+H)$^+$; $^1$H NMR (400 MHz, DMSO-d6) δ 11.84 (s, 1H), 8.67 (s, 1H), 8.49 (d, J=4.9 Hz, 2H), 8.02-7.96 (m, 2H), 7.93-7.88 (m, 1H), 7.43-7.34 (m, 3H), 7.05-6.98 (m, 1H), 6.92 (d, J=8.6 Hz, 1H), 4.26-4.19 (m, 1H), 4.16-4.07 (m, 1H), 4.04-3.97 (m, 1H), 2.22-2.12 (m, 1H), 2.09-2.01 (m, 1H).

Example-53/54: (S&R)-4-(2-(1H-1,2,3-Triazol-1-yl)-4-(trifluoromethyl)phenyl)-N-(pyridazin-3-yl) chromane-7-sulfonamide

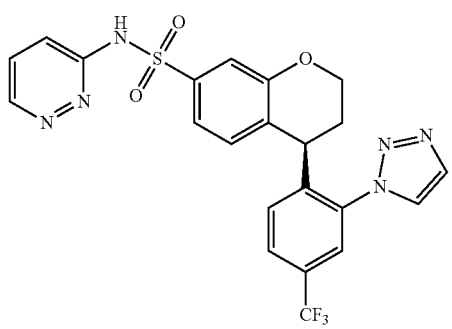

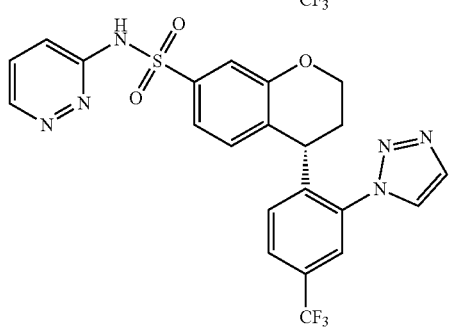

The title compounds were prepared by following the similar procedure as described in Example-1/2 using Intermediate-12 and pyridazin-3-amine.

Further the enantiomers were separated using chiral preparative HPLC (Column: ChiralPak IA; Mobile phase: A=(Hexane+0.1% TFA), B=(IPA:MeOH=1:1), A:B=50:50 to afford isomer-1 and isomer-2. These isomers were obtained at retention time 6.00 min (Example-53) and retention time 7.33 min (Example-54).

LCMS: m/z 502.96 (M+H)$^+$; $^1$H NMR (400 MHz, DMSO-d6) δ 14.54 (s, 1H), 8.69 (s, 1H), 8.31 (s, 1H), 8.05-7.96 (m, 2H), 7.94-7.84 (m, 2H), 7.75-7.66 (m, 1H), 7.40 (d, J=8.3 Hz, 1H), 7.25 (d, J=9.4 Hz, 2H), 6.90 (d, J=7.9 Hz, 1H), 4.27-4.19 (m, 1H), 4.15-4.07 (m, 1H), 4.03-3.97 (m, 1H), 2.21-2.12 (m, 1H), 2.09-2.00 (m, 1H).

Example-55/56: (S&R)-4-(2-(1H-1,2,3-Triazol-1-yl)-4-(trifluoromethyl)phenyl)-N-(5-fluoro pyrimidin-2-yl) chromane-7-sulfonamide

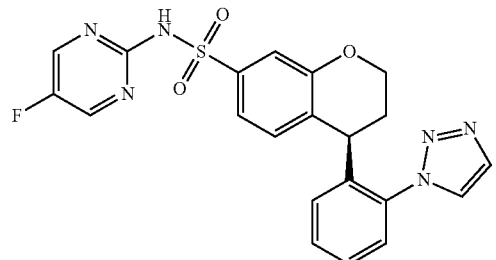

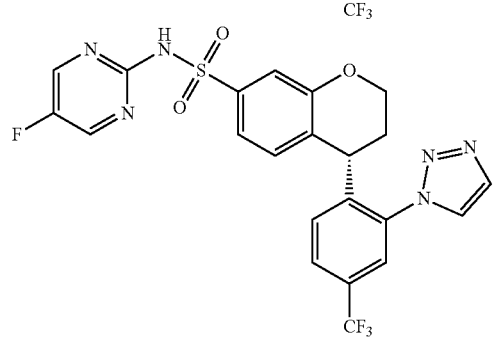

The title compounds were prepared by following the similar procedure as described in Example-1/2 using Intermediate-12 and 5-fluoropyrimidin-2-amine.

Further the enantiomers were separated using chiral preparative HPLC (Column: ChiralPak IA; Mobile phase: A=(Hexane+0.1% TFA), B=(IPA:MeOH=1:1), A:B=50:50 to afford isomer-1 and isomer-2. These isomers were obtained at retention time 5.53 min (Example-55) and retention time 7.82 min (Example-56).

LCMS: m/z 520.98 (M+H)$^+$; $^1$H NMR (400 MHz, DMSO-d6) δ 11.89 (s, 1H), 8.70-8.63 (m, 3H), 8.00 (d, J=7.4 Hz, 2H), 7.91 (d, J=8.3 Hz, 1H), 7.44-7.34 (m, 3H), 6.96 (d, J=8.5 Hz, 1H), 4.30-4.20 (m, 1H), 4.18-4.08 (m, 1H), 4.02 (t, J=7.2 Hz, 1H), 2.20-2.15 (m, 1H), 2.09-1.99 (m, 1H).

Example-57/58: (S&R)-4-(2-(1H-1,2,3-Triazol-1-yl)-4-(trifluoromethyl)phenyl)-N-(pyrimidin-4-yl) chromane-7-sulfonamide

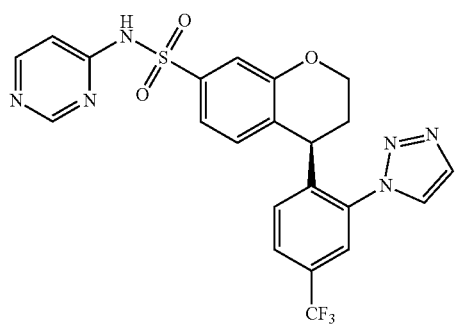

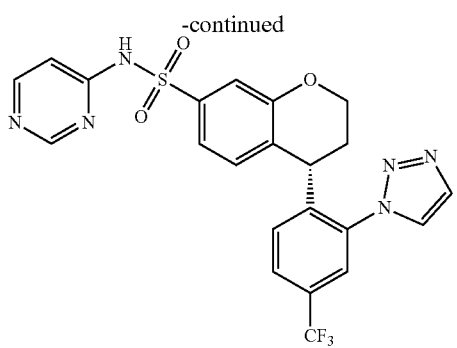

The title compounds were prepared by following the similar procedure as described in Example-1/2 using Intermediate-12 and pyrimidin-4-amine.

Further the enantiomers were separated using chiral preparative HPLC (Column: ChiralPak IA; Mobile phase: A=(Hexane+0.1% TFA), B=(IPA:MeOH=1:1), A:B=50:50 to afford isomer-1 and isomer-2. These isomers were obtained at retention time 5.18 min (Example-57) and retention time 7.17 min (Example-58).

LCMS: m/z 502.94 (M+H)$^+$; $^1$H NMR (400 MHz, DMSO-d6) δ 8.66-8.58 (m, 2H), 8.30 (s, 1H), 7.97 (d, J=11.7 Hz, 2H), 7.91 (dd, J=8.3, 1.9 Hz, 1H), 7.40 (d, J=8.3 Hz, 1H), 7.34-7.26 (m, 2H), 7.01 (s, 1H), 6.91 (d, J=8.0 Hz, 1H), 4.27-4.19 (m, 1H), 4.10 (t, J=9.9 Hz, 1H), 3.99 (t, J=7.4 Hz, 1H), 2.18-2.14 (m, 1H), 2.10-1.96 (m, 1H).

Example-59/60: (S&R)-4-(2-(1H-1,2,3-Triazol-1-yl)-4-(trifluoromethyl)phenyl)-N-(6-fluoropyridin-2-yl) chromane-7-sulfonamide

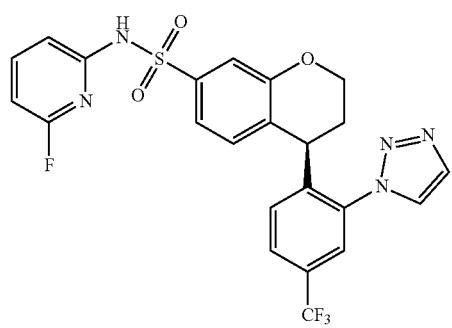

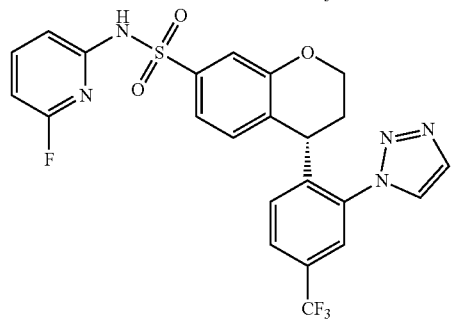

The title compounds were prepared by following the similar procedure as described in Example-1/2 using Intermediate-12 and 6-fluoropyridin-2-amine.

The enantiomers were separated using chiral preparative HPLC (Column: ChiralPak IA; Mobile phase: A=(Hexane+0.1% TFA), B=(EtOH:MeOH=1:1), A:B=60:40 to afford isomer-1 and isomer-2. These isomers were obtained at retention time 5.40 min (Example-59) and retention time 6.20 min (Example-60).

LCMS: m/z 520.02 (M+H)$^+$; $^1$H NMR (400 MHz, DMSO-d6) δ 11.39 (s, 1H), 8.66 (s, 1H), 7.99 (d, J=4.2 Hz, 2H), 7.94-7.81 (m, 2H), 7.43-7.30 (m, 3H), 6.97 (d, J=8.1 Hz, 2H), 6.77 (dd, J=8.2, 2.3 Hz, 1H), 4.29-4.19 (m, 1H), 4.13 (t, J=10.1 Hz, 1H), 4.02 (t, J=7.4 Hz, 1H), 2.22-2.13 (m, 1H), 2.11-1.97 (m, 1H).

Example-61/62: (S&R)—N-(6-Fluoropyridin-2-yl)-4-(2-(2-methylthiazol-4-yl)-4-(trifluoromethyl)phenylchroman-7-sulfonamide

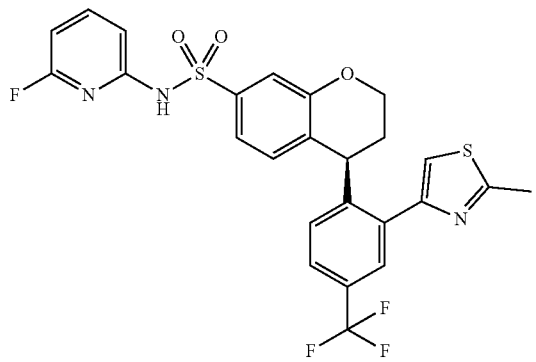

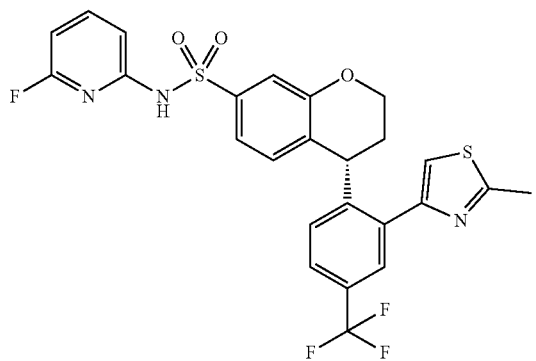

The title compounds were prepared by following the similar procedure as described in Example-1/2 using Intermediate-14 and 6-fluoropyridin-2-amine.

Further the enantiomers were separated using chiral preparative HPLC (Column: ChiralPak ID; Mobile phase: A=(Hexane+0.1% TFA), B=(EtOH:MeOH=1:1), A:B=70:30 to afford isomer-1 and isomer-2. These isomers were obtained at retention time 5.99 min (Example-61) and retention time 7.00 min (Example-62).

LCMS(ESI): m/z 549.95 (M+H)$^+$; $^1$H NMR (400 MHz, DMSO-d6) δ 11.38 (s, 1H), 7.87 (d, J=8.2 Hz, 1H), 7.85-7.78 (m, 2H), 7.67 (d, J=8.3 Hz, 1H), 7.36 (d, J=1.9 Hz, 1H), 7.35-7.27 (m, 1H), 7.19 (d, J=8.2 Hz, 1H), 7.01-6.93 (m, 1H), 6.89 (d, J=8.1 Hz, 1H), 6.81-6.70 (m, 1H), 4.86 (t, 1H), 4.30-4.15 (m, 2H), 2.69 (s, 3H), 2.31-2.16 (m, 1H), 2.14-2.02 (m, 1H).

Example-63/64: (S&R)-4-(2-(2-Methylthiazol-4-yl)-4-(trifluoromethyl)phenyl)-N-(pyrimidin-2-yl)chroman-7-sulfonamide

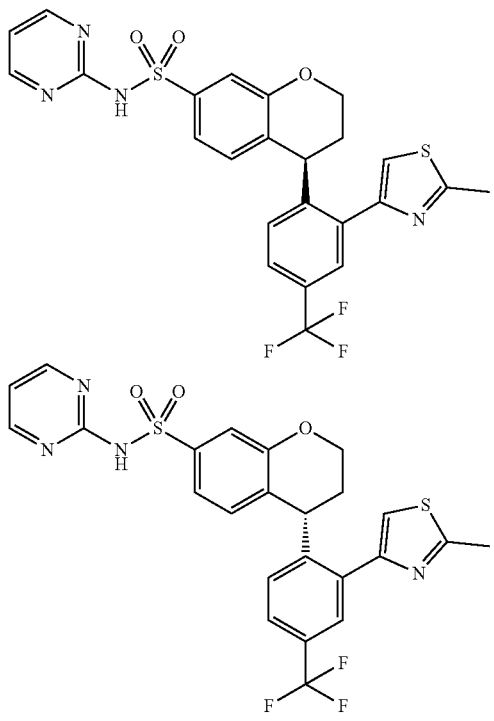

The title compounds were prepared by following the similar procedure as described in Example-1/2 using Intermediate-14 and pyrimidin-2-amine.

Further the enantiomers were separated using chiral preparative HPLC (Column: ChiralPak ID; Mobile phase: A=(Hexane+0.1% TFA), B=(MeOH:DCM=1:1), A:B=70:30 to afford isomer-1 and isomer-2. These isomers were obtained at retention time 7.36 min (Example-63) and retention time 8.21 min (Example-64).

LCMS(ESI): m/z 533.07 (M+H)$^+$; $^1$H NMR (400 MHz, DMSO-d6) δ 11.74 (s, 1H), 8.60-8.50 (m, 2H), 7.85-7.80 (m, 2H), 7.68 (d, J=8.6 Hz, 1H), 7.45-7.35 (m, 2H), 7.20 (d, J=8.3 Hz, 1H), 7.09 (s, 1H), 6.87 (d, J=8.2 Hz, 1H), 4.87 (t, J=7.2 Hz, 1H), 4.26-4.15 (m, 2H), 2.70 (s, 3H), 2.29-2.20 (m, 1H), 2.09-2.04 (m, 1H).

Example-65/66: (S&R)—N-(5-Fluoropyrimidin-2-yl)-4-(2-(2-methylthiazol-4-yl)-4-(trifluoromethyl)phenyl)chroman-7-sulfonamide

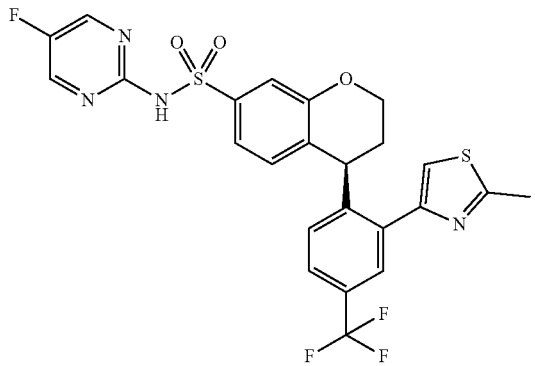

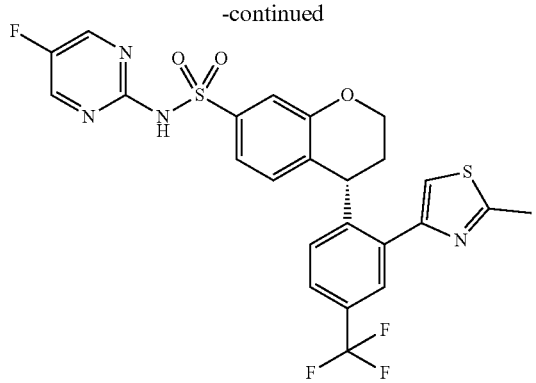

The title compounds were prepared by following the similar procedure as described in Example-1/2 using Intermediate-14 and 5-fluoropyrimidin-2-amine.

Further the enantiomers were separated using chiral preparative HPLC (Column: ChiralPak IA; Mobile phase: A=(Hexane+0.1% TFA), B=(MeOH:DCM=1:1), A:B=75:25 to afford isomer-1 and isomer-2. These isomers were obtained at retention time 7.06 min (Example-65) and retention time 8.00 min (Example-66).

LCMS(ESI): m/z 550.70 (M+H)$^+$; $^1$H NMR (400 MHz, DMSO-d6) δ 11.88 (s, 1H), 8.65 (s, 2H), 7.89-7.77 (m, 2H), 7.68 (dd, J=8.2, 2.1 Hz, 1H), 7.44-7.31 (m, 2H), 7.20 (d, J=8.2 Hz, 1H), 6.87 (d, J=8.1 Hz, 1H), 4.91-4.82 (m, 1H), 4.29-4.14 (m, 2H), 2.70 (s, 3H), 2.31-1.99 (m, 2H).

Example-67/68: (S&R)-4-(2-(2-Methylthiazol-4-yl)-4-(trifluoromethyl)phenyl)-N-(pyrimidin-4-yl)chroman-7-sulfonamide

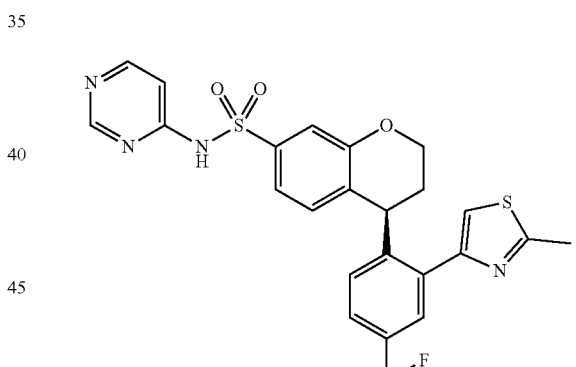

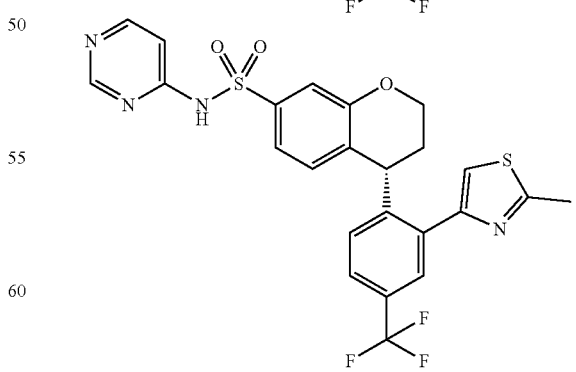

The title compounds were prepared by following the similar procedure as described in Example-1/2 using Intermediate-14 and pyrimidin-4-amine.

Further the enantiomers were separated using chiral preparative HPLC (Column: ChiralPak IA; Mobile phase: A=(Hexane+0.1% TFA), B=(MeOH:DCM=1:1), A:B=75:25 to afford isomer-1 and isomer-2. These isomers were obtained at retention time 6.82 min (Example-67) and retention time 7.72 min (Example-68).

LCMS (ESI): m/z 533.06 (M+H)$^+$; $^1$H NMR (400 MHz, DMSO-d6) δ 8.66 (s, 1H), 8.37 (s, 1H), 7.85-7.79 (m, 2H), 7.72-7.64 (m, 1H), 7.35-7.27 (m, 2H), 7.20 (d, J=8.3 Hz, 1H), 7.06 (s, 1H), 6.86 (d, J=8.0 Hz, 1H), 4.86 (t, J=7.3 Hz, 1H), 4.27-4.15 (m, 2H), 2.70 (s, 3H), 2.27-2.18 (m, 1H), 2.09-2.04 (m, 1H).

Example-69/70: (S&R)-4-(2-(2-Methylthiazol-4-yl)-4-(trifluoromethyl)phenyl)-N-(pyridazin-3-yl)chroman-7-sulfonamide

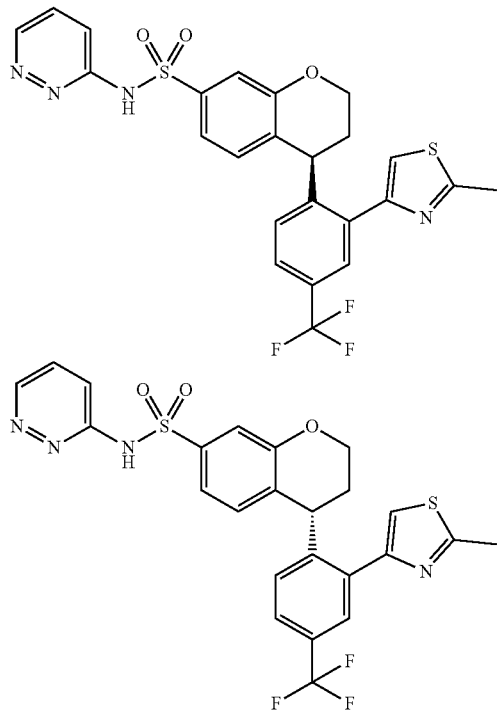

The title compounds were prepared by following the similar procedure as described in Example-1/2 using Intermediate-14 and pyridazin-3-amine.

Further the enantiomers were separated using chiral preparative HPLC (Column: ChiralPak ID; Mobile phase: A=(Hexane+0.1% TFA), B=(MeOH:DCM=1:1), A:B=75:25 to afford isomer-1 and isomer-2. These isomers were obtained at retention time 9.94 min (Example-69) and retention time 10.92 min (Example-70).

LCMS (ESI): m/z 533.08 (M+H)$^+$; $^1$H NMR (400 MHz, DMSO-d6) δ 8.33 (s, 1H), 7.94-7.81 (m, 3H), 7.75-7.65 (m, 2H), 7.29-7.17 (m, 3H), 6.83 (d, J=8.0 Hz, 1H), 4.85 (t, J=7.1 Hz, 1H), 4.29-4.12 (m, 2H), 2.71 (s, 3H), 2.27-2.06 (m, 2H).

Example-71/72: (S&R)—N-(5-Fluoropyrimidin-2-yl)-4-(2-(2-methyloxazol-4-yl)-4-(trifluoromethyl)phenyl)chroman-7-sulfonamide

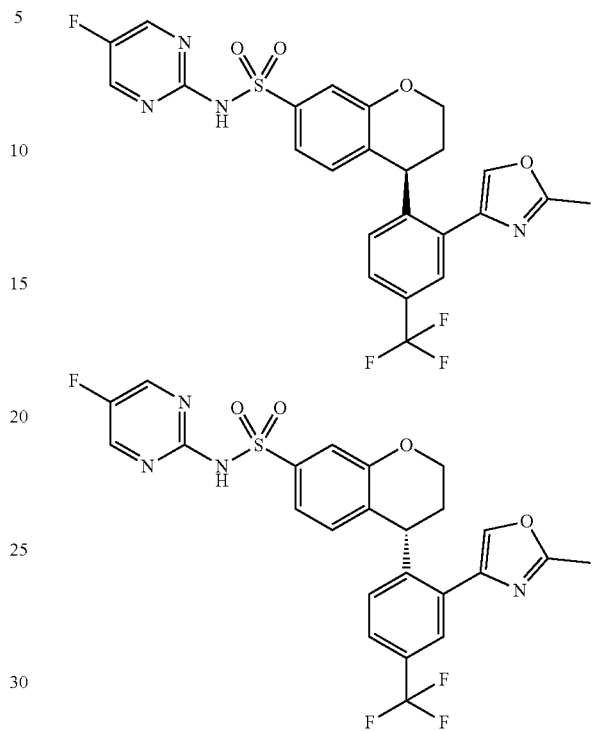

The title compounds were prepared by following the similar procedure as described in Example-1/2 using Intermediate-16 and 5-fluoropyrimidin-2-amine.

Further the enantiomers were separated using chiral preparative HPLC (Column: ChiralPak IF; Mobile phase: A=(Hexane+0.1% TFA), B=(MeOH:DCM=1:1), A:B=70:30 to afford isomer-1 and isomer-2. These isomers were obtained at retention time 6.59 min (Example-71) and retention time 7.90 min (Example-72).

LCMS (ESI): m/z 534.82 (M+H)$^+$; $^1$H NMR (400 MHz, DMSO-d$_6$) δ 11.89 (s, 1H), 8.66 (s, 2H), 8.43 (s, 1H), 8.01 (s, 1H), 7.64 (d, J=8.2 Hz, 1H), 7.45-7.32 (m, 2H), 7.14 (d, J=8.2 Hz, 1H), 6.90 (d, J=8.1 Hz, 1H), 4.91 (t, J=6.7 Hz, 1H), 4.30-4.15 (m, 2H), 2.48 (s, 3H), 2.36-2.25 (m, 1H), 2.06-1.95 (m, 1H).

Example-73/74: (S&R)—N-(6-Fluoropyridin-2-yl)-4-(2-(2-methyloxazol-4-yl)-4-(trifluoromethyl)phenyl)chroman-7-sulfonamide

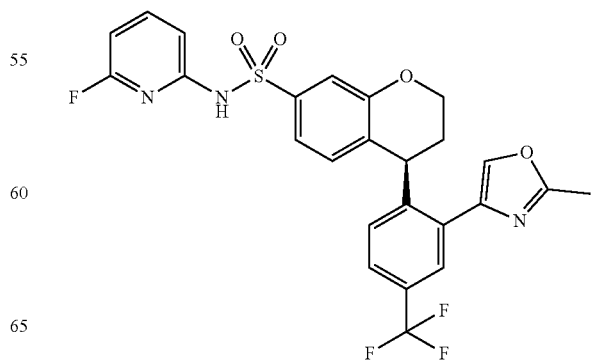

-continued

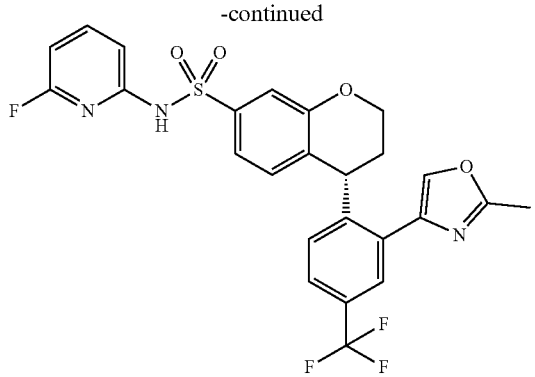

The title compounds were prepared by following the similar procedure as described in Example-1/2 using Intermediate-16 and 6-fluoropyridin-2-amine.

Further the enantiomers were separated using chiral preparative HPLC (Column: ChiralPak IF; Mobile phase: A=(Hexane+0.1% TFA), B=(EtOH:MeOH=1:1), A:B=60:40 to afford retention time 6.06 min (Example-73) and retention time 7.73 min (Example-74).

LCMS (ESI): m/z 534.07 (M+H)$^+$; $^1$H NMR (400 MHz, Chloroform-d) δ 7.83-7.69 (m, 3H), 7.52 (d, J=8.3 Hz, 1H), 7.44 (d, J=2.0 Hz, 1H), 7.34-7.23 (m, 2H), 7.05 (d, J=8.2 Hz, 1H), 6.89 (d, J=8.2 Hz, 1H), 6.64 (dd, J=8.0, 2.3 Hz, 1H), 4.89 (t, J=6.9 Hz, 1H), 4.33-4.10 (m, 2H), 2.55 (s, 3H), 2.36-2.28 (m, 1H), 2.12-2.05 (m, 1H).

Example-75/76: (S&R)-4-(2-(2-methyloxazol-4-yl)-4-(trifluoromethyl)phenyl)-N-(pyrimidin-2-yl)chroman-7-sulfonamide

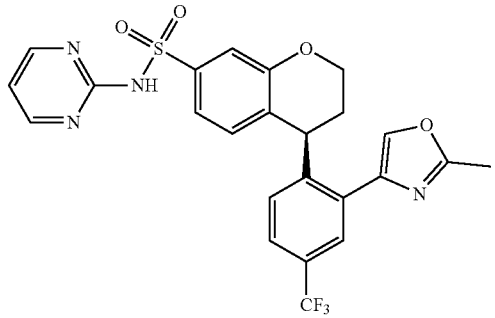

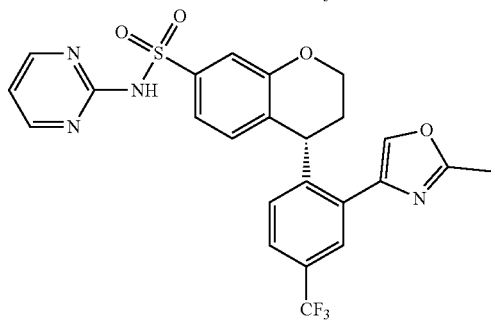

The title compounds were prepared by following the similar procedure as described in Example-1/2 using Intermediate-16 and pyrimidin-2-amine.

Further the enantiomers were separated using chiral preparative HPLC (Column: ChiralPak ID; Mobile phase: A=(Hexane+0.1% TFA), B=(MeOH:DCM=1:1), A:B=70:30 to afford retention time 7.82 min (Example-75) and retention time 8.96 min (Example-76).

LCMS (ESI): m/z 517.04 (M+H)$^+$; $^1$H NMR (400 MHz, DMSO-d$_6$) δ 11.76 (s, 1H), 8.61-8.51 (m, 2H), 8.44 (s, 1H), 8.01 (d, J=1.9 Hz, 1H), 7.64 (d, J=7.9 Hz, 1H), 7.46-7.34 (m, 2H), 7.18-7.06 (m, 2H), 6.89 (d, J=8.2 Hz, 1H), 4.91 (t, J=6.7 Hz, 1H), 4.28-4.16 (m, 2H), 2.5 (s, 3H), 2.37-1.95 (m, 2H).

Example-77/78: (S&R)-4-(2-(2-methyloxazol-4-yl)-4-(trifluoromethyl)phenyl)-N-(pyrimidin-4-yl)chroman-7-sulfonamide

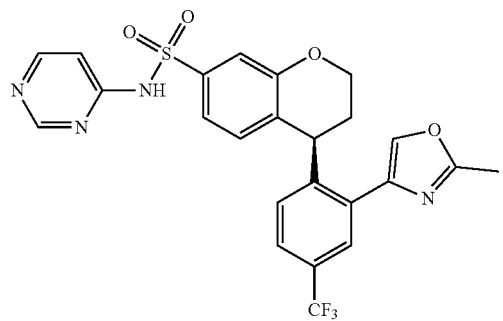

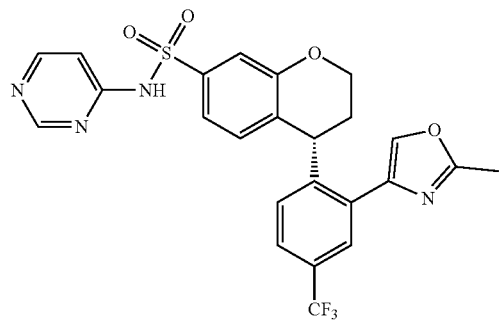

The title compounds were prepared by following the similar procedure as described in Example-1/2 using Intermediate-16 and pyrimidin-4-amine.

Further the enantiomers were separated using chiral preparative HPLC (Column: ChiralPak ID; Mobile phase: A=(Hexane+0.1% TFA), B=(MeOH:DCM=1:1), A:B=75:25 to afford retention time 7.19 min (Example-77) and retention time 8.12 min (Example-78).

LCMS (ESI): m z 516.82 (M+H)$^+$; $^1$H NMR (400 MHz, DMSO-d$_6$) δ 8.66 (s, 1H), 8.44 (s, 1H), 8.37 (s, 1H), 8.00 (d, J=2.0 Hz, 1H), 7.64 (d, J=8.3 Hz, 1H), 7.39-7.29 (m, 2H), 7.17-7.02 (m, 2H), 6.88 (d, J=8.1 Hz, 1H), 4.90 (t, J=6.8 Hz, 1H), 4.23 (d, J=10.7 Hz, 2H), 2.53 (s, 3H), 2.30-2.00 (m, 2H).

Example-79/80: (S&R)-4-(2-(2-methyloxazol-4-yl)-4-(trifluoromethyl)phenyl)-N-(pyridazin-3-yl)chroman-7-sulfonamide

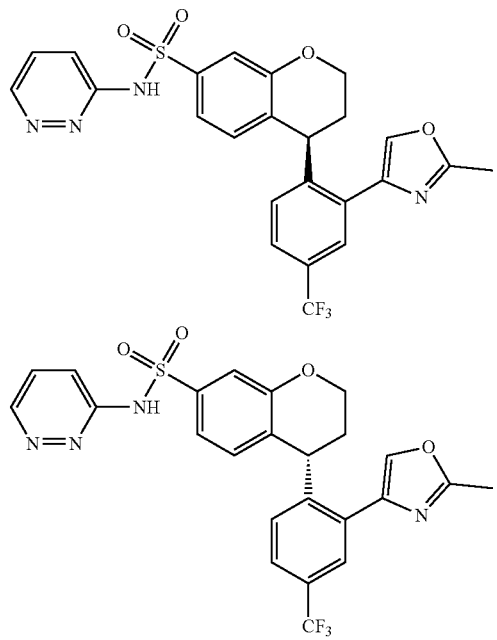

The title compounds were prepared by following the similar procedure as described in Example-1/2 using Intermediate-16 and pyridazin-3-amine.

Further the enantiomers were separated using chiral preparative HPLC (Column: ChiralPak ID; Mobile phase: A=(Hexane+0.1% TFA), B=(MeOH:DCM=1:1), A:B=70:30 to afford retention time 7.71 min (Example-79) and retention time 8.58 min (Example-80).

LCMS (ESI): m/z 516.82 (M+H)[+]; $^1$H NMR (400 MHz, DMSO-d6) δ 14.53 (s, 1H), 8.44 (s, 1H), 8.31 (s, 1H), 8.04-7.87 (m, 2H), 7.75-7.60 (m, 2H), 7.32-7.22 (m, 2H), 7.14 (d, J=8.2 Hz, 1H), 6.84 (d, J=8.0 Hz, 1H), 4.89 (t, J=6.6 Hz, 1H), 4.27-4.13 (m, 2H), 2.55 (s, 3H), 2.38-1.95 (m, 2H).

Example-81/82: (S&R)—N-(6-Fluoropyridin-2-yl)-4-(2-(2-(methylsulfonyl)ethyl)-4-(trifluoromethyl)phenyl)chroman-7-sulfonamide

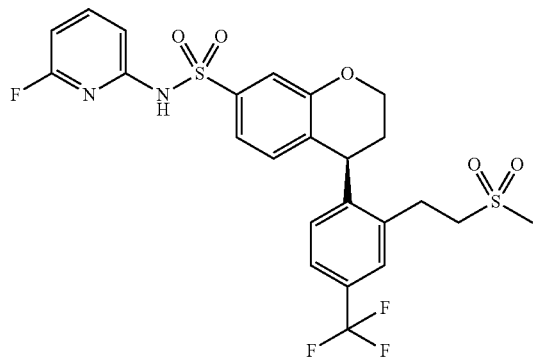

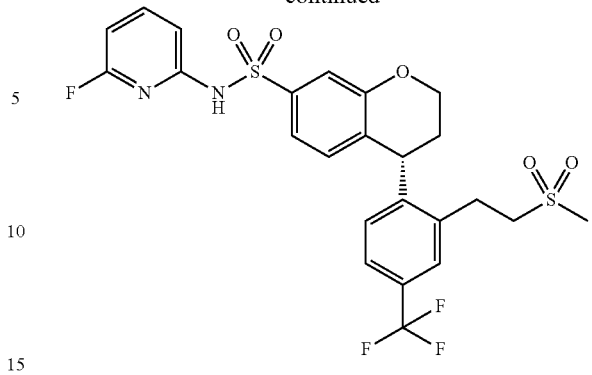

The title compounds were prepared by following the similar procedure as described in Example-1/2 using perfluorophenyl Intermediate-18 and 6-fluoropyridin-2-amine.

Further the enantiomers were separated using chiral preparative HPLC (Column: ChiralPak IA; Mobile phase: A=(Hexane+0.1% TFA), B=(EtOH:DCM=1:1), A:B=60:40 to afford isomer-1 and isomer-2. These isomers were obtained at retention time 5.62 min (Example-81) and retention time 7.40 min (Example-82).

LCMS (ESI): m/z 559.22 (M+H)[+]; $^1$H NMR (400 MHz, DMSO-d$_6$) δ 11.38 (s, 1H), 7.92-7.81 (m, 1H), 7.75 (s, 1H), 7.52 (d, J=8.2 Hz, 1H), 7.39 (d, J=1.9 Hz, 1H), 7.33 (dd, J=8.1, 1.9 Hz, 1H), 7.03-6.95 (m, 2H), 6.92 (d, J=8.2 Hz, 1H), 6.77 (dd, J=8.1, 2.4 Hz, 1H), 4.61 (t, 1H), 4.31-4.18 (m, 2H), 3.63-3.45 (m, 2H), 3.30-3.13 (m, 2H), 3.05 (s, 3H), 2.35-2.23 (m, 1H), 2.09-1.91 (m, 1H).

Example-83/84: (S&R)-4-(2-(2-(Methylsulfonyl)ethyl)-4-(trifluoromethyl)phenyl)-N-(pyrimidin-2-yl)chroman-7-sulfonamide

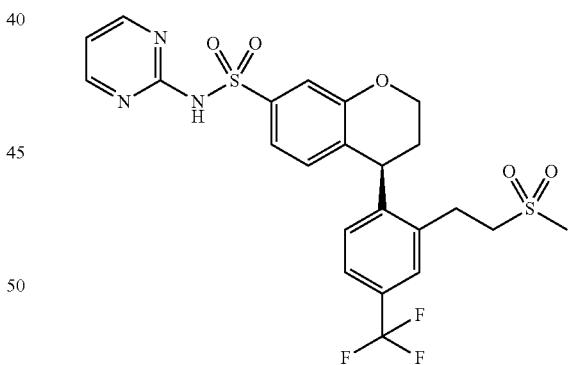

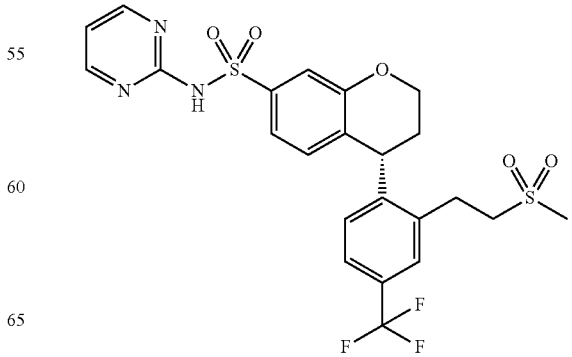

The title compounds were prepared by following the similar procedure as described in Example-1/2 using Intermediate-18 and pyrimidin-2-amine.

Further the enantiomers were separated using chiral preparative HPLC (Column: ChiralPak IA; Mobile phase: A=(Hexane+0.1% TFA), B=(EtOH:DCM=1:1), A:B=50:50 to afford isomer-1 and isomer-2. These isomers were obtained at retention time 5.49 min (Example-83) and retention time 6.83 min (Example-84).

LCMS (ESI): m/z 542.06 (M+H)$^+$; $^1$H NMR (400 MHz, DMSO-d$_6$) δ 11.77 (s, 1H), 8.54 (d, J=4.9 Hz, 2H), 7.75 (d, J=2.0 Hz, 1H), 7.52 (dd, J=8.3, 2.0 Hz, 1H), 7.45-7.33 (m, 2H), 7.11-6.95 (m, 2H), 6.89 (d, J=8.2 Hz, 1H), 4.61 (t, J=6.8 Hz, 1H), 4.34-4.18 (m, 2H), 3.64-3.46 (m, 2H), 3.29-3.14 (m, 2H), 3.05 (s, 3H), 2.36-2.25 (m, 1H), 2.07-1.94 (m, 1H).

Example-85/86: (S&R)—N-(5-Fluoropyrimidin-2-yl)-4-(2-(2-(methylsulfonyl)ethyl)-4-(trifluoromethyl)phenyl)chroman-7-sulfonamide

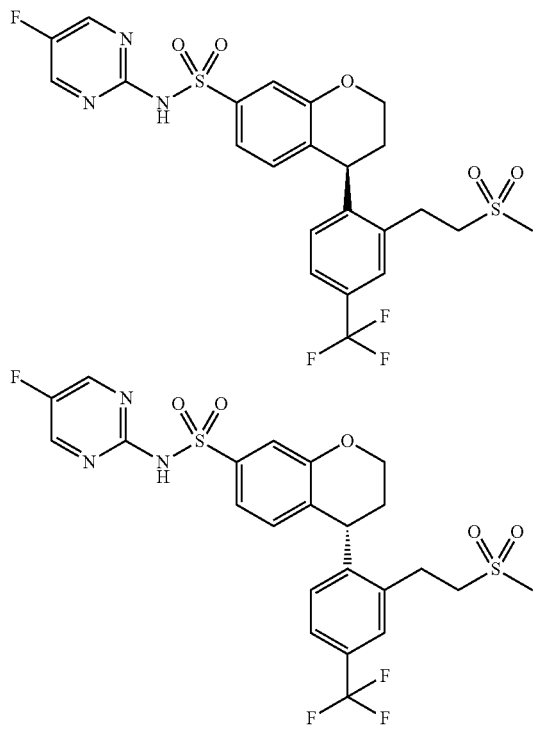

The title compounds were prepared by following the similar procedure as described in Example-1/2 using Intermediate-18 and 5-fluoropyrimidin-2-amine.

Further the enantiomers were separated using chiral preparative HPLC (Column: ChiralPak IA; Mobile phase: A=(Hexane+0.1% TFA), B=(EtOH:DCM=1:1), A:B=50:50 to afford isomer-1 and isomer-2. These isomers were obtained at retention time 4.96 min (Example-85) and retention time 6.00 min (Example-86).

LCMS (ESI): m/z 560.01 (M+H)$^+$; $^1$H NMR (400 MHz, DMSO-d$_6$) δ 8.62 (s, 2H), 7.73 (s, 1H), 7.57-7.48 (m, 1H), 7.46-7.30 (m, 2H), 7.00 (d, J=8.2 Hz, 1H), 6.88 (d, J=8.2 Hz, 1H), 4.59 (t, J=6.9 Hz, 1H), 4.32-4.19 (m, 2H), 3.55-3.45 (m, 2H) 3.32-3.12 (m, 2H), 3.03 (s, 3H), 2.37-2.23 (m, 1H), 2.07-1.93 (m, 1H).

Example-87/88: (S&R)-4-(2-(2-(Methylsulfonyl)ethyl)-4-(trifluoromethyl)phenyl)-N-(pyrimidin-4-yl)chroman-7-sulfonamide

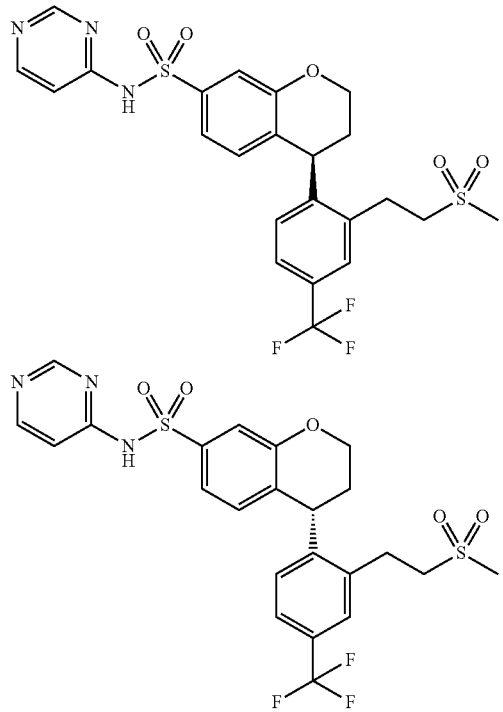

The title compounds were prepared by following the similar procedure as described in Example-1/2 using Intermediate-18 and pyrimidin-4-amine.

Further the enantiomers were separated using chiral preparative HPLC (Column: ChiralPak IA; Mobile phase: A=(Hexane+0.1% TFA), B=(EtOH:DCM=1:1), A:B=50:50 to afford isomer-1 and isomer-2. These isomers were obtained at retention time 4.53 min (Example-87) and retention time 6.96 min (Example-88).

LCMS (ESI): m/z 542.06 (M+H)$^+$; $^1$H NMR (400 MHz, DMSO-d$_6$) δ 8.65 (s, 1H), 8.36 (s, 1H), 7.75 (s, 1H), 7.53 (d, J=8.2 Hz, 1H), 7.38-7.23 (m, 2H), 7.11-6.98 (m, 2H), 6.89 (d, J=8.1 Hz, 1H), 4.60 (t, J=6.9 Hz, 1H), 4.35-4.19 (m, 2H), 3.64-3.46 (m, 2H), 3.30-3.15 (m, 2H), 3.06 (s, 3H), 2.37-2.24 (m, 1H), 2.10-1.95 (m, 1H).

Example-89/90: (S&R)-4-(2-(1H-pyrazol-1-yl)-4-(trifluoromethyl)phenyl)-N-(6-fluoropyridin-2-yl)chroman-7-sulfonamide

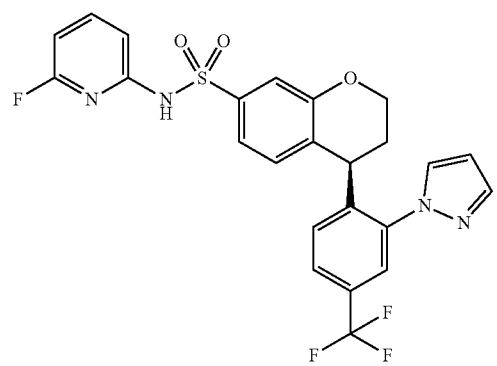

-continued

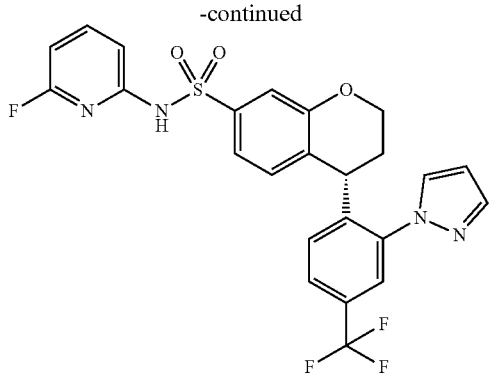

The title compounds were prepared by following the similar procedure as described in Example-1/2 using Intermediate-20 and 6-fluoropyridin-2-amine.

Further the enantiomers were separated using chiral preparative HPLC (Column: ChiralPak IA; Mobile phase: A=(Hexane+0.1% TFA), B=(EtOH:MeOH=1:1), A:B=70:30, to afford isomer-1 and isomer-2. These isomers were obtained at retention time 6.02 min (Example-89) and retention time 6.82 min (Example-90).

LCMS(ESI): m/z 519.19 (M+H)$^+$; $^1$H NMR (400 MHz, DMSO-d$_6$) δ 11.39 (s, 1H), 8.23 (d, J=2.4 Hz, 1H), 7.92-7.72 (m, 4H), 7.38-7.27 (m, 3H), 7.01-6.92 (m, 2H), 6.77 (dd, J=8.0, 2.4 Hz, 1H), 6.58-6.51 (m, 1H), 4.39-4.08 (m, 3H), 2.24-1.97 (m, 2H).

Example-91/92: (S&R)—N-(5-fluoropyrimidin-2-yl)-4-(2-(thiazol-2-yl)-4-(trifluoromethyl)phenyl)chroman-7-sulfonamide

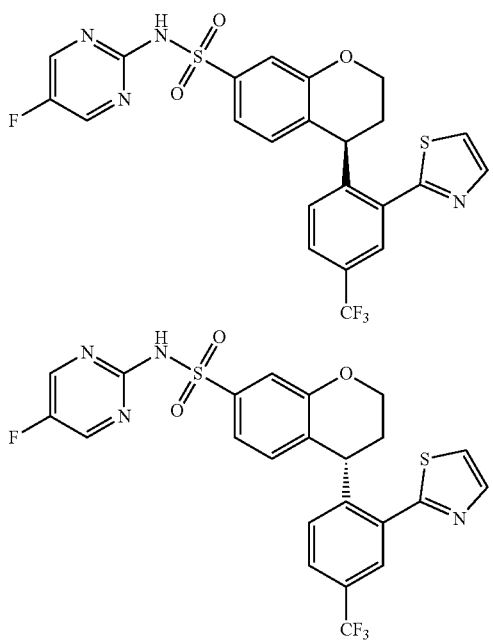

The title compounds were prepared by following the similar procedure as described in Example-1/2 using Intermediate-22 and 5-fluoropyrimidin-2-amine.

Further the enantiomers were separated using chiral preparative HPLC (Column: ChiralPak IE; Mobile phase: A=(Hexane+0.1% TFA), B=(EtOH:MeOH=1:1), A:B=50:50, to afford isomer-1 and isomer-2. These isomers were obtained at retention time 6.43 min (Example-91) and retention time 7.23 min (Example-92).

LCMS(ESI): m/z 523.19 (M+H)$^+$; $^1$H NMR (400 MHz, DMSO-d$_6$) δ 11.89 (s, 1H), 8.66 (s, 2H), 8.07-7.92 (m, 3H), 7.79 (dd, J=8.5, 2.1 Hz, 1H), 7.42-7.33 (m, 2H), 7.30 (d, J=8.4 Hz, 1H), 6.92 (d, J=8.1 Hz, 1H), 5.07 (t, J=7.2 Hz, 1H), 4.31-4.13 (m, 2H), 2.28-2.03 (m, 2H).

Example-93: (R/S)—N-(pyrimidin-2-yl)-4-(2-(thiazol-2-yl)-4-(trifluoromethyl)phenyl)chroman-7-sulfonamide

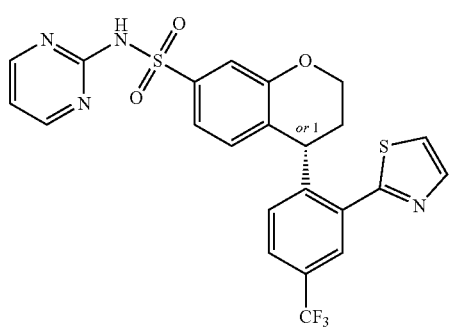 [SMILES: O=S(=O)(Nc1ncccn1)c1ccc2c(c1)OCC[C@@H]2c1ccc(C(F)(F)F)cc1-c1nccs1]

The title compound was prepared by following the similar procedure as described in Example-1/2 using Intermediate-22b and pyrimidin-2-amine.

LCMS(ESI): m/z 518.95 (M+H)$^+$; $^1$H NMR (400 MHz, DMSO-d$_6$) δ 11.75 (s, 1H), 8.54 (d, J=4.9 Hz, 2H), 8.06-7.93 (m, 3H), 7.79 (d, J=8.3 Hz, 1H), 7.43-7.33 (m, 2H), 7.29 (d, J=8.3 Hz, 1H), 7.08 (t, J=4.9 Hz, 1H), 6.91 (d, J=8.2 Hz, 1H), 5.07 (t, J=7.2 Hz, 1H), 4.30-4.09 (m, 2H), 2.32-2.05 (m, 2H).

Example-94: (R/S)—N-(pyrimidin-4-yl)-4-(2-(thiazol-2-yl)-4-(trifluoromethyl)phenyl)chroman-7-sulfonamide

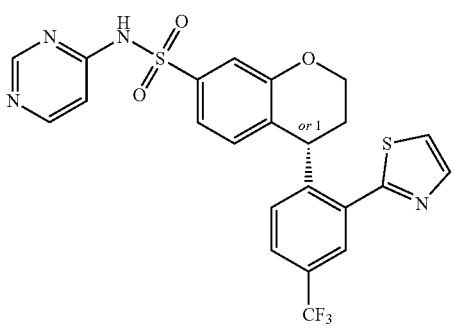 [SMILES: O=S(=O)(Nc1ccncn1)c1ccc2c(c1)OCC[C@@H]2c1ccc(C(F)(F)F)cc1-c1nccs1]

The title compound was prepared by following the similar procedure as described in Example-1/2 using Intermediate-22b and pyrimidin-4-amine.

LCMS(ESI): m/z 518.96 (M+H)$^+$; $^1$H NMR (400 MHz, DMSO-d$_6$) δ 8.65 (s, 1H), 8.36 (s, 1H), 8.12-7.93 (m, 3H), 7.79 (d, J=8.3 Hz, 1H), 7.40-7.23 (m, 3H), 7.05 (s, 1H), 6.90 (d, J=8.1 Hz, 1H), 5.06 (t, J=7.1 Hz, 1H), 4.30-4.12 (m, 2H), 2.31-2.05 (m, 2H).

Example-95: (R/S)—N-(pyridazin-3-yl)-4-(2-(thiazol-2-yl)-4-(trifluoromethyl)phenyl)chroman-7-sulfonamide

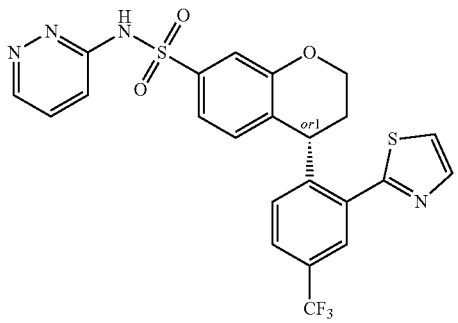 [SMILES: O=S(=O)(Nc1cccnn1)c1ccc2c(c1)OCC[C@@H]2c1ccc(C(F)(F)F)cc1-c1nccs1]

The title compound was prepared by following the similar procedure as described in Example-1/2 using Intermediate-22b and pyridazin-3-amine.

LCMS(ESI): m/z 518.88 (M+H)⁺; ¹H NMR (400 MHz, DMSO-d₆) δ 14.52 (s, 1H), 8.30 (s, 1H), 8.10-7.87 (m, 4H), 7.79 (dd, J=8.2, 2.0 Hz, 1H), 7.70 (dd, J=9.5, 3.7 Hz, 1H), 7.37-7.14 (m, 3H), 6.87 (d, J=8.0 Hz, 1H), 5.05 (t, J=7.1 Hz, 1H), 4.30-4.12 (m, 2H), 2.30-2.07 (m, 2H).

Example-96: (R/S)—N-(6-fluoropyridin-2-yl)-4-(2-(thiazol-2-yl)-4-(trifluoromethyl)phenyl)chroman-7-sulfonamide

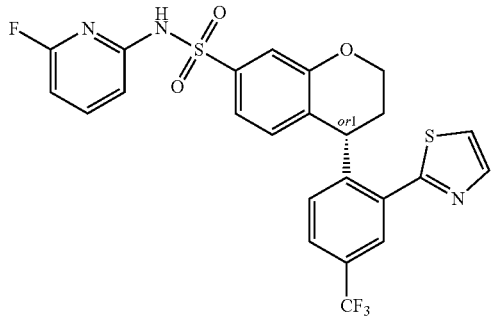 [SMILES: O=S(=O)(Nc1cccc(F)n1)c1ccc2c(c1)OCC[C@@H]2c1ccc(C(F)(F)F)cc1-c1nccs1]

The title compound was prepared by following the similar procedure as described in Example-1/2 using Intermediate-22b and 6-fluoropyridin-2-amine.

LCMS(ESI): m/z 535.94 (M+H)⁺; ¹H NMR (400 MHz, DMSO-d₆) δ 11.37 (s, 1H), 8.05-7.93 (m, 3H), 7.87 (dd, J=8.2 Hz, 1H), 7.78 (dd, J=8.3, 2.0 Hz, 1H), 7.39-7.26 (m, 3H), 7.01-6.89 (m, 2H), 6.77 (dd, J=7.9, 2.4 Hz, 1H), 5.07 (t, J=8.2, 6.1 Hz, 1H), 4.31-4.13 (m, 2H), 2.31-2.08 (m, 2H).

Example-97/98: (S&R)-4-(2-(6-isopropoxypyridin-3-yl)-4-(trifluoromethyl)phenyl)-N-(pyrimidin-2-yl)chroman-7-sulfonamide

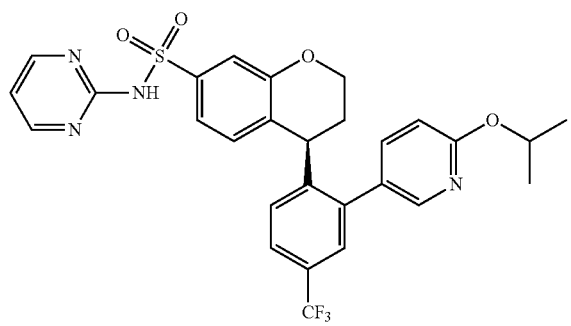

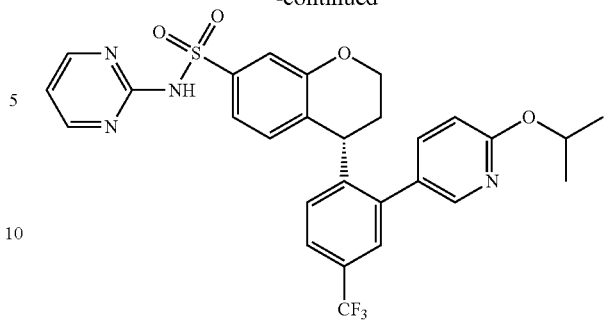

The title compounds were prepared by following the similar procedure as described in Example-1/2 using Intermediate-24 and pyrimidin-2-amine.

Further the enantiomers were separated using chiral preparative HPLC (Column: ChiralPak IE; Mobile phase: A=(Hexane+0.1% TFA), B=(IPA:DCM=1:1), A:B=60:40, to afford isomer-1 and isomer-2. These isomers were obtained at retention time 9.69 min (Example-97) and retention time 10.74 min (Example-98).

LCMS(ESI): m/z 571.14 (M+H)⁺; ¹H NMR (400 MHz, DMSO-d₆) δ 11.74 (s, 1H), 8.53 (d, J=4.8 Hz, 2H), 8.26 (s, 1H), 7.82 (d, J=8.8 Hz, 1H), 7.68 (d, J=8.3 Hz, 1H), 7.62 (s, 1H), 7.36 (d, J=8.7 Hz, 2H), 7.22 (d, J=8.3 Hz, 1H), 7.08 (s, 1H), 6.92 (d, J=8.1 Hz, 1H), 6.84 (d, J=8.5 Hz, 1H), 5.33-5.23 (m, 1H), 4.34-4.10 (m, 3H), 2.17-1.96 (m, 2H), 1.32 (d, 3H), 1.24 (d, 3H).

Example-99/100: (S&R)—N-(5-fluoropyrimidin-2-yl)-4-(2-(6-isopropoxypyridin-3-yl)-4-(trifluoromethyl)phenyl)chroman-7-sulfonamide

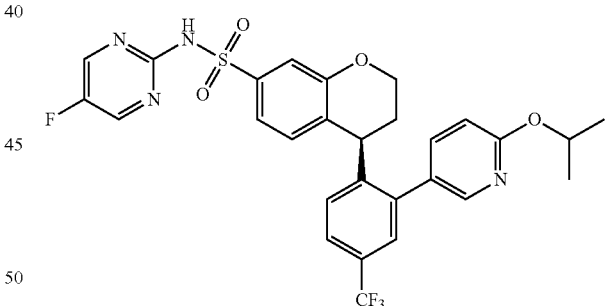

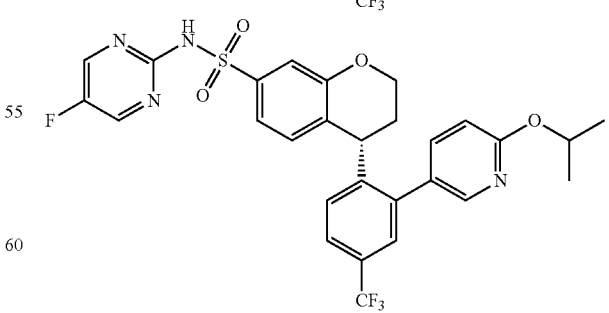

The title compounds were prepared by following the similar procedure as described in Example-1/2 using Intermediate-24 and 5-fluoropyrimidin-2-amine.

Further the enantiomers were separated using chiral preparative HPLC (Column: ChiralPak IE; Mobile phase: (MeOH+0.1% TFA) to afford isomer-1 and isomer-2. These isomers were obtained at retention time 5.67 min (Example-99) and retention time 6.21 min (Example-100). LCMS (ESI): m/z 588.83 (M+H)⁺; ¹H NMR (400 MHz, DMSO-d₆) δ 11.88 (s, 1H), 8.65 (s, 2H), 8.25 (s, 1H), 7.89-7.52 (m, 3H), 7.42-7.28 (m, 2H), 7.22 (d, J=8.2 Hz, 1H), 6.89 (dd, J=36.7, 8.3 Hz, 2H), 5.29 (quint, J=6.3 Hz, 1H), 4.37-4.04 (m, 3H), 2.22-1.93 (m, 2H), 1.32 (d, 6H).

Example-101/102: (S&R)-4-(2-(6-ethoxypyridin-3-yl)-4-(trifluoromethyl)phenyl)-N-(5-fluoropyrimidin-2-yl)chroman-7-sulfonamide

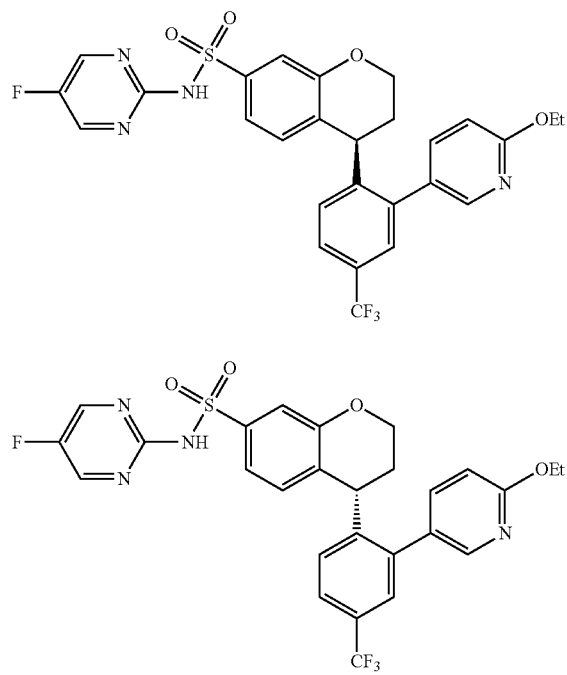 [SMILES: CCOc1ccc(-c2cc(C(F)(F)F)ccc2[C@@H]2CCOc3cc(S(=O)(=O)Nc4ncc(F)cn4)ccc32)cn1 ; CCOc1ccc(-c2cc(C(F)(F)F)ccc2[C@H]2CCOc3cc(S(=O)(=O)Nc4ncc(F)cn4)ccc32)cn1]

The title compounds were prepared by following the similar procedure as described in Example-1/2 using Intermediate-26 and 5-fluoropyrimidin-2-amine.

Further the enantiomers were separated using chiral preparative HPLC (Column: ChiralPak IE; Mobile phase: (MeOH+0.1% TFA) to afford isomer-1 and isomer-2. These isomers were obtained at retention time 6.25 min (Example-101) and retention time 7.25 min (Example-102).

LCMS(ESI): m/z 575.26 (M+H)⁺; ¹H NMR (400 MHz, DMSO-d₆) δ 11.87 (s, 1H), 8.65 (s, 2H), 8.26 (d, J=2.5 Hz, 1H), 7.83 (dd, J=8.6, 2.5 Hz, 1H), 7.69 (dd, J=8.4, 2.1 Hz, 1H), 7.62 (d, J=2.0 Hz, 1H), 7.39-7.32 (m, 2H), 7.22 (d, J=8.3 Hz, 1H), 6.99-6.85 (m, 2H), 4.35 (q, 2H), 4.31-4.20 (m, 2H), 4.17-4.08 (m, 1H), 2.21-1.96 (m, 2H), 1.34 (t, J=7.0 Hz, 3H).

Example-103: (R/S)-4-(2-(6-ethoxypyridin-3-yl)-4-(trifluoromethyl)phenyl)-N-(pyrimidin-2-yl)chroman-7-sulfonamide

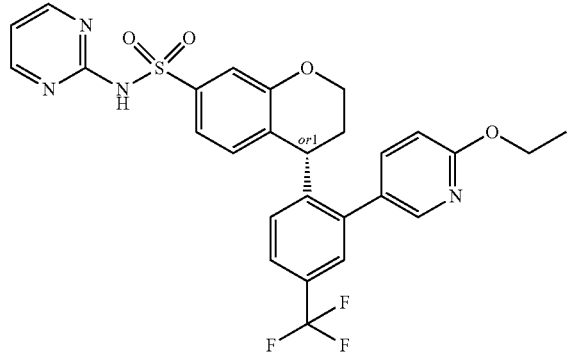 [SMILES: CCOc1ccc(-c2cc(C(F)(F)F)ccc2[C@H]2CCOc3cc(S(=O)(=O)Nc4ncccn4)ccc32)cn1]

To the stirred solution of (R/S)-4-(2-(6-fluoropyridin-3-yl)-4-(trifluoromethyl)phenyl)-N-(pyrimidin-2-yl)chroman-7-sulfonamide (Example-36) (0.10 g, 0.19 mmol) in EtOH (5 ml), K₂CO₃ (0.078 g, 0.57 mmol) was added at room temperature and reaction was stirred for 15 h at 100° C. After completion of reaction as indicated by TLC, reaction mixture was poured in to water and extract with ethyl acetate. The organic layer was dried over Na₂SO₄ and evaporated under vacuum. The crude product was purified by column chromatography followed by chiral preparative HPLC to obtain title compound (0.020 g, 19.06%). LCMS(ESI): m/z 557.12 (M+H)⁺; ¹H NMR (400 MHz, DMSO-d₆) δ 11.75 (s, 1H), 8.53 (d, J=4.9 Hz, 2H), 8.26 (d, J=2.4 Hz, 1H), 7.83 (dd, J=8.4, 2.5 Hz, 1H), 7.69 (d, J=8.3 Hz, 1H), 7.62 (s, 1H), 7.36 (d, J=8.1 Hz, 2H), 7.22 (d, J=8.2 Hz, 1H), 7.07 (d, J=6.2 Hz, 1H), 6.95-6.85 (m, 2H), 4.34 (q, J=6.9 Hz, 2H), 4.32-4.08 (m, 3H), 2.18-1.97 (m, 2H), 1.34 (t, J=7.0 Hz, 3H).

Example-104: (S/R)-4-(2-Chloro-4-(trifluoromethyl)phenyl)-N-(pyrimidin-2-yl)chroman-7-sulfonamide

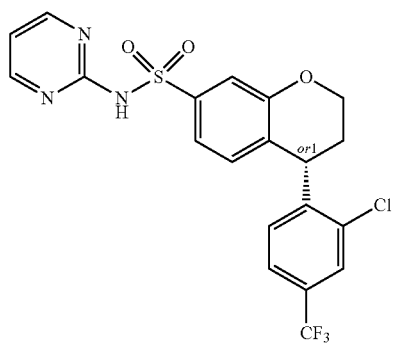 [SMILES: O=S(=O)(Nc1ncccn1)c1ccc2c(c1)OCC[C@@H]2c1ccc(C(F)(F)F)cc1Cl]

To a stirred solution of pyrimidine-2-amine (0.027 g, 0.286 mmol) in THF (5 ml) was added LiHMDS (0.272 ml, 1M in THF, 0.272 mmol) at 0° C. and stirred for 10 min.

Intermediate-27b (0.080 g, 0.143 mmol) in THF (5 ml) was added to the above reaction mixture at 0° C. After completion of reaction as indicated by TLC, reaction mixture was quenched with citric acid solution and extracted with ethyl acetate. The combined organic layer was washed with brine, dried over Na$_2$SO$_4$ and concentrated under vacuum. The crude was purified by column chromatography to obtain title compound as white solid (0.025 g, 37%). LCMS (ESI): m/z 470.05 (M+H)$^+$; $^1$H NMR (400 MHz, DMSO-d6) δ 11.80 (s, 1H), 8.54 (d, J=4.8 Hz, 2H), 7.95 (s, 1H), 7.66 (d, J=8.2 Hz, 1H), 7.46-7.37 (m, 2H), 7.16 (d, J=8.2 Hz, 1H), 7.09 (t, J=4.9 Hz, 1H), 6.96 (d, J=8.1 Hz, 1H), 4.74 (t, J=6.5 Hz, 1H), 4.34-4.22 (m, 1H), 4.20-4.08 (m, 1H), 2.32-2.23 (m, 1H), 2.15-2.04 (m, 1H).

Example-105: (S/R)-4-(2-Chloro-4-(trifluoromethyl)phenyl)-N-(5-fluoropyrimidin-2-yl)chroman-7-sulfonamide

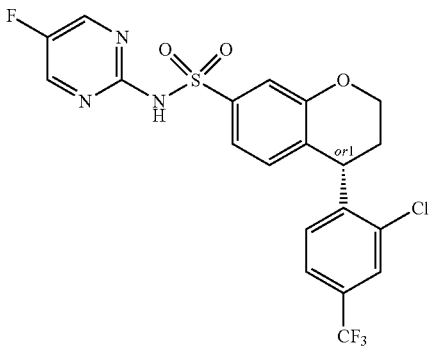 [SMILES: O=S(=O)(Nc1ncc(F)cn1)c1ccc2c(c1)OCC[C@@H]2c1ccc(C(F)(F)F)cc1Cl]

The title compound was prepared by following the similar procedure as described in Example-104 using Intermediate-27b and 5-fluoropyrimidin-2-amine. LCMS(ESI): m/z 487.92 (M+H)$^+$; $^1$H NMR (400 MHz, DMSO-d6) δ 11.91 (s, 1H), 8.67 (s, 2H), 7.95 (d, J=1.9 Hz, 1H), 7.66 (dd, J=8.2, 2.0 Hz, 1H), 7.45-7.36 (m, 2H), 7.17 (d, J=8.1 Hz, 1H), 6.97 (d, J=8.1 Hz, 1H), 4.74 (t, J=6.5 Hz, 1H), 4.28 (ddd, J=10.9, 7.4, 2.9 Hz, 1H), 4.15 (ddd, J=11.0, 7.3, 3.1 Hz, 1H), 2.29 (d, J=12.9 Hz, 1H), 2.10 (d, J=15.1 Hz, 1H).

Example-106: (S/R)-4-(2-Chloro-4-(trifluoromethyl)phenyl)-N-(pyrimidin-4-yl)chroman-7-sulfonamide

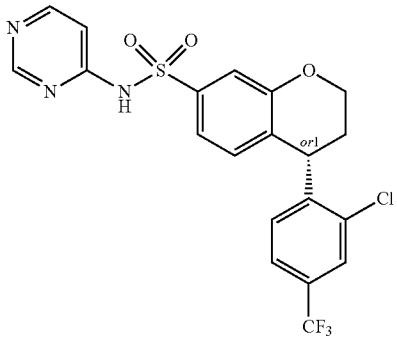 [SMILES: O=S(=O)(Nc1ccncn1)c1ccc2c(c1)OCC[C@@H]2c1ccc(C(F)(F)F)cc1Cl]

The title compound was prepared by following the similar procedure as described in Example-104 using Intermediate-27b and pyrimidin-4-amine. LCMS (ESI): m/z 469.98 (M+H)$^+$; $^1$H NMR (400 MHz, DMSO-d6) δ 8.66 (s, 1H), 8.39 (s, 1H), 7.95 (d, J=1.9 Hz, 1H), 7.71-7.59 (m, 1H), 7.40-7.30 (m, 2H), 7.22-7.02 (m, 2H), 6.95 (d, J=8.1 Hz, 1H), 4.80-4.66 (m, 1H), 4.33-4.22 (m, 1H), 4.20-4.08 (m, 1H), 2.34-2.26 (m, 1H), 2.14-2.04 (m, 1H).

Example-107: (S/R)-4-(2-Chloro-4-(trifluoromethyl)phenyl)-N-(pyridazin-3-yl)chroman-7-sulfonamide

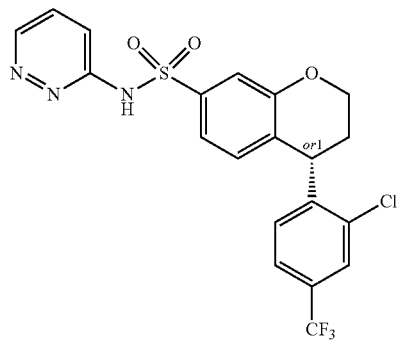 [SMILES: O=S(=O)(Nc1cccnn1)c1ccc2c(c1)OCC[C@@H]2c1ccc(C(F)(F)F)cc1Cl]

The title compound was prepared by following the similar procedure as described in Example-104 using Intermediate-27b and pyridazin-3-amine. LCMS(ESI): m/z 470.03 (M+H)$^+$; $^1$H NMR (400 MHz, DMSO-d6) δ 14.54 (s, 1H), 8.31 (s, 1H), 7.98-7.89 (m, 2H), 7.75-7.63 (m, 2H), 7.32-7.24 (m, 2H), 7.16 (d, J=8.2 Hz, 1H), 6.92 (d, J=7.9 Hz, 1H), 4.77-4.68 (m, 1H), 4.31-4.22 (m, 1H), 4.17-4.10 (m, 1H), 2.32-2.24 (m, 1H), 2.14-2.06 (m, 1H).

Example-108: (S/R)-4-(2-chloro-4-(trifluoromethyl)phenyl)-N-(6-fluoropyridin-2-yl)chroman-7-sulfonamide

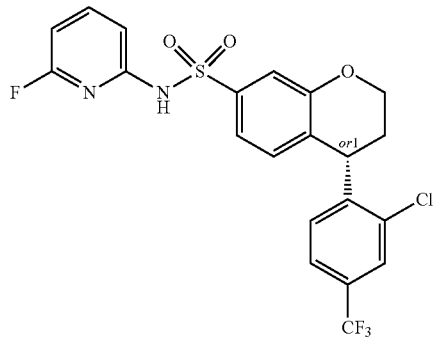 [SMILES: O=S(=O)(Nc1cccc(F)n1)c1ccc2c(c1)OCC[C@@H]2c1ccc(C(F)(F)F)cc1Cl]

The title compound was prepared by following the similar procedure as described in Example-104 using Intermediate-27b and 6-fluoropyridin-2-amine. LCMS(ESI): m/z 486.97 (M+H)$^+$; $^1$H NMR (400 MHz, DMSO-d$_6$) δ 11.39 (s, 1H), 7.97-7.82 (m, 2H), 7.65 (dd, J=8.3, 1.9 Hz, 1H), 7.43-7.32 (m, 2H), 7.17 (d, J=8.2 Hz, 1H), 7.02-6.94 (m, 2H), 6.77 (dd, J=8.0, 2.4 Hz, 1H), 4.74 (t, J=6.5 Hz, 1H), 4.33-4.23 (m, 1H), 4.21-4.10 (m, 1H), 2.31-2.05 (m, 2H).

Example-109/110: (S&R)—N-(pyrimidin-2-yl)-4-(2-(tetrahydro-2H-pyran-4-yl)-4-(trifluoromethyl)phenyl)chroman-7-sulfonamide

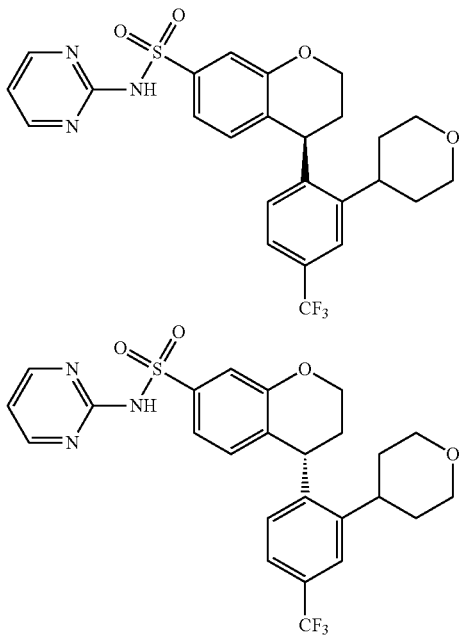

The title compounds were prepared by following the similar procedure as described in Example-1/2 using Intermediate-29 and pyrimidin-2-amine.

Further the enantiomers were separated using chiral preparative HPLC (Column: ChiralPak IA; Mobile phase: A=(Hexane+0.1% TFA), B=(IPA:DCM=1:1), A:B=70:30, to afford isomer-1 and isomer-2. These isomers were obtained at retention time 9.22 min (Example-109) and retention time 10.20 min (Example-110).

LCMS(ESI): m/z 520.08 (M+H)$^+$; $^1$H NMR (400 MHz, DMSO-d$_6$) δ 11.71 (s, 1H), 8.59-8.49 (m, 2H), 7.62 (s, 1H), 7.52-7.34 (m, 3H), 7.18-7.04 (m, 2H), 6.82 (d, J=8.1 Hz, 1H), 4.80-4.66 (m, 1H), 4.37-4.22 (m, 2H), 3.92 (d, J=11.4 Hz, 1H), 3.80-3.08 (m, 4H), 2.30-2.18 (m, 1H), 2.06-1.93 (m, 1H), 1.84-1.51 (m, 4H).

Example-111/112: (S&R)—N-(6-Fluoropyridin-2-yl)-4-(2-(2-oxopyrrolidin-1-yl)-4-(trifluoromethyl)phenyl)chroman-7-sulfonamide

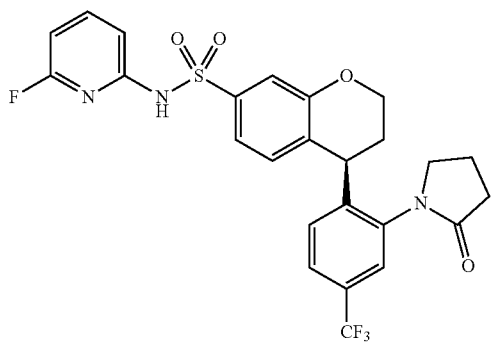

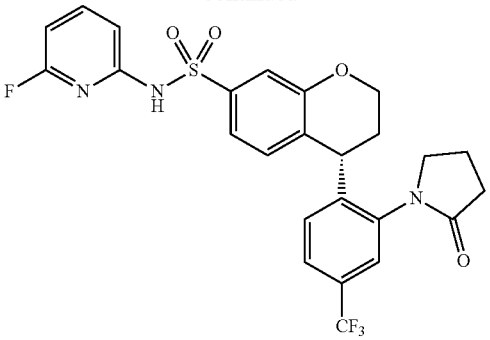

The title compounds were prepared by following the similar procedure as described in Example-1/2 using Intermediate-31 and 6-fluoropyridin-2-amine.

Further the enantiomers were separated using chiral preparative HPLC (Column: ChiralPak IC; Mobile phase: A=(Hexane+0.1% DEA), B=(EtOH:DCM=1:1), A:B=60:40 to afford isomer-1 and isomer-2. These isomers were obtained at retention time 7.85 min (Example-111) and retention time 8.90 min (Example-112).

LCMS (ESI): m/z 535.99 (M+H)$^+$; $^1$H NMR (400 MHz, Chloroform-d) δ 7.75 (dd, J=8.0 Hz, 1H), 7.55-7.48 (m, 2H), 7.43 (d, J=1.9 Hz, 1H), 7.29-7.25 (m, 3H), 7.09 (d, J=8.1 Hz, 1H), 6.64 (dd, J=8.0, 2.4 Hz, 1H), 4.35-4.26 (m, 2H), 4.26-4.11 (m, 1H), 3.94-3.70 (m, 2H), 2.64 (t, J=8.1 Hz, 2H), 2.44-2.24 (m, 3H), 2.15-1.99 (m, 1H).

Example-113/114: (S&R)—N-(5-fluoropyrimidin-2-yl)-4-(2-(2-oxopyrrolidin-1-yl)-4-(trifluoromethyl)phenyl)chroman-7-sulfonamide

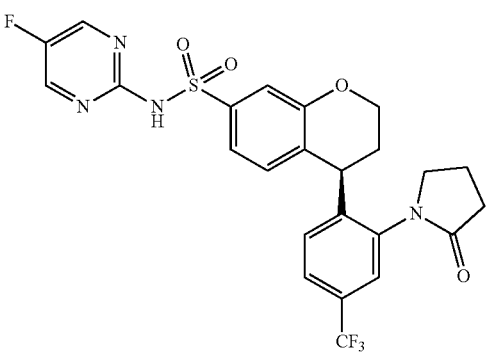

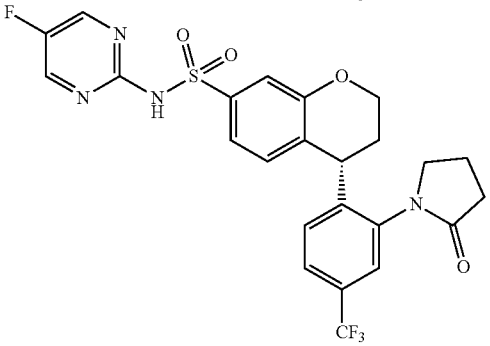

The title compounds were prepared by following the similar procedure as described in Example-1/2 using Intermediate-31a & 31b respectively and 5-fluoropyrimidin-2-amine.

LCMS(ESI): m/z 536.94 (M+H)⁺; ¹H NMR (400 MHz, DMSO-d6) δ 11.88 (s, 1H), 8.66 (s, 2H), 7.79 (s, 1H), 7.63 (d, J=8.3 Hz, 1H), 7.39 (s, 1H), 7.35 (d, J=8.0 Hz, 1H), 7.19 (d, J=8.2 Hz, 1H), 6.91 (d, J=8.2 Hz, 1H), 4.41 (t, J=7.4 Hz, 1H), 4.30-4.20 (m, 2H), 3.87-3.66 (m, 2H), 2.32-2.19 (m, 3H), 2.18-2.08 (m, 2H), 2.04-1.95 (m, 1H).

Example-115: (R/S)-4-(2-(2-oxopyrrolidin-1-yl)-4-(trifluoromethyl)phenyl)-N-(pyrimidin-2-yl)chroman-7-sulfonamide

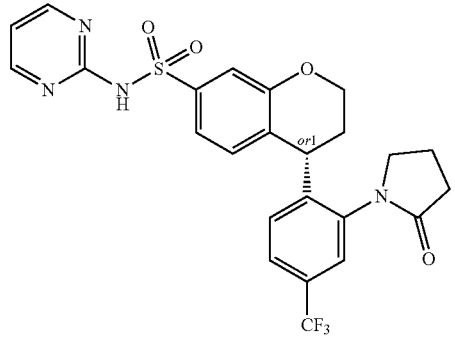 [SMILES: O=C1CCCN1c1cc(C(F)(F)F)ccc1[C@H]1CCOc2cc(S(=O)(=O)Nc3ncccn3)ccc21]

The title compound was prepared by following the similar procedure as described in Example-1/2 using Intermediate-31b and pyrimidin-2-amine. LCMS(ESI): m/z 518.94 (M+H)⁺; ¹H NMR (400 MHz, DMSO-d6) δ 11.74 (s, 1H), 8.54 (d, J=4.9 Hz, 2H), 7.79 (s, 1H), 7.63 (d, J=8.3 Hz, 1H), 7.40 (s, 1H), 7.36 (d, J=8.0 Hz, 1H), 7.19 (d, J=8.3 Hz, 1H), 7.13-7.03 (m, 1H), 6.90 (d, J=8.2 Hz, 1H), 4.41 (t, J=7.3 Hz, 1H), 4.30-4.19 (m, 2H), 3.84-3.67 (m, 2H), 2.47-2.39 (m, 2H), 2.31-2.18 (m, 1H), 2.18-2.07 (m, 2H), 2.07-1.94 (m, 1H).

Example-116: (R/S)-4-(2-(2-oxopyrrolidin-1-yl)-4-(trifluoromethyl)phenyl)-N-(pyrimidin-4-yl)chroman-7-sulfonamide

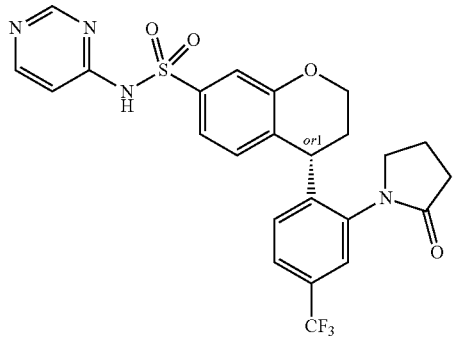 [SMILES: O=C1CCCN1c1cc(C(F)(F)F)ccc1[C@H]1CCOc2cc(S(=O)(=O)Nc3ccncn3)ccc21]

The title compound was prepared by following the similar procedure as described in Example-1/2 using Intermediate-31b and pyrimidin-4-amine. LCMS(ESI): m/z 519.04 (M+H)⁺; ¹H NMR (400 MHz, DMSO-d6) δ 8.66 (s, 1H), 8.38 (brs, 1H), 7.79 (s, 1H), 7.63 (d, J=8.2 Hz, 1H), 7.39-7.25 (m, 2H), 7.19 (d, J=8.4 Hz, 1H), 7.07 (s, 1H), 6.90 (d, J=8.0 Hz, 1H), 4.41 (t, J=7.4 Hz, 1H), 4.34-4.22 (m, 2H), 3.87-3.67 (m, 2H), 2.49-2.40 (m, 2H), 2.29-2.07 (m, 3H), 2.07-1.94 (m, 1H).

Example-117: (R/S)-4-(2-(2-oxopyrrolidin-1-yl)-4-(trifluoromethyl)phenyl)-N-(pyridazin-3-yl)chromane-7-sulfonamide

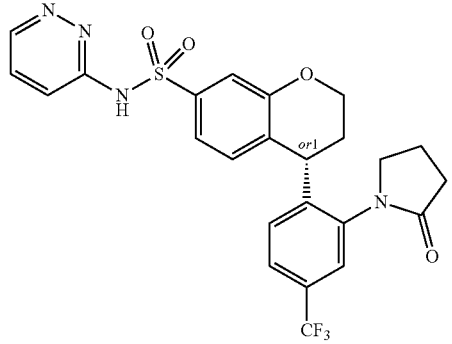 [SMILES: O=C1CCCN1c1cc(C(F)(F)F)ccc1[C@H]1CCOc2cc(S(=O)(=O)Nc3cccnn3)ccc21]

The title compound was prepared by following the similar procedure as described in Example-1/2 using Intermediate-31b and pyridazin-3-amine.

LCMS(ESI): m/z 518.94 (M+H)⁺; ¹H NMR (400 MHz, DMSO-d6) δ 8.35 (s, 1H), 7.88 (d, J=9.6 Hz, 1H), 7.78 (s, 1H), 7.70 (dd, J=9.5, 4.2 Hz, 1H), 7.63 (d, J=7.3 Hz, 1H), 7.28-7.21 (m, 2H), 7.18 (d, J=8.2 Hz, 1H), 6.86 (d, J=8.1 Hz, 1H), 4.39 (t, J=7.2 Hz, 1H), 4.30-4.19 (m, 2H), 3.85-3.67 (m, 2H), 2.48-2.39 (m, 2H), 2.28-2.19 (m, 1H), 2.18-2.08 (m, 2H), 2.03-1.95 (m, 1H).

Example-118/119: (S&R)-4-(2-morpholino-4-(trifluoromethyl)phenyl)-N-(pyrimidin-2-yl)chroman-7-sulfonamide

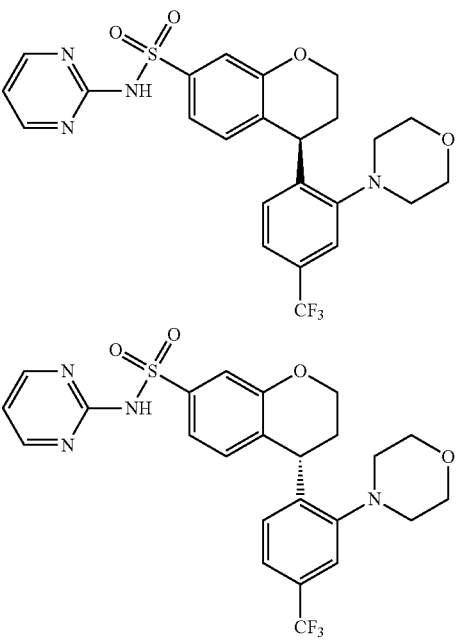

The title compounds were prepared by following the similar procedure as described in Example-1/2 using Intermediate-33 and pyrimidin-2-amine.

Further the enantiomers were separated using chiral preparative HPLC (Column: ChiralPak IA; Mobile phase: A=(Hexane+0.1% TFA), B=(IPA:DCM=1:1), A:B=70:30, to afford isomer-1 and isomer-2. These isomers were obtained at retention time 8.18 min (Example-118) and retention time 9.46 min (Example-119).

LCMS(ESI): m/z 521.09 (M+H)+; 1H NMR (400 MHz, DMSO-d6) δ 8.54 (d, J=4.9 Hz, 2H), 7.58 (d, J=1.9 Hz, 1H), 7.47-7.31 (m, 3H), 7.19-7.02 (m, 2H), 6.80 (d, J=8.1 Hz, 1H), 4.79 (t, 1H), 4.33-4.23 (m, 2H), 3.74-3.58 (m, 4H), 3.03-2.74 (m, 4H), 2.26-2.05 (m, 2H).

Example-120: (S/R)—N-(5-fluoropyrimidin-2-yl)-4-(2-morpholino-4-(trifluoromethyl)phenyl)chroman-7-sulfonamide

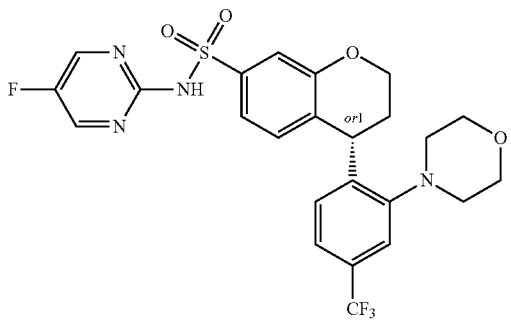 [SMILES: O=S(=O)(Nc1ncc(F)cn1)c1ccc2c(c1)OCC[C@@H]2c1ccc(C(F)(F)F)cc1N1CCOCC1]

The title compound was prepared by following the similar procedure as described in Example-1/2 using Intermediate-33b and 5-fluoropyrimidin-2-amine. LCMS(ESI): m/z 539.07 (M+H)+; 1H NMR (400 MHz, DMSO-d6) δ 11.86 (s, 1H), 8.66 (s, 2H), 7.58 (s, 1H), 7.47-7.31 (m, 3H), 7.12 (d, J=8.1 Hz, 1H), 6.81 (d, J=8.1 Hz, 1H), 4.79 (t, 1H), 4.32-4.24 (m, 2H), 3.73-3.57 (m, 4H), 3.00-2.75 (m, 4H), 2.28-2.07 (m, 2H).

Example-121: (R/S)-4-(2-morpholino-4-(trifluoromethyl)phenyl)-N-(pyrimidin-4-yl)chroman-7-sulfonamide

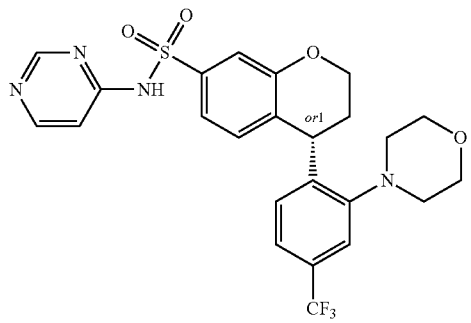 [SMILES: O=S(=O)(Nc1ccncn1)c1ccc2c(c1)OCC[C@@H]2c1ccc(C(F)(F)F)cc1N1CCOCC1]

The title compound was prepared by following the similar procedure as described in Example-1/2 using Intermediate-33b and pyrimidin-4-amine. LCMS(ESI): m/z 521.06 (M+H)+; 1H NMR (400 MHz, DMSO-d6) δ 8.66 (s, 1H), 8.37 (s, 1H), 7.58 (d, J=1.8 Hz, 1H), 7.43 (d, J=8.3 Hz, 1H), 7.36-7.26 (m, 2H), 7.19-6.99 (m, 2H), 6.79 (d, J=8.1 Hz, 1H), 4.79 (t, J=7.5 Hz, 1H), 4.33-4.22 (m, 2H), 3.75-3.56 (m, 4H), 3.02-2.76 (m, 4H), 2.27-2.05 (m, 2H).

Example-122: (R/S)-4-(2-morpholino-4-(trifluoromethyl)phenyl)-N-(pyridazin-3-yl)chroman-7-sulfonamide

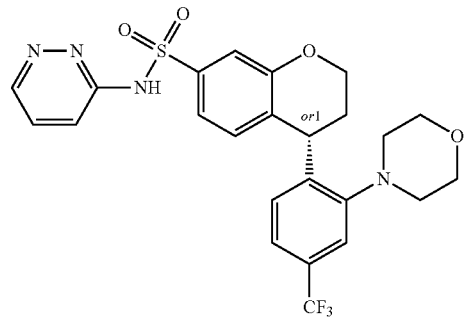 [SMILES: O=S(=O)(Nc1cccnn1)c1ccc2c(c1)OCC[C@@H]2c1ccc(C(F)(F)F)cc1N1CCOCC1]

The title compound was prepared by following the similar procedure as described in Example-1/2 using Intermediate-33b and pyridazin-3-amine. LCMS(ESI): m/z 521.05 (M+H)+; 1H NMR (400 MHz, DMSO-d6) δ 8.34 (s, 1H), 7.90 (s, 1H), 7.73-7.41 (m, 3H), 7.30-7.06 (m, 3H), 6.75 (d, J=8.2 Hz, 1H), 4.81-4.76 (m, 1H), 4.33-4.22 (m, 2H), 3.77-3.62 (m, 4H), 3.00-2.76 (m, 4H), 2.27-2.04 (m, 2H).

Example-123: (R/S)—N-(6-fluoropyridin-2-yl)-4-(2-morpholino-4-(trifluoromethyl)phenyl)chroman-7-sulfonamide

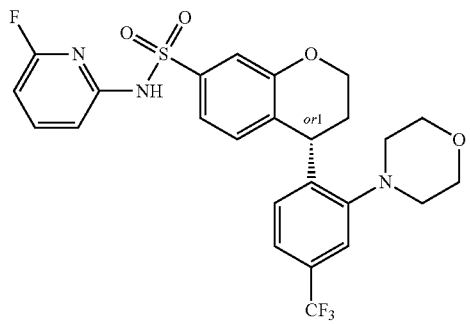 [SMILES: O=S(=O)(Nc1cccc(F)n1)c1ccc2c(c1)OCC[C@@H]2c1ccc(C(F)(F)F)cc1N1CCOCC1]

The title compound was prepared by following the similar procedure as described in Example-1/2 using Intermediate-33b and 6-fluoropyridin-2-amine. LCMS(ESI): m/z 538.06 (M+H)+; 1H NMR (400 MHz, DMSO-d6) δ 11.36 (s, 1H), 7.87 (dd, J=8.2 Hz, 1H), 7.58 (s, 1H), 7.43 (d, J=8.2 Hz, 1H), 7.39-7.27 (m, 2H), 7.12 (d, J=8.1 Hz, 1H), 6.98 (dd, J=7.9, 2.1 Hz, 1H), 6.85-6.73 (m, 2H), 4.78 (t, J=7.4 Hz, 1H), 4.32-4.24 (m, 2H), 3.73-3.53 (m, 4H), 2.98-2.73 (m, 4H), 2.27-2.04 (m, 2H).

Example-124/125: (S&R)-4-(2-(2-methoxyethoxy)-4-(trifluoromethyl)phenyl)-N-(pyrimidin-2-yl)chroman-7-sulfonamide

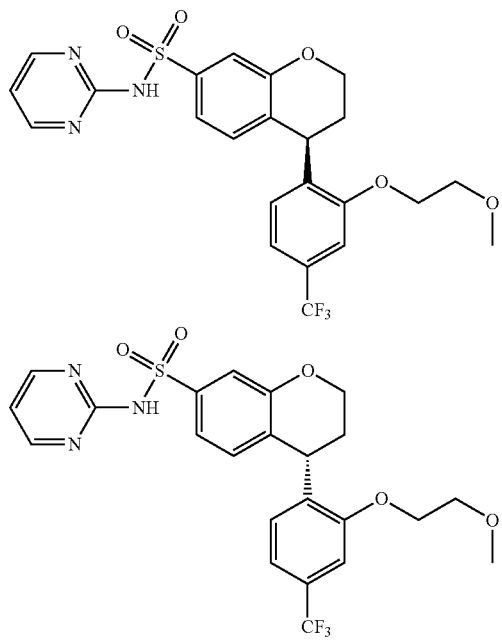

The title compounds were prepared by following the similar procedure as described in Example-1/2 using Intermediate-35a & Intermediate-35b respectively and pyrimidin-2-amine.

LCMS(ESI): m/z 510.05 (M+H)+; $^1$H NMR (400 MHz, DMSO-d$_6$) δ 11.73 (s, 1H), 8.54 (d, J=4.9 Hz, 2H), 7.45-7.31 (m, 3H), 7.25 (d, J=7.9 Hz, 1H), 7.13-7.02 (m, 2H), 6.91 (d, J=8.1 Hz, 1H), 4.55 (t, J=6.6 Hz, 1H), 4.27-4.00 (m, 4H), 3.56-3.46 (m, 1H), 3.45-3.37 (m, 1H), 3.21 (s, 3H), 2.20-2.10 (m, 2H).

Example-126: (R/S)—N-(5-fluoropyrimidin-2-yl)-4-(2-(2-methoxyethoxy)-4-(trifluoromethyl)phenyl)chroman-7-sulfonamide

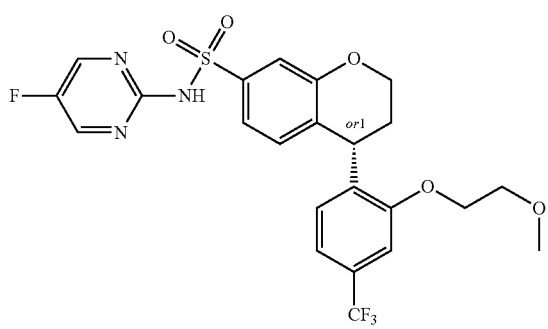 [SMILES: COCCOc1cc(C(F)(F)F)ccc1[C@H]1CCOc2cc(S(=O)(=O)Nc3ncc(F)cn3)ccc21]

The title compound was prepared by following the similar procedure as described in Example-1/2 using Intermediate-35b and 5-fluoropyrimidin-2-amine.

LCMS(ESI): m/z 528.03 (M+H)+; $^1$H NMR (400 MHz, DMSO-d$_6$) δ 11.86 (s, 1H), 8.66 (s, 2H), 7.41-7.32 (m, 3H), 7.26 (d, J=7.9 Hz, 1H), 7.06 (d, J=7.9 Hz, 1H), 6.92 (d, J=8.0 Hz, 1H), 4.56 (t, J=6.7 Hz, 1H), 4.29-4.00 (m, 4H), 3.55-3.37 (m, 2H), 3.21 (s, 3H), 2.22-2.09 (m, 2H).

Example-127: (R/S)-4-(2-(2-methoxyethoxy)-4-(trifluoromethyl)phenyl)-N-(pyrimidin-4-yl)chroman-7-sulfonamide

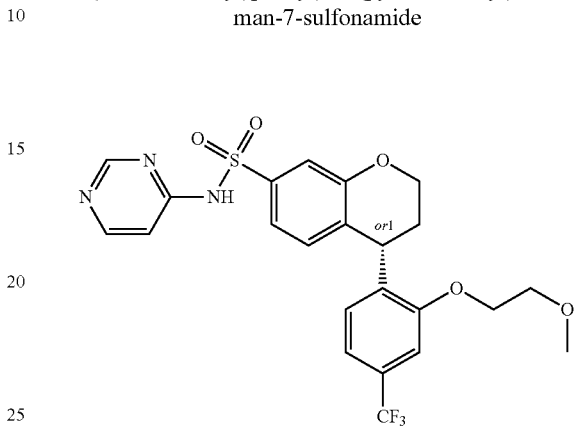

The title compound was prepared by following the similar procedure as described in Example-1/2 using Intermediate-35b and pyrimidin-4-amine.

LCMS(ESI): m/z 510.04 (M+H)+; $^1$H NMR (400 MHz, DMSO-d$_6$) δ 8.66 (s, 1H), 8.39 (s, 1H), 7.44-7.29 (m, 3H), 7.26 (d, J=7.9 Hz, 1H), 7.18-7.01 (m, 2H), 6.92 (d, J=8.0 Hz, 1H), 4.56 (t, J=6.6 Hz, 1H), 4.32-4.05 (m, 4H), 3.58-3.37 (m, 2H), 3.22 (s, 3H), 2.21-2.11 (m, 2H).

Example-128: (R/S)-4-(2-(2-methoxyethoxy)-4-(trifluoromethyl)phenyl)-N-(pyridazin-3-yl)chroman-7-sulfonamide

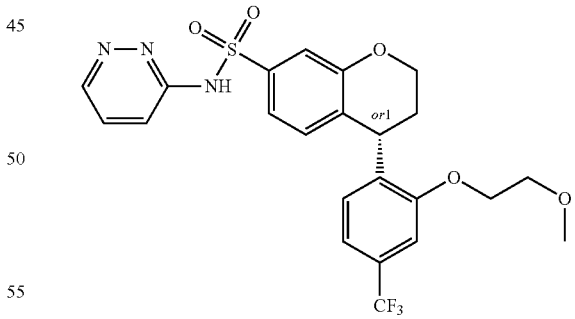

The title compound was prepared by following the similar procedure as described in Example-1/2 using Intermediate-35b and pyridazin-3-amine.

LCMS(ESI): m/z 510.04 (M+H)+; $^1$H NMR (400 MHz, DMSO-d$_6$) δ 14.52 (s, 1H), 8.31 (s, 1H), 7.92 (s, 1H), 7.70 (dd, J=9.5, 4.2 Hz, 1H), 7.34 (d, J=1.8 Hz, 1H), 7.31-7.18 (m, 3H), 7.02 (d, J=7.9 Hz, 1H), 6.89 (d, J=8.4 Hz, 1H), 4.56 (t, J=6.4 Hz, 1H), 4.34-4.07 (m, 4H), 3.62-3.44 (m, 2H), 3.24 (s, 3H), 2.26-2.07 (m, 2H).

Example-129: (R/S)—N-(6-fluoropyridin-2-yl)-4-(2-(2-methoxyethoxy)-4-(trifluoromethyl)phenyl)chroman-7-sulfonamide

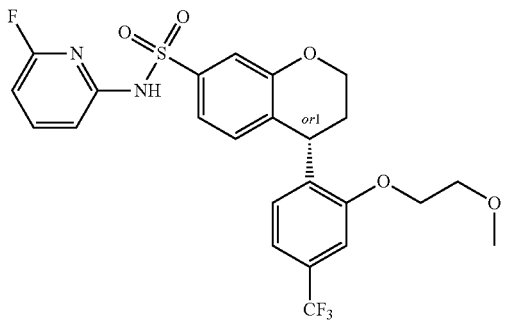

The title compound was prepared by following the similar procedure as described in Example-1/2 using Intermediate-35b and 6-fluoropyridin-2-amine. LCMS(ESI): m/z 527.04 (M+H)$^+$; $^1$H NMR (400 MHz, DMSO-d$_6$) δ 11.36 (s, 1H), 7.87 (dd, J=8.1 Hz, 1H), 7.42-7.29 (m, 3H), 7.25 (d, J=7.9 Hz, 1H), 7.06 (d, J=7.9 Hz, 1H), 6.98 (dd, J=8.0, 2.1 Hz, 1H), 6.93 (d, J=8.1 Hz, 1H), 6.77 (dd, J=8.0, 2.4 Hz, 1H), 4.55 (t, J=6.8 Hz, 1H), 4.29-3.99 (m, 4H), 3.55-3.35 (m, 2H), 3.20 (s, 3H), 2.24-2.08 (m, 2H).

Example-130/131: (S&R)-4-(2-(3-methoxypropoxy)-4-(trifluoromethyl)phenyl)-N-(pyrimidin-2-yl)chroman-7-sulfonamide

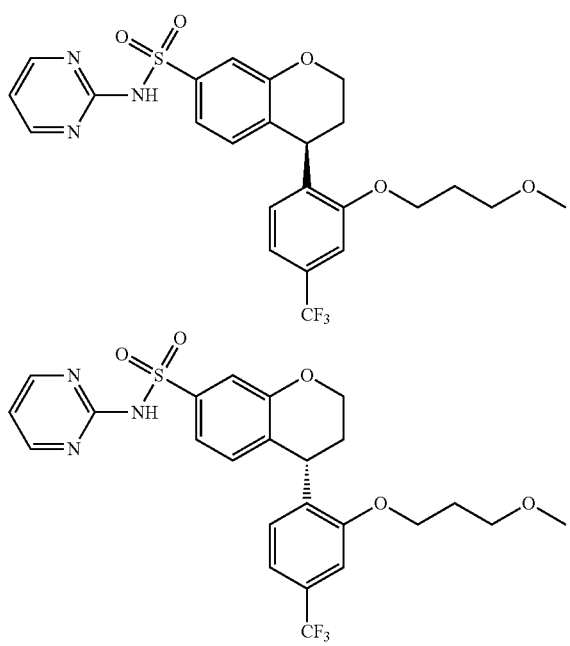

The title compounds were prepared by following the similar procedure as described in Example-1/2 using Intermediate-37 and pyrimidin-2-amine.

Further the enantiomers were separated using chiral preparative HPLC (Column: ChiralPak IA; Mobile phase: A=(Hexane+0.1% TFA), B=(IPA:MeOH=1:1), A:B=40:60, to afford isomer-1 and isomer-2. These isomers were obtained at retention time 6.43 min (Example-130) and retention time 7.76 min (Example-131).

LCMS(ESI): m/z 524.11 (M+H)$^+$; $^1$H NMR (400 MHz, DMSO-d$_6$) δ 11.73 (s, 1H), 8.53 (d, J=4.9 Hz, 2H), 7.42-7.33 (m, 2H), 7.30-7.22 (m, 2H), 7.16-7.05 (m, 2H), 6.89 (d, J=8.0 Hz, 1H), 4.53 (t, 1H), 4.28-4.17 (m, 2H), 4.15-3.91 (m, 2H), 3.33-3.19 (m, 2H), 3.16 (s, 3H), 2.22-2.11 (m, 2H), 1.78-1.63 (m, 2H).

Example-132: (R/S)—N-(5-fluoropyrimidin-2-yl)-4-(2-(3-methoxypropoxy)-4-(trifluoromethyl)phenyl)chroman-7-sulfonamide

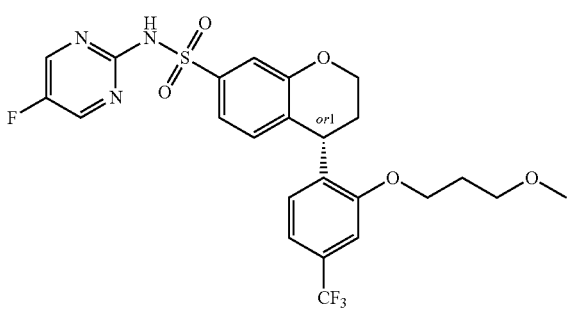 [SMILES: COCCCOc1cc(C(F)(F)F)ccc1[C@H]1CCOc2cc(S(=O)(=O)Nc3ncc(F)cn3)ccc21]

The title compound was prepared by following the similar procedure as described in Example-1/2 using Intermediate-37b and 5-fluoropyrimidin-2-amine. LCMS(ESI): m/z 542.01 (M+H)$^+$; $^1$H NMR (400 MHz, DMSO-d$_6$) δ 11.85 (s, 1H), 8.66 (s, 2H), 7.40-7.33 (m, 2H), 7.31-7.24 (m, 2H), 7.13 (d, J=7.9 Hz, 1H), 6.90 (d, J=8.0 Hz, 1H), 4.53 (t, J=7.0 Hz, 1H), 4.27-4.18 (m, 2H), 4.13-3.94 (m, 2H), 3.31-3.20 (m, 2H), 3.16 (s, 3H), 2.21-2.13 (m, 2H), 1.78-1.64 (m, 2H).

Example-133: (R/S)-4-(2-(3-methoxypropoxy)-4-(trifluoromethyl)phenyl)-N-(pyridazin-3-yl)chroman-7-sulfonamide

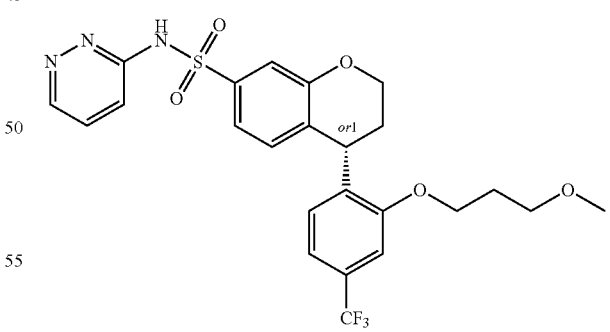

The title compound was prepared by following the similar procedure as described in Example-1/2 using Intermediate-37b and pyridazin-3-amine. LCMS(ESI): m/z 523.94 (M+H)$^+$; $^1$H NMR (400 MHz, DMSO-d$_6$) δ 14.51 (s, 1H), 8.30 (s, 1H), 7.92 (s, 1H), 7.74-7.66 (m, 1H), 7.31-7.22 (m, 4H), 7.09 (d, J=7.8 Hz, 1H), 6.86 (d, J=8.4 Hz, 1H), 4.53 (t, J=6.7 Hz, 1H), 4.22-3.99 (m, 4H), 3.33-3.24 (m, 2H), 3.18 (s, 3H), 2.18-2.12 (m, 2H), 1.84-1.73 (m, 2H).

Example-134: (R/S)—N-(6-fluoropyridin-2-yl)-4-(2-(3-methoxypropoxy)-4-(trifluoromethyl)phenyl)chroman-7-sulfonamide

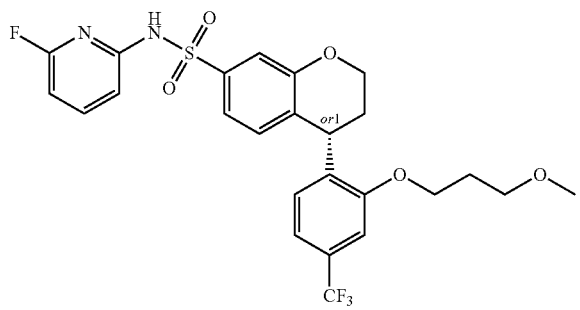 [SMILES: COCCCOc1cc(C(F)(F)F)ccc1[C@H]1CCOc2cc(S(=O)(=O)Nc3cccc(F)n3)ccc21]

The title compound was prepared by following the similar procedure as described in Example-1/2 using Intermediate-37b and 6-fluoropyridin-2-amine. LCMS(ESI): m/z 541.07 (M+H)⁺; ¹H NMR (400 MHz, DMSO-d₆) δ 11.36 (s, 1H), 7.87 (dd, J=8.2 Hz, 1H), 7.38-7.29 (m, 2H), 7.29-7.22 (m, 2H), 7.13 (d, J=7.8 Hz, 1H), 6.98 (dd, J=7.9, 2.1 Hz, 1H), 6.91 (d, J=8.1 Hz, 1H), 6.76 (dd, J=8.0, 2.4 Hz, 1H), 4.53 (t, J=7.0 Hz, 1H), 4.27-4.17 (m, 2H), 4.14-3.91 (m, 2H), 3.33-3.16 (m, 2H), 3.15 (s, 3H), 2.21-2.11 (m, 2H), 1.79-1.60 (m, 2H).

Example-135: (R/S)-4-(2-(2-methoxyethyl)-4-(trifluoromethyl)phenyl)-N-(pyrimidin-2-yl)chroman-7-sulfonamide

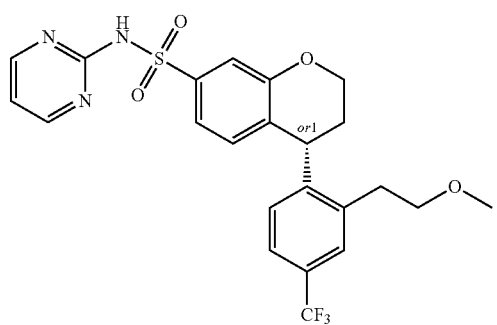 [SMILES: COCCc1cc(C(F)(F)F)ccc1[C@H]1CCOc2cc(S(=O)(=O)Nc3ncccn3)ccc21]

The title compound was prepared by following the similar procedure as described in Example-1/2 using Intermediate-39b and pyrimidin-2-amine.

LCMS(ESI): m/z 494.02 (M+H)⁺; ¹H NMR (400 MHz, DMSO-d₆) δ 11.73 (s, 1H), 8.54 (d, J=4.9 Hz, 2H), 7.65 (d, J=2.0 Hz, 1H), 7.47 (dd, J=8.2, 2.0 Hz, 1H), 7.41 (d, J=1.9 Hz, 1H), 7.37 (dd, J=8.1, 1.9 Hz, 1H), 7.08 (t, J=5.0 Hz, 1H), 6.99 (d, J=8.2 Hz, 1H), 6.81 (d, J=8.2 Hz, 1H), 4.66 (t, J=7.1 Hz, 1H), 4.28-4.22 (m, 2H), 3.60 (t, J=6.5 Hz, 2H), 3.24 (s, 3H), 3.14-3.06 (m, 1H), 3.05-2.96 (m, 1H), 2.30-2.19 (m, 1H), 2.03-1.92 (m, 1H).

Example-136: (R/S)—N-(5-fluoropyrimidin-2-yl)-4-(2-(2-methoxyethyl)-4-(trifluoromethyl)phenyl)chroman-7-sulfonamide

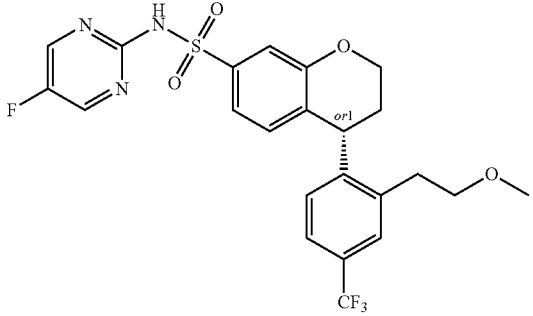 [SMILES: COCCc1cc(C(F)(F)F)ccc1[C@H]1CCOc2cc(S(=O)(=O)Nc3ncc(F)cn3)ccc21]

The title compound was prepared by following the similar procedure as described in Example-1/2 using Intermediate-39b and 5-fluoropyrimidin-2-amine. LCMS(ESI): m/z 512.00 (M+H)⁺; ¹H NMR (400 MHz, DMSO-d₆) δ 11.87 (s, 1H), 8.66 (s, 2H), 7.65 (d, J=2.1 Hz, 1H), 7.47 (dd, J=8.3, 2.0 Hz, 1H), 7.40 (d, J=1.9 Hz, 1H), 7.36 (dd, J=8.1, 2.0 Hz, 1H), 6.99 (d, J=8.2 Hz, 1H), 6.82 (d, J=8.1 Hz, 1H), 4.66 (t, J=7.0 Hz, 1H), 4.32-4.20 (m, 2H), 3.60 (t, J=6.5 Hz, 2H), 3.24 (s, 3H), 3.15-3.06 (m, 1H), 3.06-2.97 (m, 1H), 2.32-2.21 (m, 1H), 2.04-1.94 (m, 1H).

Example-137: (R/S)—N-(6-fluoropyridin-2-yl)-4-(2-(2-methoxyethyl)-4-(trifluoromethyl)phenyl)chroman-7-sulfonamide

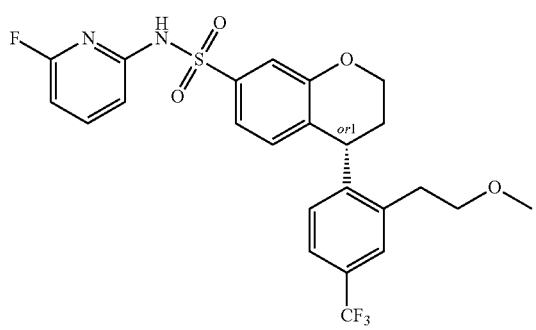 [SMILES: COCCc1cc(C(F)(F)F)ccc1[C@H]1CCOc2cc(S(=O)(=O)Nc3cccc(F)n3)ccc21]

The title compound was prepared by following the similar procedure as described in Example-1/2 using Intermediate-39b and 6-fluoropyridin-2-amine. LCMS(ESI): m/z 511.01 (M+H)⁺; ¹H NMR (400 MHz, DMSO-d₆) δ 11.37 (s, 1H), 7.87 (dd, J=8.2 Hz, 1H), 7.65 (d, J=2.0 Hz, 1H), 7.46 (dd, J=8.3, 2.0 Hz, 1H), 7.37 (d, J=1.9 Hz, 1H), 7.33 (dd, J=8.1, 2.0 Hz, 1H), 6.98 (dd, J=7.9, 1.9 Hz, 2H), 6.83 (d, J=8.2 Hz, 1H), 6.77 (dd, J=8.0, 2.4 Hz, 1H), 4.66 (t, J=7.1 Hz, 1H), 4.30-4.23 (m, 2H), 3.59 (t, J=6.5 Hz, 2H), 3.23 (s, 3H), 3.15-3.05 (m, 1H), 3.05-2.95 (m, 1H), 2.29-2.19 (m, 1H), 2.03-1.92 (m, 1H).

Example-138: (R/S)-4-(2-(2-methoxyethyl)-4-(trifluoromethyl)phenyl)-N-(pyrimidin-4-yl)chroman-7-sulfonamide

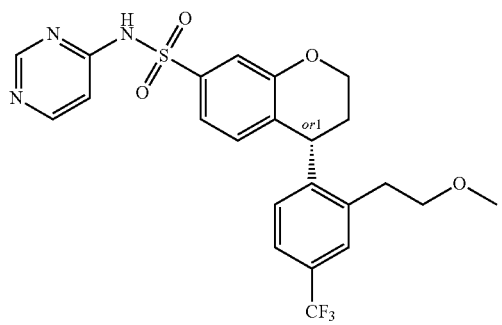 [SMILES: COCCc1cc(C(F)(F)F)ccc1[C@H]1CCOc2cc(S(=O)(=O)Nc3ccncn3)ccc21]

The title compound was prepared by following the similar procedure as described in Example-1/2 using Intermediate-39b and pyrimidin-4-amine.

LCMS(ESI): m/z 493.91 (M+H)$^+$; $^1$H NMR (400 MHz, DMSO-d$_6$) δ 8.66 (s, 1H), 7.65 (d, J=2.0 Hz, 1H), 8.42 (s, 1H), 7.47 (d, J=8.3 Hz, 1H), 7.39-7.27 (m, 2H), 7.18-6.96 (m, 2H), 6.81 (d, J=8.1 Hz, 1H), 4.66 (t, J=7.0 Hz, 1H), 4.32-4.20 (m, 2H), 3.60 (t, J=6.5 Hz, 2H), 3.24 (s, 3H), 3.17-2.94 (m, 2H), 2.30-2.16 (m, 1H), 2.09-1.91 (m, 1H).

Example-139: (R/S)-4-(2-(2-methoxyethyl)-4-(trifluoromethyl)phenyl)-N-(pyridazin-3-yl)chroman-7-sulfonamide

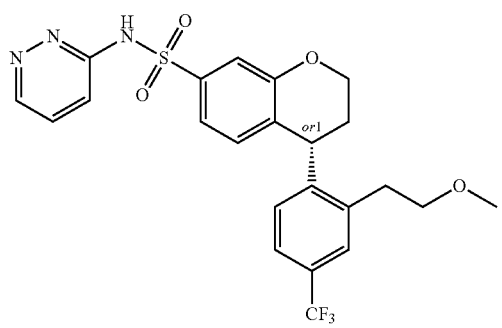 [SMILES: COCCc1cc(C(F)(F)F)ccc1[C@H]1CCOc2cc(S(=O)(=O)Nc3cccnn3)ccc21]

The title compound was prepared by following the similar procedure as described in Example-1/2 using Intermediate-39b and pyridazin-3-amine.

LCMS(ESI): m/z 493.91 (M+H)$^+$; $^1$H NMR (400 MHz, DMSO-d$_6$) δ 14.52 (s, 1H), 8.30 (s, 1H), 7.93 (s, 1H), 7.74-7.61 (m, 2H), 7.51-7.44 (m, 1H), 7.30-7.20 (m, 2H), 6.99 (d, J=8.2 Hz, 1H), 6.77 (d, J=7.9 Hz, 1H), 4.64 (t, J=6.9 Hz, 1H), 4.31-4.19 (m, 2H), 3.60 (t, J=6.5 Hz, 2H), 3.24 (s, 3H), 3.15-2.95 (m, 2H), 2.30-2.20 (m, 1H), 2.06-1.90 (m, 1H).

Example-140/141: (S&R)-4-(2-(3-methoxypropyl)-4-(trifluoromethyl)phenyl)-N-(pyrimidin-2-yl)chroman-7-sulfonamide

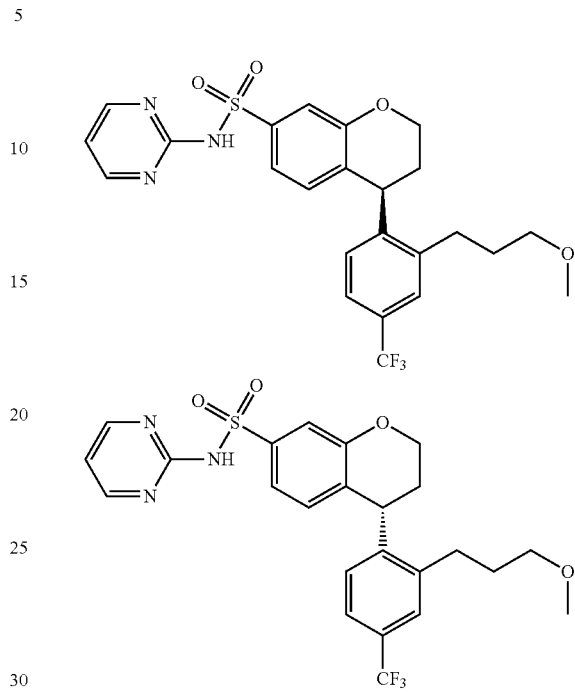

The title compounds were prepared by following the similar procedure as described in Example-1/2 using Intermediate-41a and Intermediate-41b respectively and pyrimidin-2-amine.

LCMS(ESI): m/z 508.22 (M+H)$^+$; $^1$H NMR (400 MHz, DMSO-d$_6$) δ 11.74 (s, 1H), 8.54 (d, J=4.9 Hz, 2H), 7.60 (s, 1H), 7.51-7.34 (m, 3H), 7.14-6.96 (m, 2H), 6.80 (d, J=8.2 Hz, 1H), 4.59 (t, J=7.1 Hz, 1H), 4.35-4.23 (m, 2H), 3.38-3.30 (m, 2H), 3.23 (s, 3H), 2.93-2.74 (m, 2H), 2.31-2.17 (m, 1H), 2.09-1.94 (m, 1H), 1.89-1.73 (m, 2H).

Example-142: (R/S)—N-(5-fluoropyrimidin-2-yl)-4-(2-(3-methoxypropyl)-4-(trifluoro methyl)phenyl)chroman-7-sulfonamide

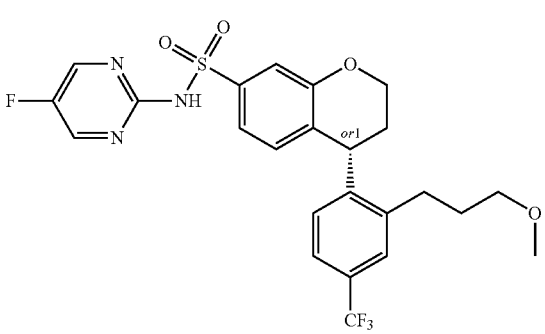 [SMILES: COCCCc1cc(C(F)(F)F)ccc1[C@H]1CCOc2cc(S(=O)(=O)Nc3ncc(F)cn3)ccc21]

The title compound was prepared by following the similar procedure as described in Example-1/2 using Intermediate-41b and 5-fluoropyrimidin-2-amine. LCMS(ESI): m/z 526.24 (M+H)$^+$; $^1$H NMR (400 MHz, DMSO-d$_6$) δ 11.87 (s, 1H), 8.66 (s, 2H), 7.61-7.45 (m, 2H), 7.43-7.32 (m, 2H), 7.02 (d, J=8.3 Hz, 1H), 6.81 (d, J=8.2 Hz, 1H), 4.59 (t, J=7.2 Hz, 1H), 4.32-4.24 (m, 2H), 3.38-3.34 (m, 2H), 3.23 (s, 3H), 2.90-2.74 (m, 2H), 2.26-2.19 (m, 1H), 2.04-1.97 (m, 1H), 1.90-1.74 (m, 2H).

Example-143: (R/S)-4-(2-(3-methoxypropyl)-4-(trifluoromethyl)phenyl)-N-(pyrimidin-4-yl)chroman-7-sulfonamide

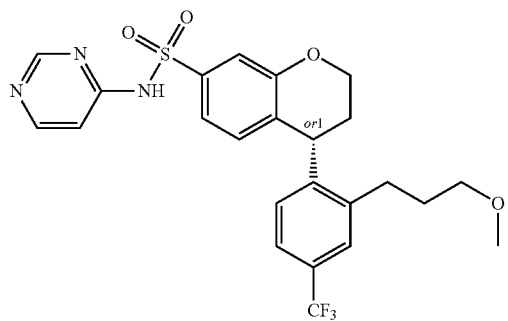 [SMILES: COCCCc1cc(C(F)(F)F)ccc1[C@H]1CCOc2cc(S(=O)(=O)Nc3ccncn3)ccc21]

The title compound was prepared by following the similar procedure as described in Example-1/2 using Intermediate-41b and pyrimidin-4-amine.

LCMS(ESI): m/z 507.94 (M+H)+; 1H NMR (400 MHz, DMSO-d6) δ 8.66 (s, 1H), 8.42 (s, 1H), 7.60 (d, J=2.0 Hz, 1H), 7.47 (dd, J=8.3, 2.0 Hz, 1H), 7.37-7.26 (m, 2H), 7.15-6.99 (m, 2H), 6.79 (d, J=8.1 Hz, 1H), 4.59 (t, 1H), 4.32-4.24 (m, 2H), 3.38-3.28 (m, 2H), 3.23 (s, 3H), 2.96-2.72 (m, 2H), 2.29-2.20 (m, 1H), 2.04-1.97 (m, 1H), 1.85-1.72 (m, 2H).

Example-144: (R/S)-4-(2-(3-methoxypropyl)-4-(trifluoromethyl)phenyl)-N-(pyridazin-3-yl)chroman-7-sulfonamide

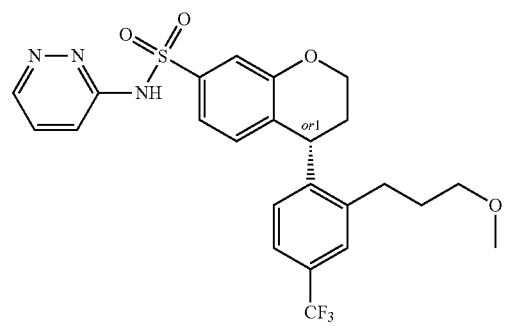 [SMILES: COCCCc1cc(C(F)(F)F)ccc1[C@H]1CCOc2cc(S(=O)(=O)Nc3cccnn3)ccc21]

The title compound was prepared by following the similar procedure as described in Example-1/2 using Intermediate-41b and pyridazin-3-amine.

LCMS(ESI): m/z 507.94 (M+H)+; 1H NMR (400 MHz, DMSO-d6) δ 14.52 (s, 1H), 8.30 (s, 1H), 7.92 (s, 1H), 7.70 (dd, J=9.6, 4.1 Hz, 1H), 7.59 (d, J=2.0 Hz, 1H), 7.47 (dd, J=8.4, 2.0 Hz, 1H), 7.29-7.21 (m, 2H), 7.02 (d, J=8.2 Hz, 1H), 6.76 (d, J=8.0 Hz, 1H), 4.58 (t, J=7.1 Hz, 1H), 4.33-4.22 (m, 2H), 3.40-3.34 (m, 2H), 3.23 (s, 3H), 2.93-2.76 (m, 2H), 2.31-2.20 (m, 1H), 2.05-1.97 (m, 1H), 1.86-1.81 (m, 2H).

Example-145: (R/S)—N-(6-fluoropyridin-2-yl)-4-(2-(3-methoxypropyl)-4-(trifluoromethyl)phenyl)chroman-7-sulfonamide

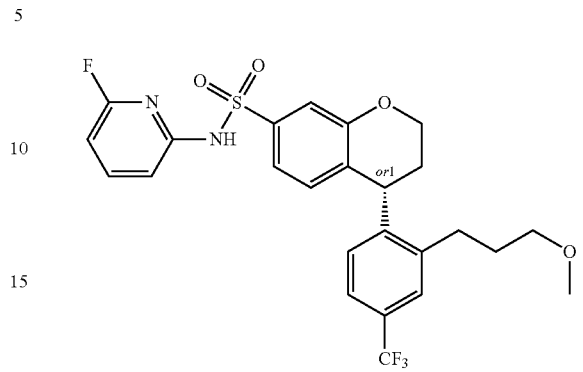

The title compound was prepared by following the similar procedure as described in Example-1/2 using Intermediate-41b and 6-fluoropyridin-2-amine LCMS(ESI): m/z 524.94 (M+H)+; 1H NMR (400 MHz, DMSO-d6) δ 11.37 (s, 1H), 7.88 (dd, J=8.2 Hz, 1H), 7.59 (d, J=2.1 Hz, 1H), 7.46 (d, J=8.1 Hz, 1H), 7.41-7.29 (m, 2H), 7.04-6.94 (m, 2H), 6.85-6.73 (m, 2H), 4.59 (t, J=7.2 Hz, 1H), 4.34-4.24 (m, 2H), 3.39-3.34 (m, 2H), 3.22 (s, 3H), 2.89-2.75 (m, 2H), 2.30-2.19 (m, 1H), 2.05-1.95 (m, 1H), 1.88-1.76 (m, 2H).

Example-146/147: (S&R)-4-(2-(4-methoxybutyl)-4-(trifluoromethyl)phenyl)-N-(pyrimidin-2-yl)chroman-7-sulfonamide

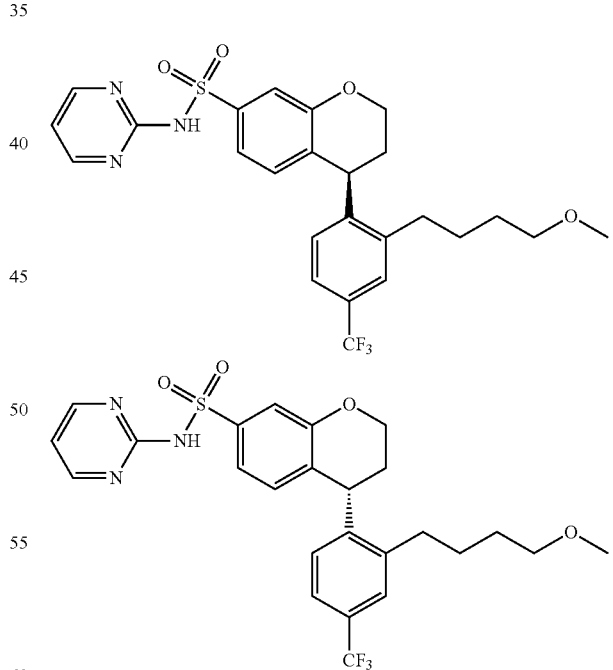

The title compounds were prepared by following the similar procedure as described in Example-1/2 using Intermediate-43 and pyrimidin-2-amine.

Further the enantiomers were separated using chiral preparative HPLC (Column: ChiralPak IA; Mobile phase: A=(Hexane+0.1% TFA), B=(IPA:DCM=1:1), A:B=70:30, to afford isomer-1 and isomer-2. These isomers were obtained at retention time 6.90 min (Example-146) and retention time 7.69 min (Example-147).

LCMS(ESI): m/z 522.09 (M+H)$^+$; $^1$H NMR (400 MHz, DMSO-d$_6$) δ 8.54 (d, J=4.9 Hz, 2H), 7.59 (s, 1H), 7.50-7.33 (m, 3H), 7.12-6.98 (m, 2H), 6.78 (d, J=8.1 Hz, 1H), 4.60 (t, J=8.2, 6.3 Hz, 1H), 4.32-4.24 (m, 2H), 3.35-3.29 (m, 2H), 3.19 (s, 3H), 2.86-2.69 (m, 2H), 2.29-2.01 (m, 2H), 1.70-1.49 (m, 4H).

Example-148: (R/S)—N-(5-fluoropyrimidin-2-yl)-4-(2-(4-methoxybutyl)-4-(trifluoromethyl)phenyl)chroman-7-sulfonamide

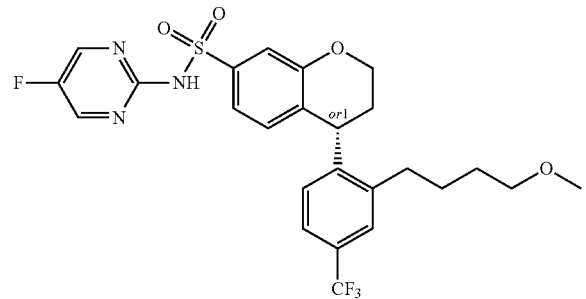 [SMILES: COCCCCc1cc(C(F)(F)F)ccc1[C@H]1CCOc2cc(S(=O)(=O)Nc3ncc(F)cn3)ccc21]

The title compound was prepared by following the similar procedure as described in Example-1/2 using Intermediate-43 and 5-fluoropyrimidin-2-amine.

Further the enantiomers were separated using chiral preparative HPLC (Column: ChiralPak IA; Mobile phase: A=(Hexane+0.1% TFA), B=(IPA:DCM=1:1), A:B=80:20, to afford isomer-1 and isomer-2. These isomers were obtained at retention time 7.52 min and retention time 8.87 min (Example-148).

LCMS(ESI): m/z 540.07 (M+H)$^+$; $^1$H NMR (400 MHz, DMSO-d$_6$) δ 11.88 (s, 1H), 8.66 (s, 2H), 7.60 (s, 1H), 7.46 (dd, J=8.3, 2.0 Hz, 1H), 7.42-7.32 (m, 2H), 7.02 (d, J=8.2 Hz, 1H), 6.79 (d, J=8.1 Hz, 1H), 4.60 (t, J=7.1 Hz, 1H), 4.35-4.24 (m, 2H), 3.36-3.28 (m, 2H) 3.20 (s, 3H), 2.90-2.70 (m, 2H), 2.27-1.94 (m, 2H), 1.67-1.48 (m, 4H).

Example-149: (R/S)-4-(2-(4-methoxybutyl)-4-(trifluoromethyl)phenyl)-N-(pyrimidin-4-yl)chroman-7-sulfonamide

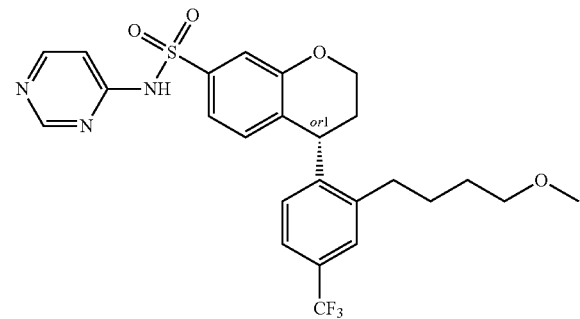 [SMILES: COCCCCc1cc(C(F)(F)F)ccc1[C@H]1CCOc2cc(S(=O)(=O)Nc3ccncn3)ccc21]

The title compound was prepared by following the similar procedure as described in Example-1/2 using Intermediate-43 and pyrimidin-4-amine.

Further the enantiomers were separated using chiral preparative HPLC (Column: ChiralPak IA; Mobile phase: A=(Hexane+0.1% TFA), B=(IPA:DCM=1:1), A:B=70:30, to afford isomer-1 and isomer-2. These isomers were obtained at retention time 5.81 min and retention time 6.75 min (Example-149).

LCMS(ESI): m/z 522.07 (M+H)$^+$; $^1$H NMR (400 MHz, DMSO-d$_6$) δ 8.67 (s, 1H), 8.39 (s, 1H), 7.60 (s, 1H), 7.47 (d, J=8.2 Hz, 1H), 7.37-7.25 (m, 2H), 7.18-6.97 (m, 2H), 6.78 (d, J=8.1 Hz, 1H), 4.59 (t, J=7.2 Hz, 1H), 4.32-4.24 (m, 2H), 3.35-3.30 (m, 2H), 3.20 (s, 3H), 2.89-2.71 (m, 2H), 2.30-1.98 (m, 2H), 1.70-1.53 (m, 4H).

Example-150: (R/S)-4-(2-(4-methoxybutyl)-4-(trifluoromethyl)phenyl)-N-(pyridazin-3-yl)chroman-7-sulfonamide

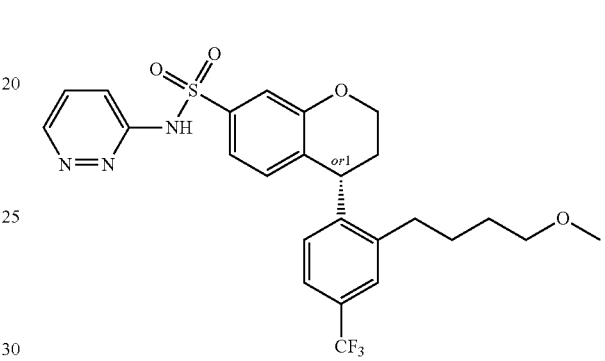

The title compound was prepared by following the similar procedure as described in Example-1/2 using Intermediate-43 and pyridazin-3-amine.

Further the enantiomers were separated using chiral preparative HPLC (Column: ChiralPak IA; Mobile phase: A=(Hexane+0.1% TFA), B=(IPA:DCM=1:1), A:B=70:30, to afford isomer-1 and isomer-2. These isomers were obtained at retention time 5.47 min and retention time 6.57 min (Example-150).

LCMS(ESI): m/z 521.94 (M+H)$^+$; $^1$H NMR (400 MHz, DMSO-d$_6$) δ 8.34 (s, 1H), 7.90 (s, 1H), 7.70 (dd, J=9.5, 4.2 Hz, 1H), 7.60 (s, 1H), 7.47 (d, J=8.3 Hz, 1H), 7.32-7.22 (m, 2H), 7.02 (d, J=8.3 Hz, 1H), 6.74 (d, J=8.0 Hz, 1H), 4.58 (t, J=7.1 Hz, 1H), 4.36-4.16 (m, 2H), 3.36-3.31 (m, 2H), 3.20 (s, 3H), 2.87-2.70 (m, 2H), 2.29-2.14 (m, 1H), 2.02-1.96 (m, 1H), 1.72-1.46 (m, 4H).

Example-151/152: (S&R)—N-(6-fluoropyridin-2-yl)-4-(2-(4-methoxybutyl)-4-(trifluoromethyl)phenyl)chroman-7-sulfonamide

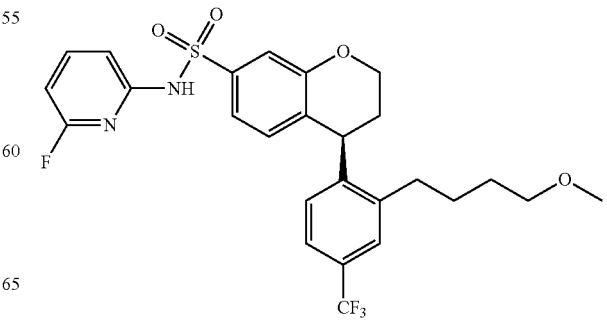

157

-continued

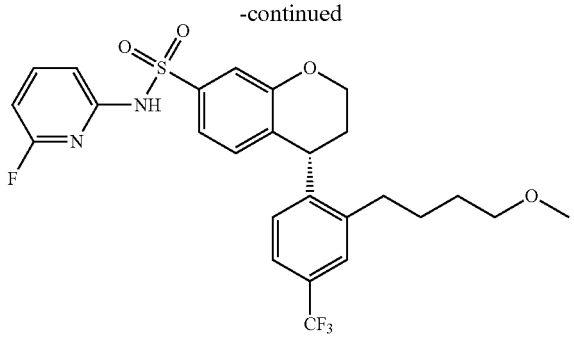

The title compounds were prepared by following the similar procedure as described in Example-1/2 using Intermediate-43 and 6-fluoropyridin-2-amine.

Further the enantiomers were separated using chiral preparative HPLC (Column: ChiralPak ID; Mobile phase: A=(Hexane+0.1% TFA), B=(IPA:DCM=1:1), A:B=75:25, to afford isomer-1 and isomer-2. These isomers were obtained at retention time 7.65 min (Example-151) and retention time 8.69 min (Example-152).

LCMS(ESI): m z 539.08 (M+H)$^+$; $^1$H NMR (400 MHz, DMSO-d6) δ 11.38 (s, 1H), 7.87 (dd, J=8.2 Hz, 1H), 7.59 (s, 1H), 7.46 (d, J=8.3 Hz, 1H), 7.38 (d, J=1.9 Hz, 1H), 7.32 (dd, J=8.1, 2.0 Hz, 1H), 7.06-6.94 (m, 2H), 6.84-6.73 (m, 2H), 4.60 (t, J=7.3 Hz, 1H), 4.35-4.25 (m, 2H), 3.35-3.24 (m, 2H), 3.19 (s, 3H), 2.82-2.60 (m, 2H), 2.29-2.17 (m, 1H), 2.05-1.95 (m, 1H), 1.75-1.50 (m, 4H).

Example-153: (R/S)-4-(2-(2-fluoroethyl)-4-(trifluoromethyl)phenyl)-N-(pyrimidin-2-yl)chroman-7-sulfonamide

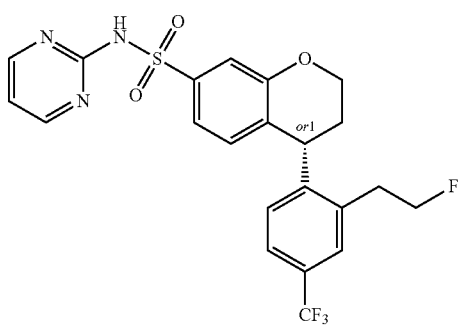 [SMILES: O=S(=O)(Nc1ncccn1)c1ccc2c(c1)OCC[C@@H]2c1ccc(C(F)(F)F)cc1CCF]

The title compound was prepared by following the similar procedure as described in Example-1/2 using Intermediate-45b and pyrimidin-2-amine. LCMS(ESI): m z 482.80 (M+H)$^+$; $^1$H NMR (400 MHz, DMSO-d$_6$) δ 11.73 (s, 1H), 8.54 (d, J=4.9 Hz, 2H), 7.71 (d, J=2.1 Hz, 1H), 7.52 (d, J=8.2 Hz, 1H), 7.45-7.27 (m, 2H), 7.15-6.95 (m, 2H), 6.81 (d, J=8.1 Hz, 1H), 4.78 (t, J=6.2 Hz, 1H), 4.72-4.56 (m, 2H), 4.36-4.20 (m, 2H), 3.29-3.06 (m, 2H), 2.31-2.21 (m, 1H), 2.02-1.92 (m, 1H).

158

Example-154: (R/S)-4-(2-(2-fluoroethyl)-4-(trifluoromethyl)phenyl)-N-(5-fluoropyrimidin-2-yl)chroman-7-sulfonamide

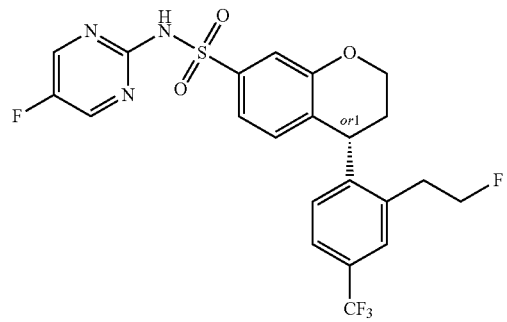 [SMILES: O=S(=O)(Nc1ncc(F)cn1)c1ccc2c(c1)OCC[C@@H]2c1ccc(C(F)(F)F)cc1CCF]

The title compound was prepared by following the similar procedure as described in Example-1/2 using Intermediate-45b and 5-fluoropyrimidin-2-amine. LCMS(ESI): m/z 500.07 (M+H)$^+$; $^1$H NMR (400 MHz, DMSO-d$_6$) δ 11.89 (s, 1H), 8.66 (s, 2H), 7.72 (s, 1H), 7.52 (d, J=8.2 Hz, 1H), 7.43-7.33 (m, 2H), 7.03 (d, J=8.3 Hz, 1H), 6.82 (d, J=8.1 Hz, 1H), 4.78 (t, J=6.2 Hz, 1H), 4.70-4.62 (m, 2H), 4.31-4.20 (m, 2H), 3.32-3.12 (m, 2H), 2.30-2.20 (m, 1H), 2.07-1.95 (m, 1H).

Example-155: (R/S)-4-(2-(2-fluoroethyl)-4-(trifluoromethyl)phenyl)-N-(pyrimidin-4-yl)chroman-7-sulfonamide

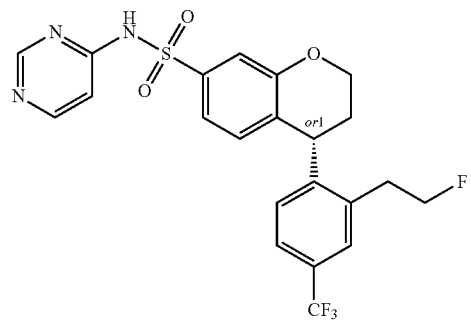 [SMILES: O=S(=O)(Nc1ccncn1)c1ccc2c(c1)OCC[C@@H]2c1ccc(C(F)(F)F)cc1CCF]

The title compound was prepared by following the similar procedure as described in Example-1/2 using Intermediate-45b and pyrimidin-4-amine. LCMS(ESI): m/z 482.27 (M+H)$^+$; $^1$H NMR (400 MHz, DMSO-d$_6$) δ 8.66 (s, 1H), 8.36 (s, 1H), 7.71 (s, 1H), 7.57-7.47 (m, 1H), 7.39-7.24 (m, 2H), 7.10-6.95 (m, 2H), 6.80 (d, J=8.0 Hz, 1H), 4.78 (t, J=6.2 Hz, 1H), 4.71-4.60 (m, 2H), 4.31-4.21 (m, 2H), 3.32-3.15 (m, 2H), 2.28-2.18 (m, 1H), 2.03-1.93 (m, 1H).

Example-156: (R/S)-4-(2-(2-fluoroethyl)-4-(trifluoromethyl)phenyl)-N-(pyridazin-3-yl)chroman-7-sulfonamide

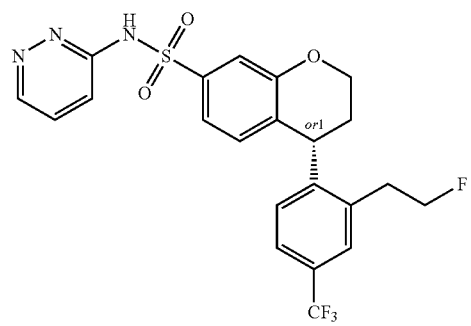 [SMILES: O=S(=O)(Nc1cccnn1)c1ccc2c(c1)OCC[C@@H]2c1ccc(C(F)(F)F)cc1CCF]

The title compound was prepared by following the similar procedure as described in Example-1/2 using Intermediate-45b and pyridazin-3-amine. LCMS(ESI): m/z 482.03 (M+H)⁺; ¹H NMR (400 MHz, DMSO-d₆) δ 14.52 (s, 1H), 8.31 (s, 1H), 7.92 (s, 1H), 7.77-7.65 (m, 2H), 7.52 (d, J=8.3 Hz, 1H), 7.32-7.19 (m, 2H), 7.03 (d, J=8.2 Hz, 1H), 6.77 (d, J=8.1 Hz, 1H), 4.79 (t, J=6.2 Hz, 1H), 4.72-4.56 (m, 2H), 4.32-4.19 (m, 2H), 3.31-3.12 (m, 2H), 2.31-2.18 (m, 1H), 2.02-1.92 (m, 1H).

Example-157: (R/S)-4-(2-(2-fluoroethyl)-4-(trifluoromethyl)phenyl)-N-(6-fluoropyridin-2-yl)chroman-7-sulfonamide

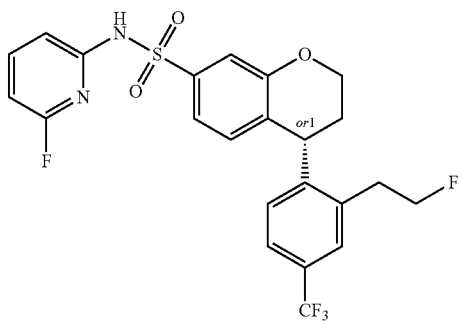 [SMILES: O=S(=O)(Nc1cccc(F)n1)c1ccc2c(c1)OCC[C@@H]2c1ccc(C(F)(F)F)cc1CCF]

The title compound was prepared by following the similar procedure as described in Example-1/2 using Intermediate-45b and 6-fluoropyridin-2-amine. LCMS(ESI): m/z 499.07 (M+H)⁺; ¹H NMR (400 MHz, DMSO-d₆) δ 11.39 (s, 1H), 7.92-7.83 (m, 1H), 7.71 (d, J=2.0 Hz, 1H), 7.51 (dd, J=8.2, 2.0 Hz, 1H), 7.38 (d, J=2.0 Hz, 1H), 7.32 (dd, J=8.1, 2.0 Hz, 1H), 7.06-6.95 (m, 2H), 6.83 (d, J=8.1 Hz, 1H), 6.77 (dd, J=8.0, 2.5 Hz, 1H), 4.77 (t, J=6.2 Hz, 1H), 4.70-4.59 (m, 2H), 4.35-4.19 (m, 2H), 3.31-3.08 (m, 2H), 2.31-2.17 (m, 1H), 2.04-1.91 (m, 1H).

Example-158: (R/S)-4-(2-(3-fluoropropyl)-4-(trifluoromethyl)phenyl)-N-(pyrimidin-2-yl)chroman-7-sulfonamide

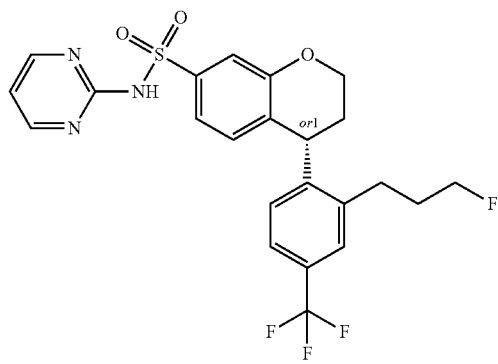 [SMILES: O=S(=O)(Nc1ncccn1)c1ccc2c(c1)OCC[C@@H]2c1ccc(C(F)(F)F)cc1CCCF]

The title compound was prepared by following the similar procedure as described in Example-1/2 using Intermediate-47b and pyrimidin-2-amine LCMS(ESI): m/z 496.08 (M+H)⁺; ¹H NMR (400 MHz, DMSO-d₆) δ 11.75 (s, 1H), 8.60-8.46 (m, 2H), 7.64 (s, 1H), 7.49 (d, J=8.3 Hz, 1H), 7.45-7.33 (m, 2H), 7.15-6.99 (m, 2H), 6.81 (d, J=8.2 Hz, 1H), 4.64-4.52 (m, 2H), 4.48-4.40 (m, 1H), 4.33-4.22 (m, 2H), 2.98-2.81 (m, 2H), 2.28-2.17 (m, 1H), 2.07-1.91 (m, 3H).

Example-159: (R/S)-4-(2-(3-fluoropropyl)-4-(trifluoromethyl)phenyl)-N-(5-fluoropyrimidin-2-yl)chroman-7-sulfonamide

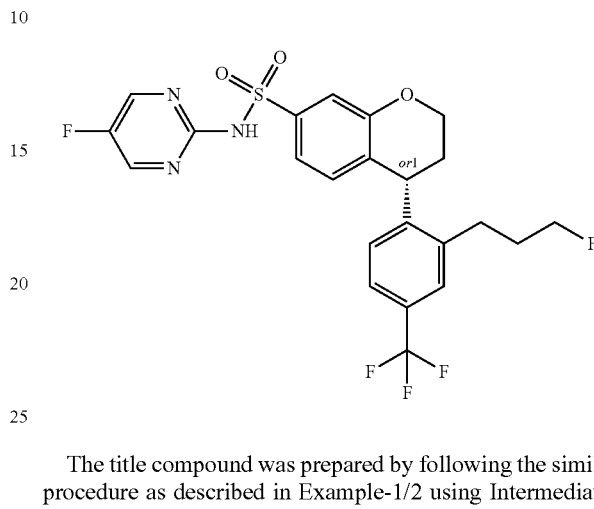

The title compound was prepared by following the similar procedure as described in Example-1/2 using Intermediate-47b and 5-fluoropyrimidin-2-amine. LCMS(ESI): m/z 513.94 (M+H)⁺; ¹H NMR (400 MHz, DMSO-d₆) δ 11.89 (s, 1H), 8.66 (s, 2H), 7.64 (d, J=1.9 Hz, 1H), 7.48 (d, 1H), 7.43-7.29 (m, 2H), 7.03 (d, J=8.2 Hz, 1H), 6.82 (d, J=8.2 Hz, 1H), 4.64-4.52 (m, 2H), 4.44 (t, J=5.9 Hz, 1H), 4.33-4.23 (m, 2H), 2.97-2.80 (m, 2H), 2.30-2.21 (m, 1H), 2.08-1.90 (m, 3H).

Example-160: (R/S)-4-(2-(3-fluoropropyl)-4-(trifluoromethyl)phenyl)-N-(pyrimidin-4-yl)chroman-7-sulfonamide

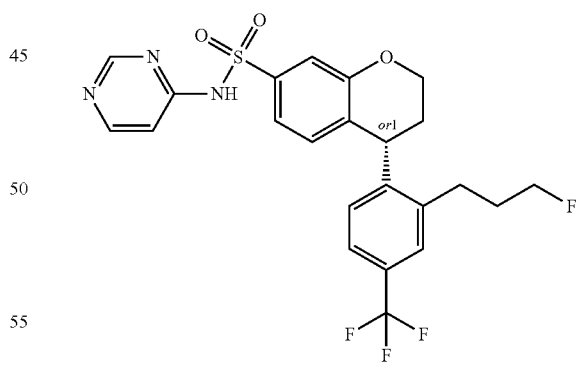

The title compound was prepared by following the similar procedure as described in Example-1/2 using Intermediate-47b and pyrimidin-4-amine. LCMS(ESI): m/z 496.10 (M+H)⁺; ¹H NMR (400 MHz, DMSO-d₆) δ 8.59 (s, 1H), 8.29 (d, J=6.3 Hz, 1H), 7.62 (d, J=2.0 Hz, 1H), 7.54-7.44 (m, 1H), 7.34-7.24 (m, 2H), 7.06-6.96 (m, 2H), 6.77 (d, J=8.1 Hz, 1H), 4.62-4.52 (m, 2H), 4.44 (t, J=5.9 Hz, 1H), 4.30-4.22 (m, 2H), 2.95-2.77 (m, 2H), 2.29-2.20 (m, 1H), 2.07-1.87 (m, 3H).

Example-161: (R/S)-4-(2-(3-fluoropropyl)-4-(trifluoromethyl)phenyl)-N-(pyridazin-3-yl)chroman-7-sulfonamide

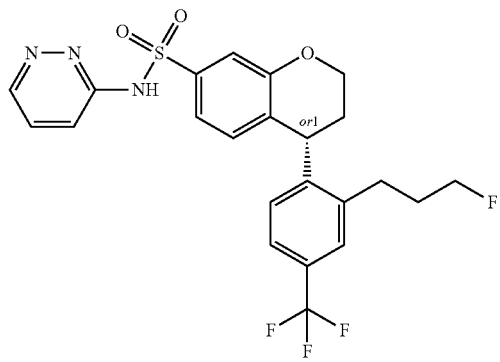 [SMILES: O=S(=O)(Nc1cccnn1)c1ccc2c(c1)OCC[C@@H]2c1ccc(C(F)(F)F)cc1CCCF]

The title compound was prepared by following the similar procedure as described in Example-1/2 using Intermediate-47b and pyridazin-3-amine. LCMS(ESI): m/z 495.95 (M+H)$^+$; $^1$H NMR (400 MHz, DMSO-d$_6$) δ 14.52 (s, 1H), 8.34-8.29 (m, 1H), 7.97-7.86 (m, 1H), 7.70 (dd, J=9.6, 4.2 Hz, 1H), 7.63 (s, 1H), 7.49 (d, J=8.2 Hz, 1H), 7.29-7.21 (m, 2H), 7.03 (d, J=8.2 Hz, 1H), 6.77 (d, J=8.0 Hz, 1H), 4.63-4.53 (m, 2H), 4.45 (t, J=5.9 Hz, 1H), 4.31-4.23 (m, 2H), 2.98-2.83 (m, 2H), 2.30-2.21 (m, 1H), 2.07-1.89 (m, 3H).

Example-162: (R/S)-4-(2-(3-fluoropropyl)-4-(trifluoromethyl)phenyl)-N-(6-fluoropyridin-2-yl)chroman-7-sulfonamide

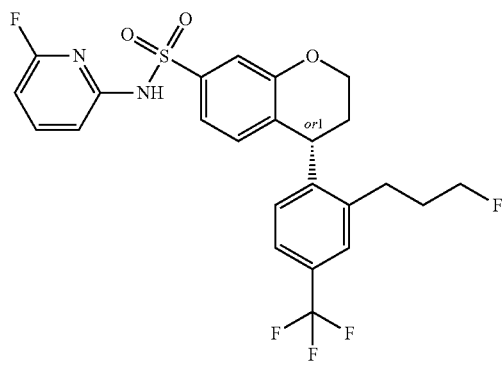 [SMILES: O=S(=O)(Nc1cccc(F)n1)c1ccc2c(c1)OCC[C@@H]2c1ccc(C(F)(F)F)cc1CCCF]

The title compound was prepared by following the similar procedure as described in Example-1/2 using Intermediate-47b and 6-fluoropyridin-2-amine. LCMS(ESI): m/z 513.08 (M+H)$^+$; $^1$H NMR (400 MHz, DMSO-d$_6$) δ 11.38 (s, 1H), 7.93-7.82 (m, 1H), 7.64 (s, 1H), 7.48 (d, J=8.2 Hz, 1H), 7.41-7.29 (m, 2H), 7.06-6.94 (m, 2H), 6.87-6.73 (m, 2H), 4.65-4.52 (m, 2H), 4.44 (t, J=6.0 Hz, 1H), 4.36-4.19 (m, 2H), 2.95-2.81 (m, 2H), 2.30-2.19 (m, 1H), 2.07-1.88 (m, 3H).

Example-163: (R/S)-4-(2-(4-fluorobutyl)-4-(trifluoromethyl)phenyl)-N-(pyrimidin-2-yl)chroman-7-sulfonamide

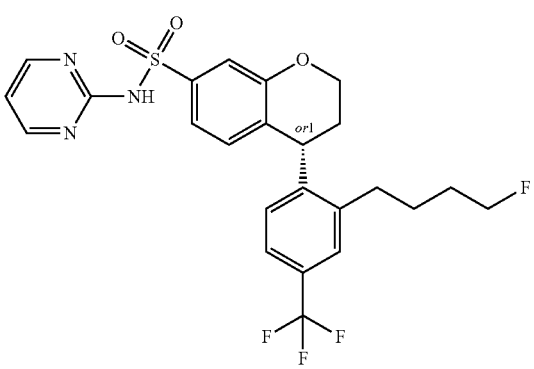 [SMILES: O=S(=O)(Nc1ncccn1)c1ccc2c(c1)OCC[C@@H]2c1ccc(C(F)(F)F)cc1CCCCF]

The title compound was prepared by following the similar procedure as described in Example-1/2 using Intermediate-49b and pyrimidin-2-amine. LCMS(ESI): m/z 510.11 (M+H)$^+$; $^1$H NMR (400 MHz, DMSO-d$_6$) δ 11.74 (s, 1H), 8.54 (d, J=4.8 Hz, 2H), 7.62 (s, 1H), 7.51-7.24 (m, 3H), 7.21-6.99 (m, 2H), 6.79 (d, J=8.2 Hz, 1H), 4.68-4.50 (m, 2H), 4.44-4.17 (m, 3H), 2.95-2.71 (m, 2H), 2.30-1.95 (m, 2H), 1.79-1.44 (m, 4H).

Example-164: (R/S)-4-(2-(4-fluorobutyl)-4-(trifluoromethyl)phenyl)-N-(5-fluoropyrimidin-2-yl)chroman-7-sulfonamide

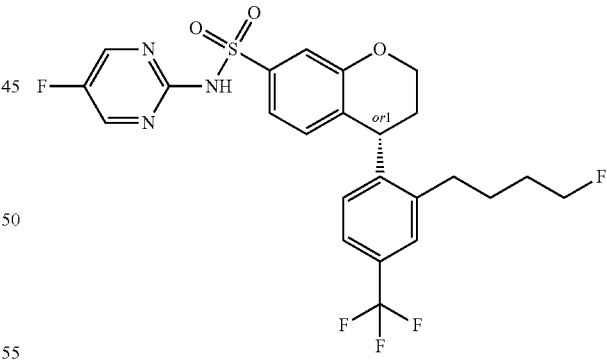

The title compound was prepared by following the similar procedure as described in Example-1/2 using Intermediate-49b and 5-fluoropyrimidin-2-amine. LCMS(ESI): m/z 528.12 (M+H)$^+$; $^1$H NMR (400 MHz, DMSO-d$_6$) δ 11.88 (s, 1H), 8.66 (s, 2H), 7.62 (s, 1H), 7.47 (d, J=8.2 Hz, 1H), 7.43-7.34 (m, 2H), 7.02 (d, J=8.2 Hz, 1H), 6.80 (d, J=8.1 Hz, 1H), 4.65-4.50 (m, 2H), 4.45-4.25 (m, 3H), 2.95-2.73 (m, 2H), 2.30-2.18 (m, 1H), 2.07-1.94 (m, 1H), 1.81-1.53 (m, 4H).

Example-165: (R/S)-4-(2-(4-fluorobutyl)-4-(trifluoromethyl)phenyl)-N-(pyrimidin-4-yl)chroman-7-sulfonamide

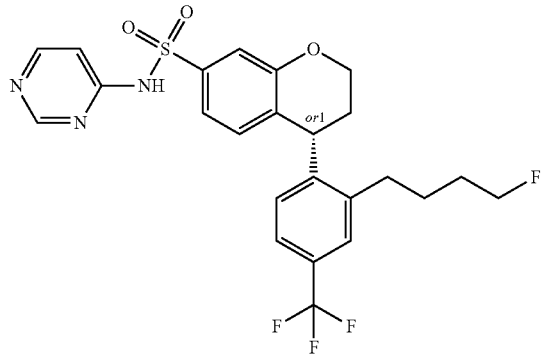 [SMILES: O=S(=O)(Nc1ccncn1)c1ccc2c(c1)OCC[C@@H]2c1ccc(C(F)(F)F)cc1CCCCF]

The title compound was prepared by following the similar procedure as described in Example-1/2 using Intermediate-49b and pyrimidin-4-amine. LCMS(ESI): m/z 510.05 (M+H)$^+$; $^1$H NMR (400 MHz, DMSO-d$_6$) δ 8.66 (s, 1H), 8.40 (s, 1H), 7.62 (d, J=2.0 Hz, 1H), 7.49-7.45 (m, 1H), 7.38-7.24 (m, 2H), 7.03 (d, J=8.2 Hz, 2H), 6.78 (d, J=8.2 Hz, 1H), 4.60 (t, J=7.2 Hz, 1H), 4.53 (t, J=5.8 Hz, 1H), 4.44-4.39 (m, 1H), 4.35-4.22 (m, 2H), 2.91-2.74 (m, 2H), 2.29-2.20 (m, 1H), 2.06-1.95 (m, 1H), 1.84-1.59 (m, 4H).

Example-166: (R/S)-4-(2-(4-fluorobutyl)-4-(trifluoromethyl)phenyl)-N-(pyridazin-3-yl)chroman-7-sulfonamide

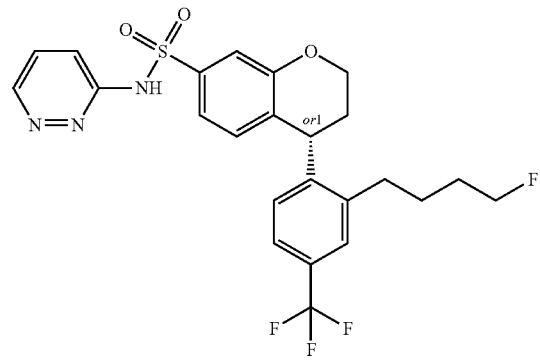 [SMILES: O=S(=O)(Nc1cccnn1)c1ccc2c(c1)OCC[C@@H]2c1ccc(C(F)(F)F)cc1CCCCF]

The title compound was prepared by following the similar procedure as described in Example-1/2 using Intermediate-49b and pyridazin-3-amine. LCMS(ESI): m/z 510.07 (M+H)$^+$; $^1$H NMR (400 MHz, DMSO-d$_6$) δ 14.52 (s, 1H), 8.32 (s, 1H), 7.91 (s, 1H), 7.70 (dd, J=9.5, 4.1 Hz, 1H), 7.62 (d, J=2.0 Hz, 1H), 7.47 (dd, J=8.3, 2.0 Hz, 1H), 7.32-7.20 (m, 2H), 7.09-6.99 (m, 1H), 6.75 (d, J=8.0 Hz, 1H), 4.63-4.49 (m, 2H), 4.47-4.39 (m, 1H), 4.34-4.21 (m, 2H), 2.94-2.73 (m, 2H), 2.25-2.19 (m, 1H), 2.07-1.97 (m, 1H), 1.82-1.59 (m, 4H).

Example-167: (R/S)-4-(2-(4-fluorobutyl)-4-(trifluoromethyl)phenyl)-N-(6-fluoropyridin-2-yl)chroman-7-sulfonamide

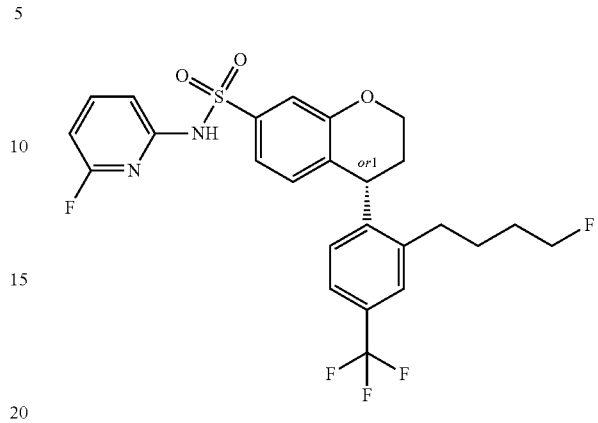

The title compound was prepared by following the similar procedure as described in Example-1/2 using Intermediate-49b and 6-fluoropyridin-2-amine. LCMS(ESI): m/z 527.06 (M+H)$^+$; $^1$H NMR (400 MHz, DMSO-d$_6$) δ 11.37 (s, 1H), 7.87 (dd, J=8.2 Hz, 1H), 7.62 (d, J=2.0 Hz, 1H), 7.49-7.44 (m, 1H), 7.38 (d, J=1.9 Hz, 1H), 7.32 (dd, J=8.2, 1.9 Hz, 1H), 7.05-6.94 (m, 2H), 6.84-6.74 (m, 2H), 4.61 (t, J=7.2 Hz, 1H), 4.53 (t, J=5.8 Hz, 1H), 4.44-4.37 (m, 1H), 4.33-4.22 (m, 2H), 2.92-2.71 (m, 2H), 2.30-2.16 (m, 1H), 2.06-1.97 (m, 1H), 1.85-1.49 (m, 4H).

Example-168/169: (R&S)—N-(pyrimidin-2-yl)-4-(2-((tetrahydro-2H-pyran-4-yl)oxy)-4-(trifluoromethyl)phenyl)chroman-7-sulfonamide

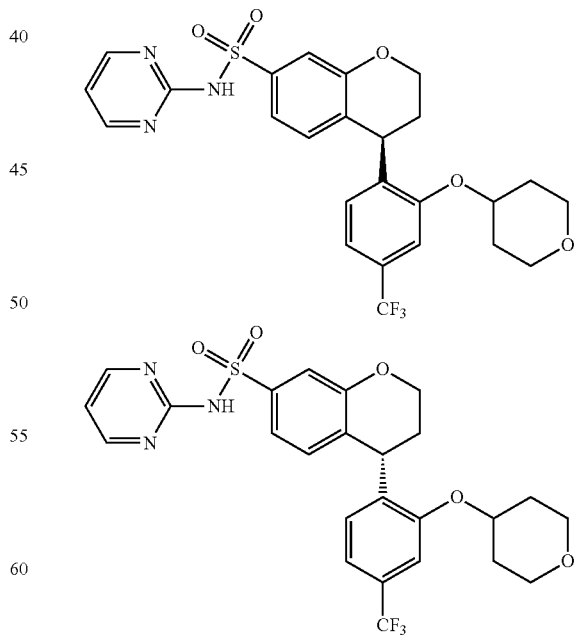

The title compounds were prepared by following the similar procedure as described in Example-1/2 using Intermediate-51 and pyrimidin-2-amine.

Further the enantiomers were separated using chiral preparative HPLC (Column: ChiralPak ID; Mobile phase: (Acetonitrile+0.1% TFA), to afford isomer-1 and isomer-2. These isomers were obtained at retention time 4.82 min (Example-168) and retention time 5.99 min (Example-169).

LCMS(ESI): m/z 535.94 (M+H)+; $^1$H NMR (400 MHz, Chloroform-d) δ 8.66 (d, J=4.9 Hz, 2H), 7.68 (d, J=1.9 Hz, 1H), 7.56 (dd, J=8.2, 1.9 Hz, 1H), 7.14 (d, J=7.9 Hz, 1H), 7.09-6.89 (m, 4H), 4.65-4.53 (m, 2H), 4.30-4.19 (m, 2H), 3.90-3.70 (m, 2H), 3.65-3.53 (m, 2H), 2.29-2.18 (m, 2H), 2.10-2.01 (m, 1H), 1.97-1.75 (m, 2H), 1.60-1.40 (m, 1H).

Example-170/171: (R&S)—N-(5-fluoropyrimidin-2-yl)-4-(2-((tetrahydro-2H-pyran-4-yl)oxy)-4-(trifluoromethyl)phenyl)chroman-7-sulfonamide

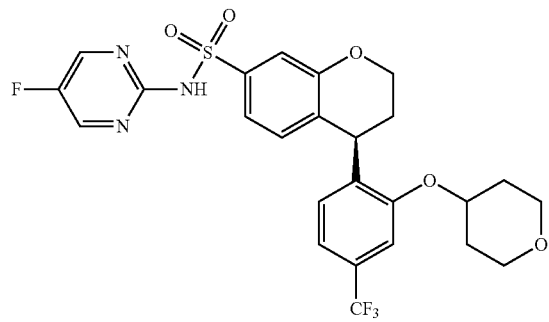

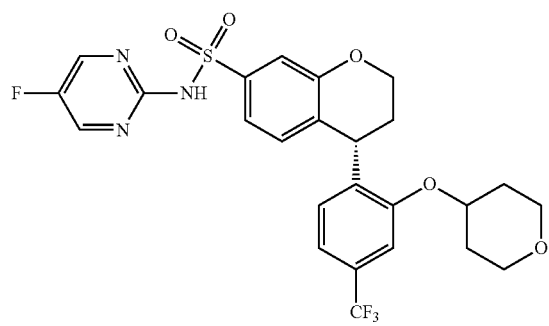

The title compounds were prepared by following the similar procedure as described in Example-1/2 using Intermediate-51 and 5-fluoropyrimidin-2-amine.

Further the enantiomers were separated using chiral preparative HPLC (Column: ChiralPak IA; Mobile phase: A=(Hexane+0.1% TFA), B=(IPA:MeOH=1:1), A:B=50:50, to afford isomer-1 and isomer-2. These isomers were obtained at retention time 6.37 min (Example-170) and retention time 7.90 min (Example-171).

LCMS(ESI): m/z 553.95 (M+H)+; $^1$H NMR (400 MHz, DMSO-d$_6$) δ 11.84 (s, 1H), 8.65 (s, 2H), 7.39 (d, J=2.0 Hz, 1H), 7.35 (dd, J=8.1, 1.9 Hz, 1H), 7.32 (s, 1H), 7.24 (d, J=6.4 Hz, 2H), 6.88 (d, J=8.1 Hz, 1H), 4.75-4.65 (m, 1H), 4.53 (t, J=7.3 Hz, 1H), 4.30-4.17 (m, 2H), 3.63 (d, J=7.9 Hz, 1H), 3.50-3.38 (m, 3H), 2.32-2.06 (m, 2H), 1.90-1.84 (m, 1H), 1.68-1.41 (m, 2H), 1.24-1.06 (m, 1H).

Example-172/173: (R&S)—N-(pyrimidin-4-yl)-4-(2-((tetrahydro-2H-pyran-4-yl)oxy)-4-(trifluoromethyl)phenyl)chroman-7-sulfonamide

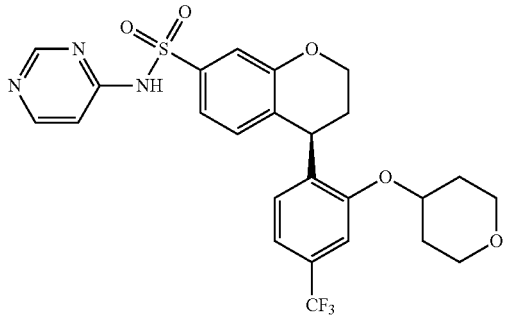

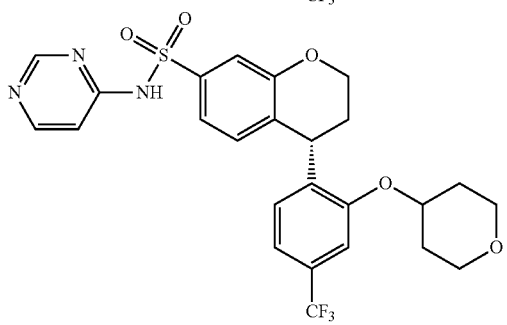

The title compounds were prepared by following the similar procedure as described in Example-1/2 using Intermediate-51 and pyrimidin-4-amine.

Further the enantiomers were separated using chiral preparative HPLC (Column: ChiralPak IE; Mobile phase: A=(Hexane+0.1% TFA), B=(IPA:MeOH=1:1), A:B=40:60, to afford isomer-1 and isomer-2. These isomers were obtained at retention time 7.07 min (Example-172) and retention time 8.09 min (Example-173).

LCMS(ESI): m/z 535.94 (M+H)+; $^1$H NMR (400 MHz, DMSO-d$_6$) δ 8.66 (s, 1H), 8.38 (s, 1H), 7.32 (d, J=2.8 Hz, 3H), 7.23 (q, J=8.0 Hz, 2H), 7.07 (s, 1H), 6.87 (d, J=7.9 Hz, 1H), 4.75-4.65 (m, 1H), 4.53 (t, J=7.3 Hz, 1H), 4.28-4.10 (m, 2H), 3.71-3.19 (m, 4H), 2.30-2.05 (m, 2H), 1.95-1.85 (m, 1H), 1.71-1.45 (m, 2H), 1.19-1.02 (m, 1H).

Example-174/175: (R&S)—N-(pyridazin-3-yl)-4-(2-((tetrahydro-2H-pyran-4-yl)oxy)-4-(trifluoromethyl)phenyl)chroman-7-sulfonamide

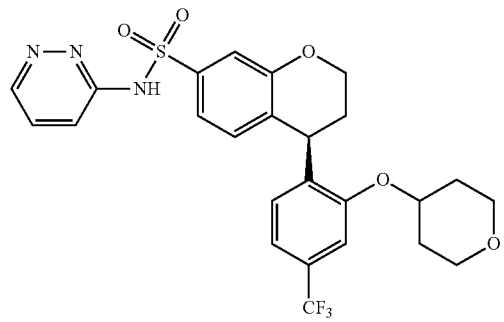

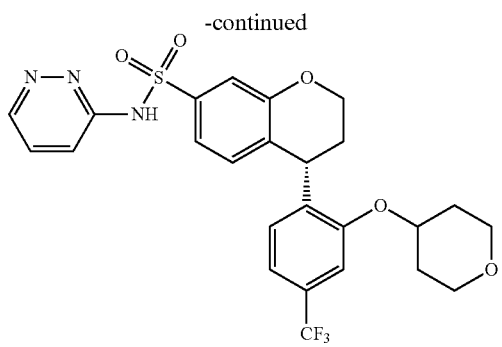

The title compounds were prepared by following the similar procedure as described in Example-1/2 using Intermediate-51 and pyridazin-3-amine.

Further the enantiomers were separated using chiral preparative HPLC (Column: ChiralPak ID; Mobile phase: A=(Hexane+0.1% TFA), B=(IPA:MeOH=1:1), A:B=40:60, to afford isomer-1 and isomer-2. These isomers were obtained at retention time 8.71 min (Example-174) and retention time 10.18 min (Example-175).

LCMS(ESI): m/z 535.94 (M+H)+; 1H NMR (400 MHz, DMSO-d6) δ 14.52 (s, 1H), 8.31 (s, 1H), 7.89 (s, 1H), 7.69 (dd, J=9.5, 4.2 Hz, 1H), 7.32 (s, 1H), 7.28-7.12 (m, 4H), 6.84 (d, J=8.1 Hz, 1H), 4.75-4.70 (m, 1H), 4.53 (t, J=7.0 Hz, 1H), 4.25-4.17 (m, 2H), 3.68-3.63 (m, 1H), 3.52-3.42 (m, 3H), 2.25-2.07 (m, 2H), 1.94-1.88 (m, 1H), 1.69-1.49 (m, 2H), 1.35-1.05 (m, 1H).

Example-176/177: (R&S)—N-(6-fluoropyridin-2-yl)-4-(2-((tetrahydro-2H-pyran-4-yl)oxy)-4-(trifluoromethyl)phenyl)chroman-7-sulfonamide

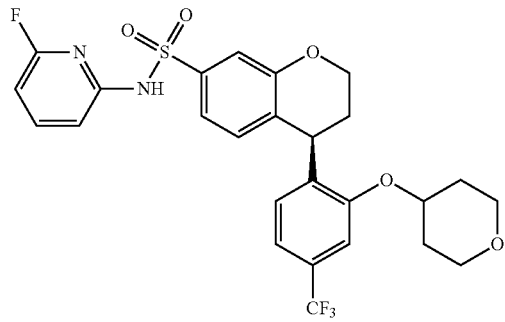

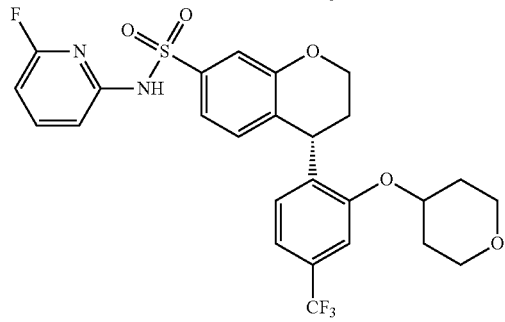

The title compounds were prepared by following the similar procedure as described in Example-1/2 using Intermediate-51 and 6-fluoropyridin-2-amine.

Further the enantiomers were separated using chiral preparative HPLC (Column: ChiralPak ID; Mobile phase: A=(Hexane+0.1% TFA), B=(IPA:MeOH=1:1), A:B=60:40, to afford isomer-1 and isomer-2. These isomers were obtained at retention time 6.98 min (Example-176) and retention time 8.06 min (Example-177).

LCMS(ESI): m/z 552.82 (M+H)+; 1H NMR (400 MHz, DMSO-d6) δ 11.35 (s, 1H), 7.86 (dd, J=8.2 Hz, 1H), 7.38-7.17 (m, 5H), 6.97 (dd, J=7.9, 2.1 Hz, 1H), 6.89 (d, J=8.1 Hz, 1H), 6.76 (dd, J=8.0, 2.4 Hz, 1H), 4.72-4.65 (m, 1H), 4.53 (t, J=7.3 Hz, 1H), 4.30-4.16 (m, 2H), 3.70-3.61 (m, 1H), 3.52-3.42 (m, 2H), 3.32-3.23 (m, 1H), 2.28-2.07 (m, 2H), 1.94-1.86 (m, 1H), 1.62-1.48 (m, 2H), 1.13-0.99 (m, 1H).

Example-178/179: (R&S)—N-(pyrimidin-2-yl)-4-(2-(((S)-tetrahydrofuran-3-yl)oxy)-4-(trifluoromethyl)phenyl)chroman-7-sulfonamide

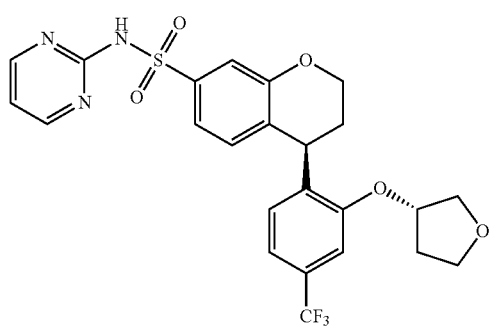

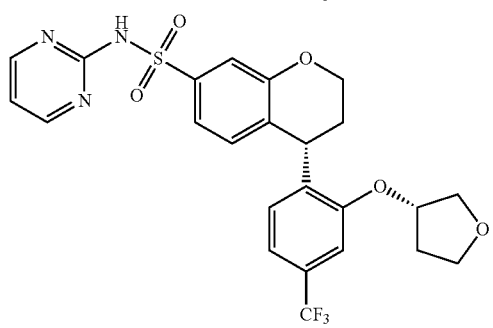

The title compounds were prepared by following the similar procedure as described in Example-1/2 using Intermediate-53 and pyrimidin-2-amine.

Further the enantiomers were separated using chiral preparative HPLC (Column: ChiralPak ID; Mobile phase: A=(Hexane+0.1% TFA), B=(IPA:MeOH=1:1), A:B=30:70, to afford isomer-1 and isomer-2. These isomers were obtained at retention time 7.21 min (Example-178) and retention time 9.80 min (Example-179).

LCMS(ESI): m/z 522.04 (M+H)+; 1H NMR (400 MHz, DMSO-d6) δ 11.75 (s, 1H), 8.53 (d, J=5.0 Hz, 2H), 7.42-7.33 (m, 2H), 7.32-7.24 (m, 2H), 7.14-7.05 (m, 2H), 6.89 (d, J=8.0 Hz, 1H), 5.20-5.12 (m, 1H), 4.52 (t, J=6.8 Hz, 1H), 4.27-4.12 (m, 2H), 3.79-3.55 (m, 4H), 2.24-1.95 (m, 4H).

Example-180/181: (R&S)—N-(6-fluoropyridin-2-yl)-4-(2-(((S)-tetrahydrofuran-3-yl)oxy)-4-(trifluoromethyl)phenyl)chroman-7-sulfonamide

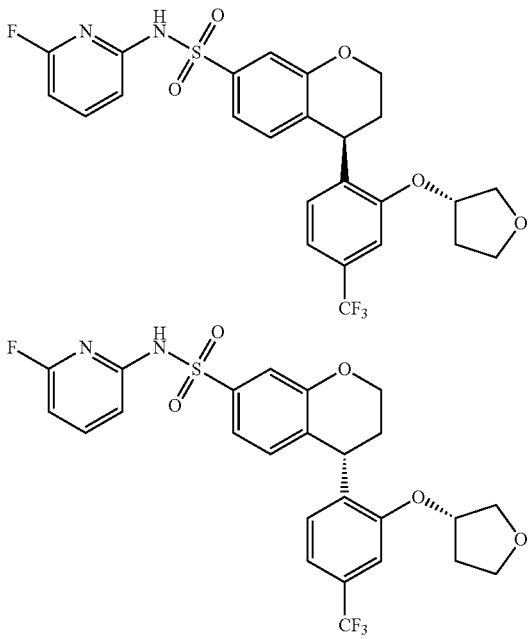

The title compounds were prepared by following the similar procedure as described in Example-1/2 using Intermediate-53 and 6-fluoropyridin-2-amine.

Further the enantiomers were separated using chiral preparative HPLC (Column: ChiralPak ID; Mobile phase: A=(Hexane+0.1% TFA), B=(IPA:MeOH=1:1), A:B=65:35, to afford isomer-1 and isomer-2. These isomers were obtained at retention time 7.07 min (Example-180) and retention time 7.84 min (Example-181).

LCMS(ESI): m/z 539.10 (M+H)+; $^1$H NMR (400 MHz, DMSO-$d_6$) δ 11.36 (s, 1H), 7.87 (dd, J=8.1 Hz, 1H), 7.36 (d, J=1.9 Hz, 1H), 7.33-7.18 (m, 4H), 6.98 (dd, J=7.9, 2.1 Hz, 1H), 6.89 (d, J=8.1 Hz, 1H), 6.76 (dd, J=8.1, 2.5 Hz, 1H), 5.11 (d, J=5.7 Hz, 1H), 4.48 (t, J=7.2 Hz, 1H), 4.27-4.15 (m, 2H), 3.85 (dd, J=10.1, 4.4 Hz, 1H), 3.69 (d, J=10.1 Hz, 1H), 3.61-3.41 (m, 2H), 2.20-2.05 (m, 2H), 1.91-1.80 (m, 1H), 1.58-1.44 (m, 1H).

Example-182: (S/R)—N-(5-fluoropyrimidin-2-yl)-4-(2-(((S)-tetrahydrofuran-3-yl)oxy)-4-(trifluoromethyl)phenyl)chroman-7-sulfonamide

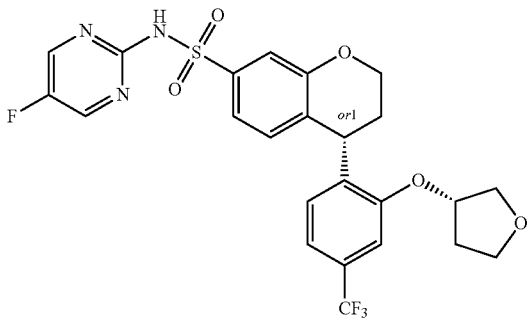 [SMILES: O=S(=O)(Nc1ncc(F)cn1)c1ccc2c(c1)OCC[C@@H]2c1ccc(C(F)(F)F)cc1O[C@H]1CCOC1]

The title compound was prepared by following the similar procedure as described in Example-1/2 using Intermediate-53b and 5-fluoropyrimidin-2-amine.

LCMS(ESI): m/z 540.07 (M+H)+; $^1$H NMR (400 MHz, DMSO-$d_6$) δ 11.86 (s, 1H), 8.65 (s, 2H), 7.38 (d, J=1.9 Hz, 1H), 7.34 (dd, J=8.1, 2.0 Hz, 1H), 7.30-7.24 (m, 2H), 7.19 (d, J=7.8 Hz, 1H), 6.88 (d, J=8.1 Hz, 1H), 5.14 (t, J=5.2 Hz, 1H), 4.49 (t, J=7.2 Hz, 1H), 4.26-4.14 (m, 2H), 3.87 (dd, J=10.1, 4.4 Hz, 1H), 3.69 (d, J=10.1 Hz, 1H), 3.61-3.53 (m, 1H), 3.48-3.39 (m, 1H), 2.22-2.08 (m, 2H), 1.97-1.87 (m, 1H), 1.51-1.39 (m, 1H).

Example-183: (S/R)—N-(pyrimidin-4-yl)-4-(2-(((S)-tetrahydrofuran-3-yl)oxy)-4-(trifluoromethyl)phenyl)chroman-7-sulfonamide

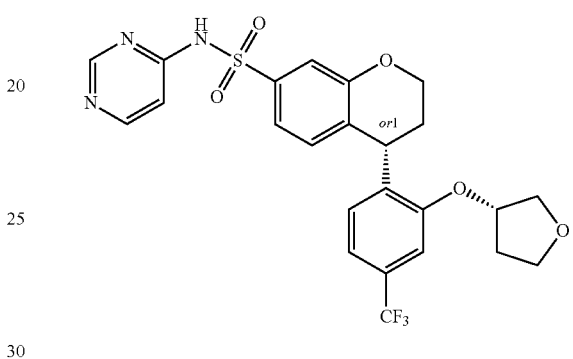

The title compound was prepared by following the similar procedure as described in Example-1/2 using Intermediate-53b and pyrimidin-4-amine. LCMS(ESI): m/z 540.07 (M+H)+; $^1$H NMR (400 MHz, DMSO-$d_6$) δ 8.67 (s, 1H), 8.38 (s, 1H), 7.40-7.23 (m, 4H), 7.19 (d, J=8.0 Hz, 1H), 7.07 (s, 1H), 6.88 (d, J=8.0 Hz, 1H), 5.20-5.06 (m, 1H), 4.49 (t, J=7.3 Hz, 1H), 4.25-4.14 (m, 2H), 3.87 (dd, J=10.2, 4.6 Hz, 1H), 3.78-3.54 (m, 3H), 2.22-2.07 (m, 2H), 1.98-1.84 (m, 1H), 1.59-1.35 (m, 1H).

Example-184: (S/R)—N-(pyridazin-3-yl)-4-(2-(((S)-tetrahydrofuran-3-yl)oxy)-4-(trifluoromethyl)phenyl)chroman-7-sulfonamide

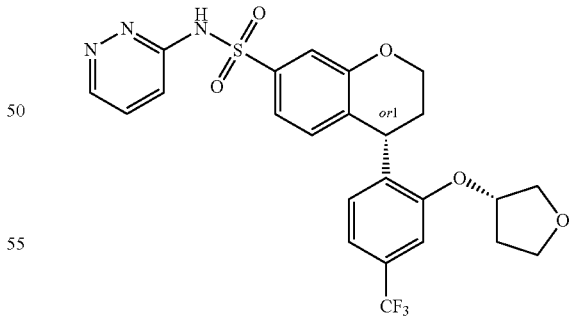

The title compound was prepared by following the similar procedure as described in Example-1/2 using Intermediate-53b and pyridazin-3-amine. LCMS(ESI): m/z 522.08 (M+H)+; $^1$H NMR (400 MHz, DMSO-$d_6$) δ 8.31 (s, 1H), 7.93 (s, 1H), 7.71 (s, 1H), 7.36-7.20 (m, 4H), 7.15 (d, J=8.0 Hz, 1H), 6.85 (d, J=8.1 Hz, 1H), 5.22-5.12 (m, 1H), 4.55-4.45 (m, 1H), 4.26-4.11 (m, 2H), 3.95-3.43 (m, 4H), 2.25-2.07 (m, 3H), 1.65-1.48 (m, 1H).

Example-185/186: (S&R)—N-(pyrimidin-2-yl)-4-(2-(((R)-tetrahydrofuran-3-yl)oxy)-4-(trifluoromethyl)phenyl)chroman-7-sulfonamide

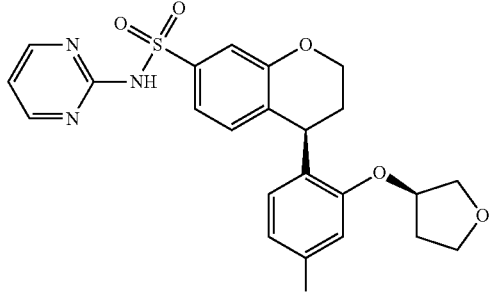

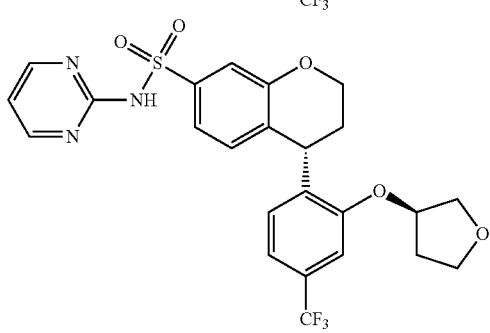

The title compounds were prepared by following the similar procedure as described in Example-1/2 using Intermediate-55 and pyrimidin-2-amine.

Further the enantiomers were separated using chiral preparative HPLC (Column: ChiralPak ID; Mobile phase: A=(Hexane+0.1% TFA), B=(IPA:MeOH=1:1), A:B=30:70, to afford isomer-1 and isomer-2. These isomers were obtained at retention time 7.08 min (Example-185) and retention time 9.87 min (Example-186).

LCMS(ESI): m/z 522.15 (M+H)$^+$; $^1$H NMR (400 MHz, DMSO-$d_6$) δ 11.72 (s, 1H), 8.53 (d, J=4.9 Hz, 2H), 7.42-7.32 (m, 2H), 7.31-7.23 (m, 2H), 7.19 (d, J=7.9 Hz, 1H), 7.08 (t, J=4.9 Hz, 1H), 6.88 (d, J=8.1 Hz, 1H), 5.12 (s, 1H), 4.49 (t, J=7.1 Hz, 1H), 4.20 (t, J=5.0 Hz, 2H), 3.86 (dd, J=10.2, 4.4 Hz, 1H), 3.70 (d, J=10.2 Hz, 1H), 3.62-3.52 (m, 1H), 3.51-3.40 (m, 1H), 2.17-2.07 (m, 2H), 1.94-1.85 (m, 1H), 1.49-1.41 (m, 1H).

Example-187/188: (S&R)-2'-(7-(N-(pyrimidin-2-yl)sulfamoyl)chroman-4-yl)-5'-(trifluoromethyl)-[1,1'-biphenyl]-4-carboxylic acid

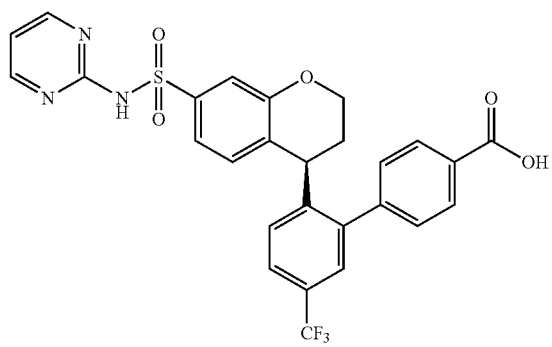

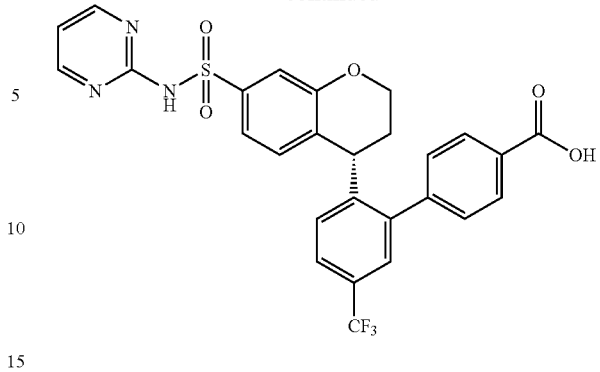

Step-1: (S&R)-tert-butyl 2'-(7-(N-(pyrimidin-2-yl)sulfamoyl)chroman-4-yl)-5'-(trifluoromethyl)-[1,1'-biphenyl]-4-carboxylate

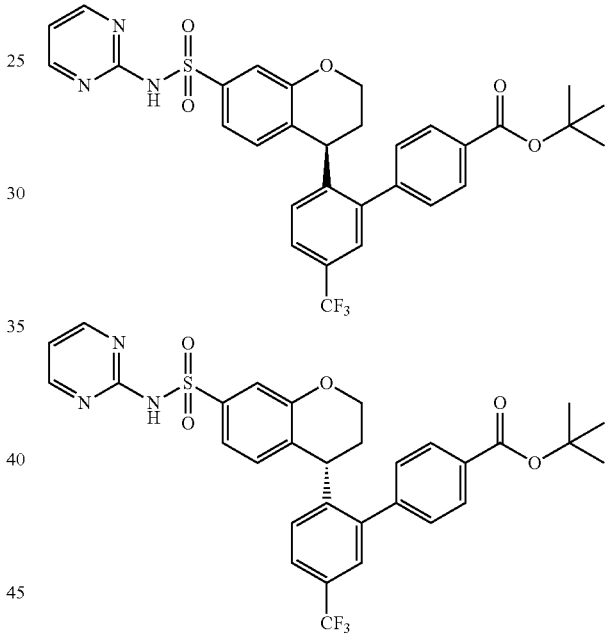

The title compounds were prepared by following the similar procedure as described in Example-1/2 using Intermediate-57 and pyrimidin-2-amine.

Further the enantiomers were separated using chiral preparative HPLC (Column: ChiralPak IA; Mobile phase: A=(Hexane+0.1% TFA), B=(MeOH:DCM=1:1), A:B=80:20, to afford isomer-1 and isomer-2. These isomers were obtained at retention time 8.96 min and retention time 10.18 min respectively.

LCMS (ESI): m/z 612.14 (M+H)$^+$;

Step-2: (S&R)-2'-(7-(N-(pyrimidin-2-yl)sulfamoyl)chroman-4-yl)-5'-(trifluoromethyl)-[1,1'-biphenyl]-4-carboxylic acid To a stirred solution of (S/R)-tert-butyl 2'-(7-(N-(pyrimidin-2-yl)sulfamoyl)chroman-4-yl)-5'-(trifluoromethyl)-[1,1'-biphenyl]-4-carboxylate (Isomer-1) (0.045 g, 0.074 mmol) in DCM (10 ml), TFA (0.057 ml, 0.736 mmol) was added and stirred for 4 h at room temperature. After completion of reaction as indicated by TLC, the reaction mixture was evaporated to dryness and washed with pentane to obtain white solid (0.035 g, 86%) (Example-187).

Similarly Isomer-2 of step 1 was treated with TFA and got the Example-188.

LCMS(ESI): m/z 555.82 (M+H)$^+$; $^1$H NMR (400 MHz, DMSO-d$_6$) δ 8.52 (d, J=4.9 Hz, 2H), 8.04 (d, J=8.0 Hz, 2H), 7.71 (d, J=8.3 Hz, 1H), 7.65-7.58 (m, 3H), 7.41-7.33 (m, 2H), 7.24 (d, J=8.3 Hz, 1H), 7.07 (t, J=4.9 Hz, 1H), 6.92 (d, J=8.7 Hz, 1H), 4.33-4.20 (m, 2H), 4.10 (t, J=10.2 Hz, 1H), 2.14-1.97 (m, 2H).

Example-189/190: (S&R)-2'-(7-(N-(5-fluoropyrimidin-2-yl)sulfamoyl)chroman-4-yl)-5'-(trifluoromethyl)-[1,1'-biphenyl]-4-carboxylic acid

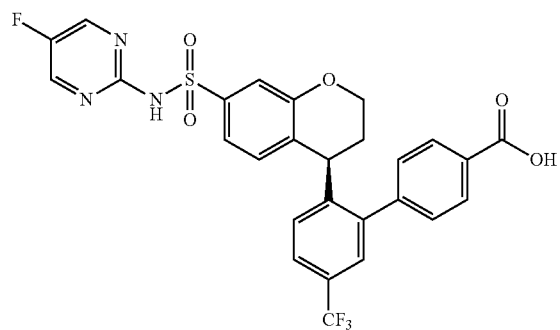

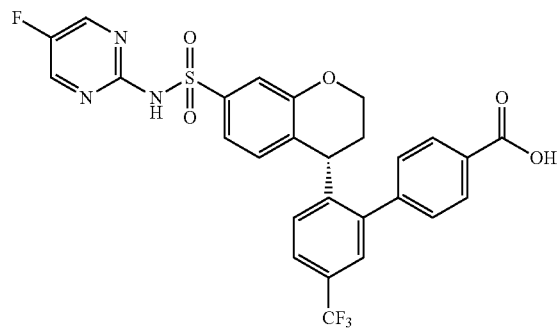

Step-1: (S&R)-tert-butyl 2'-(7-(N-(5-fluoropyrimidin-2-yl)sulfamoyl)chroman-4-yl)-5'-(trifluoromethyl)-[1,1'-biphenyl]-4-carboxylate

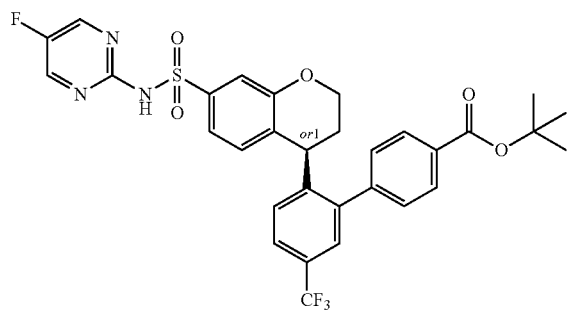

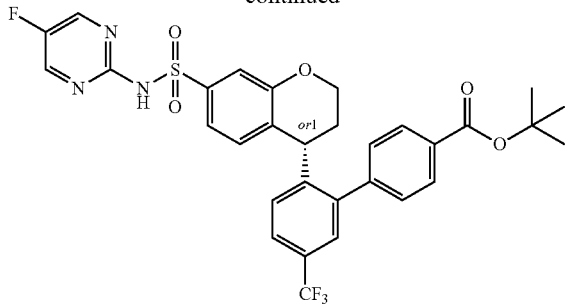

The title compounds were prepared by following the similar procedure as described in Example-1/2 using Intermediate-57 and 5-fluoropyrimidin-2-amine).

Further the enantiomers were separated using chiral preparative HPLC (Column: ChiralPak IE; Mobile phase: A=(Hexane+0.1% TFA), B=(MeOH:DCM=1:1), A:B=80:20, to afford isomer-1 and isomer-2. These isomers were obtained at retention time 8.02 min and retention time 9.26 min respectively.

LCMS (ESI): m/z 652.12 (M+Na)$^+$;

Step-2: (S&R)-2'-(7-(N-(5-fluoropyrimidin-2-yl)sulfamoyl)chroman-4-yl)-5'-(trifluoromethyl)-[1,1'-biphenyl]-4-carboxylic acid The title compound was prepared by following similar procedure as described in Example-187/188 (Step-2) using step-1 intermediates.

LCMS(ESI): m/z 573.82 (M+H)$^+$; $^1$H NMR (400 MHz, DMSO-d$_6$) δ 11.88 (s, 1H), 8.64 (s, 2H), 8.04 (d, J=7.9 Hz, 2H), 7.77-7.67 (m, 1H), 7.65-7.60 (m, 3H), 7.40-7.33 (m, 2H), 7.24 (d, J=8.3 Hz, 1H), 6.93 (d, J=8.5 Hz, 1H), 4.34-4.20 (m, 2H), 4.10 (t, J=10.2 Hz, 1H), 2.13-1.98 (m, 2H).

Example-191: (R/S)-2'-(7-(N-(pyridazin-3-yl)sulfamoyl)chroman-4-yl)-5'-(trifluoromethyl)-[1,1'-biphenyl]-4-carboxylic acid

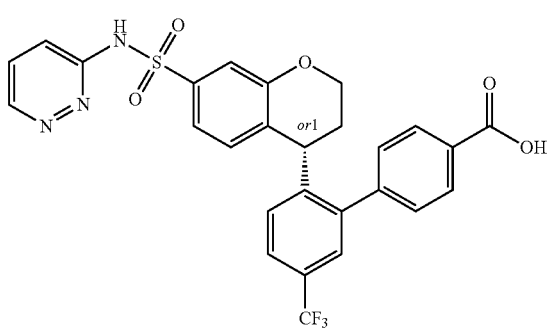 [SMILES: O=C(O)c1ccc(-c2cc(C(F)(F)F)ccc2[C@H]2CCOc3cc(S(=O)(=O)Nc4cccnn4)ccc32)cc1]

Step-1: tert-butyl (R/S)-2'-(7-(N-(pyridazin-3-yl)sulfamoyl)chroman-4-yl)-5'-(trifluoromethyl)-[1,1'-biphenyl]-4-carboxylate

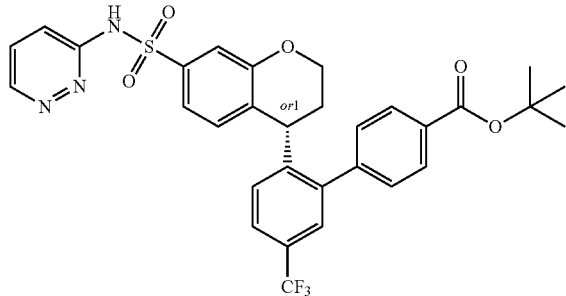 [SMILES: CC(C)(C)OC(=O)c1ccc(-c2cc(C(F)(F)F)ccc2[C@H]2CCOc3cc(S(=O)(=O)Nc4cccnn4)ccc32)cc1]

The title compound was prepared by following the similar procedure as described in Example-1/2 using Intermediate-57b and pyridazin-3-amine.
LCMS (ESI): m/z 612.14 (M+H)+;

Step-2: (R/S)-2'-(7-(N-(pyridazin-3-yl)sulfamoyl)chroman-4-yl)-5'-(trifluoromethyl)-[1,1'-biphenyl]-4-carboxylic acid The tert-butyl deprotection was carried out as described in Example-187/188 using TFA to obtain title compound. LCMS(ESI): m/z 555.82 (M+H)+; $^1$H NMR (400 MHz, DMSO-$d_6$) δ 8.34 (s, 1H), 8.05 (d, J=8.0 Hz, 2H), 7.87 (d, J=9.6 Hz, 1H), 7.76-7.66 (m, 2H), 7.65-7.57 (m, 3H), 7.28-7.20 (m, 3H), 6.87 (d, J=8.0 Hz, 1H), 4.27-4.02 (m, 3H), 2.15-1.98 (m, 2H).

Example-192: (R/S)-2'-(7-(N-(6-fluoropyridin-2-yl)sulfamoyl)chroman-4-yl)-5'-(trifluoromethyl)-[1,1'-biphenyl]-4-carboxylic acid

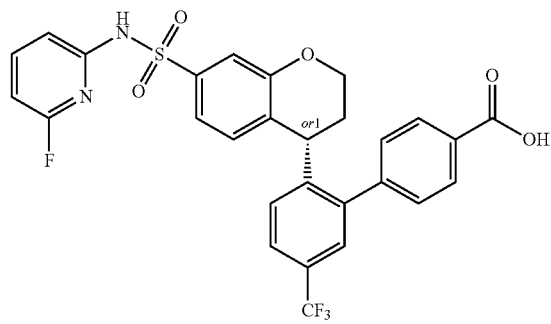 [SMILES: O=C(O)c1ccc(-c2cc(C(F)(F)F)ccc2[C@H]2CCOc3cc(S(=O)(=O)Nc4cccc(F)n4)ccc32)cc1]

Step-1: tert-Butyl (R/S)-2'-(7-(N-(6-fluoropyridin-2-yl)sulfamoyl)chroman-4-yl)-5'-(trifluoromethyl)-[1,1'-biphenyl]-4-carboxylate

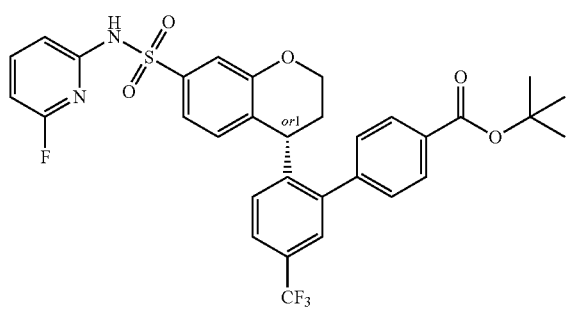 [SMILES: CC(C)(C)OC(=O)c1ccc(-c2cc(C(F)(F)F)ccc2[C@H]2CCOc3cc(S(=O)(=O)Nc4cccc(F)n4)ccc32)cc1]

The title compound was prepared by following the similar procedure as described in Example-1/2 using Intermediate-57b and 6-fluoropyridin-2-amine. LCMS (ESI): m/z 628.71 (M+H)+;

Step-2: (R/S)-2'-(7-(N-(6-fluoropyridin-2-yl)sulfamoyl)chroman-4-yl)-5'-(trifluoromethyl)-[1,1'-biphenyl]-4-carboxylic acid The tert-butyl deprotection was carried out as described in Example-187 using TFA to obtain title compound. $^1$H NMR (400 MHz, DMSO-$d_6$) δ 13.09 (s, 1H), 11.37 (s, 1H), 8.03 (d, J=7.9 Hz, 2H), 7.86 (dd, J=8.2 Hz, 1H), 7.70 (d, 1H), 7.65-7.57 (m, 3H), 7.37-7.28 (m, 2H), 7.22 (d, J=8.3 Hz, 1H), 7.00-6.92 (m, 2H), 6.75 (dd, J=7.9, 2.4 Hz, 1H), 4.35-4.18 (m, 2H), 4.10 (t, J=10.2 Hz, 1H), 2.18-1.97 (m, 2H).

Example-193/194: (S&R)-4-(2-(5-fluoropyridin-2-yl)-4-(trifluoromethyl)phenyl)-N-(pyrimidin-2-yl)chroman-7-sulfonamide

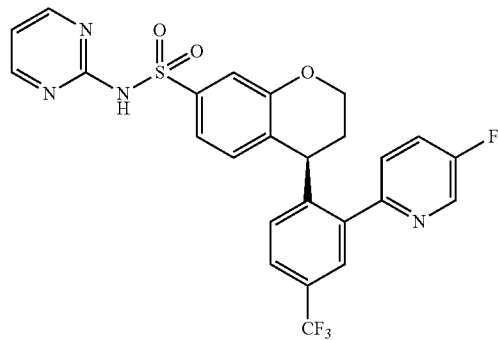

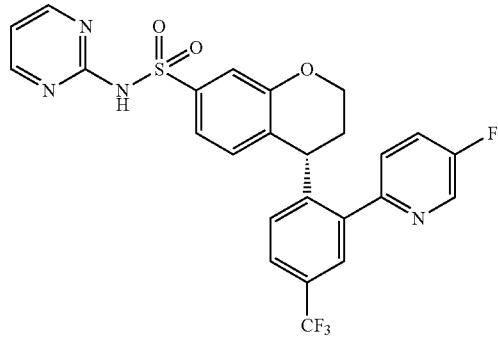

The title compounds were prepared by following the similar procedure as described in Example-1/2 using Intermediate-59 and pyrimidin-2-amine.
Further the enantiomers were separated using chiral preparative HPLC (Column: ChiralPak ID; Mobile phase: A=(Hexane+0.1% TFA), B=(IPA:MeOH=1:1), A:B=30:70, to afford isomer-1 and isomer-2. These isomers were obtained at retention time 6.49 min (Example-193) and retention time 7.80 min (Example-194).
LCMS(ESI): m/z 531.02 (M+H)+; $^1$H NMR (400 MHz, DMSO-d6) δ 11.79 (s, 1H), 8.69 (d, J=2.9 Hz, 1H), 8.53 (d, J=4.9 Hz, 2H), 7.89 (td, J=8.7, 3.0 Hz, 1H), 7.79 (dd, J=8.7, 4.5 Hz, 1H), 7.76-7.69 (m, 2H), 7.41-7.34 (m, 2H), 7.24 (d, J=8.1 Hz, 1H), 7.07 (t, J=4.9 Hz, 1H), 6.91 (d, J=8.2 Hz, 1H), 4.57 (t, J=7.2 Hz, 1H), 4.29-4.21 (m, 1H), 4.16-4.09 (m, 1H), 2.21-2.15 (m, 1H), 2.11-2.03 (m, 1H).

Example-195/196: (S&R)-4-(2-(5-fluoropyridin-2-yl)-4-(trifluoromethyl)phenyl)-N-(5-fluoropyrimidin-2-yl)chroman-7-sulfonamide

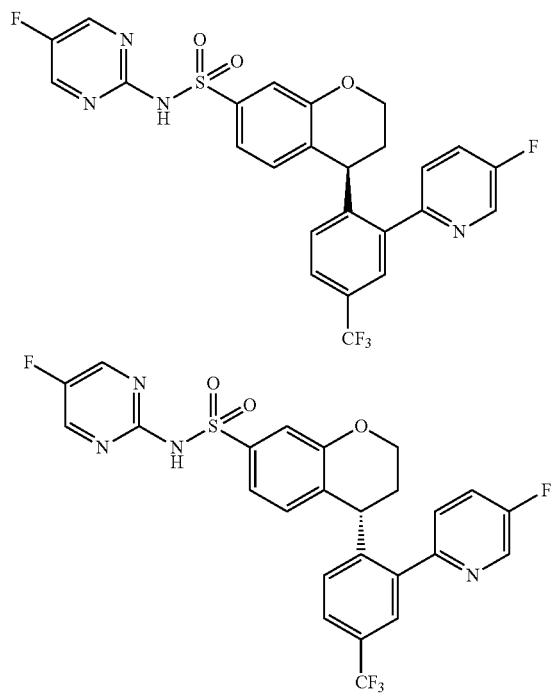

The title compounds were prepared by following the similar procedure as described in Example-1/2 using Intermediate-59 and 5-fluoropyrimidin-2-amine.

Further the enantiomers were separated using chiral preparative HPLC (Column: ChiralPak ID; Mobile phase: A=(Hexane+0.1% TFA), B=(IPA:MeOH=1:1), A:B=30:70, to afford isomer-1 and isomer-2. These isomers were obtained at retention time 4.97 min (Example-195) and retention time 5.72 min (Example-196).

LCMS(ESI): m/z 548.70 (M+H)$^+$; $^1$H NMR (400 MHz, DMSO-d6) δ 11.88 (s, 1H), 8.69 (d, J=2.8 Hz, 1H), 8.61 (s, 2H), 7.93-7.85 (m, 1H), 7.79 (dd, J=8.8, 4.4 Hz, 1H), 7.76-7.70 (m, 2H), 7.39-7.30 (m, 2H), 7.24 (d, J=8.3 Hz, 1H), 6.90 (d, J=8.3 Hz, 1H), 4.56 (t, J=7.6 Hz, 1H), 4.30-4.19 (m, 1H), 4.15-4.05 (m, 1H), 2.22-2.11 (m, 1H), 2.11-2.00 (m, 1H).

Example-197/198: (S&R)-4-(2-(5-fluoropyridin-2-yl)-4-(trifluoromethyl)phenyl)-N-(pyrimidin-4-yl)chroman-7-sulfonamide

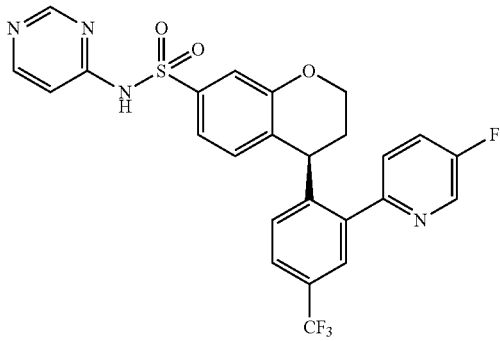

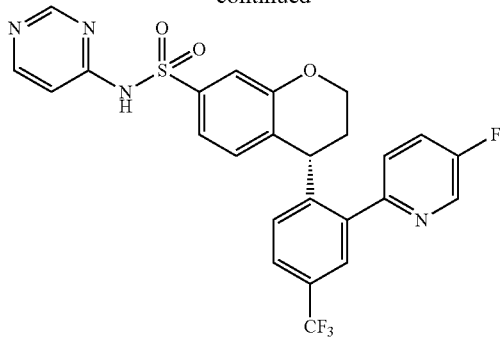

The title compounds were prepared by following the similar procedure as described in Example-1/2 using Intermediate-59 and pyrimidin-4-amine.

Further the enantiomers were separated using chiral preparative HPLC (Column: ChiralPak IE; Mobile phase: (MeOH+0.1% TFA) to afford isomer-1 and isomer-2. These isomers were obtained at retention time 6.96 min (Example-197) and retention time 7.61 min (Example-198).

LCMS(ESI): m/z=531.22 (M+H)$^+$; $^1$H NMR (400 MHz, DMSO-d6) δ 14.52 (s, 1H), 8.70 (d, J=2.9 Hz, 1H), 8.30 (s, 1H), 7.90 (td, J=8.9, 3.1 Hz, 2H), 7.79 (dd, J=8.7, 4.5 Hz, 1H), 7.76-7.67 (m, 3H), 7.28-7.19 (m, 3H), 6.87 (d, J=7.9 Hz, 1H), 4.59-4.50 (m, 1H), 4.27-4.19 (m, 1H), 4.14-4.07 (m, 1H), 2.25-2.12 (m, 1H), 2.10-1.99 (m, 1H).

Example-199/200: (S&R)-4-(2-(5-fluoropyridin-2-yl)-4-(trifluoromethyl)phenyl)-N-(pyridazin-3-yl)chroman-7-sulfonamide

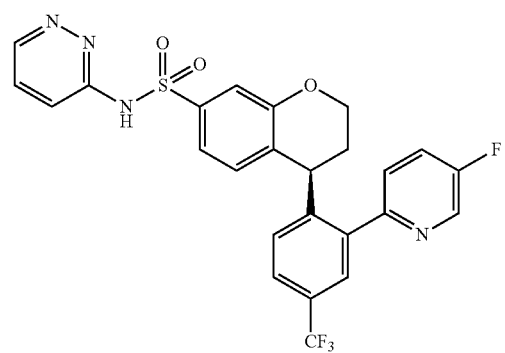

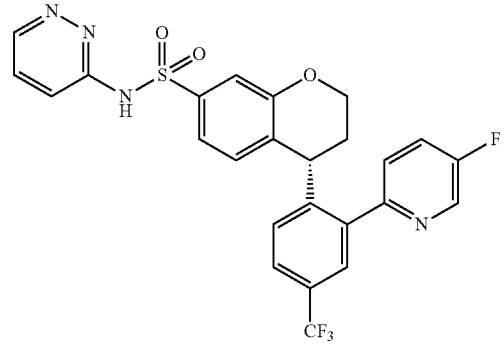

The title compounds were prepared by following the similar procedure as described in Example-1/2 using Intermediate-59 and pyridazin-3-amine.

Further the enantiomers were separated using chiral preparative HPLC (Column: ChiralPak ID; Mobile phase: A=(Hexane+0.1% TFA), B=(IPA:DCM=1:1), A:B=60:40, to afford isomer-1 and isomer-2. These isomers were obtained at retention time 7.20 min (Example-199) and retention time 8.24 min ((Example-200).

LCMS(ESI): m/z 531.09 (M+H)⁺; ¹H NMR (400 MHz, DMSO-d6) δ 8.69 (d, J=2.9 Hz, 1H), 8.65 (s, 1H), 8.37 (s, 1H), 7.89 (td, J=8.7, 3.0 Hz, 1H), 7.79 (dd, J=8.7, 4.5 Hz, 1H), 7.76-7.70 (m, 2H), 7.30 (s, 2H), 7.25 (d, J=8.3 Hz, 1H), 7.06 (s, 1H), 6.91 (d, J=7.6 Hz, 1H), 4.56 (t, 1H), 4.29-4.21 (m, 1H), 4.12 (t, J=9.6 Hz, 1H), 2.23-2.11 (m, 1H), 2.11-1.98 (m, 1H).

Example-201: (S)-4-(2-(6-methylpyridin-3-yl)-4-(trifluoromethyl)phenyl)-N-(pyrimidin-2-yl)chromane-7-sulfonamide

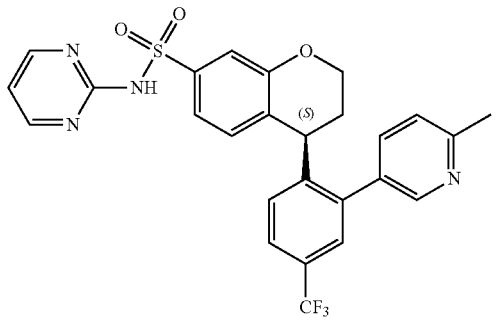

Step-1

(S/R)-perfluorophenyl-4-(2-(6-methylpyridin-3-yl)-4-(trifluoromethyl)phenyl)chromane-7-sulfonate A solution of 2-methyl-5-(4,4,5,5-tetramethyl-1,3,2-dioxaborolan-2-yl)pyridine (0.16 g, 0.716 mmol) and (R/S)-perfluorophenyl 4-(2-chloro-4-(trifluoromethyl)phenyl)chroman-7-sulfonate (Intermediate-27a) (0.20 g, 0.358 mmol) in 1,4-dioxane (5 ml) was purged with N₂ for 10 min and then added into potassium phosphate dibasic (0.19 g, 1.074 mmol), tri tert butylphosphanium tetrafluoroborate (0.010 g, 0.036 mmol) and PdCl₂(dppf)-CH₂Cl₂ adduct (0.044 g, 0.054 mmol). The reaction mixture was heated in sealed tube at 100° C. for 1 h. After completion of reaction, as indicated by TLC, reaction mixture was poured into water and extracted with ethyl acetate. The organic phase was dried over sodium sulphate and evaporated under vacuum. The crude was purified by column chromatography to obtain title compound (0.11 g, 49%).

¹H NMR (400 MHz, Chloroform-d) δ 8.59 (d, J=2.3 Hz, 1H), 7.70-7.61 (m, 2H), 7.58 (s, 1H), 7.49 (d, J=1.9 Hz, 1H), 7.40-7.32 (m, 2H), 7.13 (d, J=8.2 Hz, 1H), 6.95 (d, J=8.2 Hz, 1H), 4.42-4.31 (m, 2H), 4.19-4.10 (m, 1H), 2.70 (s, 3H), 2.30-1.85 (m, 2H).

Step-2: (S)-4-(2-(6-methylpyridin-3-yl)-4-(trifluoromethyl)phenyl)-N-(pyrimidin-2-yl)chromane-7-sulfonamide The title compound was prepared by following similar procedure as described in Example-1/2 using the product from step-1and pyrimidin-2-amine.

LCMS(ESI): m/z 527.03 (M+H)⁺; ¹H NMR (400 MHz, DMSO-d₆) δ 8.57 (d, J=2.3 Hz, 1H), 8.53 (d, J=4.9 Hz, 2H), 7.84 (d, J=7.9 Hz, 1H), 7.71 (d, J=8.3 Hz, 1H), 7.61 (d, J=2.0 Hz, 1H), 7.41-7.34 (m, 3H), 7.23 (d, J=8.2 Hz, 1H), 7.07 (t, J=4.9 Hz, 1H), 6.93 (d, J=8.4 Hz, 1H), 4.33-4.19 (m, 2H), 4.16-4.07 (m, 1H), 2.53 (s, 3H), 2.17-2.10 (m, 1H), 2.06-2.00 (m, 1H).

The absolute stereochemistry of Example-201 was assigned to be S using vibrational circular dichroism (VCD) spectra.

Example-202: (R)-4-(2-(6-methylpyridin-3-yl)-4-(trifluoromethyl)phenyl)-N-(pyrimidin-2-yl)chroman-7-sulfonamide

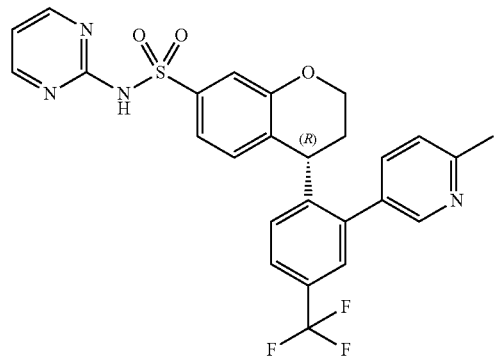

To a solution of pyrimidin-2-amine (0.021 g, 0.219 mmol) in dry THF (2 ml) was added LiHMDS (0.190 ml, 1M in THF, 0.190 mmol) at 0° C., and stirred for 10 min, then Intermediate-61 (0.09 g, 0.146 mmol) in THF (3 ml) was added. The resultant mixture was stirred for 1 h. After completion of reaction as indicated by TLC, reaction mixture was poured into water and extracted with ethyl acetate. The combined organic layer was washed with water, brine dried over Na₂SO₄ and concentrated under vacuum. The crude product was purified by column chromatography to obtain title compound as white solid (0.02 g, 26%). LCMS (ESI): m/z 527.11 (M+H)⁺; ¹H NMR (400 MHz, DMSO-d6) δ 11.80 (s, 1H), 8.56 (d, J=2.3 Hz, 1H), 8.53 (d, J=4.9 Hz, 2H), 7.82 (dd, J=7.9, 2.4 Hz, 1H), 7.70 (dd, J=8.3, 2.0 Hz, 1H), 7.62 (d, J=2.0 Hz, 1H), 7.41-7.32 (m, 3H), 7.23 (d, J=8.3 Hz, 1H), 7.07 (t, J=4.9 Hz, 1H), 6.93 (d, J=8.5 Hz, 1H), 4.31-4.19 (m, 2H), 4.16-4.07 (m, 1H), 2.53 (s, 3H), 2.19-2.08 (m, 1H), 2.07-2.00 (m, 1H).

The absolute stereochemistry of Example-202 was assigned to be R using vibrational circular dichroism (VCD) spectra. The compound having alpha configuration provided better in vitro activity against Na_v1.7.

Example-203: (R/S)—N-(5-fluoropyrimidin-2-yl)-4-(2-(6-methylpyridin-3-yl)-4-(trifluoromethyl)phenyl)chroman-7-sulfonamide

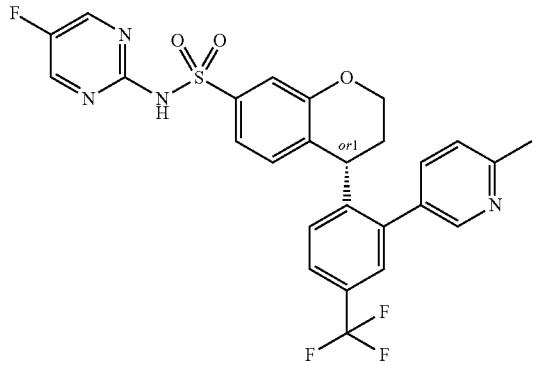

The title compound was prepared by following similar procedure as described for Example-202 using Intermediate-61 and 5-fluoropyrimidin-2-amine. LCMS(ESI): m/z 545.09 (M+H)+; 1H NMR (400 MHz, DMSO-d6) δ 11.88 (s, 1H), 8.65 (s, 2H), 8.58 (s, 1H), 7.87 (d, J=7.9 Hz, 1H), 7.71 (d, J=8.3 Hz, 1H), 7.63 (s, 1H), 7.41 (d, J=8.0 Hz, 1H), 7.38-7.32 (m, 2H), 7.24 (d, J=8.2 Hz, 1H), 6.94 (d, J=8.5 Hz, 1H), 4.30-4.19 (m, 2H), 4.12 (t, J=10.2 Hz, 1H), 2.55 (s, 3H), 2.19-2.08 (m, 1H), 2.08-1.95 (m, 1H).

Example-204: (R/S)-4-(2-(6-methylpyridin-3-yl)-4-(trifluoromethyl)phenyl)-N-(pyrimidin-4-yl)chroman-7-sulfonamide

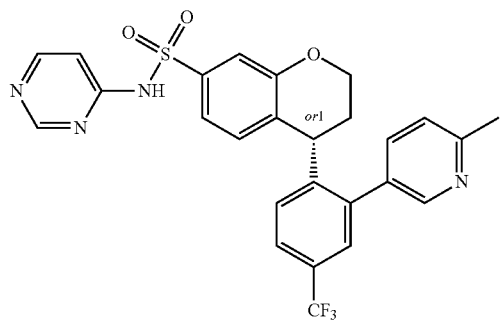

The title compound was prepared by following similar procedure as described for Example-202 using Intermediate-61 and pyrimidin-4-amine. LCMS(ESI): m/z 527.04 (M+H)+; 1H NMR (400 MHz, DMSO-d6) δ 8.65 (s, 1H), 8.56 (s, 1H), 8.40 (s, 1H), 7.83 (d, J=8.0 Hz, 1H), 7.71 (d, J=8.5 Hz, 1H), 7.62 (s, 1H), 7.38 (d, J=8.0 Hz, 1H), 7.30 (s, 2H), 7.24 (d, J=8.5 Hz, 1H), 7.10 (s, 1H), 6.97-6.86 (m, 1H), 4.33-4.18 (m, 2H), 4.18-4.06 (m, 1H), 2.54 (s, 3H), 2.22-2.08 (m, 1H), 2.08-1.95 (m, 1H).

Example-205: (R/S)-4-(2-(6-methylpyridin-3-yl)-4-(trifluoromethyl)phenyl)-N-(pyridazin-3-yl)chroman-7-sulfonamide

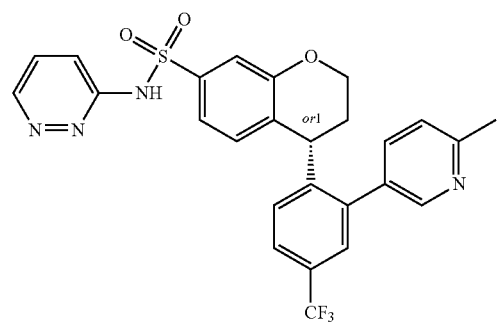

The title compound was prepared by following similar procedure as described for Example-202 using Intermediate-61 and pyridazin-3-amine. LCMS(ESI): m/z 527.06 (M+H)+; 1H NMR (400 MHz, DMSO-d6) δ 8.65 (s, 1H), 8.56 (s, 1H), 8.40 (s, 1H), 7.83 (d, J=8.0 Hz, 1H), 7.71 (d, J=8.5 Hz, 1H), 7.62 (s, 1H), 7.38 (d, J=8.0 Hz, 1H), 7.30 (s, 2H), 7.24 (d, J=8.5 Hz, 1H), 7.10 (s, 1H), 6.97-6.86 (m, 1H), 4.33-4.18 (m, 2H), 4.18-4.06 (m, 1H), 2.54 (s, 3H), 2.22-2.08 (m, 1H), 2.08-1.95 (m, 1H).

Example-206: (R/S)—N-(6-fluoropyridin-2-yl)-4-(2-(6-methylpyridin-3-yl)-4-(trifluoromethyl)phenyl)chroman-7-sulfonamide

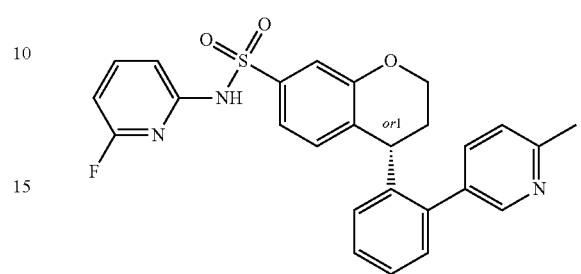

Step-1: Perfluorophenyl 4-(2-(6-methylpyridin-3-yl)-4-(trifluoromethyl)phenyl)chroman-7-sulfonate

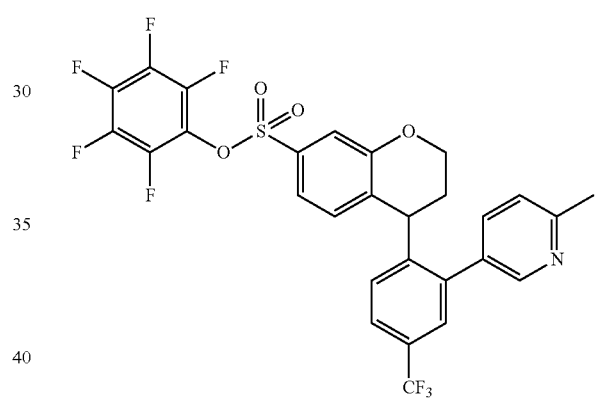

A solution of 2-methyl-5-(4,4,5,5-tetramethyl-1,3,2-dioxaborolan-2-yl)pyridine (3 g, 13.69 mmol) and Intermediate-27 (4.5 g, 8.05 mmol) in 1,4-dioxane (100 ml) was purged with nitrogen for 10 min. After which potassium phosphate dibasic (4.21 g, 24.16 mmol), tri-tert-butylphosphanium tetrafluoroborate (0.23 g, 0.805 mmol) and PdCl2 (dppf)-CH2Cl2 adduct (0.99 g, 1.208 mmol) was added then heated in sealed tube at 114° C. for 2 h. After completion of reaction as indicated by TLC, reaction mixture was poured into water and extracted with ethyl acetate. The combined organic layer was washed with water, brine, dried over Na2SO4 and concentrated under vacuum. The crude product was purified by column chromatography to obtain title compound (1.9 g, 38%). 1H NMR (400 MHz, Chloroform-d) δ 8.60 (s, 1H), 7.72 (d, J=7.9 Hz, 1H), 7.64 (d, J=8.2 Hz, 1H), 7.57 (s, 1H), 7.51-7.47 (m, 1H), 7.43-7.34 (m, 2H), 7.13 (d, J=8.2 Hz, 1H), 6.95 (d, J=8.2 Hz, 1H), 4.40-4.31 (m, 2H), 4.20-4.12 (m, 1H), 2.73 (s, 3H), 2.30-1.85 (m, 2H).

Step-2: (R/S)—N-(6-fluoropyridin-2-yl)-4-(2-(6-methylpyridin-3-yl)-4-(trifluoromethyl)phenyl)chroman-7-sulfonamide The title compound was prepared by following similar procedure as described for Example-202 using Perfluorophenyl 4-(2-(6-methylpyridin-3-yl)-4-(trifluoromethyl)phenyl)chroman-7-sulfonate (Step-1) and 6-fluoropyridin-2-amine.

Further the enantiomers were separated using chiral preparative HPLC (Column: ChiralPak IE; Mobile phase: A=(Hexane+0.1% TFA), B=(IPA:MeOH=1:1), A:B=60:40, to afford isomer-1 and isomer-2. These isomers were obtained at retention time 8.27 min and retention time 9.50 min (Example-206).

LCMS(ESI): m/z 544.03 (M+H)$^+$; $^1$H NMR (400 MHz, DMSO-d6) δ 11.37 (s, 1H), 8.55 (d, J=2.3 Hz, 1H), 7.90-7.78 (m, 2H), 7.70 (dd, J=8.4, 1.9 Hz, 1H), 7.62 (s, 1H), 7.36 (d, J=8.0 Hz, 1H), 7.34-7.29 (m, 2H), 7.22 (d, J=8.2 Hz, 1H), 6.95 (d, J=8.0 Hz, 2H), 6.73 (d, J=8.0 Hz, 1H), 4.31-4.19 (m, 2H), 4.12 (t, J=10.2 Hz, 1H), 2.53 (s, 3H), 2.16-2.08 (m, 1H), 2.05-1.95 (m, 1H).

Example-207: (R/S)-4-(2-(2-oxooxazolidin-3-yl)-4-(trifluoromethyl)phenyl)-N-(pyrimidin-2-yl)chroman-7-sulfonamide

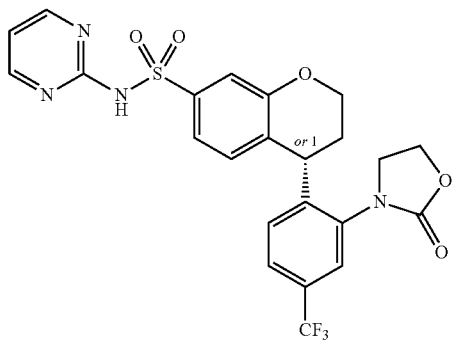 [SMILES: O=C1OCCN1c1cc(C(F)(F)F)ccc1[C@H]1CCOc2cc(S(=O)(=O)Nc3ncccn3)ccc21]

The title compound was prepared by following the similar procedure as described in Example-1/2 using Intermediate-63b and pyrimidin-2-amine. LCMS(ESI): m/z 520.94 (M+H)$^+$; $^1$H NMR (400 MHz, DMSO-d6) δ 11.74 (s, 1H), 8.54 (d, J=4.9 Hz, 2H), 7.99 (s, 1H), 7.66 (d, J=8.2 Hz, 1H), 7.41 (s, 1H), 7.36 (dd, J=8.1, 1.9 Hz, 1H), 7.22 (d, J=8.2 Hz, 1H), 7.08 (t, J=4.9 Hz, 1H), 6.87 (d, J=8.1 Hz, 1H), 4.61 (t, J=8.7, 6.1 Hz, 1H), 4.54-4.41 (m, 2H), 4.33-4.23 (m, 2H), 4.11-3.90 (m, 2H), 2.31-2.19 (m, 1H), 2.10-1.96 (m, 1H).

Example-208: (R/S)—N-(5-fluoropyrimidin-2-yl)-4-(2-(2-oxooxazolidin-3-yl)-4-(trifluoromethyl)phenyl)chroman-7-sulfonamide

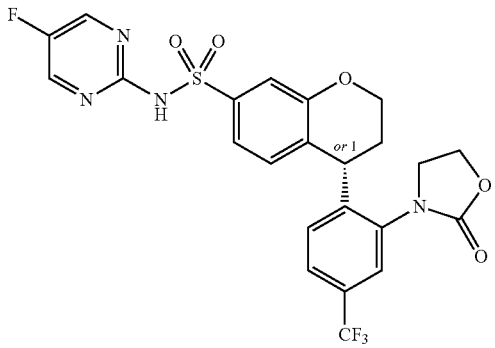 [SMILES: O=C1OCCN1c1cc(C(F)(F)F)ccc1[C@H]1CCOc2cc(S(=O)(=O)Nc3ncc(F)cn3)ccc21]

The title compound was prepared by following the similar procedure as described in Example-1/2 using Intermediate-63b and 5-fluoropyrimidin-2-amine. LCMS(ESI): m/z 539.02 (M+H)$^+$; $^1$H NMR (400 MHz, DMSO-d6) δ 11.88 (s, 1H), 8.66 (s, 2H), 7.99 (s, 1H), 7.66 (d, J=8.2 Hz, 1H), 7.44-7.30 (m, 2H), 7.21 (d, J=8.2 Hz, 1H), 6.88 (d, J=8.2 Hz, 1H), 4.61 (t, J=7.6 Hz, 1H), 4.56-4.41 (m, 2H), 4.34-4.22 (m, 2H), 4.12-4.01 (m, 1H), 4.01-3.90 (m, 1H), 2.30-2.20 (m, 1H), 2.08-1.97 (m, 1H).

Example-209: (R/S)-4-(2-(2-oxooxazolidin-3-yl)-4-(trifluoromethyl)phenyl)-N-(pyridazin-3-yl)chroman-7-sulfonamide

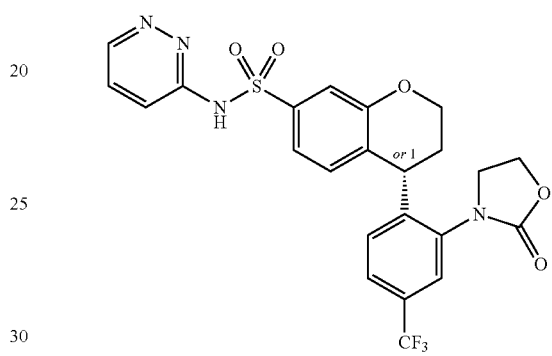

The title compound was prepared by following the similar procedure as described in Example-1/2 using Intermediate-63b and pyridazin-3-amine.

LCMS(ESI): m/z 520.94 (M+H)$^+$; $^1$H NMR (400 MHz, DMSO-d6) δ 14.52 (s, 1H), 8.33 (s, 1H), 8.02-7.96 (m, 1H), 7.89 (s, 1H), 7.75-7.63 (m, 2H), 7.28-7.18 (m, 3H), 6.83 (d, J=8.0 Hz, 1H), 4.59 (t, J=7.3 Hz, 1H), 4.54-4.46 (m, 2H), 4.30-4.21 (m, 2H), 4.12-3.94 (m, 2H), 2.32-2.20 (m, 1H), 2.08-2.00 (m, 1H).

Example-210: (R/S)—N-(6-fluoropyridin-2-yl)-4-(2-(2-oxooxazolidin-3-yl)-4-(trifluoromethyl)phenyl)chromane-7-sulfonamide

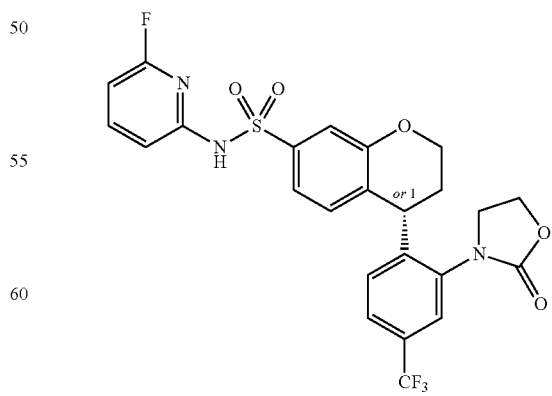

The title compound was prepared by following the similar procedure as described in Example-1/2 using Intermediate- 63b and 6-fluoropyridin-2-amine. LCMS(ESI): m/z 537.95 (M+H)⁺; ¹H NMR (400 MHz, DMSO-d₆) δ 11.40 (s, 1H), 7.99 (s, 1H), 7.93-7.81 (m, 1H), 7.66 (d, J=8.3 Hz, 1H), 7.39-7.28 (m, 2H), 7.21 (d, J=8.3 Hz, 1H), 6.96 (d, J=8.0 Hz, 1H), 6.88 (d, J=8.2 Hz, 1H), 6.75 (d, J=8.0 Hz, 1H), 4.61 (t, J=7.5 Hz, 1H), 4.54-4.40 (m, 2H), 4.35-4.24 (m, 2H), 4.12-3.88 (m, 2H), 2.30-2.19 (m, 1H), 2.11-1.95 (m, 1H).

Example-211: (R/S)-4-(2-(3,3-difluoropropyl)-4-(trifluoromethyl)phenyl)-N-(pyrimidin-2-yl)chroman-7-sulfonamide

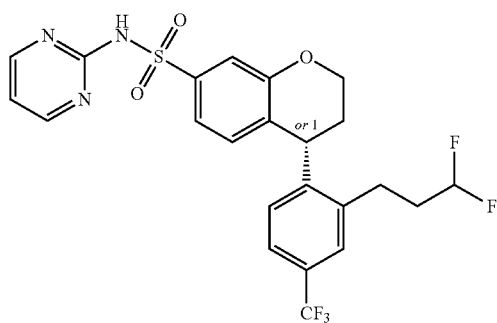 [SMILES: O=S(=O)(Nc1ncccn1)c1ccc2c(c1)OCC[C@@H]2c1ccc(C(F)(F)F)cc1CCC(F)F]

The title compound was prepared by following the similar procedure as described in Example-1/2 using Intermediate-65b and pyrimidin-2-amine. LCMS(ESI): m/z 513.94 (M+H)⁺; ¹H NMR (400 MHz, DMSO-d₆) δ 11.75 (s, 1H), 8.54 (d, J=4.9 Hz, 2H), 7.68 (d, J=2.0 Hz, 1H), 7.57-7.31 (m, 3H), 7.14-6.93 (m, 2H), 6.83 (d, J=8.1 Hz, 1H), 6.23 (t, 1H), 4.59 (t, J=7.0 Hz, 1H), 4.37-4.16 (m, 2H), 2.95-2.85 (m, 2H), 2.32-1.94 (m, 4H).

Example-212: (R/S)-4-(2-(3,3-difluoropropyl)-4-(trifluoromethyl)phenyl)-N-(5-fluoropyrimidin-2-yl)chroman-7-sulfonamide

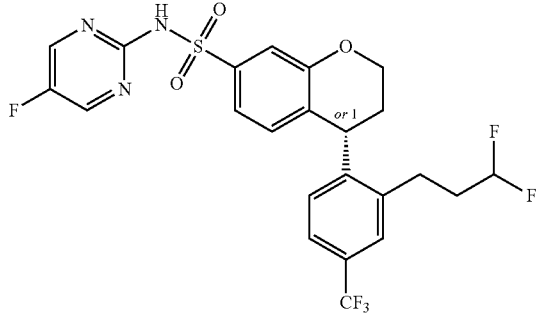 [SMILES: O=S(=O)(Nc1ncc(F)cn1)c1ccc2c(c1)OCC[C@@H]2c1ccc(C(F)(F)F)cc1CCC(F)F]

The title compound was prepared by following the similar procedure as described in Example-1/2 using Intermediate-65b and 5-fluoropyrimidin-2-amine. LCMS(ESI): m/z 532.05 (M+H)⁺; ¹H NMR (400 MHz, DMSO-d₆) δ 11.88 (s, 1H), 8.66 (s, 2H), 7.68 (d, J=2.0 Hz, 1H), 7.50 (dd, J=8.2, 2.1 Hz, 1H), 7.43-7.32 (m, 2H), 7.03 (d, J=8.2 Hz, 1H), 6.84 (d, J=8.1 Hz, 1H), 6.09 (t, J=56.6 Hz, 1H), 4.60 (t, J=7.0 Hz, 1H), 4.35-4.21 (m, 2H), 2.99-2.86 (m, 2H), 2.30-1.94 (m, 4H).

Example-213: (R/S)-4-(2-(3,3-difluoropropyl)-4-(trifluoromethyl)phenyl)-N-(pyrimidin-4-yl)chroman-7-sulfonamide

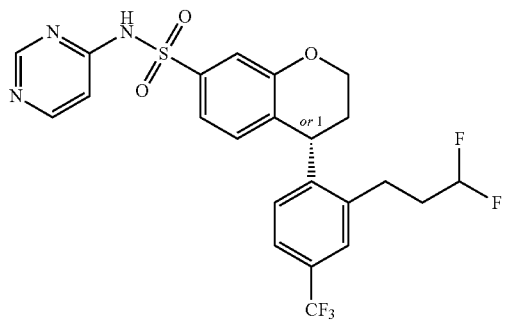 [SMILES: O=S(=O)(Nc1ccncn1)c1ccc2c(c1)OCC[C@@H]2c1ccc(C(F)(F)F)cc1CCC(F)F]

The title compound was prepared by following the similar procedure as described in Example-1/2 using Intermediate-65b and pyrimidin-4-amine. LCMS(ESI): m/z 513.94 (M+H)⁺; ¹H NMR (400 MHz, DMSO-d₆) δ 8.66 (s, 1H), 8.38 (s, 1H), 7.68 (d, J=2.0 Hz, 1H), 7.50 (dd, J=8.2, 2.0 Hz, 1H), 7.40-7.27 (m, 2H), 7.17-7.00 (m, 2H), 6.83 (d, J=8.1 Hz, 1H), 6.16 (t, 1H), 4.59 (t, 1H), 4.34-4.21 (m, 2H), 3.05-2.83 (m, 2H), 2.30-1.93 (m, 4H).

Example-214: (R/S)-4-(2-(3,3-difluoropropyl)-4-(trifluoromethyl)phenyl)-N-(pyridazin-3-yl)chroman-7-sulfonamide

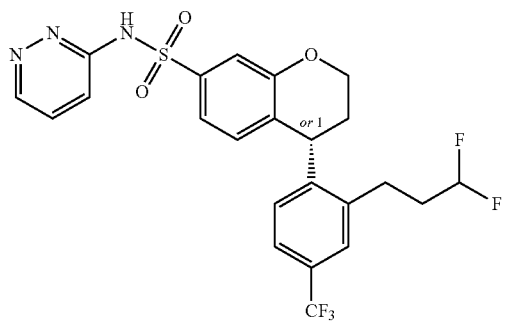 [SMILES: O=S(=O)(Nc1cccnn1)c1ccc2c(c1)OCC[C@@H]2c1ccc(C(F)(F)F)cc1CCC(F)F]

The title compound was prepared by following the similar procedure as described in Example-1/2 using Intermediate-65b and pyridazin-3-amine. LCMS(ESI): m/z 513.94 (M+H)⁺; ¹H NMR (400 MHz, DMSO-d₆) δ 14.52 (s, 1H), 8.30 (s, 1H), 7.92 (d, J=9.3 Hz, 1H), 7.81-7.62 (m, 2H), 7.60-7.47 (m, 1H), 7.38-7.13 (m, 2H), 7.04 (d, J=8.2 Hz, 1H), 6.79 (d, J=8.0 Hz, 1H), 6.17 (t, 1H), 4.57 (t, 1H), 4.44-4.12 (m, 2H), 3.10-2.71 (m, 2H), 2.35-1.94 (m, 4H).

Example-215: (R/S)-4-(2-(3,3-difluoropropyl)-4-(trifluoromethyl)phenyl)-N-(6-fluoropyridin-2-yl)chromane-7-sulfonamide

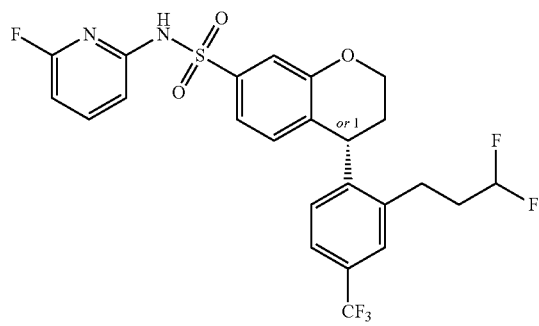 [SMILES: O=S(=O)(Nc1cccc(F)n1)c1ccc2c(c1)OCC[C@@H]2c1ccc(C(F)(F)F)cc1CCC(F)F]

The title compound was prepared by following the similar procedure as described in Example-1/2 using Intermediate-65b and 6-fluoropyridin-2-amine. LCMS(ESI): m/z 531.02 (M+H)⁺; ¹H NMR (400 MHz, DMSO-d₆) δ 11.37 (s, 1H), 7.87 (q, J=8.2 Hz, 1H), 7.68 (d, J=2.0 Hz, 1H), 7.49 (d, J=8.2 Hz, 1H), 7.44-7.27 (m, 2H), 7.07-6.92 (m, 2H), 6.92-6.66 (m, 2H), 6.16 (t, J=59.2, 54.7 Hz, 1H), 4.59 (t, J=7.1 Hz, 1H), 4.35-4.18 (m, 2H), 3.00-2.80 (m, 2H), 2.27-2.01 (m, 4H).

Example-216/217: (R&S)-4-(2-(oxetan-3-yloxy)-4-(trifluoromethyl)phenyl)-N-(pyrimidin-2-yl)chroman-7-sulfonamide

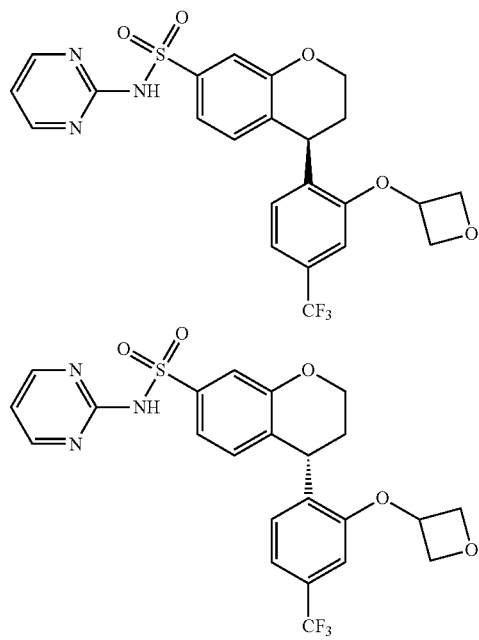

The title compounds were prepared by following the similar procedure as described in Example-1/2 using Intermediate-67 and pyrimidin-2-amine.

Further the enantiomers were separated using chiral preparative HPLC (Column: ChiralPak ID; Mobile phase: (IPA: MeOH=1:1) to afford isomer-1 and isomer-2. These isomers were obtained at retention time 5.17 min (Example-216) and retention time 6.74 min (Example-217).

LCMS(ESI): m/z 508.06 (M+H)⁺; ¹H NMR (400 MHz, DMSO-d₆) δ 8.53 (d, J=4.9 Hz, 2H), 7.46-7.34 (m, 2H), 7.30 (d, J=8.0 Hz, 1H), 7.16-7.05 (m, 2H), 6.98-6.89 (m, 2H), 5.42 (t, 1H), 4.88 (t, J=6.6 Hz, 1H), 4.77 (t, J=6.6 Hz, 1H), 4.64 (t, J=6.7 Hz, 1H), 4.45 (t, J=6.1 Hz, 1H), 4.31 (t, J=6.0 Hz, 1H), 4.21 (dd, J=20.9, 6.5 Hz, 2H), 2.25-2.14 (m, 2H).

Example-218: (S/R)—N-(5-fluoropyrimidin-2-yl)-4-(2-(oxetan-3-yloxy)-4-(trifluoromethyl)phenyl)chroman-7-sulfonamide

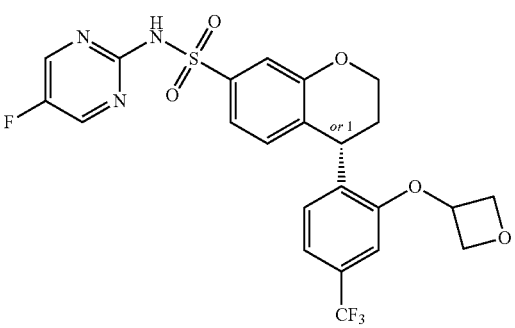 [SMILES: O=S(=O)(Nc1ncc(F)cn1)c1ccc2c(c1)OCC[C@@H]2c1ccc(C(F)(F)F)cc1OC1COC1]

The title compound was prepared by following the similar procedure as described in Example-1/2 using Intermediate-67b and 5-fluoropyrimidin-2-amine. LCMS(ESI): m/z 526.00 (M+H)⁺; ¹H NMR (400 MHz, DMSO-d₆) δ 11.86 (s, 1H), 8.65 (s, 2H), 7.43-7.33 (m, 2H), 7.30 (d, J=8.0 Hz, 1H), 7.14 (d, J=7.9 Hz, 1H), 6.98-6.89 (m, 2H), 5.42 (quintet, J=5.4 Hz, 1H), 4.86 (t, J=6.7 Hz, 1H), 4.76 (t, J=6.6 Hz, 1H), 4.64 (t, J=6.8 Hz, 1H), 4.41 (t, 1H), 4.31-4.16 (m, 3H), 2.23-2.13 (m, 2H).

Example-219: (S/R)—N-(6-fluoropyridin-2-yl)-4-(2-(oxetan-3-yloxy)-4-(trifluoromethyl)phenyl)chromane-7-sulfonamide

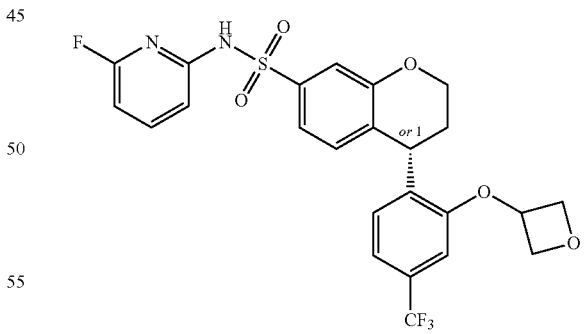

The title compound was prepared by following the similar procedure as described in Example-1/2 using Intermediate-67b and 6-fluoropyridin-2-amine. LCMS(ESI): m/z 524.94 (M+H)⁺; ¹H NMR (400 MHz, DMSO-d₆) δ 11.36 (s, 1H), 7.87 (dd, J=8.2 Hz, 1H), 7.40-7.23 (m, 3H), 7.11 (d, J=8.0 Hz, 1H), 7.01-6.94 (m, 2H), 6.91 (s, 1H), 6.76 (dd, J=8.0, 2.4 Hz, 1H), 5.41 (quint, J=5.4 Hz, 1H), 4.87 (t, J=6.6 Hz, 1H), 4.76 (t, J=6.7 Hz, 1H), 4.64 (t, J=6.8 Hz, 1H), 4.44 (dd, J=7.2, 4.9 Hz, 1H), 4.36-4.12 (m, 3H), 2.24-2.13 (m, 2H).

Example-220/221: (S&R)-4-(2-(3-fluoropropoxy)-4-(trifluoromethyl)phenyl)-N-(pyrimidin-2-yl)chroman-7-sulfonamide

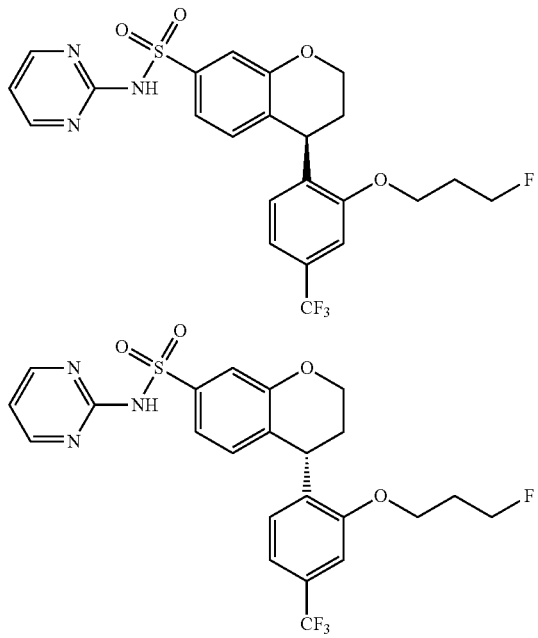

The title compounds were prepared by following the similar procedure as described in Example-1/2 using Intermediate-69 and pyrimidin-2-amine.

Further the enantiomers were separated using chiral preparative HPLC (Column: ChiralPak IA; Mobile phase: A=(Hexane+0.1% TFA), B=(IPA:MeOH=1:1), A:B=30:70, to afford isomer-1 and isomer-2. These isomers were obtained at retention time 5.72 min (Example-220) and retention time 7.90 min (Example-221).

LCMS(ESI): m/z 512.03 (M+H)$^+$; $^1$H NMR (400 MHz, DMSO-d$_6$) δ 8.54 (d, J=4.9 Hz, 2H), 7.43-7.34 (m, 2H), 7.32-7.24 (m, 2H), 7.14-7.06 (m, 2H), 6.91 (d, J=8.1 Hz, 1H), 4.55 (t, J=7.0 Hz, 1H), 4.50-4.30 (m, 2H), 4.24-4.10 (m, 4H), 2.14 (d, J=5.6 Hz, 2H), 1.93-1.76 (m, 2H).

Example-222: (R/S)-4-(2-(5-fluoro-6-methylpyridin-2-yl)-4-(trifluoromethyl)phenyl)-N-(pyrimidin-2-yl)chroman-7-sulfonamide

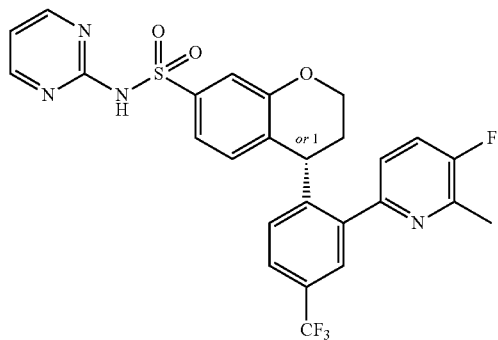 [SMILES: Cc1nc(-c2cc(C(F)(F)F)ccc2[C@H]2CCOc3cc(S(=O)(=O)Nc4ncccn4)ccc32)ccc1F]

The title compound was prepared by following the similar procedure as described in Example-1/2 using Intermediate-71b and pyrimidin-2-amine. LCMS(ESI): m/z 543.94 (M+H)$^+$; $^1$H NMR (400 MHz, DMSO-d$_6$) δ 11.74 (s, 1H), 8.53 (d, J=4.9 Hz, 2H), 7.80-7.68 (m, 3H), 7.59 (dd, J=8.5, 3.6 Hz, 1H), 7.40-7.32 (m, 2H), 7.24 (d, J=8.5 Hz, 1H), 7.08 (t, J=4.9 Hz, 1H), 6.90 (d, J=8.0 Hz, 1H), 4.62-4.54 (m, 1H), 4.31-4.23 (m, 1H), 4.20-4.10 (m, 1H), 2.46 (d, J=2.9 Hz, 3H), 2.28-2.18 (m, 1H), 2.16-2.04 (m, 1H).

Example-223: (R/S)-4-(2-(5-fluoro-6-methylpyridin-2-yl)-4-(trifluoromethyl)phenyl)-N-(5-fluoropyrimidin-2-yl)chroman-7-sulfonamide

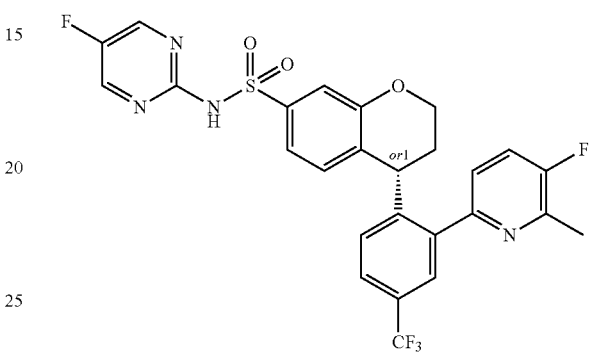

The title compound was prepared by following the similar procedure as described in Example-1/2 using Intermediate-71b and 5-fluoropyrimidin-2-amine. LCMS(ESI): m/z 563.07 (M+H)$^+$; $^1$H NMR (400 MHz, DMSO-d6) δ 11.87 (s, 1H), 8.65 (s, 2H), 7.83-7.68 (m, 3H), 7.59 (dd, J=8.5, 3.6 Hz, 1H), 7.40-7.31 (m, 2H), 7.24 (d, J=8.7 Hz, 1H), 6.90 (d, J=8.0 Hz, 1H), 4.58 (dd, J=8.6, 6.2 Hz, 1H), 4.31-4.24 (m, 1H), 4.21-4.11 (m, 1H), 2.46 (d, J=2.9 Hz, 3H), 2.29-2.18 (m, 1H), 2.18-2.07 (m, 1H).

Example-224: (R/S)-4-(2-(5-fluoro-6-methylpyridin-2-yl)-4-(trifluoromethyl)phenyl)-N-(pyridazin-3-yl)chroman-7-sulfonamide

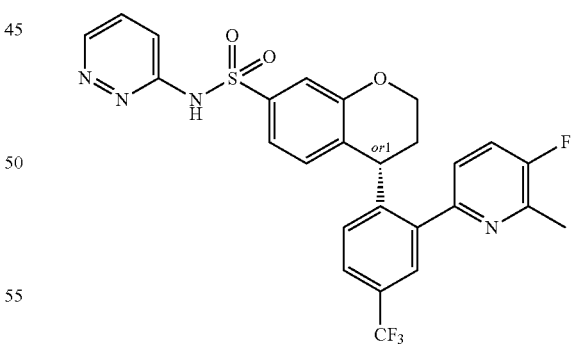

The title compound was prepared by following the similar procedure as described in Example-1/2 using Intermediate-71b and pyridazin-3-amine. LCMS(ESI): m/z 543.94 (M+H)$^+$; $^1$H NMR (400 MHz, DMSO-d6) δ 14.51 (s, 1H), 8.30 (s, 1H), 7.91 (s, 1H), 7.81-7.66 (m, 4H), 7.60 (dd, J=8.4, 3.6 Hz, 1H), 7.23 (dd, J=8.4, 5.3 Hz, 3H), 6.86 (d, J=8.5 Hz, 1H), 4.60-4.52 (m, 1H), 4.31-4.20 (m, 1H), 4.18-4.09 (m, 1H), 2.47 (d, J=2.9 Hz, 3H), 2.28-2.19 (m, 1H), 2.15-2.03 (m, 1H).

Example-225: (R/S)-4-(2-(5-fluoro-6-methylpyridin-2-yl)-4-(trifluoromethyl)phenyl)-N-(6-fluoropyridin-2-yl)chroman-7-sulfonamide

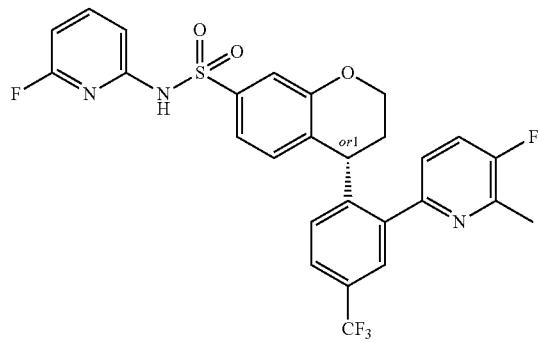 [SMILES: Cc1nc(-c2cc(C(F)(F)F)ccc2[C@H]2CCOc3cc(S(=O)(=O)Nc4cccc(F)n4)ccc32)ccc1F]

The title compound was prepared by following the similar procedure as described in Example-1/2 using Intermediate-71b and 6-fluoropyridin-2-amine. LCMS(ESI): m/z 561.95 (M+H)$^+$; $^1$H NMR (400 MHz, DMSO-d6) δ 11.37 (s, 1H), 7.92-7.83 (m, 1H), 7.81-7.64 (m, 3H), 7.58 (dd, J=8.6, 3.6 Hz, 1H), 7.38-7.27 (m, 2H), 7.24 (d, J=8.3 Hz, 1H), 6.96 (dd, J=7.9, 2.0 Hz, 1H), 6.91 (d, J=8.1 Hz, 1H), 6.76 (dd, J=8.2, 2.4 Hz, 1H), 4.57 (t, J=7.5 Hz, 1H), 4.32-4.22 (m, 1H), 4.15 (t, J=10.0, Hz, 1H), 2.45 (d, J=2.9 Hz, 3H), 2.27-2.18 (m, 1H), 2.17-2.05 (m, 1H).

Example-226/227: (S&R)-4-(2-methoxy-4-(trifluoromethyl)phenyl)-N-(pyrimidin-2-yl)chroman-7-sulfonamide

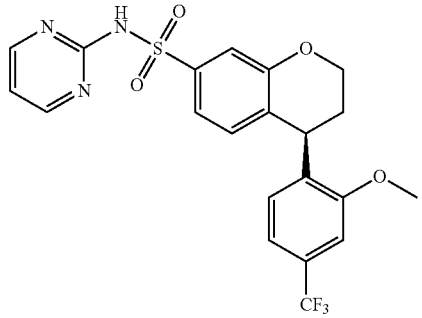

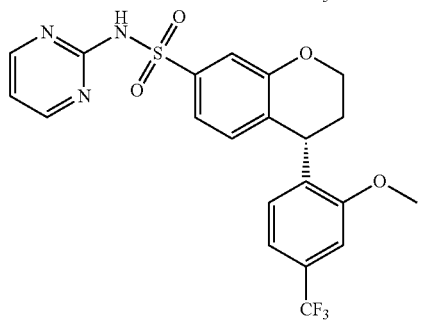

The title compounds were prepared by following the similar procedure as described in Example-1/2 using Intermediate-72 and pyrimidin-2-amine.

Further the enantiomers were separated using chiral preparative HPLC (Column: ChiralPak ID; Mobile phase: A=(Hexane+0.1% TFA), B=(IPA:DCM=1:1), A:B=70:30, to afford isomer-1 and isomer-2. These isomers were obtained at retention time 6.74 min (Example-226) and retention time 7.36 min (Example-227).

LCMS(ESI): m/z 465.99 (M+H)$^+$; $^1$H NMR (400 MHz, DMSO-d$_6$) δ 11.73 (s, 1H), 8.54 (d, J=4.9 Hz, 2H), 7.43-7.35 (m, 2H), 7.32 (d, J=1.7 Hz, 1H), 7.24 (d, J=8.0 Hz, 1H), 7.12-7.06 (m, 1H), 6.98-6.90 (m, 2H), 4.59 (t, J=6.3 Hz, 1H), 4.30-4.19 (m, 1H), 4.15-4.04 (m, 1H), 3.87 (s, 3H), 2.25-1.99 (m, 2H).

Example-228/229: (S&R)-N-(6-fluoropyridin-2-yl)-4-(2-methoxy-4-(trifluoromethyl)phenyl)chroman-7-sulfonamide

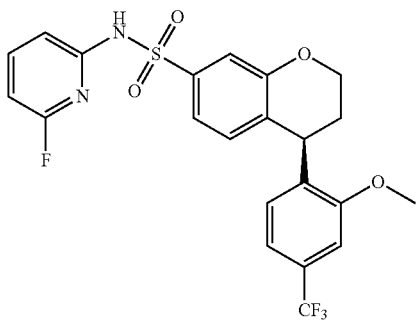

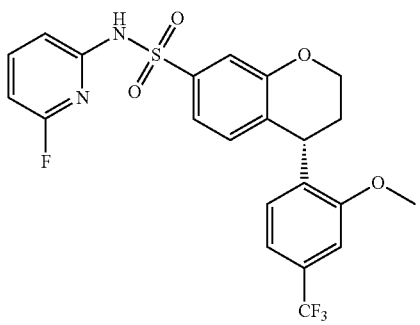

The title compounds were prepared by following the similar procedure as described in Example-1/2 using Intermediate-72 and 6-fluoropyridin-2-amine.

Further the enantiomers were separated using chiral preparative HPLC (Column: ChiralPak ID; Mobile phase: A=(Hexane+0.1% TFA), B=(IPA:DCM=1:1), A:B=60:40, to afford isomer-1 and isomer-2. These isomers were obtained at retention time 8.31 min (Example-228) and retention time 9.37 min (Example-229).

LCMS(ESI): m/z 482.99 (M+H)$^+$; $^1$H NMR (400 MHz, DMSO-d$_6$) δ 11.38 (s, 1H), 7.87 (dd, J=8.2 Hz, 1H), 7.42-7.28 (m, 3H), 7.24 (d, J=8.0 Hz, 1H), 6.96 (ddd, J=12.8, 8.1, 2.5 Hz, 3H), 6.77 (dd, J=8.0, 2.4 Hz, 1H), 4.58 (t, J=6.2 Hz, 1H), 4.28-4.19 (m, 1H), 4.14-4.04 (m, 1H), 3.85 (s, 3H), 2.22-2.02 (m, 2H).

Example-230/231: (S&R)-4-(2-(3-oxomorpholino)-4-(trifluoromethyl)phenyl)-N-(pyrimidin-2-yl)chroman-7-sulfonamide

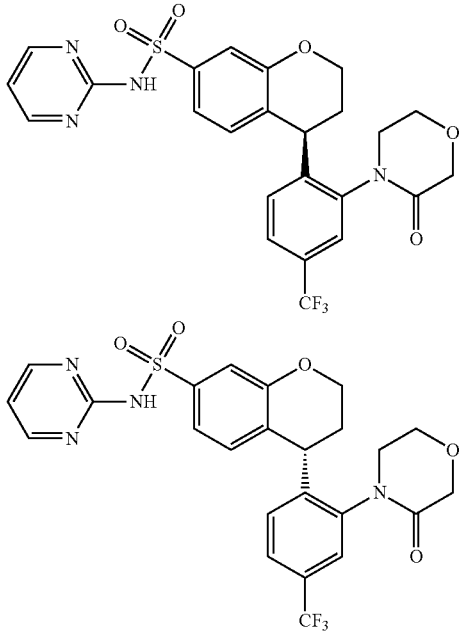

The title compounds were prepared by following the similar procedure as described in Example-1/2 using Intermediate-74 and pyrimidin-2-amine.

Further the enantiomers were separated using chiral preparative HPLC (Column: ChiralPak ID; Mobile phase: A=(Hexane+0.1% TFA), B=(IPA:DCM=1:1), A:B=60:40, to afford isomer-1 and isomer-2. These isomers were obtained at retention time 5.65 min (Example-230) and retention time 6.45 min (Example-231).

LCMS(ESI): m/z 535.0 (M+H)$^+$; $^1$H NMR (400 MHz, DMSO-d$_6$) δ 11.75 (s, 1H), 8.54 (d, J=4.9 Hz, 2H), 7.88 (s, 1H), 7.70-7.62 (m, 1H), 7.44-7.30 (m, 2H), 7.19 (d, J=8.3 Hz, 1H), 7.12-7.05 (m, 1H), 7.00-6.82 (m, 1H), 4.50-4.16 (m, 5H), 4.08-3.98 (m, 2H), 3.95-3.85 (m, 1H), 3.65-3.49 (m, 1H), 2.29-2.15 (m, 1H), 2.04-1.95 (m, 1H).

Example-232/233: (S&R)-4-(2-(1,1-dioxidothiomorpholino)-4-(trifluoromethyl)phenyl)-N-(pyrimidin-2-yl)chroman-7-sulfonamide

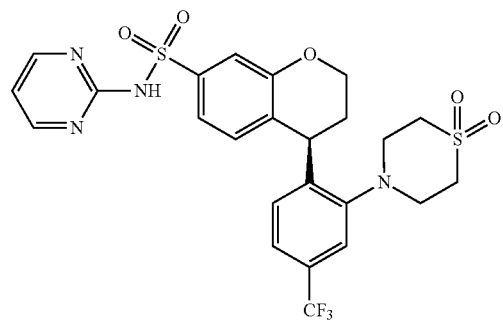

-continued

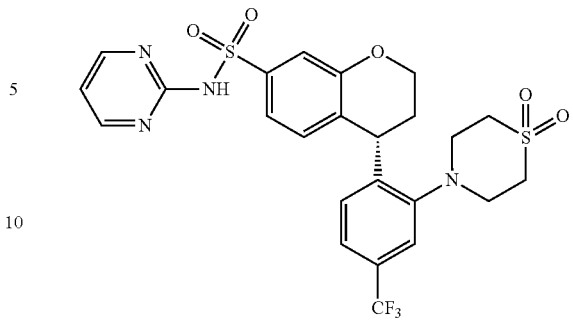

The title compounds were prepared by following the similar procedure as described in Example-1/2 using Intermediate-76 and pyrimidin-2-amine.

Further the enantiomers were separated using chiral preparative HPLC (Column: ChiralPak IA; Mobile phase: A=(Hexane+0.1% TFA), B=(IPA:DCM=1:1), A:B=50:50, to afford isomer-1 and isomer-2. These isomers were obtained at retention time 5.23 min (Example-232) and retention time 5.99 min (Example-233).

LCMS(ESI): m/z 569.07 (M+H)$^+$; $^1$H NMR (400 MHz, DMSO-d$_6$) δ 11.74 (s, 1H), 8.54 (d, J=4.8 Hz, 2H), 7.71 (d, J=1.8 Hz, 1H), 7.46 (d, J=8.1 Hz, 1H), 7.41 (d, J=1.9 Hz, 1H), 7.35 (dd, J=8.1, 2.0 Hz, 1H), 7.12-7.03 (m, 2H), 6.85 (d, J=8.1 Hz, 1H), 4.85 (t, 1H), 4.40-4.16 (m, 2H), 3.52-3.14 (m, 8H), 2.32-2.22 (m, 1H), 2.12-1.96 (m, 1H).

Example-234: (R/S)-4-(2-(1,1-dioxidothiomorpholino)-4-(trifluoromethyl)phenyl)-N-(5-fluoropyrimidin-2-yl)chroman-7-sulfonamide

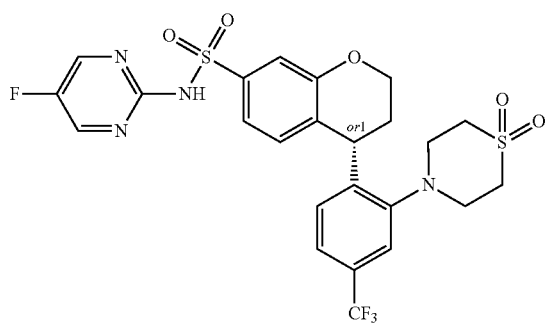 [SMILES: O=S1(=O)CCN(c2cc(C(F)(F)F)ccc2[C@H]2CCOc3cc(S(=O)(=O)Nc4ncc(F)cn4)ccc32)CC1]

The title compound was prepared by following the similar procedure as described in Example-1/2 using Intermediate-76b and 5-fluoropyrimidin-2-amine. LCMS(ESI): m/z 586.83 (M+H)$^+$; $^1$H NMR (400 MHz, DMSO-d$_6$) δ 11.86 (s, 1H), 8.66 (s, 2H), 7.72 (s, 1H), 7.46 (d, J=8.2 Hz, 1H), 7.42-7.30 (m, 2H), 7.13-7.06 (m, 1H), 6.86 (d, J=8.2 Hz, 1H), 4.87-4.82 (m, 1H), 4.39-4.19 (m, 2H), 3.51-3.18 (m, 8H), 2.33-2.23 (m, 1H), 2.11-1.97 (m, 1H).

Example-235: (R/S)-4-(2-(1,1-dioxidothiomorpholino)-4-(trifluoromethyl)phenyl)-N-(6-fluoropyridin-2-yl)chroman-7-sulfonamide

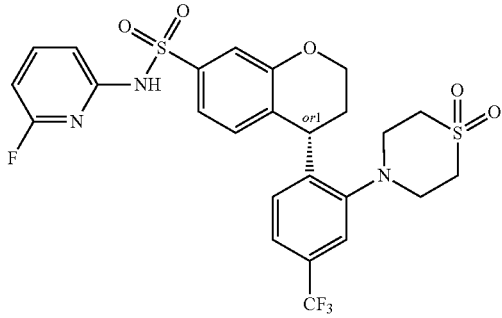 [SMILES: O=S1(=O)CCN(c2cc(C(F)(F)F)ccc2[C@H]2CCOc3cc(S(=O)(=O)Nc4cccc(F)n4)ccc32)CC1]

The title compounds were prepared by following the similar procedure as described in Example-1/2 using Intermediate-76b and 6-fluoropyridin-2-amine. LCMS(ESI): m/z 585.95 (M+H)⁺; ¹H NMR (400 MHz, DMSO-d₆) δ 11.37 (s, 1H), 7.87 (dd, J=8.2 Hz, 1H), 7.71 (s, 1H), 7.45 (d, J=8.0 Hz, 1H), 7.37 (d, J=2.0 Hz, 1H), 7.31 (dd, J=8.2, 2.0 Hz, 1H), 7.08 (s, 1H), 6.98 (dd, J=8.0, 2.1 Hz, 1H), 6.86 (d, J=8.1 Hz, 1H), 6.77 (dd, J=8.0, 2.4 Hz, 1H), 4.90-4.79 (m, 1H), 4.39-4.21 (m, 2H), 3.50-3.21 (m, 8H), 2.33-2.21 (m, 1H), 2.11-2.00 (m, 1H).

Example-236: (R/S)-4-(2-(1,1-dioxidothiomorpholino)-4-(trifluoromethyl)phenyl)-N-(pyridazin-3-yl)chroman-7-sulfonamide

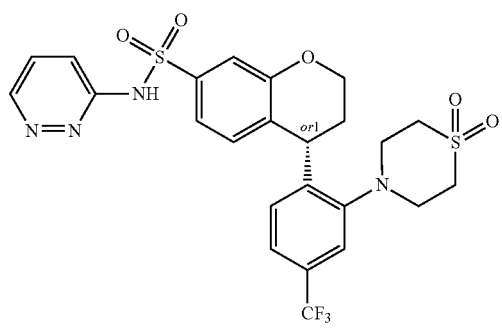 [SMILES: O=S1(=O)CCN(c2cc(C(F)(F)F)ccc2[C@H]2CCOc3cc(S(=O)(=O)Nc4cccnn4)ccc32)CC1]

The title compound was prepared by following the similar procedure as described in Example-1/2 using Intermediate-76b and pyridazin-3-amine. LCMS(ESI): m/z 568.95 (M+H)⁺; ¹H NMR (400 MHz, DMSO-d₆) δ 14.51 (s, 1H), 8.30 (s, 1H), 7.93 (s, 1H), 7.71 (s, 2H), 7.46 (d, J=8.5 Hz, 1H), 7.30-7.20 (m, 2H), 7.09 (d, J=8.2 Hz, 1H), 6.80 (d, J=8.1 Hz, 1H), 4.88-4.79 (m, 1H), 4.38-4.19 (m, 2H), 3.52-3.21 (m, 8H), 2.30-2.20 (m, 1H), 2.08-1.95 (m, 1H).

Example-237: (R/S)-4-(2-(1,1-dioxidothiomorpholino)-4-(trifluoromethyl)phenyl)-N-(pyrimidin-4-yl)chromane-7-sulfonamide

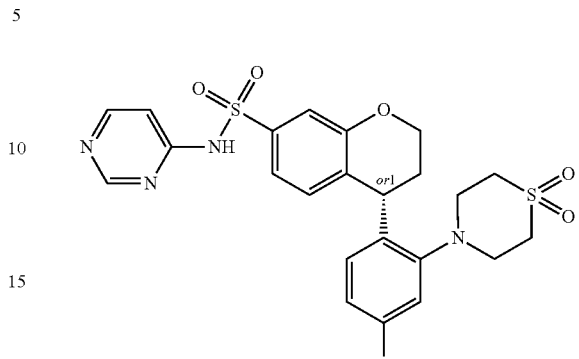

The title compound was prepared by following the similar procedure as described in Example-1/2 using (R/S)-perfluorophenyl 4-(2-(1,1-dioxidothiomorpholino)-4-(trifluoromethyl)phenyl)chroman-7-sulfonate (Intermediate-76b) and pyrimidin-4-amine. LCMS(ESI): m/z 568.95 (M+H)⁺; ¹H NMR (400 MHz, DMSO-d₆) δ 8.78-8.36 (m, 2H), 7.71 (d, J=1.7 Hz, 1H), 7.46 (d, J=8.2 Hz, 1H), 7.38-7.23 (m, 2H), 7.19-7.05 (m, 2H), 6.84 (d, J=8.1 Hz, 1H), 4.91-4.80 (m, 1H), 4.40-4.18 (m, 2H), 3.52-3.19 (m, 8H), 2.30-2.19 (m, 1H), 2.10-1.95 (m, 1H).

Example-238/239: (S&R)-4-(2-propyl-4-(trifluoromethyl)phenyl)-N-(pyrimidin-2-yl)chroman-7-sulfonamide

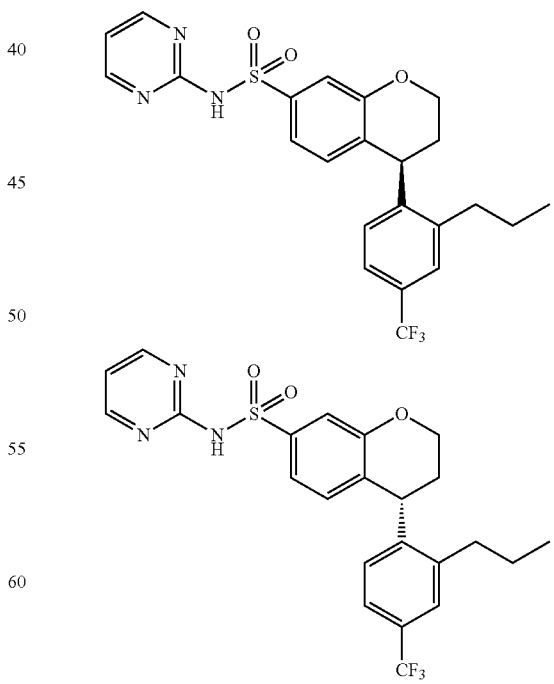

The title compounds were prepared by following the similar procedure as described in Example-1/2 using Intermediate-79 and pyrimidin-2-amine. Further the enantiomers were separated using chiral preparative HPLC (Column: ChiralPak IE; Mobile phase: A=(Hexane+0.1% TFA), B=(IPA:MeOH=1:1), A:B=30:70, to afford isomer-1 and isomer-2. These isomers were obtained at retention time 6.79 min (Example-238) and retention time 8.33 min (Example-239). LCMS(ESI): m/z 478.04 (M+H)$^+$; $^1$H NMR (400 MHz, DMSO-d$_6$) δ 11.73 (s, 1H), 8.54 (d, J=4.9 Hz, 2H), 7.59 (d, J=2.1 Hz, 1H), 7.46 (d, J=8.2 Hz, 1H), 7.41 (d, J=1.9 Hz, 1H), 7.37 (dd, J=8.1, 2.0 Hz, 1H), 7.13-6.98 (m, 2H), 6.78 (d, J=8.2 Hz, 1H), 4.60 (t, J=7.2 Hz, 1H), 4.33-4.22 (m, 2H), 2.76 (dd, J=33.8, 8.5 Hz, 2H), 2.29-2.17 (m, 1H), 2.09-1.94 (m, 1H), 1.67-1.55 (m, 2H), 0.93 (t, J=7.2 Hz, 3H).

Example-240/241: (S&R)—N-(5-fluoropyrimidin-2-yl)-4-(2-propyl-4-(trifluoromethyl)phenyl)chroman-7-sulfonamide

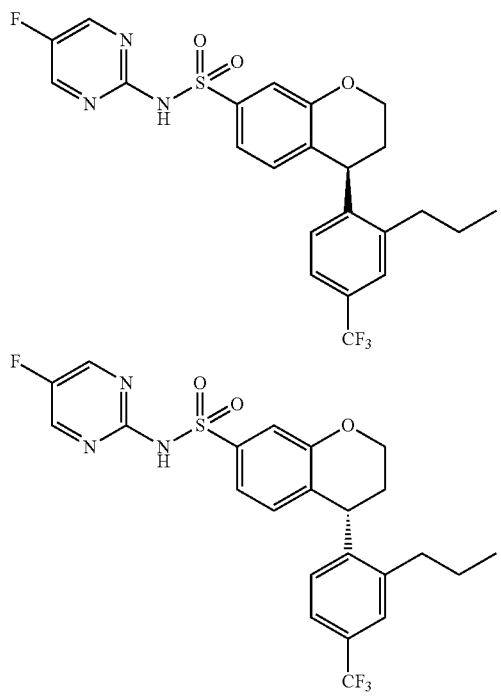

The title compounds were prepared by following the similar procedure as described in Example-1/2 using Intermediate-79 and 5-fluoropyrimidin-2-amine. Further the enantiomers were separated using chiral preparative HPLC (Column: ChiralPak ID; Mobile phase: A=(Hexane+0.1% TFA), B=(IPA:MeOH=1:1), A:B=30:70, to afford isomer-1 and isomer-2. These isomers were obtained at retention time 4.61 min (Example-240) and retention time 5.49 min (Example-241). LCMS(ESI): m/z 496.01 (M+H)$^+$; $^1$H NMR (400 MHz, DMSO-d$_6$) δ 11.88 (s, 1H), 8.66 (s, 2H), 7.60 (s, 1H), 7.50-7.32 (m, 3H), 7.02 (d, J=8.2 Hz, 1H), 6.79 (d, J=8.1 Hz, 1H), 4.64-4.56 (m, 1H), 4.36-4.22 (m, 2H), 2.84-2.68 (m, 2H), 2.28-2.19 (m, 1H), 2.03-1.97 (m, 1H), 1.67-1.54 (m, 2H), 0.94 (t, J=7.3 Hz, 3H).

Example-242/243: (S&R)-4-(2-propyl-4-(trifluoromethyl)-N-(pyridazin-3-yl)chroman-7-sulfonamide

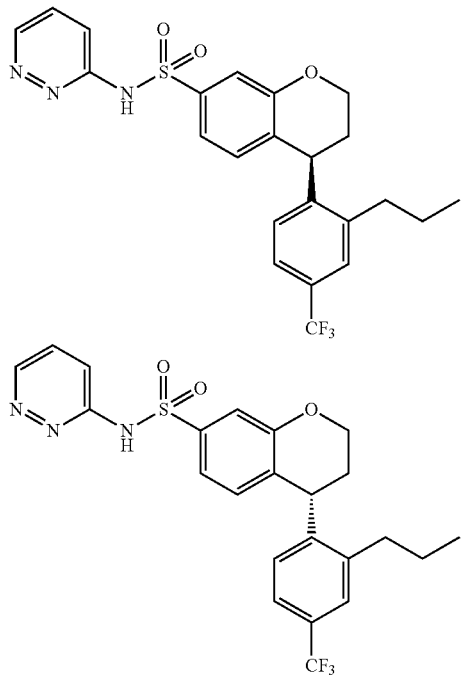

The title compounds were prepared by following the similar procedure as described in Example-1/2 using Intermediate-79 and pyridazin-3-amine. Further the enantiomers were separated using chiral preparative HPLC (Column: ChiralPak IE; Mobile phase: A=(Hexane+0.1% TFA), B=(IPA:MeOH=1:1), A:B=30:70, to afford isomer-1 and isomer-2. These isomers were obtained at retention time 6.57 min (Example-242) and retention time 7.67 min (Example-243). LCMS(ESI): m/z 478.03 (M+H)$^+$; $^1$H NMR (400 MHz, DMSO-d$_6$) δ 14.53 (s, 1H), 8.31 (s, 1H), 7.91 (s, 1H), 7.70 (dd, J=9.5, 4.1 Hz, 1H), 7.59 (d, J=2.0 Hz, 1H), 7.46 (d, J=8.2 Hz, 1H), 7.34-7.18 (m, 2H), 7.02 (d, J=8.2 Hz, 1H), 6.74 (d, J=8.0 Hz, 1H), 4.58 (t, J=7.1 Hz, 1H), 4.34-4.20 (m, 2H), 2.88-2.70 (m, 2H), 2.30-2.19 (m, 1H), 2.06-1.93 (m, 1H), 1.71-1.52 (m, 2H), 0.95 (t, J=7.3 Hz, 3H).

Example-244/245: (S&R)—N-(6-fluoropyridin-2-yl)-4-(2-propyl-4-(trifluoromethyl)phenyl)chroman-7-sulfonamide

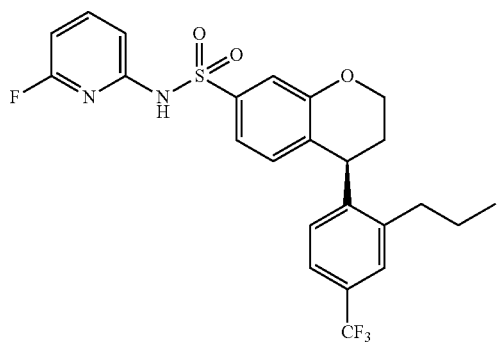

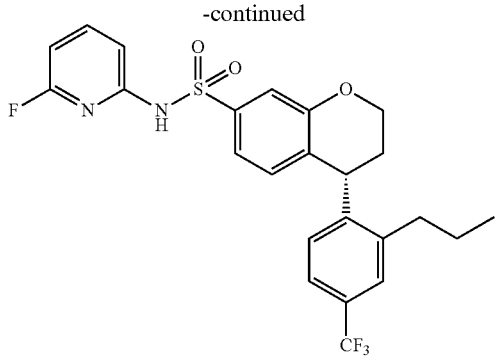

The title compounds were prepared by following the similar procedure as described in Example-1/2 using Intermediate-79 and 6-fluoropyridin-2-amine. Further the enantiomers were separated using chiral preparative HPLC (Column: ChiralPak IE; Mobile phase: A=(Hexane+0.1% TFA), B=(IPA:MeOH=1:1), A:B=50:50, to afford isomer-1 and isomer-2. These isomers were obtained at retention time 4.91 min (Example-244) and retention time 5.64 min (Example-245). LCMS(ESI): m/z 495.06 (M+H)$^+$; $^1$H NMR (400 MHz, DMSO-$d_6$) δ 11.38 (s, 1H), 7.87 (dd, J=8.2 Hz, 1H), 7.59 (d, J=2.0 Hz, 1H), 7.49-7.42 (m, 1H), 7.38 (d, J=1.9 Hz, 1H), 7.32 (dd, J=8.2, 2.0 Hz, 1H), 7.05-6.93 (m, 2H), 6.83-6.74 (m, 2H), 4.60 (t, J=7.2 Hz, 1H), 4.36-4.22 (m, 2H), 2.86-2.65 (m, 2H), 2.28-2.16 (m, 1H), 2.07-1.94 (m, 1H), 1.72-1.48 (m, 2H), 0.93 (t, J=7.3 Hz, 3H).

PHARMACOLOGICAL ACTIVITY

Certain illustrative compounds within the scope of the invention are screened for Nay activity according to the procedure given below. The screening of the compounds may be carried by other methods and procedures known to skilled in the art.

Analysis of Inhibition of Sodium Channels by Test Compounds:

HEK-293 cells overexpressing the channel of interest were seeded in a 96-well plate at a density of 30000 cells/well and incubated at 37° C./5% CO$_2$ for 48 hr. The assay was carried out using the Red Membrane Potential Dye (Molecular Devices) following the manufacturer's instructions. Briefly, the cells were incubated with 1× red membrane potential dye for 1.5 hour. The cells were then treated with various concentrations of the test compounds for 15-20 min followed by depolarization with 10-30 µM Veratridine. The fluorescence was read following excitation at 510-545 nm and emission at 565-625 nm in FLIPR. The "max-min" fluorescence values were used to calculate the % inhibition. IC$_{50}$ values were calculated by plotting % inhibition against concentration and curve fitting into a sigmoidal dose response.

Through the use of the above described assay procedure, compounds were found to exhibit functional activity against Na$_v$1.7 in vitro and particularly well suited for the treatment of diseases or disorders as described herein above. The IC$_{50}$ (nM) values of the representative compounds for Na$_v$1.7 and Na$_v$1.5 in vitro are set forth in Table-1

TABLE 1

| Ex. No | Na$_v$1.7 IC$_{50}$ nM or inhibition @ 10 µM | Na$_v$1.5 IC$_{50}$ nM or % inhibition @ 10 µM |
|---|---|---|
| 1 | 48 | >10 µM |
| 2 | 0.3 | 62% |
| 3 | 1241 | >10 µM |
| 4 | 1 | 57% |
| 5 | 733 | 58% |
| 6 | 17 | 46% |
| 7 | 4323 | >10 µM |
| 8 | 20 | >10 µM |
| 9 | 1358 | >10 µM |
| 10 | 3 | >10 µM |
| 11 | 96% | >10 µM |
| 12 | 86 | >10 µM |
| 13 | 74% | >10 µM |
| 14 | 33 | 15% |
| 15 | 96% | >10 µM |
| 16 | 17 | >10 µM |
| 17 | 96% | >10 µM |
| 18 | 759 | >10 µM |
| 19 | 1008 | >10 µM |
| 20 | 245 | — |
| 21 | 4274 | 57% |
| 22 | 2057 | 74% |
| 23 | 3691 | 59% |
| 24 | 816 | 3921 |
| 25 | 221 | >10 µM |
| 26 | 685 | >10 µM |
| 27 | 80% | >10 µM |
| 28 | 1574 | >10 µM |
| 29 | 91% | >10 µM |
| 30 | 72% | >10 µM |
| 31 | 2054 | >10 µM |
| 32 | 151 | >10 µM |
| 33 | 514 | >10 µM |
| 34 | 57 | >10 µM |
| 35 | 86% | >10 µM |
| 36 | 12 | 74% |
| 37 | 248 | >10 µM |
| 38 | 2 | >10 µM |
| 39 | 182 | >10 µM |
| 40 | 0.04 | >10 µM |
| 41 | 622 | >10 µM |
| 42 | 0.2 | 644 |
| 43 | 1071 | — |
| 44 | 16 | 770 |
| 45 | 2294 | >10 µM |
| 46 | 162 | >10 µM |
| 47 | 64% | >10 µM |
| 48 | 802 | >10 µM |
| 49 | 793 | >10 µM |
| 50 | 77 | 38% |
| 51 | >10 µM | >10 µM |
| 52 | 698 | >10 µM |
| 53 | 70% | 44% |
| 54 | 706 | >10 µM |
| 55 | 4326 | >10 µM |
| 56 | 601 | >10 µM |
| 57 | 2673 | >10 µM |
| 58 | 54 | >10 µM |
| 59 | 187 | >10 µM |
| 60 | 0.3 | >10 µM |
| 61 | 568 | >10 µM |
| 62 | 5 | 42% |
| 63 | 526 | >10 µM |
| 64 | 3 | >10 µM |
| 65 | 16 | >10 µM |
| 66 | 8 | >10 µM |
| 67 | 30 | >10 µM |
| 68 | 0.9 | 29% |
| 70 | 115 | >10 µM |
| 71 | 1512 | >10 µM |
| 72 | 15 | >10 µM |
| 73 | 842 | 44% |
| 74 | 0.2 | 44% |
| 75 | 86% | >10 µM |
| 76 | 46 | >10 µM |

TABLE 1-continued

| Ex. No | Na$_v$1.7 IC$_{50}$ nM or inhibition @ 10 μM | Na$_v$1.5 IC$_{50}$ nM or % inhibition @ 10 μM |
|---|---|---|
| 77 | 858 | >10 μM |
| 78 | 1 | 1168 |
| 79 | 2515 | >10 μM |
| 80 | 114 | 53% |
| 81 | 993 | 34% |
| 82 | 20 | >10 μM |
| 83 | 71% | >10 μM |
| 84 | 2575 | >10 μM |
| 85 | 2723 | >10 μM |
| 86 | 2387 | >10 μM |
| 87 | 58% | >10 μM |
| 88 | 626 | >10 μM |
| 89 | 108 | >10 μM |
| 90 | 15 | >10 μM |
| 91 | 1116 | >10 μM |
| 92 | 11 | >10 μM |
| 93 | 4 | 56% |
| 94 | 3 | 51% |
| 95 | 11 | 74% |
| 96 | 8 | 70% |
| 97 | 170 | 71% |
| 98 | 11 | 432 |
| 99 | 1065 | 80% |
| 100 | 75 | >10 μM |
| 101 | 2594 | 51% |
| 102 | 39 | >10 μM |
| 103 | 10 | 932 |
| 104 | 184 | >10 μM |
| 105 | 1505 | >10 μM |
| 106 | 147 | >10 μM |
| 107 | 229 | >10 μM |
| 108 | 57 | 2184 |
| 109 | 740 | >10 μM |
| 110 | 156 | 1748 |
| 111 | 814 | 67% |
| 112 | 801 | 65% |
| 113 | 65% | >10 μM |
| 114 | 624 | >10 μM |
| 115 | 41 | >10 μM |
| 116 | 1957 | >10 μM |
| 117 | 106 | >10 μM |
| 118 | 727 | >10 μM |
| 119 | 5 | 30% |
| 120 | 11 | >10 μM |
| 121 | 3 | 248 |
| 122 | 38 | 54% |
| 123 | 1 | 103 |
| 124 | 2234 | 71% |
| 125 | 395 | 2636 |
| 126 | 140 | >10 μM |
| 127 | 4 | 37% |
| 128 | 145 | 55% |
| 129 | 16 | 62% |
| 130 | 1689 | >10 μM |
| 131 | 53 | 66% |
| 132 | 163 | >10 μM |
| 133 | 128 | 66% |
| 134 | 31 | 1345 |
| 135 | 708 | >10 μM |
| 136 | 655 | 33% |
| 137 | 12 | 3641 |
| 138 | 588 | >10 μM |
| 139 | 33 | >10 μM |
| 140 | 1741 | >10 μM |
| 141 | 69 | 65% |
| 142 | 179 | >10 μM |
| 143 | 16 | 534 |
| 144 | 86 | 2683 |
| 145 | 19 | 2407 |
| 146 | 790 | >10 μM |
| 147 | 199 | 60% |
| 148 | 172 | >10 μM |
| 149 | 21 | 58% |
| 150 | 31 | 1428 |
| 151 | 390 | 57% |
| 152 | 40 | 67% |
| 153 | 39 | 35% |
| 154 | 83 | >10 μM |
| 155 | 4 | >10 μM |
| 156 | 42 | 36% |
| 157 | 42 | >10 μM |
| 158 | 130 | 505 |
| 159 | 10 | 943 |
| 160 | 0.7 | 61% |
| 161 | 12 | 1352 |
| 162 | 0.7 | 2637 |
| 163 | 42 | 307 |
| 164 | 61 | 81% |
| 165 | 5 | 303 |
| 166 | 50 | 134 |
| 167 | 58 | 241 |
| 168 | 3903 | >10 μM |
| 169 | 43 | 4887 |
| 170 | 1092 | >10 μM |
| 171 | 125 | 53% |
| 172 | 2740 | >10 μM |
| 173 | 12 | 63% |
| 174 | 2456 | >10 μM |
| 175 | 248 | 1686 |
| 176 | 1310 | 57% |
| 177 | 11 | 232 |
| 178 | 149 | >10 μM |
| 179 | 38 | 64% |
| 180 | 831 | >10 μM |
| 181 | 0.9 | 43% |
| 182 | 55 | 30% |
| 183 | 11 | >10 μM |
| 184 | 170 | 67% |
| 185 | 1025 | >10 μM |
| 186 | 83 | 46% |
| 187 | 2599 | — |
| 188 | 67 | >10 μM |
| 189 | 1811 | >10 μM |
| 190 | 257 | >10 μM |
| 191 | 671 | >10 μM |
| 192 | 8 | >10 μM |
| 193 | 80 | >10 μM |
| 194 | 1 | 65% |
| 195 | 478 | >10 μM |
| 196 | 1 | >10 μM |
| 197 | 551 | >10 μM |
| 198 | 7 | 2516 |
| 199 | 355 | >10 μM |
| 200 | 0.5 | >10 μM |
| 201 | 85 | >10 μM |
| 202 | 0.5 | >10 μM |
| 203 | 6 | >10 μM |
| 204 | 8 | 1103 |
| 205 | 8 | 250 |
| 206 | 4 | 1312 |
| 207 | 49 | >10 μM |
| 208 | 46 | >10 μM |
| 209 | 47 | 28% |
| 210 | 48 | >10 μM |
| 211 | 7 | 777 |
| 212 | 18 | >10 μM |
| 213 | 34 | 65% |
| 214 | 2 | 635 |
| 215 | 38 | 1354 |
| 216 | 2728 | >10 μM |
| 217 | 152 | 50% |
| 218 | 43 | >10 μM |
| 219 | 34 | 40% |
| 220 | >10 μM | >10 μM |
| 221 | 42 | 1466 |
| 222 | 63 | 73% |
| 223 | 82 | 33% |
| 224 | 51 | 2124 |
| 225 | 12 | 1496 |
| 226 | 2346 | 86% |

TABLE 1-continued

| Ex. No | $Na_v1.7$ $IC_{50}$ nM or inhibition @ 10 μM | $Na_v1.5$ $IC_{50}$ nM or % inhibition @ 10 μM |
|---|---|---|
| 227 | 177 | >10 μM |
| 228 | 55% | >10 μM |
| 229 | 156 | 42% |
| 230 | 4421 | >10 μM |
| 231 | 559 | >10 μM |
| 232 | 36% | >10 μM |
| 233 | 164 | >10 μM |
| 234 | 83 | >10 μM |
| 235 | 173 | >10 μM |
| 236 | 113 | >10 μM |
| 237 | 19 | >10 μM |
| 238 | 1757 | >10 μM |
| 239 | 124 | 62% |
| 240 | 2737 | >10 μM |
| 241 | 172 | >10 μM |
| 242 | 1055 | 3654 |
| 243 | 92 | 2407 |
| 244 | 474 | 69% |
| 245 | 41 | 75% |

The invention claimed is:

1. A compound having the Formula (I):

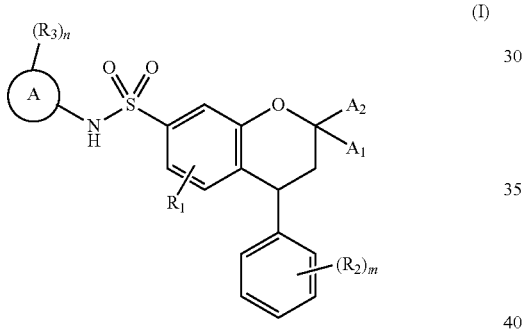

(I)

wherein, $A_1$ and $A_2$ are independently hydrogen or substituted or unsubstituted ($C_1$-$C_6$)alkyl; or $A_1$ and $A_2$, together with the carbon atom to which they are attached, form a substituted or unsubstituted 3- to 6-membered cycloalkyl ring or 4- to 6-membered heterocyclic ring;

$R_1$ is selected from the group consisting of hydrogen, halogen, cyano, substituted or unsubstituted ($C_1$-$C_6$) alkyl and substituted or unsubstituted ($C_1$-$C_6$) alkoxy;

$R_2$, which may be same or different at each occurrence, is independently selected from the group consisting of halogen, cyano, substituted or unsubstituted ($C_1$-$C_6$)alkyl, ($C_1$-$C_6$)haloalkyl, —($CH_2$)$_{0-2}$—$S(O)_2$-alkyl, —O—$R_6$, substituted or unsubstituted alkoxyalkyl, substituted or unsubstituted ($C_3$-$C_8$) cycloalkyl, substituted or unsubstituted ($C_6$-$C_{10}$) aryl, substituted or unsubstituted 5- to 6-membered monocyclic heteroaryl, substituted or unsubstituted 4- to 6-membered monocyclic heterocyclyl, —C(O) OH, —C(O)O-alkyl and —C(O)$NR_4R_5$;

ring A is monocyclic six membered heteroaryl containing 1- to 3-nitrogen atoms in the ring;

$R_3$, which may be same or different at each occurrence, is independently selected from the group consisting of halogen, cyano, substituted or unsubstituted ($C_1$-$C_6$)alkyl and substituted or unsubstituted ($C_1$-$C_6$) alkoxy;

$R_4$ and $R_5$ are independently selected from hydrogen or substituted or unsubstituted ($C_1$-$C_6$)alkyl; or $R_4$ and $R_5$ together with the nitrogen atom to which they are attached, form substituted or unsubstituted 5- to 6-membered heterocylic ring;

$R_6$ is selected from the group consisting of hydrogen, substituted or unsubstituted ($C_1$-$C_6$)alkyl, ($C_1$-$C_6$) haloalkyl, substituted or unsubstituted alkoxyalkyl, substituted or unsubstituted ($C_3$-$C_8$)cycloalkyl, substituted or unsubstituted ($C_6$-$C_{10}$)aryl, substituted or unsubstituted 5- to 6-membered monocyclic heteroaryl and substituted or unsubstituted 4- to 6-membered monocyclic heterocyclyl;

'm' is an integer ranging from 0 to 3, both inclusive;

'n' is an integer ranging from 0 to 3, both inclusive;

wherein the substituents for substituted or unsubstituted alkyl, substituted or unsubstituted alkoxy, substituted or unsubstituted cycloalkyl, substituted or unsubstituted aryl, substituted or unsubstituted heteroaryl, substituted or unsubstituted heterocyclyl, substituted or unsubstituted heterocyclic ring, substituted or unsubstituted alkoxyalkyl are one or more same or different and independently selected from the group consisting of hydroxy, halogen, carboxy, cyano, nitro, oxo (=O), ($C_1$-$C_6$)alkyl, ($C_1$-$C_6$)haloalkyl, hydroxy ($C_1$-$C_6$)alkyl, alkoxyalkyl, ($C_2$-$C_6$) alkenyl, ($C_2$-$C_6$)alkynyl, ($C_6$-$C_{10}$)aryl, arylalkyl, ($C_3$-$C_8$)cycloalkyl, cycloalkylalkyl, 5 to 10 membered heteroaryl, 4 to 10 membered heterocyclic ring, 3 to 10 membered heterocyclylalkyl, heteroarylalkyl, —C(O)$OR_x$, —C(O)$R_y$, —C(S)$R_y$, —C(O) $NR_xR_z$, —$NR_xC(O)NR_xR_z$, —N($R_x$)$S(O)_2R_y$, —$NR_xR_z$, —$NR_xC(O)R_y$, —$NR_xC(S)R_y$, —$NR_xC$ $(S)NR_xR_z$, —$S(O)_2NR_xR_z$, —$OR_x$, —$OC(O)R_y$, —$C(R_aR_b)_{1-3}C(O)OR_x$, —$C(R_aR_b)_{1-3}C(O)NR_xR_z$, —$OC(R_aR_b)_{2-3}$—$OR_x$, —$OC(R_aR_b)_{2-3}$—$NR_xR_z$, —$OC(R_aR_b)_{2-3}$—$S(O)_{0-2}R_y$, —$C(R_aR_b)_{1-3}$—$NR_xR_z$, —$C(R_aR_b)_{1-3}$—$S(O)_{0-2}R_y$, —$OC$ $(R_aR_b)_{1-3}$—$C(O)NR_xR_z$, —$OC(R_aR_b)_{1-3}$—$C(O)$ $OR_x$ and —$S(O)_{0-2}R_y$;

each of $R_x$ is selected from the group consisting hydrogen, ($C_1$-$C_6$)alkyl, ($C_1$-$C_6$)haloalkyl, ($C_2$-$C_6$)alkenyl, ($C_2$-$C_6$)alkynyl, ($C_6$-$C_{10}$)aryl, arylalkyl, ($C_3$-$C_8$)cycloalkyl, ($C_3$-$C_8$)cycloalkenyl, 5 to 10 membered heteroaryl, heterocyclic ring, heterocyclylalkyl and heteroarylalkyl;

each of $R_y$ is selected from the group consisting ($C_1$-$C_6$)alkyl, ($C_1$-$C_6$)haloalkyl, ($C_2$-$C_6$)alkenyl, ($C_2$-$C_6$) alkynyl, ($C_6$-$C_{10}$)aryl, arylalkyl, ($C_3$-$C_8$)cycloalkyl, ($C_3$-$C_8$)cycloalkenyl, 5 to 10 membered heteroaryl, heterocyclic ring, heterocyclylalkyl and heteroarylalkyl;

each of $R_z$ is selected from the group consisting hydrogen, ($C_1$-$C_6$)alkyl, ($C_1$-$C_6$)haloalkyl, ($C_2$-$C_6$)alkenyl, ($C_2$-$C_6$)alkynyl, ($C_6$-$C_{10}$)aryl, arylalkyl, ($C_3$-$C_8$)cycloalkyl, ($C_3$-$C_8$)cycloalkenyl, 5 to 10 membered heteroaryl, heterocyclic ring, heterocyclylalkyl and heteroarylalkyl; or $R_x$ and $R_z$ together with the nitrogen atom to which they are attached form a substituted or unsubstituted, saturated or unsaturated 4- to 8-membered cyclic ring, wherein the unsaturated cyclic ring may have one or two double bonds; and each of $R_a$ and $R_b$ are independently selected from the group consisting of hydrogen, halogen and substituted or unsubstituted $(C_1-C_6)$alkyl;
or N-oxides thereof or a pharmaceutically acceptable salt thereof or stereoisomer thereof.

2. The compound of claim-1 having the Formula (II):

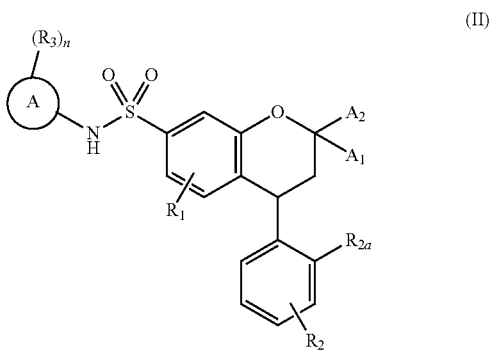

(II)

or N-oxides thereof or a pharmaceutically acceptable salt thereof or stereoisomer thereof;
wherein,
ring A is monocyclic six membered heteroaryl containing 1- to 2-nitrogen atoms in the ring;
$A_1$ and $A_2$ are independently hydrogen or substituted or unsubstituted $(C_1-C_6)$alkyl;
$R_{2a}$ is selected from halogen, cyano, substituted or unsubstituted $(C_1-C_6)$alkyl, $(C_1-C_6)$haloalkyl, —$(CH_2)_{0-2}$—$S(O)_2$-alkyl, —O—$R_6$, substituted or unsubstituted $(C_3-C_8)$cycloalkyl, substituted or unsubstituted $(C_6-C_{10})$aryl, substituted or unsubstituted 5- to 6-membered monocyclic heteroaryl, substituted or unsubstituted 4- to 6-membered monocyclic heterocyclyl, —C(O)OH, —C(O)O-alkyl and —C(O)NR$_4$R$_5$ where R$_4$ and R$_5$ are hydrogen or $(C_1-C_6)$alkyl;
$R_6$ is selected from the group consisting of hydrogen, substituted or unsubstituted $(C_1-C_6)$alkyl, $(C_1-C_6)$haloalkyl, substituted or unsubstituted alkoxyalkyl, substituted or unsubstituted $(C_3-C_8)$cycloalkyl, substituted or unsubstituted $(C_6-C_{10})$aryl, substituted or unsubstituted 5- to 6-membered monocyclic heteroaryl, and substituted or unsubstituted 4- to 6-membered monocyclic heterocyclyl;
$R_1$, $R_2$, $R_3$ and 'n' are as defined in claim-1.

3. The compound of claim-1 having the Formula (III)

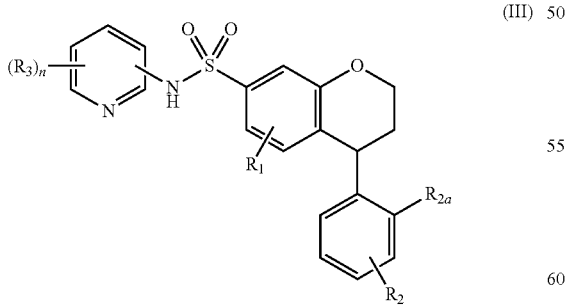

(III)

or N-oxides thereof or a pharmaceutically acceptable salt thereof or stereoisomer thereof;
wherein,
$R_{2a}$ is selected from halogen, cyano, substituted or unsubstituted $(C_1-C_6)$alkyl, $(C_1-C_6)$haloalkyl, —$(CH_2)_{0-2}$—$S(O)_2$-alkyl, —O—$R_6$, substituted or unsubstituted alkoxyalkyl, $(C_3-C_8)$cycloalkyl, substituted or unsubstituted $(C_6-C_{10})$aryl, substituted or unsubstituted 5- to 6-membered monocyclic heteroaryl, substituted or unsubstituted 4- to 6-membered monocyclic heterocyclyl, —C(O)OH, —C(O)O-alkyl and —C(O)NR$_4$R$_5$ where R$_4$ and R$_5$ are hydrogen or $(C_1-C_6)$alkyl;
$R_6$ is selected from the group consisting of hydrogen, substituted or unsubstituted $(C_1-C_6)$alkyl, $(C_1-C_6)$haloalkyl, substituted or unsubstituted alkoxyalkyl, substituted or unsubstituted $(C_3-C_8)$cycloalkyl, substituted or unsubstituted $(C_6-C_{10})$aryl, substituted or unsubstituted 5- to 6-membered monocyclic heteroaryl, and substituted or unsubstituted 4- to 6-membered monocyclic heterocyclyl;
$R_1$, $R_2$, $R_3$ and 'n' are as defined in claim-1.

4. The compound of claim-1 having the Formula (IV)

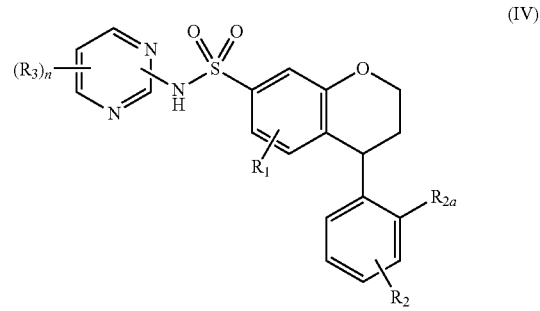

(IV)

or N-oxides thereof or a pharmaceutically acceptable salt thereof or stereoisomer thereof;
wherein,
$R_{2a}$ is selected from halogen, cyano, substituted or unsubstituted $(C_1-C_6)$alkyl, $(C_1-C_6)$haloalkyl, —$(CH_2)_{0-2}$—$S(O)_2$-alkyl, —O—$R_6$, substituted or unsubstituted alkoxyalkyl, $(C_3-C_8)$cycloalkyl, substituted or unsubstituted $(C_6-C_{10})$aryl, substituted or unsubstituted 5- to 6-membered monocyclic heteroaryl, substituted or unsubstituted 4- to 6-membered monocyclic heterocyclyl, —C(O)OH, —C(O)O-alkyl and —C(O)NR$_4$R$_5$ where R$_4$ and R$_5$ are hydrogen or $(C_1-C_6)$alkyl;
$R_6$ is selected from the group consisting of hydrogen, substituted or unsubstituted $(C_1-C_6)$alkyl, $(C_1-C_6)$haloalkyl, substituted or unsubstituted alkoxyalkyl, $(C_3-C_8)$cycloalkyl, substituted or unsubstituted $(C_6-C_{10})$aryl, substituted or unsubstituted 5- to 6-membered monocyclic heteroaryl, and substituted or unsubstituted 4- to 6-membered monocyclic heterocyclyl;
$R_1$, $R_2$, $R_3$ and 'n' are as defined in claim-1.

5. The compound of claim-1 having the Formula (V)

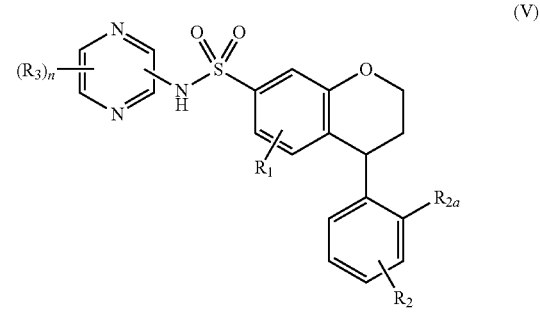

(V)

or N-oxides thereof or a pharmaceutically acceptable salt thereof or stereoisomer thereof;

wherein,

R$_{2a}$ is selected from halogen, cyano, substituted or unsubstituted (C$_1$-C$_6$)alkyl, (C$_1$-C$_6$)haloalkyl, —(CH$_2$)$_{0-2}$—S(O)$_2$-alkyl, —O—R$_6$, substituted or unsubstituted alkoxyalkyl, (C$_3$-C$_8$)cycloalkyl, substituted or unsubstituted (C$_6$-C$_{10}$)aryl, substituted or unsubstituted 5- to 6-membered monocyclic heteroaryl, substituted or unsubstituted 4- to 6-membered monocyclic heterocyclyl, —C(O)OH, —C(O)O-alkyl and —C(O)NR$_4$R$_5$ where R$_4$ and R$_5$ are hydrogen or (C$_1$-C$_6$)alkyl;

R$_6$ is selected from the group consisting of hydrogen, substituted or unsubstituted (C$_1$-C$_6$)alkyl, (C$_1$-C$_6$)haloalkyl, substituted or unsubstituted alkoxyalkyl, (C$_3$-C$_8$)cycloalkyl, substituted or unsubstituted (C$_6$-C$_{10}$)aryl, substituted or unsubstituted 5- to 6-membered monocyclic heteroaryl and substituted or unsubstituted 4- to 6-membered monocyclic heterocyclyl;

R$_1$, R$_2$, R$_3$ and 'n' are as defined in claim-1.

6. The compound of claim-1 having the Formula (VI)

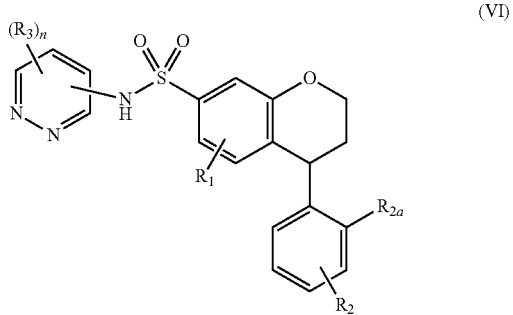

(VI)

or N-oxides thereof or a pharmaceutically acceptable salt thereof or stereoisomer thereof;

wherein,

R$_{2a}$ is selected from halogen, cyano, substituted or unsubstituted (C$_1$-C$_6$)alkyl, (C$_1$-C$_6$)haloalkyl, —(CH$_2$)$_{0-2}$—S(O)$_2$-alkyl, —O—R$_6$, substituted or unsubstituted alkoxyalkyl, (C$_3$-C$_8$)cycloalkyl, substituted or unsubstituted (C$_6$-C$_{10}$)aryl, substituted or unsubstituted 5- to 6-membered monocyclic heteroaryl, substituted or unsubstituted 4- to 6-membered monocyclic heterocyclyl, —C(O)OH, —C(O)O-alkyl and —C(O)NR$_4$R$_5$ where R$_4$ and R$_5$ are hydrogen or (C$_1$-C$_6$)alkyl;

R$_6$ is selected from the group consisting of hydrogen, substituted or unsubstituted (C$_1$-C$_6$)alkyl, (C$_1$-C$_6$)haloalkyl, substituted or unsubstituted alkoxyalkyl, substituted or unsubstituted (C$_3$-C$_8$)cycloalkyl, substituted or unsubstituted (C$_6$-C$_{10}$)aryl, substituted or unsubstituted 5- to 6-membered monocyclic heteroaryl and substituted or unsubstituted 4- to 6-membered monocyclic heterocyclyl;

R$_1$, R$_2$, R$_3$ and 'n' are as defined in claim-1.

7. The compound of claim 1 wherein R$_1$ is hydrogen, halogen or (C$_1$-C$_6$)alkyl.

8. The compound of claim-1 wherein ring A is selected from

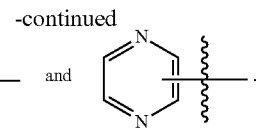

9. The compound of claim 1 wherein R$_3$ is halogen, cyano, substituted or unsubstituted (C$_1$-C$_6$)alkyl and substituted or unsubstituted (C$_1$-C$_6$)alkoxy; and 'n' is 0 or 1.

10. The compound of claim-1 wherein A$_1$ and A$_2$ are independently hydrogen or substituted or unsubstituted (C$_1$-C$_6$) alkyl.

11. The compound of claim-1 wherein A$_1$ and A$_2$ together with the carbon atom to which they are attached, form a substituted or unsubstituted 3- to 6-membered cycloalkyl ring.

12. The compound of claim 1 wherein R$_2$ is selected from halogen, cyano, substituted or unsubstituted (C$_1$-C$_6$)alkyl, (C$_1$-C$_6$)haloalkyl, —(CH$_2$)$_{0-2}$—S(O)$_2$-alkyl, —O—R$_6$, substituted or unsubstituted alkoxyalkyl, (C$_3$-C$_8$)cycloalkyl, substituted or unsubstituted (C$_6$-C$_{10}$)aryl (e.g. phenyl), substituted or unsubstituted 5- to 6-membered monocyclic heteroaryl (e.g pyridyl, pyrazolyl, triazolyl, thiazolyl, oxazolyl), substituted or unsubstituted 4- to 6-membered monocyclic heterocyclyl (e.g. pyrrolidinone, oxazolidinone, morpholine, morpholinone, thiomorpholine1,1-dioxide, tetrahydropyran), —C(O)OH, —C(O)O— alkyl and —C(O)NR$_4$R$_5$ where R$_4$ and R$_5$ are hydrogen or (C$_1$-C$_6$)alkyl; R$_6$ is selected from the group consisting of hydrogen, substituted or unsubstituted (C$_1$-C$_6$)alkyl, (C$_1$-C$_6$)haloalkyl, substituted or unsubstituted alkoxyalkyl, (C$_3$-C$_8$)cycloalkyl, substituted or unsubstituted (C$_6$-C$_{10}$)aryl, substituted or unsubstituted 5- to 6-membered monocyclic heteroaryl, and substituted or unsubstituted 4- to 6-membered monocyclic heterocyclyl; and 'm' is 0, 1 or 2.

13. A compound of claim 2 wherein R$_2$ is halogen, (C$_1$-C$_6$)haloalkyl or O—R$_6$ where R$_6$ is hydrogen or (C$_1$-C$_6$)alkyl.

14. The compound of claim-1 having the Formula (II):

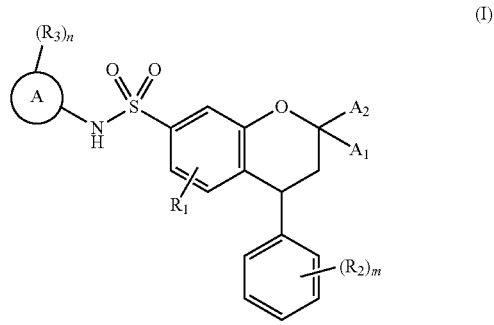

(I)

wherein A$_1$ and A$_2$ are hydrogen; R$_1$ is hydrogen; ring A is monocyclic six membered heteroaryl containing 1- to 2-nitrogen atoms in the ring -continued

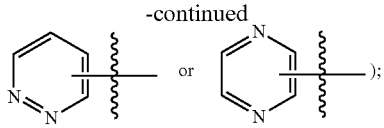

$R_2$ is halogen, $(C_1-C_6)$haloalkyl or —O—$R_6$; $R_{2a}$ is halogen, substituted or unsubstituted $(C_1-C_6)$alkyl, $(C_1-C_6)$haloalkyl, —$(CH_2)_{0-2}$—$S(O)_2$-alkyl, —O—$R_6$, substituted or unsubstituted alkoxyalkyl, substituted or unsubstituted $(C_6-C_{10})$ aryl

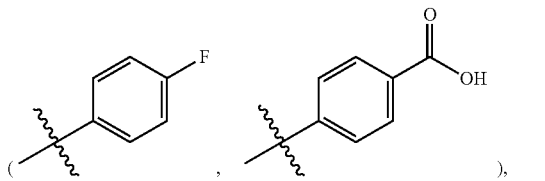 [SMILES: *c1ccc(F)cc1 ; *c1ccc(C(=O)O)cc1]

substituted or unsubstituted 5- to 6-membered monocyclic heteroaryl

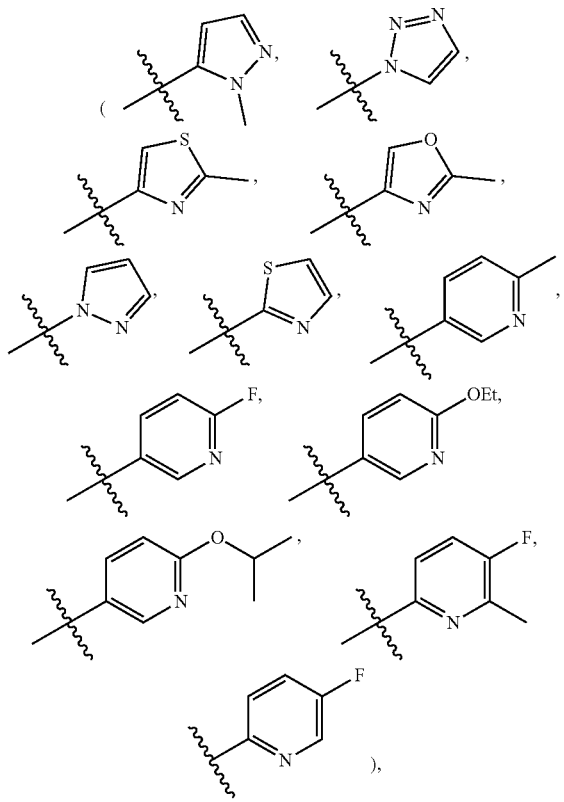

substituted or unsubstituted 4- to 6-membered monocyclic heterocyclyl

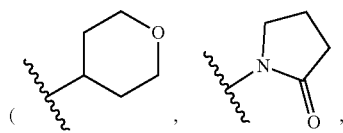

-continued

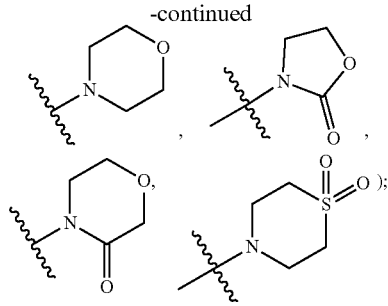

where $R_6$ is substituted or unsubstituted $(C_1-C_6)$alkyl, substituted or unsubstituted alkoxyalkyl and substituted or unsubstituted 4- to 6-membered monocyclic heterocyclyl

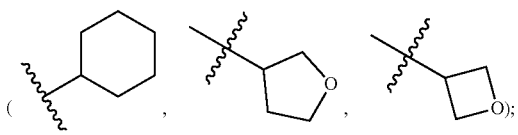

$R_3$ is halogen, substituted or unsubstituted $(C_1-C_6)$alkyl and substituted or unsubstituted $(C_1-C_6)$alkoxy;
and 'n' is 0 or 1;
or a free base thereof, N-oxide thereof, or stereoisomers thereof or a pharmaceutically acceptable salt thereof.

15. A compound which is selected from:
(S)—N-(6-Fluoropyridin-2-yl)-4-(2-(1-methyl-1H-pyrazol-5-yl)-4-(trifluoromethyl)phenyl)chroman-7-sulfonamide;
(R)—N-(6-Fluoropyridin-2-yl)-4-(2-(1-methyl-1H-pyrazol-5-yl)-4-(trifluoromethyl)phenyl)chroman-7-sulfonamide;
(S&R)—N-(4-Fluoropyridin-2-yl)-4-(2-(1-methyl-1H-pyrazol-5-yl)-4-(trifluoromethyl)phenyl)chroman-7-sulfonamide;
(S&R)—N-(5-Fluoropyridin-2-yl)-4-(2-(1-methyl-1H-pyrazol-5-yl)-4-(trifluoromethyl)phenyl)chroman-7-sulfonamide;
(S&R)—N-(5-Fluoropyrimidin-2-yl)-4-(2-(1-methyl-1H-pyrazol-5-yl)-4-(trifluoromethyl)phenyl)chroman-7-sulfonamide;
(S&R)-4-(2-(1-Methyl-1H-pyrazol-5-yl)-4-(trifluoromethyl)phenyl)-N-(pyrimidin-4-yl)chroman-7-sulfonamide;
(S&R)-4-(2-(1-Methyl-1H-pyrazol-5-yl)-4-(trifluoromethyl)phenyl)-N-(pyrazin-2-yl)chromane-7-sulfonamide;
(S&R)-4-(2-(1-Methyl-1H-pyrazol-5-yl)-4-(trifluoromethyl)phenyl)-N-(pyridazin-3-yl)chromane-7-sulfonamide;
(S&R)-4-(2-(1-Methyl-1H-pyrazol-5-yl)-4-(trifluoromethyl)phenyl)-N-(pyrimidin-2-yl)chromane-7-sulfonamide;
(S&R)—N-(3-Fluoropyridin-2-yl)-4-(2-(1-methyl-1H-pyrazol-5-yl)-4-(trifluoromethyl)phenyl)chromane-7-sulfonamide;
(S&R)-4-(2-(1-Methyl-1H-pyrazol-5-yl)-4-(trifluoromethyl)phenyl)-N-(6-methylpyridin-2-yl)chroman-7-sulfonamide;
(S&R)-4-(2-(1-Methyl-1H-pyrazol-5-yl)-4-(trifluoromethyl)phenyl)-N-(5-methylpyridin-2-yl)chroman-7-sulfonamide;

(S&R)-4-(2-(1-Methyl-1H-pyrazol-5-yl)-4-(trifluoromethyl)phenyl)-N-(4-methylpyridin-2-yl)chroman-7-sulfonamide;
(S&R)—N-(6-Isopropoxypyridin-2-yl)-4-(2-(1-methyl-1H-pyrazol-5-yl)-4-(trifluoromethyl)phenyl)chroman-7-sulfonamide;
(S&R)—N-(2-Fluoropyridin-3-yl)-4-(2-(1-methyl-1H-pyrazol-5-yl)-4-(trifluoromethyl)phenyl)chroman-7-sulfonamide;
(S&R)-4-(2-(1-Methyl-1H-pyrazol-5-yl)-4-(trifluoromethyl)phenyl)-N-(4-methylpyrimidin-2-yl)chroman-7-sulfonamide;
(S&R)-4-(4-Chloro-2-(1-methyl-1H-pyrazol-5-yl)phenyl)-N-(6-fluoropyridin-2-yl)chroman-7-sulfonamide;
(S&R)—N-(6-Fluoropyridin-2-yl)-4-(4-isopropoxy-2-(1-methyl-1H-pyrazol-5-yl)phenyl)chroman-7-sulfonamide;
(S&R)-4-(2-(6-Fluoropyridin-3-yl)-4-(trifluoromethyl)phenyl)-N-(pyrimidin-2-yl)chromane-7-sulfonamide;
(S&R)-4-(2-(6-Fluoropyridin-3-yl)-4-(trifluoromethyl)phenyl)-N-(5-fluoropyrimidin-2-yl)chromane-7-sulfonamide;
(S&R)-4-(2-(6-Fluoropyridin-3-yl)-4-(trifluoromethyl)phenyl)-N-(pyrimidin-4-yl)chromane-7-sulfonamide;
(S&R)-4-(2-(6-Fluoropyridin-3-yl)-4-(trifluoromethyl)phenyl)-N-(pyridazin-3-yl)chromane-7-sulfonamide;
(S&R)-4-(4'-Fluoro-5-(trifluoromethyl)-[1,1'-biphenyl]-2-yl)-N-(pyrimidin-2-yl)chromane-7-sulfonamide;
(S&R)-4-(4'-Fluoro-5-(trifluoromethyl)-[1,1'-biphenyl]-2-yl)-N-(5-fluoropyrimidin-2-yl)chromane-7-sulfonamide;
(S&R)-4-(4'-Fluoro-5-(trifluoromethyl)-[1,1'-biphenyl]-2-yl)-N-(pyrimidin-4-yl)chromane-7-sulfonamide;
(S&R)-4-(4'-Fluoro-5-(trifluoromethyl)-[1,1'-biphenyl]-2-yl)-N-(6-fluoropyridin-2-yl)chromane-7-sulfonamide;
(S&R)-4-(2-(1H-1,2,3-Triazol-1-yl)-4-(trifluoromethyl)phenyl)-N-(pyrimidin-2-yl)chromane-7-sulfonamide;
(S&R)-4-(2-(1H-1,2,3-Triazol-1-yl)-4-(trifluoromethyl)phenyl)-N-(pyridazin-3-yl)chromane-7-sulfonamide;
(S&R)-4-(2-(1H-1,2,3-Triazol-1-yl)-4-(trifluoromethyl)phenyl)-N-(5-fluoropyrimidin-2-yl)chromane-7-sulfonamide;
(S&R)-4-(2-(1H-1,2,3-Triazol-1-yl)-4-(trifluoromethyl)phenyl)-N-(pyrimidin-4-yl)chromane-7-sulfonamide;
(S&R)-4-(2-(1H-1,2,3-Triazol-1-yl)-4-(trifluoromethyl)phenyl)-N-(6-fluoropyridin-2-yl)chromane-7-sulfonamide;
(S&R)—N-(6-Fluoropyridin-2-yl)-4-(2-(2-methylthiazol-4-yl)-4-(trifluoromethyl)phenyl)chroman-7-sulfonamide;
(S&R)-4-(2-(2-Methylthiazol-4-yl)-4-(trifluoromethyl)phenyl)-N-(pyrimidin-2-yl)chroman-7-sulfonamide;
(S&R)—N-(5-Fluoropyrimidin-2-yl)-4-(2-(2-methylthiazol-4-yl)-4-(trifluoromethyl)phenyl)chroman-7-sulfonamide;
(S&R)-4-(2-(2-Methylthiazol-4-yl)-4-(trifluoromethyl)phenyl)-N-(pyrimidin-4-yl)chroman-7-sulfonamide;
(S&R)-4-(2-(2-Methylthiazol-4-yl)-4-(trifluoromethyl)phenyl)-N-(pyridazin-3-yl)chroman-7-sulfonamide;
(S&R)—N-(5-Fluoropyrimidin-2-yl)-4-(2-(2-methyloxazol-4-yl)-4-(trifluoromethyl)phenyl)chroman-7-sulfonamide;
(S&R)—N-(6-Fluoropyridin-2-yl)-4-(2-(2-methyloxazol-4-yl)-4-(trifluoromethyl)phenyl)chroman-7-sulfonamide;
(S&R)-4-(2-(2-Methyloxazol-4-yl)-4-(trifluoromethyl)phenyl)-N-(pyrimidin-2-yl)chroman-7-sulfonamide;
(S&R)-4-(2-(2-Methyloxazol-4-yl)-4-(trifluoromethyl)phenyl)-N-(pyrimidin-4-yl)chroman-7-sulfonamide;
(S&R)-4-(2-(2-Methyloxazol-4-yl)-4-(trifluoromethyl)phenyl)-N-(pyridazin-3-yl)chroman-7-sulfonamide;
(S&R)—N-(6-Fluoropyridin-2-yl)-4-(2-(2-(methylsulfonyl)ethyl)-4-(trifluoromethyl)phenyl)chroman-7-sulfonamide;
(S&R)-4-(2-(2-(Methylsulfonyl)ethyl)-4-(trifluoromethyl)phenyl)-N-(pyrimidin-2-yl)chroman-7-sulfonamide;
(S&R)—N-(5-Fluoropyrimidin-2-yl)-4-(2-(2-(methylsulfonyl)ethyl)-4-(trifluoromethyl)phenyl)chroman-7-sulfonamide;
(S&R)-4-(2-(2-(Methylsulfonyl)ethyl)-4-(trifluoromethyl)phenyl)-N-(pyrimidin-4-yl)chroman-7-sulfonamide;
(S&R)-4-(2-(1H-Pyrazol-1-yl)-4-(trifluoromethyl)phenyl)-N-(6-fluoropyridin-2-yl)chroman-7-sulfonamide;
(S&R)—N-(5-Fluoropyrimidin-2-yl)-4-(2-(thiazol-2-yl)-4-(trifluoromethyl)phenyl)chroman-7-sulfonamide;
(R/S)—N-(Pyrimidin-2-yl)-4-(2-(thiazol-2-yl)-4-(trifluoromethyl)phenyl)chroman-7-sulfonamide;
(R/S)—N-(Pyrimidin-4-yl)-4-(2-(thiazol-2-yl)-4-(trifluoromethyl)phenyl)chroman-7-sulfonamide;
(R/S)—N-(Pyridazin-3-yl)-4-(2-(thiazol-2-yl)-4-(trifluoromethyl)phenyl)chroman-7-sulfonamide;
(R/S)—N-(6-Fluoropyridin-2-yl)-4-(2-(thiazol-2-yl)-4-(trifluoromethyl)phenyl)chroman-7-sulfonamide;
(S&R)-4-(2-(6-Isopropoxypyridin-3-yl)-4-(trifluoromethyl)phenyl)-N-(pyrimidin-2-yl)chroman-7-sulfonamide;
(S&R)—N-(5-Fluoropyrimidin-2-yl)-4-(2-(6-isopropoxypyridin-3-yl)-4-(trifluoromethyl)phenyl)chroman-7-sulfonamide;
(S&R)-4-(2-(6-Ethoxypyridin-3-yl)-4-(trifluoromethyl)phenyl)-N-(5-fluoropyrimidin-2-yl)chroman-7-sulfonamide;
(R/S)-4-(2-(6-Ethoxypyridin-3-yl)-4-(trifluoromethyl)phenyl)-N-(pyrimidin-2-yl)chroman-7-sulfonamide;
(S/R)-4-(2-Chloro-4-(trifluoromethyl)phenyl)-N-(pyrimidin-2-yl)chroman-7-sulfonamide;
(S/R)-4-(2-Chloro-4-(trifluoromethyl) phenyl)-N-(5-fluoropyrimidin-2-yl)chroman-7-sulfonamide;
(S/R)-4-(2-Chloro-4-(trifluoromethyl)phenyl)-N-(pyrimidin-4-yl)chroman-7-sulfonamide;
(S/R)-4-(2-Chloro-4-(trifluoromethyl)phenyl)-N-(pyridazin-3-yl)chroman-7-sulfonamide;
(S/R)-4-(2-Chloro-4-(trifluoromethyl)phenyl)-N-(6-fluoropyridin-2-yl)chroman-7-sulfonamide;
(S&R)—N-(Pyrimidin-2-yl)-4-(2-(tetrahydro-2H-pyran-4-yl)-4-(trifluoromethyl)phenyl)chroman-7-sulfonamide;
(S&R)—N-(6-Fluoropyridin-2-yl)-4-(2-(2-oxopyrrolidin-1-yl)-4-(trifluoromethyl)phenyl)chroman-7-sulfonamide;
(S&R)—N-(5-Fluoropyrimidin-2-yl)-4-(2-(2-oxopyrrolidin-1-yl)-4-(trifluoromethyl)phenyl)chroman-7-sulfonamide;
(R/S)-4-(2-(2-Oxopyrrolidin-1-yl)-4-(trifluoromethyl)phenyl)-N-(pyrimidin-2-yl)chroman-7-sulfonamide;
(R/S)-4-(2-(2-Oxopyrrolidin-1-yl)-4-(trifluoromethyl)phenyl)-N-(pyrimidin-4-yl)chroman-7-sulfonamide;
(R/S)-4-(2-(2-Oxopyrrolidin-1-yl)-4-(trifluoromethyl)phenyl)-N-(pyridazin-3-yl)chromane-7-sulfonamide;

(S&R)-4-(2-Morpholino-4-(trifluoromethyl)phenyl)-N-(pyrimidin-2-yl)chroman-7-sulfonamide;
(S/R)—N-(5-Fluoropyrimidin-2-yl)-4-(2-morpholino-4-(trifluoromethyl)phenyl)chroman-7-sulfonamide;
(R/S)-4-(2-Morpholino-4-(trifluoromethyl)phenyl)-N-(pyrimidin-4-yl)chroman-7-sulfonamide;
(R/S)-4-(2-Morpholino-4-(trifluoromethyl)phenyl)-N-(pyridazin-3-yl)chroman-7-sulfonamide;
(R/S)—N-(6-Fluoropyridin-2-yl)-4-(2-morpholino-4-(trifluoromethyl)phenyl)chroman-7-sulfonamide;
(S&R)-4-(2-(2-Methoxyethoxy)-4-(trifluoromethyl)phenyl)-N-(pyrimidin-2-yl)chroman-7-sulfonamide;
(R/S)—N-(5-Fluoropyrimidin-2-yl)-4-(2-(2-methoxyethoxy)-4-(trifluoromethyl)phenyl)chroman-7-sulfonamide;
(R/S)-4-(2-(2-Methoxyethoxy)-4-(trifluoromethyl)phenyl)-N-(pyrimidin-4-yl)chroman-7-sulfonamide;
(R/S)-4-(2-(2-Methoxyethoxy)-4-(trifluoromethyl)phenyl)-N-(pyridazin-3-yl)chroman-7-sulfonamide;
(R/S)—N-(6-Fluoropyridin-2-yl)-4-(2-(2-methoxyethoxy)-4-(trifluoromethyl)phenyl)chroman-7-sulfonamide;
(S&R)-4-(2-(3-Methoxypropoxy)-4-(trifluoromethyl)phenyl)-N-(pyrimidin-2-yl)chroman-7-sulfonamide;
(R/S)—N-(5-Fluoropyrimidin-2-yl)-4-(2-(3-methoxypropoxy)-4-(trifluoromethyl)phenyl)chroman-7-sulfonamide;
(R/S)-4-(2-(3-Methoxypropoxy)-4-(trifluoromethyl)phenyl)-N-(pyridazin-3-yl)chroman-7-sulfonamide;
(R/S)—N-(6-Fluoropyridin-2-yl)-4-(2-(3-methoxypropoxy)-4-(trifluoromethyl)phenyl)chroman-7-sulfonamide;
(R/S)-4-(2-(2-Methoxyethyl)-4-(trifluoromethyl)phenyl)-N-(pyrimidin-2-yl)chroman-7-sulfonamide;
(R/S)—N-(5-Fluoropyrimidin-2-yl)-4-(2-(2-methoxyethyl)-4-(trifluoromethyl)phenyl)chroman-7-sulfonamide;
(R/S)—N-(6-Fluoropyridin-2-yl)-4-(2-(2-methoxyethyl)-4-(trifluoromethyl)phenyl)chroman-7-sulfonamide;
(R/S)-4-(2-(2-Methoxyethyl)-4-(trifluoromethyl)phenyl)-N-(pyrimidin-4-yl)chroman-7-sulfonamide;
(R/S)-4-(2-(2-Methoxyethyl)-4-(trifluoromethyl)phenyl)-N-(pyridazin-3-yl)chroman-7-sulfonamide;
(S&R)-4-(2-(3-Methoxypropyl)-4-(trifluoromethyl)phenyl)-N-(pyrimidin-2-yl)chroman-7-sulfonamide;
(R/S)—N-(5-Fluoropyrimidin-2-yl)-4-(2-(3-methoxypropyl)-4-(trifluoromethyl)phenyl)chroman-7-sulfonamide;
(R/S)-4-(2-(3-Methoxypropyl)-4-(trifluoromethyl)phenyl)-N-(pyrimidin-4-yl)chroman-7-sulfonamide;
(R/S)-4-(2-(3-Methoxypropyl)-4-(trifluoromethyl)phenyl)-N-(pyridazin-3-yl)chroman-7-sulfonamide;
(R/S)—N-(6-Fluoropyridin-2-yl)-4-(2-(3-methoxypropyl)-4-(trifluoromethyl)phenyl)chroman-7-sulfonamide;
(S&R)-4-(2-(4-Methoxybutyl)-4-(trifluoromethyl)phenyl)-N-(pyrimidin-2-yl)chroman-7-sulfonamide;
(R/S)—N-(5-Fluoropyrimidin-2-yl)-4-(2-(4-methoxybutyl)-4-(trifluoromethyl)phenyl)chroman-7-sulfonamide;
(R/S)-4-(2-(4-Methoxybutyl)-4-(trifluoromethyl)phenyl)-N-(pyrimidin-4-yl)chroman-7-sulfonamide;
(R/S)-4-(2-(4-Methoxybutyl)-4-(trifluoromethyl)phenyl)-N-(pyridazin-3-yl)chroman-7-sulfonamide;
(S&R)—N-(6-Fluoropyridin-2-yl)-4-(2-(4-methoxybutyl)-4-(trifluoromethyl)phenyl)chroman-7-sulfonamide;
(R/S)-4-(2-(2-Fluoroethyl)-4-(trifluoromethyl)phenyl)-N-(pyrimidin-2-yl)chroman-7-sulfonamide;
(R/S)-4-(2-(2-Fluoroethyl)-4-(trifluoromethyl)phenyl)-N-(5-fluoro pyrimidin-2-yl)chroman-7-sulfonamide;
(R/S)-4-(2-(2-Fluoroethyl)-4-(trifluoromethyl)phenyl)-N-(pyrimidin-4-yl)chroman-7-sulfonamide;
(R/S)-4-(2-(2-Fluoroethyl)-4-(trifluoromethyl)phenyl)-N-(pyridazin-3-yl)chroman-7-sulfonamide;
(R/S)-4-(2-(2-Fluoroethyl)-4-(trifluoromethyl)phenyl)-N-(6-fluoropyridin-2-yl)chroman-7-sulfonamide;
(R/S)-4-(2-(3-Fluoropropyl)-4-(trifluoromethyl)phenyl)-N-(pyrimidin-2-yl)chroman-7-sulfonamide;
(R/S)-4-(2-(3-Fluoropropyl)-4-(trifluoromethyl)phenyl)-N-(5-fluoropyrimidin-2-yl)chroman-7-sulfonamide;
(R/S)-4-(2-(3-Fluoropropyl)-4-(trifluoromethyl)phenyl)-N-(pyrimidin-4-yl)chroman-7-sulfonamide;
(R/S)-4-(2-(3-Fluoropropyl)-4-(trifluoromethyl)phenyl)-N-(pyridazin-3-yl)chroman-7-sulfonamide;
(R/S)-4-(2-(3-Fluoropropyl)-4-(trifluoromethyl)phenyl)-N-(6-fluoropyridin-2-yl)chroman-7-sulfonamide;
(R/S)-4-(2-(4-Fluorobutyl)-4-(trifluoromethyl)phenyl)-N-(pyrimidin-2-yl)chroman-7-sulfonamide;
(R/S)-4-(2-(4-Fluorobutyl)-4-(trifluoromethyl)phenyl)-N-(5-fluoropyrimidin-2-yl)chroman-7-sulfonamide;
(R/S)-4-(2-(4-Fluorobutyl)-4-(trifluoromethyl)phenyl)-N-(pyrimidin-4-yl)chroman-7-sulfonamide;
(R/S)-4-(2-(4-Fluorobutyl)-4-(trifluoromethyl)phenyl)-N-(pyridazin-3-yl)chroman-7-sulfonamide;
(R/S)-4-(2-(4-Fluorobutyl)-4-(trifluoromethyl)phenyl)-N-(6-fluoropyridin-2-yl)chroman-7-sulfonamide;
(R&S)—N-(Pyrimidin-2-yl)-4-(2-((tetrahydro-2H-pyran-4-yl)oxy)-4-(trifluoromethyl)phenyl)chroman-7-sulfonamide;
(R&S)—N-(5-Fluoropyrimidin-2-yl)-4-(2-((tetrahydro-2H-pyran-4-yl)oxy)-4-(trifluoromethyl)phenyl)chroman-7-sulfonamide;
(R&S)—N-(Pyrimidin-4-yl)-4-(2-((tetrahydro-2H-pyran-4-yl)oxy)-4-(trifluoromethyl)phenyl)chroman-7-sulfonamide;
(R&S)—N-(Pyridazin-3-yl)-4-(2-((tetrahydro-2H-pyran-4-yl)oxy)-4-(trifluoromethyl)phenyl)chroman-7-sulfonamide;
(R&S)—N-(6-Fluoropyridin-2-yl)-4-(2-((tetrahydro-2H-pyran-4-yl)oxy)-4-(trifluoromethyl)phenyl)chroman-7-sulfonamide;
(R&S)—N-(Pyrimidin-2-yl)-4-(2-(((S)-tetrahydrofuran-3-yl)oxy)-4-(trifluoromethyl)phenyl)chroman-7-sulfonamide;
(R&S)—N-(6-Fluoropyridin-2-yl)-4-(2-(((S)-tetrahydrofuran-3-yl)oxy)-4-(trifluoromethyl)phenyl)chroman-7-sulfonamide;
(S/R)—N-(5-Fluoropyrimidin-2-yl)-4-(2-(((S)-tetrahydrofuran-3-yl)oxy)-4-(trifluoromethyl)phenyl)chroman-7-sulfonamide;
(S/R)—N-(Pyrimidin-4-yl)-4-(2-(((S)-tetrahydrofuran-3-yl)oxy)-4-(trifluoromethyl)phenyl)chroman-7-sulfonamide;
(S/R)—N-(Pyridazin-3-yl)-4-(2-(((S)-tetrahydrofuran-3-yl)oxy)-4-(trifluoromethyl)phenyl)chroman-7-sulfonamide;
(S&R)—N-(Pyrimidin-2-yl)-4-(2-(((R)-tetrahydrofuran-3-yl)oxy)-4-(trifluoromethyl)phenyl)chroman-7-sulfonamide;
(S&R)-2'-(7-(N-(Pyrimidin-2-yl)sulfamoyl)chroman-4-yl)-5'-(trifluoromethyl)-[1,1'-biphenyl]-4-carboxylic acid;

(S&R)-2'-(7-(N-(5-Fluoropyrimidin-2-yl)sulfamoyl) chroman-4-yl)-5'-(trifluoromethyl)-[1,1'-biphenyl]-4-carboxylic acid;

(R/S)-2'-(7-(N-(Pyridazin-3-yl)sulfamoyl)chroman-4-yl)-5'-(trifluoromethyl)-[1,1'-biphenyl]-4-carboxylic acid;

(R/S)-2'-(7-(N-(6-Fluoropyridin-2-yl)sulfamoyl)chroman-4-yl)-5'-(trifluoromethyl)-[1,1'-biphenyl]-4-carboxylic acid;

(S&R)-4-(2-(5-Fluoropyridin-2-yl)-4-(trifluoromethyl)phenyl)-N-(pyrimidin-2-yl)chroman-7-sulfonamide;

(S&R)-4-(2-(5-Fluoropyridin-2-yl)-4-(trifluoromethyl)phenyl)-N-(5-fluoropyrimidin-2-yl)chroman-7-sulfonamide;

(S&R)-4-(2-(5-Fluoropyridin-2-yl)-4-(trifluoromethyl)phenyl)-N-(pyrimidin-4-yl)chroman-7-sulfonamide;

(S&R)-4-(2-(5-Fluoropyridin-2-yl)-4-(trifluoromethyl)phenyl)-N-(pyridazin-3-yl)chroman-7-sulfonamide;

(S)-4-(2-(6-Methylpyridin-3-yl)-4-(trifluoromethyl)phenyl)-N-(pyrimidin-2-yl)chroman-7-sulfonamide;

(R)-4-(2-(6-Methylpyridin-3-yl)-4-(trifluoromethyl)phenyl)-N-(pyrimidin-2-yl)chroman-7-sulfonamide;

(R/S)—N-(5-Fluoropyrimidin-2-yl)-4-(2-(6-methylpyridin-3-yl)-4-(trifluoromethyl)phenyl)chroman-7-sulfonamide;

(R/S)-4-(2-(6-Methylpyridin-3-yl)-4-(trifluoromethyl)phenyl)-N-(pyrimidin-4-yl)chroman-7-sulfonamide;

(R/S)-4-(2-(6-Methylpyridin-3-yl)-4-(trifluoromethyl)phenyl)-N-(pyridazin-3-yl)chroman-7-sulfonamide;

(R/S)—N-(6-Fluoropyridin-2-yl)-4-(2-(6-methylpyridin-3-yl)-4-(trifluoromethyl)phenyl)chroman-7-sulfonamide;

(R/S)-4-(2-(2-Oxooxazolidin-3-yl)-4-(trifluoromethyl)phenyl)-N-(pyrimidin-2-yl)chroman-7-sulfonamide;

(R/S)—N-(5-Fluoropyrimidin-2-yl)-4-(2-(2-oxooxazolidin-3-yl)-4-(trifluoro methyl)phenyl)chroman-7-sulfonamide;

(R/S)-4-(2-(2-Oxooxazolidin-3-yl)-4-(trifluoromethyl)phenyl)-N-(pyridazin-3-yl)chroman-7-sulfonamide;

(R/S)—N-(6-Fluoropyridin-2-yl)-4-(2-(2-oxooxazolidin-3-yl)-4-(trifluoromethyl)phenyl)chromane-7-sulfonamide;

(R/S)-4-(2-(3,3-Difluoropropyl)-4-(trifluoromethyl)phenyl)-N-(pyrimidin-2-yl)chroman-7-sulfonamide;

(R/S)-4-(2-(3,3-Difluoropropyl)-4-(trifluoromethyl)phenyl)-N-(5-fluoropyrimidin-2-yl)chroman-7-sulfonamide;

(R/S)-4-(2-(3,3-Difluoropropyl)-4-(trifluoromethyl)phenyl)-N-(pyrimidin-4-yl)chroman-7-sulfonamide;

(R/S)-4-(2-(3,3-Difluoropropyl)-4-(trifluoromethyl)phenyl)-N-(pyridazin-3-yl)chroman-7-sulfonamide;

(R/S)-4-(2-(3,3-Difluoropropyl)-4-(trifluoromethyl)phenyl)-N-(6-fluoropyridin-2-yl)chromane-7-sulfonamide;

(R&S)-4-(2-(Oxetan-3-yloxy)-4-(trifluoromethyl)phenyl)-N-(pyrimidin-2-yl)chroman-7-sulfonamide;

(S/R)—N-(5-Fluoropyrimidin-2-yl)-4-(2-(oxetan-3-yloxy)-4-(trifluoromethyl)phenyl)chroman-7-sulfonamide;

(S/R)—N-(6-Fluoropyridin-2-yl)-4-(2-(oxetan-3-yloxy)-4-(trifluoromethyl)phenyl)chromane-7-sulfonamide;

(S&R)-4-(2-(3-Fluoropropoxy)-4-(trifluoromethyl)phenyl)-N-(pyrimidin-2-yl)chroman-7-sulfonamide;

(R/S)-4-(2-(5-Fluoro-6-methylpyridin-2-yl)-4-(trifluoromethyl)phenyl)-N-(pyrimidin-2-yl)chroman-7-sulfonamide;

(R/S)-4-(2-(5-Fluoro-6-methylpyridin-2-yl)-4-(trifluoromethyl)phenyl)-N-(5-fluoropyrimidin-2-yl)chroman-7-sulfonamide;

(R/S)-4-(2-(5-Fluoro-6-methylpyridin-2-yl)-4-(trifluoromethyl)phenyl)-N-(pyridazin-3-yl)chroman-7-sulfonamide;

(R/S)-4-(2-(5-Fluoro-6-methylpyridin-2-yl)-4-(trifluoromethyl)phenyl)-N-(6-fluoropyridin-2-yl)chroman-7-sulfonamide;

(S&R)-4-(2-Methoxy-4-(trifluoromethyl)phenyl)-N-(pyrimidin-2-yl)chroman-7-sulfonamide;

(S&R)—N-(6-Fluoropyridin-2-yl)-4-(2-methoxy-4-(trifluoromethyl)phenyl)chroman-7-sulfonamide;

(S&R)-4-(2-(3-Oxomorpholino)-4-(trifluoromethyl)phenyl)-N-(pyrimidin-2-yl)chroman-7-sulfonamide;

(S&R)-4-(2-(1,1-Dioxidothiomorpholino)-4-(trifluoromethyl)phenyl)-N-(pyrimidin-2-yl)chroman-7-sulfonamide;

(R/S)-4-(2-(1,1-Dioxidothiomorpholino)-4-(trifluoromethyl)phenyl)-N-(5-fluoropyrimidin-2-yl)chroman-7-sulfonamide;

(R/S)-4-(2-(1,1-Dioxidothiomorpholino)-4-(trifluoromethyl)phenyl)-N-(6-fluoropyridin-2-yl)chroman-7-sulfonamide;

(R/S)-4-(2-(1,1-Dioxidothiomorpholino)-4-(trifluoromethyl)phenyl)-N-(pyridazin-3-yl)chroman-7-sulfonamide;

(R/S)-4-(2-(1,1-Dioxidothiomorpholino)-4-(trifluoromethyl)phenyl)-N-(pyrimidin-4-yl)chromane-7-sulfonamide;

(S&R)-4-(2-propyl-4-(trifluoromethyl)phenyl)-N-(pyrimidin-2-yl)chroman-7-sulfonamide;

(S&R)—N-(5-fluoropyrimidin-2-yl)-4-(2-propyl-4-(trifluoromethyl)phenyl)chroman-7-sulfonamide;

(S&R)-4-(2-propyl-4-(trifluoromethyl)phenyl)-N-(pyridazin-3-yl)chroman-7-sulfonamide; and (S&R)—N-(6-fluoropyridin-2-yl)-4-(2-propyl-4-(trifluoromethyl)phenyl)chroman-7-sulfonamide or racemate thereof, N-oxide thereof or a pharmaceutically acceptable salt thereof.

16. A pharmaceutical composition comprising one or more compounds according to claim 1, and one or more pharmaceutically acceptable excipients.

17. A method for treating, managing and/or lessening pain associated with the modulation of Nav1.7 function in a subject in need thereof wherein the method comprises administering to the subject a therapeutically effective amount of a compound according to claim 1, or a pharmaceutically acceptable salt thereof.

18. The method of claim 17, wherein the pain is neuropathic pain.

19. The method of claim 17, wherein the pain is inflammatory pain.

20. The method of claim 17, wherein the pain associated with the modulation of Nav1.7 function is selected from the group consisting of erythromelalgia, postoperative pain, arthritis pain, osteoarthritis pain, pain associated with cancer including chemotherapy pain, neuropathic pain secondary to metastatic inflammation, neuralgic, orofacial pain, burn pain, somatic pain, dental pain, sciatica pain, intestinal obstruction pain, visceral pain, colicky pain, myofascial pain, trauma pain, labour pain, trigeminal neuralgia, glossopharyngeal neuralgia, adiposis dolorosa, acute herpetic and postherpetic neuralgia, diabetic neuropathy, causalgia, brachial plexus avulsion, occipital neuralgia, reflux sympathetic dystrophy, fibromyalgia, gout, phantom limb pain, pain following stroke, thalamic lesions, radiculopathy, chronic headache, migraine pain, familial hemiplegic migraine, conditions associated with cephalic pain, sinus headache, tension headache, cardiac pain arising from an ischemic myocardium, pain following stroke, neuropathy secondary to metastatic inflammation, pain due to connective tissue damage, and other forms of neuralgic, neuropathic, and idiopathic pain syndromes.

21. A process for the preparation of compound of Formula (Ia):

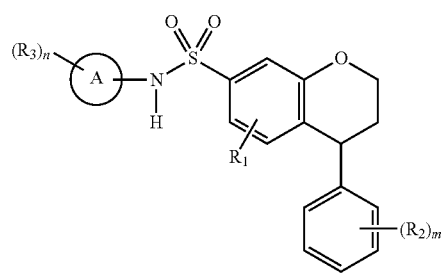

(Ia)

wherein ring A, $R_1$, $R_2$, $R_3$, 'm' and 'n' are as defined in claim-1;

the process comprising the steps of:

a) reacting a compound of formula (2) with NCS followed by pentafluorophenol gives the pentafluoro ester of formula (7)

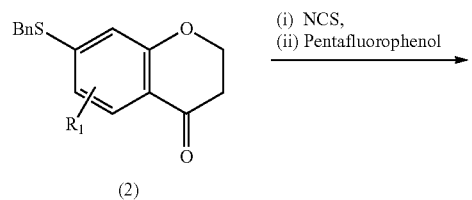

(2)

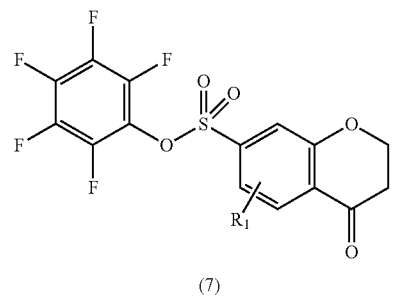

(7)

b) reacting a compound of formula (7) with p-tosyl hydrazine to give the hydrazone compound of formula (8)

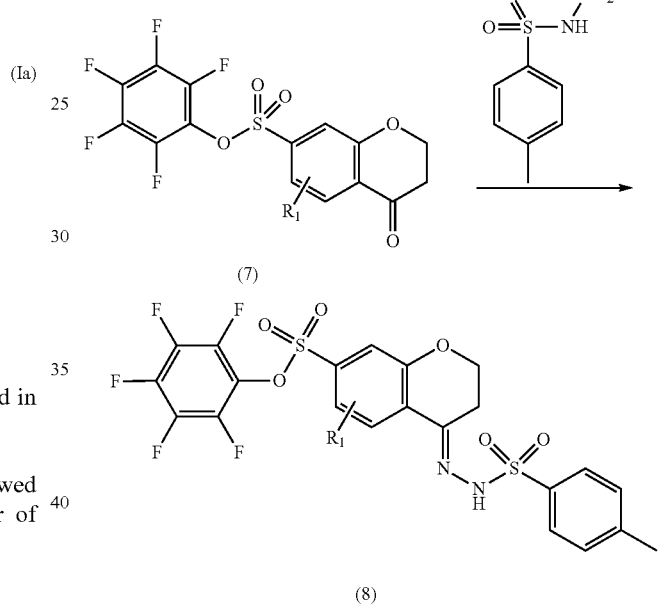

(7)

(8)

c) coupling of a compound of formula (8) with compound of formula (4) in presence of suitable Pd catalyst to give compound of formula (6) which can also be prepared from compound of formula (5) by reacting with sulfuryl chloride or NCS or dichlorohydantoin followed by pentafluorophenol

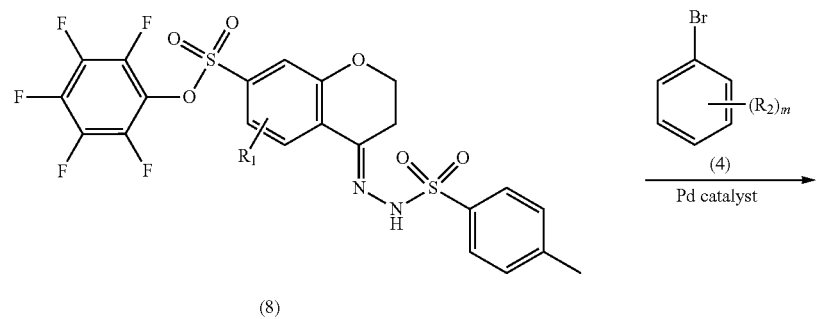

(8)

-continued
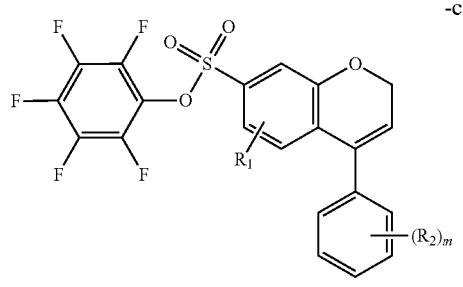 (6)
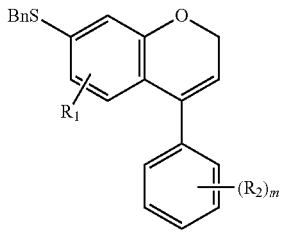 (5)
Sulfonyl ester formation
d) reducing a compound of formula (6) using Pd/C to give compound of formula (9)
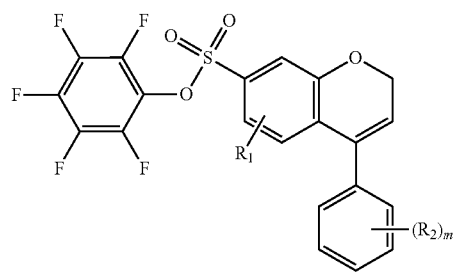
(6)
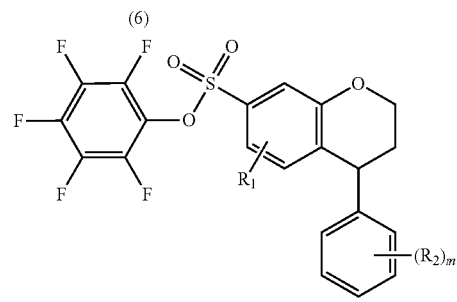
(9)
e) coupling of a compound of formula (9) with amine of formula (10) to give compound of formula (1a)
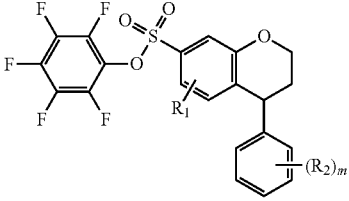
(9)
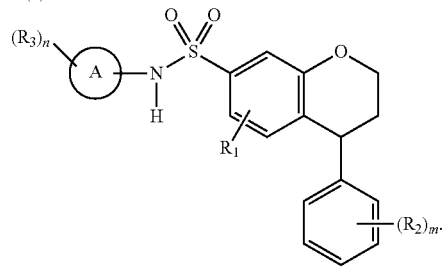
(Ia)
* * * * *